United States Patent
Chen et al.

(10) Patent No.: US 10,053,515 B2
(45) Date of Patent: Aug. 21, 2018

(54) ANTI-COAGULATION FACTOR XI ANTIBODIES

(71) Applicants: Merck Sharp & Dohme Corp., Rahway, NJ (US); Adimab, LLC, Lebanon, NH (US)

(72) Inventors: Zhu Chen, Warren, NJ (US); Kenneth P. Ellsworth, Cranbury, NJ (US); James A. Milligan, New Egypt, NJ (US); Elizabeth Oldham, Palo Alto, CA (US); Dietmar Seiffert, Lawrenceville, NJ (US); Vaishnavi Ganti, Palo Alto, CA (US); Mohammad Tabrizifard, Palo Alto, CA (US); Bianka Prinz, Lebanon, NH (US)

(73) Assignees: Merck Sharp & Dohme Corp., Rahway, NJ (US); Adimab LLC, Lebanon, NH (US)

( * ) Notice: Subject to any disclaimer, the term of this patent is extended or adjusted under 35 U.S.C. 154(b) by 0 days.

(21) Appl. No.: 15/409,607

(22) Filed: Jan. 19, 2017

(65) Prior Publication Data

US 2017/0226225 A1   Aug. 10, 2017

Related U.S. Application Data

(60) Provisional application No. 62/281,842, filed on Jan. 22, 2016.

(51) Int. Cl.
| | | |
|---|---|---|
| C07K 16/36 | (2006.01) | |
| A61K 39/395 | (2006.01) | |
| A61P 7/02 | (2006.01) | |
| C07K 16/30 | (2006.01) | |
| C07K 14/745 | (2006.01) | |
| A61K 39/00 | (2006.01) | |

(52) U.S. Cl.
CPC .......... *C07K 16/36* (2013.01); *A61K 39/3955* (2013.01); *A61P 7/02* (2018.01); *C07K 16/30* (2013.01); *A61K 2039/505* (2013.01); *C07K 14/745* (2013.01); *C07K 2317/33* (2013.01); *C07K 2317/52* (2013.01); *C07K 2317/56* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 6,391,299 B1 | 5/2002 | Blackburn et al. |
| 8,236,316 B2 | 8/2012 | Gruber et al. |
| 8,388,959 B2 | 3/2013 | Gruber et al. |
| 8,399,648 B2 | 3/2013 | Gruber et al. |
| 8,940,883 B2 | 1/2015 | Gruber et al. |
| 9,096,673 B2 | 8/2015 | Tocker et al. |
| 9,102,725 B2 | 8/2015 | Korman et al. |
| 9,102,738 B2 | 8/2015 | Terrett et al. |
| 9,119,839 B2 | 9/2015 | Huang et al. |
| 9,125,895 B2 | 9/2015 | Gruber et al. |
| 9,138,475 B2 | 9/2015 | Vistica et al. |
| 9,181,330 B2 | 11/2015 | Marks et al. |
| 9,234,043 B1 | 1/2016 | Campbell et al. |
| 9,255,153 B2 | 2/2016 | Cunningham et al. |
| 9,266,964 B2 | 2/2016 | Sexton et al. |
| 9,273,135 B2 | 3/2016 | Korman et al. |
| 9,284,589 B2 | 3/2016 | Vaughan et al. |
| 9,315,573 B2 | 4/2016 | Harding et al. |
| 9,387,247 B2 | 7/2016 | Korman et al. |
| 9,394,370 B2 | 7/2016 | Tawara et al. |
| 9,428,572 B2 | 8/2016 | Throsby et al. |
| 9,428,579 B2 | 8/2016 | Giles-Komar et al. |
| 9,481,731 B2 | 11/2016 | Cunningham et al. |
| 9,486,523 B2 | 11/2016 | Simard |
| 9,492,539 B2 | 11/2016 | Korman et al. |
| 9,492,540 B2 | 11/2016 | Korman et al. |
| 9,522,957 B2 | 12/2016 | Cunningham et al. |
| 9,540,448 B2 | 1/2017 | Scheinberg et al. |
| 9,562,108 B2 | 2/2017 | Walker et al. |
| 9,631,025 B2 | 4/2017 | Vistica et al. |
| 9,631,029 B2 | 4/2017 | Chiusaroli et al. |
| 9,636,399 B2 | 5/2017 | Gruber et al. |
| 9,637,550 B2 | 5/2017 | Gruber et al. |
| 2015/0203574 A1 | 7/2015 | Rajpal et al. |
| 2015/0259436 A1 | 9/2015 | Scheinberg et al. |
| 2015/0329641 A1 | 11/2015 | Braun et al. |
| 2016/0009796 A9 | 1/2016 | Mike et al. |
| 2016/0017036 A1 | 1/2016 | Merchant et al. |
| 2016/0024221 A1 | 1/2016 | Vistica et al. |

(Continued)

FOREIGN PATENT DOCUMENTS

| | | |
|---|---|---|
| EP | 2222707 B1 | 9/2010 |
| EP | 3002298 A1 | 4/2016 |

(Continued)

OTHER PUBLICATIONS

Rudikoff et al (Proc Natl Acad Sci USA 1982 vol. 79 pp. 1979-1983).*

Van Montfoort et al., Two Novel Inhibitor Anti-Human Factor XI Antibodies Prevent Cessation of Blood Flow in a Murine Venous Thrombosis Model, Thrombosis and Haemostasis, vol. 110, No. 5, 2013, pp. 1065-1073.

Leung et al., Inhibition of Factor XII Mediated Activation of Factor XI Provides Protection Against Experimental Acute Ischemic Stroke in Mice, Translational Stroke Research, vol. 3, No. 3, 2012, pp. 381-389.

(Continued)

*Primary Examiner* — Zachary Howard
(74) *Attorney, Agent, or Firm* — John David Reilly; Laura Ginkel

(57) ABSTRACT

Antibodies that bind the apple 2 domain of human coagulation Factor XI and inhibit activation of FXI by coagulation factor XIIa are described.

18 Claims, 34 Drawing Sheets

(56) References Cited

U.S. PATENT DOCUMENTS

| | | |
|---|---|---|
| 2016/0046707 A1 | 2/2016 | Imai et al. |
| 2016/0060343 A1 | 3/2016 | Huang et al. |
| 2016/0075782 A1 | 3/2016 | Korman et al. |
| 2016/0102150 A1 | 4/2016 | Sexton et al. |
| 2016/0115228 A1 | 4/2016 | Smith |
| 2016/0152700 A1 | 6/2016 | Comeau et al. |
| 2016/0168265 A1 | 6/2016 | Marks et al. |
| 2016/0228570 A1 | 8/2016 | Nissim et al. |
| 2016/0237147 A1 | 8/2016 | Wild, Jr. et al. |
| 2016/0251443 A1 | 9/2016 | Tocker et al. |
| 2016/0304596 A1 | 10/2016 | Wild, Jr. et al. |
| 2016/0340440 A1 | 11/2016 | Fanslow, III et al. |
| 2016/0347845 A1 | 12/2016 | Kumar et al. |
| 2017/0073408 A1 | 3/2017 | Han et al. |
| 2017/0073421 A1 | 3/2017 | Kjaergaard et al. |
| 2017/0088620 A1 | 3/2017 | Nioi et al. |
| 2017/0088630 A1 | 3/2017 | Scheinberg et al. |
| 2017/0096474 A1 | 4/2017 | Marks et al. |
| 2017/0106095 A1 | 4/2017 | Batt et al. |
| 2017/0107273 A1 | 4/2017 | Wakita et al. |
| 2017/0115307 A1 | 4/2017 | Garcia-Martinez et al. |
| 2017/0204195 A1 | 7/2017 | Gruber et al. |

FOREIGN PATENT DOCUMENTS

| | | |
|---|---|---|
| JP | H0656382 | 7/1994 |
| WO | 198912463 | 12/1989 |
| WO | 199726010 | 7/1997 |
| WO | 2009067660 | 5/2009 |
| WO | 2009154461 | 12/2009 |
| WO | 2010080623 | 7/2010 |
| WO | 2012009568 | 1/2012 |
| WO | 2013167669 | 11/2013 |
| WO | 2013173255 | 11/2013 |
| WO | 2016023019 | 2/2016 |
| WO | 2016164637 | 10/2016 |
| WO | 2016201389 | 12/2016 |
| WO | 2016207858 | 12/2016 |
| WO | 2017015619 | 1/2017 |

OTHER PUBLICATIONS

Zhu et al., FXIa and Platelet Polyphosphate as Therapeutic Targets During Human Blood Clotting on Collagen Tissue Factor Surfaces Under Flow, Blood, vol. 126, No. 12, 2015, pp. 1494-1502.

Puy et al., Blood Journal—Activated Factor XI increases the procoagulant activity of the extrinsic pathway by inactivating tissue factor pathway inhibitor, vol. 125, 2015, p. 1488.

Rudikoff et al., Proceedings National Academy of Sciences PNAS, National Academy of Sciences US, vol. 79, 1982, pp. 1979-1983.

Angal et al., A Single Amino Acid Substitution Abolishes the Heterogeneity of Chimeric Mouse/Human (IgG4) Antibody, Molec. Immunol. vol. 30, 1993, pp. 105-108.

Akiyama et al., Mechanism of Activation of Coagulation Factor XI by Factor XIIa Studied with Monoclonal Antibodies, J. Clin. Invest. vol. 78, 1986, pp. 1631-1637.

Baglia et al., A Binding Site for Thrombin in the Apple 1 Domain of Factor XI, JBC, vol. 271, 1996, pp. 3652-3658.

Baglia et al., Functional domains in the heavy-chain region of factor XI: a high molecular weight kininogen-binding site and a substrate-binding site for factor IX, Blood, vol. 74, 1989, pp. 244-251.

Fujikawa et al., Amino Acid Sequence of Human Factor XI, A Blood Coagulation factor for Tandem Repeats that are Highly Homologous with Plasma Prekallikrein, Blood, vol. 74, 1989, pp. 2417-2424.

Labrijn et al., Therapeutic IgG4 antibodies engage in Fab-arm exchange with endogenous human IgG4 in vivo, Nat. Biotechnol. vol. 27, 2009, pp. 767-771.

McMullen et al., Location of the Disulfide Bonds in Human Coagulation Factor XI: The Presence of Tandem Apple Domains, Biochem. vol. 30, 1991, pp. 2056-2060.

Nishikado et al., Murine Monoclonal Antibodies to Human Factor XI, Thromb Res. vol. 42, 1986, pp. 225-234.

Sinha et al., Functional Characterization of Human Blood Coagulation Factor XIa Using Hybridoma Antibodies, JBC, vol. 260, 1985, pp. 10714-10719.

Stern et al., Acquired Antibody to Factor XI in a Patient with Congenital Factor XI Deficiency, J. Clin. Invest. vol. 69, 1982, pp. 1270-1276.

Sun et al., Identification of a Factor IX Binding Site on the Third Apple Domain of Activated Factor XIJBC, vol. 271, 1996, pp. 29023-29028.

Leung et al., Inhibition of Factor XII Mediated Activation of Factor XI Provides Protection Against Experimental Acute Ischemic Stroke in Mice, Trans. Stroke Res. vol. 3, 2012, pp. 381-389.

Van Montfoort et al., Two Novel Inhibitory Anti-human Factor XI Antibodies Prevent Cessation of Blood Flow in Murine Venous Thrombosis Model, Thromb. and Haemo. vol. 10, 2013, pp. 1065-1073.

Puy et al., Activated Factor XI Increases the Procoagulant Activity of the Extrinsic Pathway by Inactivating Tissue Factor Pathway Inhibitor, Blood, vol. 125, 2015, pp. 1488-1496.

Rudnikoff et al., Single Amino Acid Substitution Altering Antigen-binding Specificity, Proc. Natl. Acad. Sci. USA, vol. 79, 1982, pp. 1979-1983.

Zhu et al., FXIA & Platelet Polyphosphate as Therapeutic Targets During Human Blood Clotting on Collagen/Tissue Factor Surfaces Under Flow, Blood, vol. 126, 2015, 1494-1502.

* cited by examiner

Heavy Chain variable domain of αFXI-13654p (SEQ ID NO:16)

```
         1         2         3         4         5         6         7         8         9
123456789012345678901234567890123456789012a34567890123456789012abc345678901234
EVQLVESGGGLVKPGGSLRLSCAASGFTFSSYSMNWVRQAPGKGLEWVSSISSSSSYIYYADSVKGRFTISRDNAKNSLYLQMNSLRAEDTAVYYCAR
                         |___HC-CDR1__|              |_____HC-CDR2_____|

1    1
5678 90abcde1234567890123
SYYDYDQGYGMDVWGQGTTVTVSS
|_____HC-CDR3_____|
```

Light Chain variable domain of αFXI-13654p (SEQ ID NO:17)

```
         1         2         3         4         5         6         7         8         9
123456789012345678901234567890123456789012345678901234567890123456789012345678
DIQMTQSPSSVSASVGDRVTITCRASQGISSWLAWYQQKPGKAPKLLIYAASSLQSGVPSRFSGSGSGTDFTLTISSLQPEDFATYYCQQVNSYPITF
                       |____LC-CDR1___|        |_LC-CDR2_|                           |__LC-CDR3__|

1
8901234567
GGGTKVEIK
```

FIG.7

Heavy Chain of αFXI-13654p-IgG4 (S228P) (+/-K)/kappa (SEQ ID NO:59)
*EVQLVESGGGLVKPGGSLRLSCAASGFTFSSYSMNWRQAPGKGLEWVSSISSSSSYIYYADSVKGRFTISRDNAKNSLYLQMNSLRAEDTAVYYCAR SYYDYDQGYGMDVWGQGTTVTVSSA*STKGPSVFPLAPCSRSTSESTAALGCLVKDYFPEPVTVSWNSGALTSGVHTFPAVLQSSGLYSLSSVVTVPSS SLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPR EEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENN YKTTPPVLDSDGSFFLYSRLTVDKSRWQEGNVFSCSVMHEALHNHYTQKSLSLSLGX Light Chain of αFXI-13654p-IgG4 (S228P)(+/-K)/kappa (SEQ ID NO:19)
*DIQMTQSPSSVSASVGDRVTITCRASQGISSWLAWYQQKPGKAPKLLIYAASSLQSGVPSRFSGSGSGTDFTLTISSLQPEDFATYYCQQYNSYPITF GGGTKVEIKR*TVAAPSVFIFPPSDEQLKSGTASVVCLLNNFYPREAKVQWKVDNALQSGNSQESVTEQDSKDSTYSLSSTLTLSKADYEKHKVYACEV THQGLSSPVTKSFNRGEC

FIG.8

Heavy Chain variable domain of αFXI-13716p (SEQ ID NO:20)

```
         1         2         3         4         5         6         7         8         9
1234567890123456789012345678901234567890123456789012a345678901234567890abc345678901234
QVQLVQSGAEVKKPGASVKVSCKASGYTFTSYSMHWVRQAPGQGLEWMGIINPSGGSTSYAQKFQGRVTMTRDTSTSTVYMELSSLRSEDTAVYYCAR
                         └──── HC-CDR1 ────┘           └─────── HC-CDR2 ───────┘
    1         1
567890abcdefg1234567890123
GAYLMELYYYGMDVWGQGTTVTVSS
└──── HC-CDR3 ────┘
```

Light Chain variable domain of αFXI-13716p (SEQ ID NO:21)

```
         1         2         3         4         5         6         7         8         9
123456789012345678901234567890123456789012345678901234567890123456789012345678901234568
EIVMTQSPATLSVSPGERATLSCRASQSVSSNLAWYQQKPGQAPRLLIYGASTRATGIPARFSGSGSGTEFTLTISSLQSEDFAVYYCQQFNDWPLTF
                       └──── LC-CDR1 ────┘              └─ LC-CDR2 ─┘                   └── LC-CDR3 ──┘
    1
890123456
GGGTKVEIK
```

FIG.9

Heavy Chain of αFXI-13716p-IgG4 (S228P)(+/-K)/Kappa (SEQ ID NO:60)
*QVQLVQSGAEVKKPGASVKVSCKASGYTFTSYSMHWVRQAPGQGLEWMGIINPSGGSTSYAQKFQGRVTMTRDTSTSTVYMELSSLRSE
DTAVYYCARGAYLMELYYYYGMDVWGQGTTVTVSS*ASTKGPSVFPLAPCSRSTSESTAALGCLVKDYFPEPVTVSWNSGALTSGVHTFP
AVLQSSGLYSLSSVVTVPSSSLGTKTYTCNVDHKPSNTKVDKRVESKYGPPCPPCPAPEFLGGPSVFLFPPKPKDTLMISRTPEVTCVV
VDVSQEDPEVQFNWYVDGVEVHNAKTKPREEQFNSTYRVVSVLTVLHQDWLNGKEYKCKVSNKGLPSSIEKTISKAKGQPREPQVYTLP
PSQEEMTKNQVSLTCLVKGFYPSDIAVEWESNGQPENNYKTTPPVLDSDGSFFLYSRLTVDKSRWQEGNVFSCSVMHEALHNHYTQKSL
SLSLGX Light Chain variable domain of αFXI-13716p-IgG4 (S228P)(+/-K)/Kappa (SEQ ID NO:23)
*EIVMTQSPATLSVSPGERATLSCRASQSVSSNLAWYQQKPGQAPRLLIYGASTRATGIPARFSGSGSGTEFTLTISSLQSEDFAVYYCQ
QFNDWPLTFGGGTKVEIKRT*VAAPSVFIFPPSDEQLKSGTASVVCLLNNFYPREAKVQWKVDNALQSGNSQESVTEQDSKDSTYSLSST
LTLSKADYEKHKVYACEVTHQGLSSPVTKSFNRGEC

FIG. 10

Heavy Chain variable domain of αFXI-13716 (SEQ ID NO:24)

```
         1         2         3         4          5               6         7         8           9
123456789012345678901234567890123456789012345678901 2a34567890123456789012abc34567890 1234
EVQLVQSGAEVKKPGASVKVSCKASGYTFTSYSMHWVRQAPGQGLEWMGI IINPSGGSTSYAQKFQGRVIMTRDTSTSTVYMELSSLRSEDTAVYYCAR
                              └── HC-CDR1 ──┘     └────── HC-CDR2 ──────┘
   1         1
567890abcdefg123456789 0123
GAYLLELYYYGMDVWGQGTTVTVSS
└── HC-CDR3 ──┘
```

Light Chain variable domain of αFXI-13716 (SEQ ID NO:21)

```
         1         2         3         4         5          6         7         8          9
1234567890123456789012345678901234567890123456789012345678 9012345678 901234567890123456 78
EIVMTQSPATLSVSPGERATLSCRASQSVSSNLAWYQQKPGQAPRLLIYGASTRATG IPARFSGSGSGTEFTLTISSLQSEDFAVYYCQQFNDWPLT F
                       └────── LC-CDR1 ──────┘           └── LC-CDR2 ─┘                └── LC-CDR3 ──┘
   1
8901234 56
GGGTKVEIK
```

FIG.11

Heavy Chain of αFXI-13716-IgG4 (S228P) Q1E M103L (+/-K)/Kappa (SEQ ID NO:61)
*EVQLVQSGAEVKKPGASVKVSCKASGYTFTSYSMHWVRQAPGQGLEWMGIINPSGGSTSYAQKFQGRVTMTRDTSTSTVYMELSSLRSE
DTAVYYCARGAYLLELYYYYGMDVWGQGTTVTVSS*ASTKGPSVFPLAPCSRSTSESTAALGCLVKDYFPEPVTVSWNSGALTSGVHTFP
AVLQSSGLYSLSSVVTVPSSSLGTKTYTCNVDHKPSNTKVDKRVESKYGPPCPPCPAPEFLGGPSVFLFPPKPKDTLMISRTPEVTCVV
VDVSQEDPEVQFNWYVDGVEVHNAKTKPREEQFNSTYRVVSVLTVLHQDWLNGKEYKCKVSNKGLPSSIEKTISKAKGQPREPQVYTLP
PSQEEMTKNQVSLTCLVKGFYPSDIAVEWESNGQPENNYKTTPPVLDSDGSFFLYSRLTVDKSRWQEGNVFSCSVMHEALHNHYTQKSL
SLSLGX Light Chain variable domain of αFXI-13716-IgG4 (S228P) Q1E M103L (+/-K)/Kappa (SEQ ID NO:23)
*EIVMTQSPATLSVSPGERATLSCRASQSVSSNLAWYQQKPGQAPRLLIYGASTRATGIPARFSGSGSGTEFTLTISSLQSEDFAVYYCQ
QFNDWPLTFGGGTKVEIK*RTVAAPSVFIFPPSDEQLKSGTASVVCLLNNFYPREAKVQWKVDNALQSGNSQESVTEQDSKDSTYSLSST
LTLSKADYEKHKVYACEVTHQGLSSPVTKSFNRGEC

FIG.12

Heavy Chain of aFXI-13654p-IgG1 (+/-K)/kappa (SEQ ID NO:62)
*EVQLVESGGGLVKPGGSLRLSCAASGFTFSSYSMNWVRQAPGKGLEWVSSISSSSSYIYYADSVKGRFTISRDNAKNSLYLQMNSLRAE
DTAVYYCARSYYDYDQGYGMDVWGQGTTVTVSS*ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEPKSCDKTHTCPPCPAPELLGGPSVFLFPPKPKDTL
MISRTPEVTCVVVDVSHEDPEVKFNWYVDGVEVHNAKTKPREEQYNSTYRVVSVLTVLHQDWLNGKEYKCKVSNKALPA
PIEKTISKAKGQPREPQVYTLPPSRDELTKNQVSLTCLVKGFYPSDIAVEWESNGQPENNYKTTPPVLDSDGSFFLYSKLTVD
KSRWQQGNVFSCSVMHEALHNHYTQKSLSLSPGX Light Chain of aFXI-13654p-IgG1/kappa (SEQ ID NO:19)
*DIQMTQSPSSVSASVGDRVTITCRASQGISSWLAWYQQKPGKAPKLLIYAASSLQSGVPSRFSGSGSGTDFTLTISSLQPEDFATYYCQQVNSYPITF
GGGTKVEIK*RTVAAPSVFIFPPSDEQLKSGTASVVCLLNNFYPREAKVQWKVDNALQSGNSQESVTEQDSKDSTYSLSSTLTLSKADYEKHKVYACEV
THQGLSSPVTKSFNRGEC

FIG.13

Heavy Chain of αFXI-13716p-IgG1 (+/-K)/kappa (SEQ ID NO:63)
*QVQLVQSGAEVKKPGASVKVSCKASGYTFTSYSMHWVRQAPGQGLEWMGIINPSGGSTSYAQKFQGRVTMTRDTSTSTVMELSSL
RSEDTAVYYCARGAYLMELYYYGMDVWGQGTTVTVSS*ASTKGPSVFPLAPSSKSTSGGTAALGCLVKDYFPEPVTVSWNSGAL
TSGVHTFPAVLQSSGLYSLSSVVTVPSSSLGTQTYICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYPSDIAVEWESNGQPENNYKTTPPVLDSDGSFFLYSKL
TVDKSRWQQGNVFSCSVMHEALHNHYTQKSLSLSPGX Light Chain variable domain of αFXI-13716p-IgG1 (SEQ ID NO:23)
*EIVMTQSPATLSVSPGERATLSCRASQSVSSNLAWYQQKPGQAPRLLIYGASTRATGIPARFSGSGSGTEFTLTISSLQSEDFAVYYCQ
QFNDWPLTFGGGTKVEIK*RTVAAPSVFIFPPSDEQLKSGTASVVCLLNNFYPREAKVQWKVDNALQSGNSQESVTEQDSKDSTYSLSST
LTLSKADYEKHKVYACEVTHQGLSSPVTKSFNRGEC

FIG. 14

Heavy Chain of αFXI-13716p-IgG1 (+/-K) Q1E M103L/kappa (SEQ ID NO:64)
*EVQLVQSGAEVKKPGASVKVSCKASGYTFTSYSMHWVRQAPGQGLEWMGIINPSGGSTSYAQKFQGRVTMTRDTSTSTVYMELSSLR
SEDTAVYYCARGAYLLELYYYGMDVWGQGTTVTVSS*ASTKGPSVFPLAPSSKSTSGGTAALGCLVKDYFPEPVTVSWNSGALTS
GVHTFPAVLQSSGLYSLSSVVTVPSSSLGTQTYICNVNHKPSNTKVDKKVEPKSCDKTHTCPPCPAPELLGGPSVFLFPPKPKD
TLMISRTPEVTCVVVDVSHEDPEVKFNWYVDGVEVHNAKTKPREEQYNSTYRVVSVLTVLHQDWLNGKEYKCKVSNKAL
PAPIEKTISKAKGQPREPQVYTLPPSRDELTKNQVSLTCLVKGFYPSDIAVEWESNGQPENNYKTTPPVLDSDGSFFLYSKLTV
DKSRWQQGNVFSCSVMHEALHNHYTQKSLSLSPGX Light Chain variable domain of αFXI-13716-IgG1 Q1E M103L (+/-K)/Kappa (SEQ ID NO:23)
*EIVMTQSPATLSVSPGERATLSCRASQSVSSNLAWYQQKPGQAPRLLIYGASTRATGIPARFSGSGSGTEFTLTISSLQSEDFAVYYCQ
QFNDWPLTFGGGTKVEIK*RTVAAPSVFIFPPSDEQLKSGTASVVCLLNNFYPREAKVQWKVDNALQSGNSQESVTEQDSKDSTYSLSST
LTLSKADYEKHKVYACEVTHQGLSSPVTKSFNRGEC

FIG. 15

```
                        SEQUENCE LISTING

<160> NUMBER OF SEQ ID NOS: 72

<210> SEQ ID NO 1
<211> LENGTH: 9
<212> TYPE: PRT
<213> ORGANISM: Artificial Sequence
<220> FEATURE:
<223> OTHER INFORMATION: alpha-FXI-13654p HC-CDR1

<400> SEQUENCE: 1

Phe Thr Phe Ser Ser Tyr Ser Met Asn
1               5

<210> SEQ ID NO 2
<211> LENGTH: 17
<212> TYPE: PRT
<213> ORGANISM: Artificial Sequence
```

-continued

```
<220> FEATURE:
<223> OTHER INFORMATION: alpha-FXI-13654p HC-CDR2

<400> SEQUENCE: 2

Ser Ile Ser Ser Ser Ser Ser Tyr Ile Tyr Tyr Ala Asp Ser Val Lys
1               5                   10                  15
Gly

<210> SEQ ID NO 3
<211> LENGTH: 13
<212> TYPE: PRT
<213> ORGANISM: Artificial Sequence
<220> FEATURE:
<223> OTHER INFORMATION: alpha-FXI-13654p HC-CDR3

<400> SEQUENCE: 3

Ser Tyr Tyr Asp Tyr Asp Gln Gly Tyr Gly Met Asp Val
1               5                   10

<210> SEQ ID NO 4
<211> LENGTH: 11
<212> TYPE: PRT
<213> ORGANISM: Artificial Sequence
<220> FEATURE:
<223> OTHER INFORMATION: alpha-FXI-13654p LC-CDR1

<400> SEQUENCE: 4

Arg Ala Ser Gln Gly Ile Ser Ser Trp Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: alpha-FXI-13654p LC-CDR2

<400> SEQUENCE: 5

Ala Ala Ser Ser Leu Gln Ser
1               5

<210> SEQ ID NO 6
<211> LENGTH: 9
<212> TYPE: PRT
<213> ORGANISM: Artificial Sequence
<220> FEATURE:
<223> OTHER INFORMATION: alpha-FXI-13654p LC-CDR3

<400> SEQUENCE: 6

Gln Gln Val Asn Ser Tyr Pro Ile Thr
1               5

<210> SEQ ID NO 7
<211> LENGTH: 9
<212> TYPE: PRT
<213> ORGANISM: Artificial Sequence
<220> FEATURE:
<223> OTHER INFORMATION: alpha-FXI-13716p and alpha-FXI-13716 HC-CDR1

<400> SEQUENCE: 7

Tyr Thr Phe Thr Ser Tyr Ser Met His
1               5

<210> SEQ ID NO 8
<211> LENGTH: 17
<212> TYPE: PRT
```

```
<213> ORGANISM: Artificial Sequence
<220> FEATURE:
<223> OTHER INFORMATION: alpha-FXI-13716p and alpha-FXI-13716 HC-CDR2

<400> SEQUENCE: 8

Ile Ile Asn Pro Ser Gly Gly Ser Thr Ser Tyr Ala Gln Lys Phe Gln
1               5                   10                  15

Gly

<210> SEQ ID NO 9
<211> LENGTH: 15
<212> TYPE: PRT
<213> ORGANISM: Artificial Sequence
<220> FEATURE:
<223> OTHER INFORMATION: alpha-FXI-13716p HC-CDR3

<400> SEQUENCE: 9

Gly Ala Tyr Leu Met Glu Leu Tyr Tyr Tyr Tyr Gly Met Asp Val
1               5                   10                  15

<210> SEQ ID NO 10
<211> LENGTH: 11
<212> TYPE: PRT
<213> ORGANISM: Artificial Sequence
<220> FEATURE:
<223> OTHER INFORMATION: alpha-FXI-13716p and alpha-FXI-13716 LC-CDR1

<400> SEQUENCE: 10

Arg Ala Ser Gln Ser Val Ser Ser Asn Leu Ala
1               5                   10

<210> SEQ ID NO 11
<211> LENGTH: 7
<212> TYPE: PRT
<213> ORGANISM: Artificial Sequence
<220> FEATURE:
<223> OTHER INFORMATION: alpha-FXI-136716p and alpha-FXI-13716 LC-CDR2

<400> SEQUENCE: 11

Gly Ala Ser Thr Arg Ala Thr
1               5

<210> SEQ ID NO 12
<211> LENGTH: 9
<212> TYPE: PRT
<213> ORGANISM: Artificial Sequence
<220> FEATURE:
<223> OTHER INFORMATION: alpha-FXI-13716p and alpha-FXI-13716 LC-CDR3

<400> SEQUENCE: 12

Gln Gln Phe Asn Asp Trp Pro Leu Thr
1               5

<210> SEQ ID NO 13
<211> LENGTH: 15
<212> TYPE: PRT
<213> ORGANISM: Artificial Sequence
<220> FEATURE:
<223> OTHER INFORMATION: alpha-FXI-13716 HC-CDR3

<400> SEQUENCE: 13

Gly Ala Tyr Leu Leu Glu Leu Tyr Tyr Tyr Tyr Gly Met Asp Val
1               5                   10                  15

<210> SEQ ID NO 14
<211> LENGTH: 327
```

```
<212> TYPE: PRT
<213> ORGANISM: Artificial Sequence
<220> FEATURE:
<223> OTHER INFORMATION: Human IgG4 HC constant domain: (S228P) S at
      position 108 replaced with P
<220> FEATURE:
<221> NAME/KEY: MISC_FEATURE
<222> LOCATION: (327)..(327)
<223> OTHER INFORMATION: Xaa is Lys or absent

<400> SEQUENCE: 14

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Xaa
                325

<210> SEQ ID NO 15
<211> LENGTH: 107
<212> TYPE: PRT
```

<213> ORGANISM: Artificial Sequence
<220> FEATURE:
<223> OTHER INFORMATION: Human kappa LC constant domain

<400> SEQUENCE: 15

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 16
<211> LENGTH: 122
<212> TYPE: PRT
<213> ORGANISM: Artificial Sequence
<220> FEATURE:
<223> OTHER INFORMATION: alpha-FXI-13654p HC variable region

<400> SEQUENCE: 16

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Tyr Tyr Asp Tyr Asp Gln Gly Tyr Gly Met Asp Val Trp
            100                 105                 110

Gly Gln Gly Thr Thr Val Thr Val Ser Ser
            115                 120
```

<210> SEQ ID NO 17
<211> LENGTH: 107
<212> TYPE: PRT
<213> ORGANISM: Artificial Sequence
<220> FEATURE:
<223> OTHER INFORMATION: alpha-FXI-13654p kappa LC variable region

<400> SEQUENCE: 17

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45
```

Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Val Asn Ser Tyr Pro Ile
                85                  90                  95

Thr Phe Gly Gly Gly Thr Lys Val Glu Ile Lys
            100                 105

<210> SEQ ID NO 18
<211> LENGTH: 448
<212> TYPE: PRT
<213> ORGANISM: Artificial Sequence
<220> FEATURE:
<223> OTHER INFORMATION: alpha-FXI-13654p-IgG4 HC S228P C-terminal
      K-less

<400> SEQUENCE: 18

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Ser Tyr Tyr Asp Tyr Asp Gln Gly Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val

```
            290                 295                 300
Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Gln Glu Glu Met Thr Lys Asn Gln Val Ser Leu Thr
                355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
                420                 425                 430

Ala Leu His Asn His Tyr Thr Gln Lys Ser Leu Ser Leu Ser Leu Gly
            435                 440                 445

<210> SEQ ID NO 19
<211> LENGTH: 214
<212> TYPE: PRT
<213> ORGANISM: Artificial Sequence
<220> FEATURE:
<223> OTHER INFORMATION: alpha-FXI-13654p kappa LC

<400> SEQUENCE: 19

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Asn Ser Tyr Pro Ile
                85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
```

<210> SEQ ID NO 20
<211> LENGTH: 124
<212> TYPE: PRT
<213> ORGANISM: Artificial Sequence
<220> FEATURE:
<223> OTHER INFORMATION: alpha-FXI-13716p HC variable region

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ser Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ala Tyr Leu Met Glu Leu Tyr Tyr Tyr Gly Met Asp
            100                 105                 110

Val Trp Gly Gln Gly Thr Thr Val Thr Val Ser Ser
        115                 120

<210> SEQ ID NO 21
<211> LENGTH: 107
<212> TYPE: PRT
<213> ORGANISM: Artificial Sequence
<220> FEATURE:
<223> OTHER INFORMATION: alpha-FXI-13716p and alpha-FXI-13716 Kappa
      LC variable region

<400> SEQUENCE: 21

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Phe Asn Asp Trp Pro Leu
                85                  90                  95

Thr Phe Gly Gly Gly Thr Lys Val Glu Ile Lys
            100                 105

<210> SEQ ID NO 22
<211> LENGTH: 450
<212> TYPE: PRT
<213> ORGANISM: Artificial Sequence
<220> FEATURE:
<223> OTHER INFORMATION: alpha-FXI-13716p-IgG4 HC S228P  C-terminal
      K-less

<400> SEQUENCE: 22

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ser Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ala Tyr Leu Met Glu Leu Tyr Tyr Tyr Gly Met Asp
            100                 105                 110

Val Trp Gly Gln Gly Thr Thr Val Thr Val Ser Ser Ala Ser Thr Lys
            115                 120                 125

Gly Pro Ser Val Phe Pro Leu Ala Pro Cys Ser Arg Ser Thr Ser Glu
        130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
            195                 200                 205

Val Asp His Lys Pro Ser Asn Thr Lys Val Asp Lys Arg Val Glu Ser
    210                 215                 220

Lys Tyr Gly Pro Pro Cys Pro Pro Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
```

```
                420                 425                 430

His Glu Ala Leu His Asn His Tyr Thr Gln Lys Ser Leu Ser Leu Ser
            435                 440                 445

Leu Gly
    450

<210> SEQ ID NO 23
<211> LENGTH: 214
<212> TYPE: PRT
<213> ORGANISM: Artificial Sequence
<220> FEATURE:
<223> OTHER INFORMATION: alpha-FXI-13716p and alpha-FXI-13716 Kappa LC

<400> SEQUENCE: 23

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Phe Asn Asp Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 24
<211> LENGTH: 124
<212> TYPE: PRT
<213> ORGANISM: Artificial Sequence
<220> FEATURE:
<223> OTHER INFORMATION: alpha-FXI-13716 HC variable region (Q1E M103L)

<400> SEQUENCE: 24

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ser Met His Trp Val Arg Gln Ala Pro Gly Gln Gly Leu Glu Trp Met
        35                  40                  45
```

```
Gly Ile Ile Asn Pro Ser Gly Gly Ser Thr Ser Tyr Ala Gln Lys Phe
            50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ala Tyr Leu Leu Glu Leu Tyr Tyr Tyr Gly Met Asp
                100                 105                 110

Val Trp Gly Gln Gly Thr Thr Val Thr Val Ser Ser
            115                 120
```

<210> SEQ ID NO 25
<211> LENGTH: 450
<212> TYPE: PRT
<213> ORGANISM: Artificial Sequence
<220> FEATURE:
<223> OTHER INFORMATION: alpha-FXI-13716 IgG4 HC Q1E M103L S228P
      C-terminal K-less

<400> SEQUENCE: 25

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ser Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
            50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ala Tyr Leu Leu Glu Leu Tyr Tyr Tyr Gly Met Asp
                100                 105                 110

Val Trp Gly Gln Gly Thr Thr Val Thr Val Ser Ser Ala Ser Thr Lys
            115                 120                 125

Gly Pro Ser Val Phe Pro Leu Ala Pro Cys Ser Arg Ser Thr Ser Glu
130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
            195                 200                 205

Val Asp His Lys Pro Ser Asn Thr Lys Val Asp Lys Arg Val Glu Ser
        210                 215                 220

Lys Tyr Gly Pro Pro Cys Pro Pro Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285
```

```
His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly
    450

<210> SEQ ID NO 26
<211> LENGTH: 449
<212> TYPE: PRT
<213> ORGANISM: Artificial Sequence
<220> FEATURE:
<223> OTHER INFORMATION: alpha-FXI-13654p-IgG4 HC S228P C-terminal K

<400> SEQUENCE: 26

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Tyr Tyr Asp Tyr Asp Gln Gly Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190
```

```
Val Pro Ser Ser Ser Leu Gly Thr Lys Thr Tyr Thr Cys Asn Val Asp
            195                 200                 205

His Lys Pro Ser Asn Thr Lys Val Asp Lys Arg Val Glu Ser Lys Tyr
210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
            405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
            435                 440                 445

Lys

<210> SEQ ID NO 27
<211> LENGTH: 451
<212> TYPE: PRT
<213> ORGANISM: Artificial Sequence
<220> FEATURE:
<223> OTHER INFORMATION: alpha-FXI-13716p-IgG4 HC S228P C-terminal K

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ser Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95
```

```
Ala Arg Gly Ala Tyr Leu Met Glu Leu Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
210                 215                 220

Lys Tyr Gly Pro Pro Cys Pro Pro Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly Lys
    450
```

<210> SEQ ID NO 28
<211> LENGTH: 451
<212> TYPE: PRT
<213> ORGANISM: Artificial Sequence
<220> FEATURE:
<223> OTHER INFORMATION: alpha-FXI-13716 IgG4 HC Q1E M103L S228P
      C-terminal K

<400> SEQUENCE: 28

-continued

```
Glu Val Gln Leu Val Gln Ser Gly Ala Glu Lys Lys Pro Gly Ala
1               5                   10                  15

Ser Val Lys Val Ser Cys Lys Ala Ser Gly Tyr Thr Phe Thr Ser Tyr
            20                  25                  30

Ser Met His Trp Val Arg Gln Ala Pro Gly Gln Gly Leu Glu Trp Met
            35                  40                  45

Gly Ile Ile Asn Pro Ser Gly Ser Thr Ser Tyr Ala Gln Lys Phe
50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ala Tyr Leu Leu Glu Leu Tyr Tyr Tyr Gly Met Asp
                100                 105                 110

Val Trp Gly Gln Gly Thr Thr Val Thr Val Ser Ser Ala Ser Thr Lys
            115                 120                 125

Gly Pro Ser Val Phe Pro Leu Ala Pro Cys Ser Arg Ser Thr Ser Glu
130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
            165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
            195                 200                 205

Val Asp His Lys Pro Ser Asn Thr Lys Val Asp Lys Arg Val Glu Ser
210                 215                 220

Lys Tyr Gly Pro Pro Cys Pro Pro Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
            275                 280                 285

His Asn Ala Lys Thr Lys Pro Arg Glu Glu Gln Phe Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415
```

```
Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly Lys
    450

<210> SEQ ID NO 29
<211> LENGTH: 329
<212> TYPE: PRT
<213> ORGANISM: Artificial Sequence
<220> FEATURE:
<223> OTHER INFORMATION: IgG1 HC constant domain C-terminal K-less

<400> SEQUENCE: 29

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320
```

Gln Lys Ser Leu Ser Leu Ser Pro Gly
                325

<210> SEQ ID NO 30
<211> LENGTH: 330
<212> TYPE: PRT
<213> ORGANISM: Artificial Sequence
<220> FEATURE:
<223> OTHER INFORMATION: IgG1 HC constant domain C-terminal K

<400> SEQUENCE: 30

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 31
<211> LENGTH: 448

```
<212> TYPE: PRT
<213> ORGANISM: Artificial Sequence
<220> FEATURE:
<223> OTHER INFORMATION: alpha-FXI-13654p IgG1 HC C-terminal K-less

<400> SEQUENCE: 31
```

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Tyr Tyr Asp Tyr Asp Gln Gly Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

```
Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
            405                 410                 415

Ser Arg Trp Gln Glu Gly Asn Val Phe Ser Cys Ser Val Met His Glu
        420                 425                 430

Ala Leu His Asn His Tyr Thr Gln Lys Ser Leu Ser Leu Ser Leu Gly
        435                 440                 445

<210> SEQ ID NO 32
<211> LENGTH: 449
<212> TYPE: PRT
<213> ORGANISM: Artificial Sequence
<220> FEATURE:
<223> OTHER INFORMATION: alpha-FXI-13654p IgG1 HC C-terminal K

<400> SEQUENCE: 32

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Tyr Tyr Asp Tyr Asp Gln Gly Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300
```

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 33
<211> LENGTH: 453
<212> TYPE: PRT
<213> ORGANISM: Artificial Sequence
<220> FEATURE:
<223> OTHER INFORMATION: alpha-FXI-13716p IgG1 HC C-terminal K-less

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ser Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ala Tyr Leu Met Glu Leu Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro

```
            210                 215                 220
Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
        290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Asp Glu Leu Thr Lys Asn
            355                 360                 365

Gln Val Ser Leu Thr Cys Leu Val Lys Gly Phe Tyr Pro Ser Asp Ile
        370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
            435                 440                 445

Ser Leu Ser Pro Gly
        450

<210> SEQ ID NO 34
<211> LENGTH: 454
<212> TYPE: PRT
<213> ORGANISM: Artificial Sequence
<220> FEATURE:
<223> OTHER INFORMATION: alpha-FXI-13716p IgG1 HC C-terminal K

<400> SEQUENCE: 34

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ser Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ala Tyr Leu Met Glu Leu Tyr Tyr Tyr Gly Met Asp
            100                 105                 110

Val Trp Gly Gln Gly Thr Thr Val Thr Val Ser Ser Ala Ser Thr Lys
```

```
            115                 120                 125
Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Leu Gly Thr Gln Thr Tyr Ile Cys Asn
        195                 200                 205

Val Asn His Lys Pro Ser Asn Thr Lys Val Asp Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 35
<211> LENGTH: 453
<212> TYPE: PRT
<213> ORGANISM: Artificial Sequence
<220> FEATURE:
<223> OTHER INFORMATION: alpha-FXI-13716 IgG1 HC M103L C-terminal K-less

<400> SEQUENCE: 35

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
```

```
                20                  25                  30
Ser Met His Trp Val Arg Gln Ala Pro Gly Gln Gly Leu Glu Trp Met
            35                  40                  45
Gly Ile Ile Asn Pro Ser Gly Gly Ser Thr Ser Tyr Ala Gln Lys Phe
        50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Gly Ala Tyr Leu Leu Glu Leu Tyr Tyr Tyr Gly Met Asp
            100                 105                 110
Val Trp Gly Gln Gly Thr Thr Val Thr Val Ser Ser Ala Ser Thr Lys
        115                 120                 125
Gly Pro Ser Val Phe Pro Leu Ala Pro Ser Ser Lys Ser Thr Ser Gly
    130                 135                 140
Gly Thr Ala Ala Leu Gly Cys Leu Val Lys Asp Tyr Phe Pro Glu Pro
145                 150                 155                 160
Val Thr Val Ser Trp Asn Ser Gly Ala Leu Thr Ser Gly Val His Thr
                165                 170                 175
Phe Pro Ala Val Leu Gln Ser Ser Gly Leu Tyr Ser Leu Ser Ser Val
            180                 185                 190
Val Thr Val Pro Ser Ser Ser Leu Gly Thr Gln Thr Tyr Ile Cys Asn
        195                 200                 205
Val Asn His Lys Pro Ser Asn Thr Lys Val Asp Lys Lys Val Glu Pro
    210                 215                 220
Lys Ser Cys Asp Lys Thr His Thr Cys Pro Pro Cys Pro Ala Pro Glu
225                 230                 235                 240
Leu Leu Gly Gly Pro Ser Val Phe Leu Phe Pro Pro Lys Pro Lys Asp
                245                 250                 255
Thr Leu Met Ile Ser Arg Thr Pro Glu Val Thr Cys Val Val Val Asp
            260                 265                 270
Val Ser His Glu Asp Pro Glu Val Lys Phe Asn Trp Tyr Val Asp Gly
        275                 280                 285
Val Glu Val His Asn Ala Lys Thr Lys Pro Arg Glu Glu Gln Tyr Asn
    290                 295                 300
Ser Thr Tyr Arg Val Val Ser Val Leu Thr Val Leu His Gln Asp Trp
305                 310                 315                 320
Leu Asn Gly Lys Glu Tyr Lys Cys Lys Val Ser Asn Lys Ala Leu Pro
                325                 330                 335
Ala Pro Ile Glu Lys Thr Ile Ser Lys Ala Lys Gly Gln Pro Arg Glu
            340                 345                 350
Pro Gln Val Tyr Thr Leu Pro Pro Ser Arg Asp Glu Leu Thr Lys Asn
        355                 360                 365
Gln Val Ser Leu Thr Cys Leu Val Lys Gly Phe Tyr Pro Ser Asp Ile
    370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
                405                 410                 415
Leu Thr Val Asp Lys Ser Arg Trp Gln Gln Gly Asn Val Phe Ser Cys
            420                 425                 430
Ser Val Met His Glu Ala Leu His Asn His Tyr Thr Gln Lys Ser Leu
        435                 440                 445
```

Ser Leu Ser Pro Gly
      450

<210> SEQ ID NO 36
<211> LENGTH: 454
<212> TYPE: PRT
<213> ORGANISM: Artificial Sequence
<220> FEATURE:
<223> OTHER INFORMATION: alpha-FXI-13716 IgG1 HC M103L C-terminal K

<400> SEQUENCE: 36

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ser Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ala Tyr Leu Leu Glu Leu Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

```
Pro Gln Val Tyr Thr Leu Pro Pro Ser Arg Asp Glu Leu Thr Lys Asn
            355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
            435                 440                 445

Ser Leu Ser Pro Gly Lys
    450

<210> SEQ ID NO 37
<211> LENGTH: 607
<212> TYPE: PRT
<213> ORGANISM: Homo sapiens

<400> SEQUENCE: 37

Glu Cys Val Thr Gln Leu Leu Lys Asp Thr Cys Phe Glu Gly Gly Asp
1               5                   10                  15

Ile Thr Thr Val Phe Thr Pro Ser Ala Lys Tyr Cys Gln Val Val Cys
                20                  25                  30

Thr Tyr His Pro Arg Cys Leu Leu Phe Thr Phe Thr Ala Glu Ser Pro
            35                  40                  45

Ser Glu Asp Pro Thr Arg Trp Phe Thr Cys Val Leu Lys Asp Ser Val
        50                  55                  60

Thr Glu Thr Leu Pro Arg Val Asn Arg Thr Ala Ala Ile Ser Gly Tyr
65                  70                  75                  80

Ser Phe Lys Gln Cys Ser His Gln Ile Ser Ala Cys Asn Lys Asp Ile
                85                  90                  95

Tyr Val Asp Leu Asp Met Lys Gly Ile Asn Tyr Asn Ser Ser Val Ala
            100                 105                 110

Lys Ser Ala Gln Glu Cys Gln Glu Arg Cys Thr Asp Asp Val His Cys
        115                 120                 125

His Phe Phe Thr Tyr Ala Thr Arg Gln Phe Pro Ser Leu Glu His Arg
130                 135                 140

Asn Ile Cys Leu Leu Lys His Thr Gln Thr Gly Thr Pro Thr Arg Ile
145                 150                 155                 160

Thr Lys Leu Asp Lys Val Val Ser Gly Phe Ser Leu Lys Ser Cys Ala
                165                 170                 175

Leu Ser Asn Leu Ala Cys Ile Arg Asp Ile Phe Pro Asn Thr Val Phe
            180                 185                 190

Ala Asp Ser Asn Ile Asp Ser Val Met Ala Pro Asp Ala Phe Val Cys
        195                 200                 205

Gly Arg Ile Cys Thr His His Pro Gly Cys Leu Phe Phe Thr Phe Phe
210                 215                 220

Ser Gln Glu Trp Pro Lys Glu Ser Gln Arg Asn Leu Cys Leu Leu Lys
225                 230                 235                 240

Thr Ser Glu Ser Gly Leu Pro Ser Thr Arg Ile Lys Lys Ser Lys Ala
                245                 250                 255

Leu Ser Gly Phe Ser Leu Gln Ser Cys Arg His Ser Ile Pro Val Phe
```

```
                    260                 265                 270
Cys His Ser Ser Phe Tyr His Asp Thr Asp Phe Leu Gly Glu Glu Leu
            275                 280                 285

Asp Ile Val Ala Ala Lys Ser His Glu Ala Cys Gln Lys Leu Cys Thr
        290                 295                 300

Asn Ala Val Arg Cys Gln Phe Phe Thr Tyr Thr Pro Ala Gln Ala Ser
305                 310                 315                 320

Cys Asn Glu Gly Lys Gly Lys Cys Tyr Leu Lys Leu Ser Ser Asn Gly
                325                 330                 335

Ser Pro Thr Lys Ile Leu His Gly Arg Gly Gly Ile Ser Gly Tyr Thr
            340                 345                 350

Leu Arg Leu Cys Lys Met Asp Asn Glu Cys Thr Thr Lys Ile Lys Pro
        355                 360                 365

Arg Ile Val Gly Gly Thr Ala Ser Val Arg Gly Glu Trp Pro Trp Gln
    370                 375                 380

Val Thr Leu His Thr Thr Ser Pro Thr Gln Arg His Leu Cys Gly Gly
385                 390                 395                 400

Ser Ile Ile Gly Asn Gln Trp Ile Leu Thr Ala Ala His Cys Phe Tyr
                405                 410                 415

Gly Val Glu Ser Pro Lys Ile Leu Arg Val Tyr Ser Gly Ile Leu Asn
            420                 425                 430

Gln Ser Glu Ile Lys Glu Asp Thr Ser Phe Phe Gly Val Gln Glu Ile
        435                 440                 445

Ile Ile His Asp Gln Tyr Lys Met Ala Glu Ser Gly Tyr Asp Ile Ala
    450                 455                 460

Leu Leu Lys Leu Glu Thr Thr Val Asn Tyr Thr Asp Ser Gln Arg Pro
465                 470                 475                 480

Ile Cys Leu Pro Ser Lys Gly Asp Arg Asn Val Ile Tyr Thr Asp Cys
                485                 490                 495

Trp Val Thr Gly Trp Gly Tyr Arg Lys Leu Arg Asp Lys Ile Gln Asn
            500                 505                 510

Thr Leu Gln Lys Ala Lys Ile Pro Leu Val Thr Asn Glu Glu Cys Gln
        515                 520                 525

Lys Arg Tyr Arg Gly His Lys Ile Thr His Lys Met Ile Cys Ala Gly
    530                 535                 540

Tyr Arg Glu Gly Gly Lys Asp Ala Cys Lys Gly Asp Ser Gly Gly Pro
545                 550                 555                 560

Leu Ser Cys Lys His Asn Glu Val Trp His Leu Val Gly Ile Thr Ser
                565                 570                 575

Trp Gly Glu Gly Cys Ala Gln Arg Glu Arg Pro Gly Val Tyr Thr Asn
            580                 585                 590

Val Val Glu Tyr Val Asp Trp Ile Leu Glu Lys Thr Gln Ala Val
        595                 600                 605

<210> SEQ ID NO 38
<211> LENGTH: 16
<212> TYPE: PRT
<213> ORGANISM: Artificial Sequence
<220> FEATURE:
<223> OTHER INFORMATION: Epitope-A

<400> SEQUENCE: 38

Tyr Ala Thr Arg Gln Phe Pro Ser Leu Glu His Arg Asn Ile Cys Leu
1               5                   10                  15
```

```
<210> SEQ ID NO 39
<211> LENGTH: 13
<212> TYPE: PRT
<213> ORGANISM: Artificial Sequence
<220> FEATURE:
<223> OTHER INFORMATION: Epitope-B

<400> SEQUENCE: 39

His Thr Gln Thr Gly Thr Pro Thr Arg Ile Thr Lys Leu
1               5                   10

<210> SEQ ID NO 40
<211> LENGTH: 330
<212> TYPE: PRT
<213> ORGANISM: Artificial Sequence
<220> FEATURE:
<223> OTHER INFORMATION: IgG1 HC constant domain
<220> FEATURE:
<221> NAME/KEY: MISC_FEATURE
<222> LOCATION: (330)..(330)
<223> OTHER INFORMATION: Xaa is Lys or absent

<400> SEQUENCE: 40

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Xaa
                325                 330

<210> SEQ ID NO 41
<211> LENGTH: 327
<212> TYPE: PRT
<213> ORGANISM: Artificial Sequence
<220> FEATURE:
<223> OTHER INFORMATION: Human IgG4 HC constant domain: S228P
<220> FEATURE:
<221> NAME/KEY: MISC_FEATURE
<222> LOCATION: (327)..(327)
<223> OTHER INFORMATION: Xaa is Lys or absent

<400> SEQUENCE: 41

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser

```
                 290                295                300
Cys Ser Val Met His Glu Ala Leu His Asn His Tyr Thr Gln Lys Ser
305                310                315                320
Leu Ser Leu Ser Leu Gly Xaa
                325

<210> SEQ ID NO 42
<211> LENGTH: 1344
<212> TYPE: DNA
<213> ORGANISM: Artificial Sequence
<220> FEATURE:
<223> OTHER INFORMATION: DNA encoding alpha-FXI-13654p IgG4 HC
      C-terminal K-less

<400> SEQUENCE: 42
gaagtgcagc tggtcgaaag cggcggcgga ctggtgaaac cggaggaag cctgaggctg      60 agctgtgccg ccagcggctt taccttcagc tcctactcca tgaactgggt gaggcaggct    120
cctggaaaag gcctggagtg ggtgagctcc atctccagca gctcctccta tatctactac    180
gccgactccg tgaaaggcag gttcaccatc agcagggata atgccaagaa cagcctgtac    240
ctgcagatga actccctcag ggccgaagac acagccgtgt actactgcgc caggagctat    300
tacgactacg accagggcta tggcatggac gtgtggggcc agggcaccac agtcaccgtg    360
agctccgcct ccaccaaagg accctccgtg tttcccctgg cccctgtag cagatccacc    420 agcgagagca ccgccgctct gggctgtctc gtgaaggatt acttccccga gcccgtgacc    480
gtgagctgga actctggcgc cctgacatcc ggcgtgcaca cattcccgc cgtcctgcaa    540 agcagcggcc tctatagcct gagctccgtg gtgaccgtgc cctccagcag cctgggaaca    600
aagacctaca cctgcaacgt ggaccacaaa ccctccaaca ccaaggtcga caagagagtg    660
gaaagcaagt acggccctcc ttgtccccct tgccctgctc ctgagttcct gggcggaccc    720
agcgtgttcc tgtttccccc caaacccaag acacccctga tcagcag aaccccgag        780 gtcacctgcg tcgtggtgga cgtgagccag gaggaccccg aagtgcagtt caactggtac    840
gtggacggcg tggaggtgca caacgccaag accaagccca ggaagagca attcaactcc      900 acctacaggg tggtgtccgt cctgacagtc ctccaccagg actggctgaa cggaaaggag    960
tacaaatgta aggtgtccaa caagggcctg cccagctcca tcgagaagac aatctccaag   1020
gctaagggcc agcccagaga gccccaggtg tatacccctcc ctccctccca ggaggaaatg   1080
accaagaacc aggtctccct gacctgcctg gtgaagggct tctatcccag cgacatcgcc   1140
gtggaatggg aatccaacgg ccagcccgag aacaactaca gacaacacc ccccgtgctc    1200 gattccgacg gttctttctt cctgtactcc aggctgacag tggacaaaag caggtggcag    1260
gagggcaatg tcttcagctg cagcgtgatg catgaggccc tgcacaacca ctatacccag    1320
aagagcctgt ccctgagcct gggc                                          1344

<210> SEQ ID NO 43
<211> LENGTH: 1347
<212> TYPE: DNA
<213> ORGANISM: Artificial Sequence
<220> FEATURE:
<223> OTHER INFORMATION: DNA encoding alpha-FXI-13654p IgG4 HC
      C-terminal K

<400> SEQUENCE: 43
gaagtgcagc tggtcgaaag cggcggcgga ctggtgaaac cggaggaag cctgaggctg      60 agctgtgccg ccagcggctt taccttcagc tcctactcca tgaactgggt gaggcaggct    120
```

```
cctggaaaag gcctggagtg ggtgagctcc atctccagca gctcctccta tatctactac      180
gccgactccg tgaaaggcag gttcaccatc agcagggata atgccaagaa cagcctgtac      240
ctgcagatga actccctcag ggccgaagac acagccgtgt actactgcgc caggagctat      300
tacgactacg accagggcta tggcatggac gtgtggggcc agggcaccac agtcaccgtg      360
agctccgcct ccaccaaagg accctccgtg tttcccctgg cccctgtag cagatccacc      420 agcgagagca ccgccgctct gggctgtctc gtgaaggatt acttccccga gcccgtgacc      480
gtgagctgga actctggcgc cctgacatcc ggcgtgcaca cattcccgc cgtcctgcaa      540 agcagcggcc tctatagcct gagctccgtg gtgaccgtgc cctccagcag cctgggaaca      600
aagacctaca cctgcaacgt ggaccacaaa ccctccaaca ccaaggtcga caagagagtg      660
gaaagcaagt acggccctcc ttgtccccct tgccctgctc ctgagttcct gggcggaccc      720
agcgtgttcc tgtttccccc caaacccaag gacaccctga tgatcagcag aaccccgag      780 gtcacctgcg tcgtggtgga cgtgagccag gaggaccccg aagtgcagtt caactggtac      840
gtggacggcg tggaggtgca caacgccaag accaagccca gggaagagca attcaactcc      900
acctacaggg tggtgtccgt cctgacagtc ctccaccagg actggctgaa cggaaaggag      960
tacaaatgta aggtgtccaa caagggcctg cccagctcca tcgagaagac aatctccaag     1020
gctaagggcc agcccagaga gccccaggtg tatacccctcc ctccctccca ggaggaaatg     1080
accaagaacc aggtctccct gacctgcctg gtgaagggct tctatcccag cgacatcgcc     1140
gtggaatggg aatccaacgg ccagcccgag aacaactaca agacaacacc cccgtgctc     1200 gattccgacg gttcttttctt cctgtactcc aggctgacag tggacaaaag caggtggcag     1260
gagggcaatg tcttcagctg cagcgtgatg catgaggccc tgcacaacca ctatcccag     1320 aagagcctgt ccctgagcct gggcaag                                         1347

<210> SEQ ID NO 44
<211> LENGTH: 642
<212> TYPE: DNA
<213> ORGANISM: Artificial Sequence
<220> FEATURE:
<223> OTHER INFORMATION: DNA encoding alpha-FXI-13654p LC

<400> SEQUENCE: 44
gacatccaga tgacccagag cccttcctcc gtgagcgcca gcgtcggcga cagagtgacc       60
atcacctgca gagccagcca gggcatcagc agctggctgg cttggtacca gcagaagccc      120
ggcaaggccc ccaagctgct gatctacgcc gccagcagcc tgcagagcgg cgtgccctcc      180
agatttagcg gcagcggcag cggcaccgac tttaccctca caatcagcag cctgcagccc      240
gaggacttcg ctacctacta ctgccagcag gtgaacagct accctatcac attcggcggc      300
ggcaccaagg tggagatcaa gagaaccgtg gccgccccca gcgtgttcat cttccccccc      360
tccgatgagc agctgaaaag cggcaccgcc agcgtcgtgt gcctgctgaa caacttctac      420
cccagggagg ccaaagtgca gtggaaggtc gacaacgccc tgcagtccgg caacagccaa      480
gaaagcgtca ccgagcagga cagcaaggac tccacctaca gcctgtccag caccctgacc      540
ctgagcaagg ccgactacga aagcacaag gtgtacgcct gcgaggtgac acaccagggc      600
ctgagctccc ccgtgaccaa gagcttcaat aggggcgagt gc                        642

<210> SEQ ID NO 45
<211> LENGTH: 1353
<212> TYPE: DNA
```

<213> ORGANISM: Artificial Sequence
<220> FEATURE:
<223> OTHER INFORMATION: DNA encoding alpha-FXI-13654p IgG1 HC
      C-terminal K-less

<400> SEQUENCE: 45

| | | | | | |
|---|---|---|---|---|---|
| gaggtgcagc | tggtggagtc | tgggggaggc | ctggtcaagc | ctgggggtc | cctgagactc | 60 |
| tcctgtgcag | cctctggatt | caccttcagt | agctatagca | tgaactgggt | ccgccaggct | 120 |
| ccagggaagg | ggctggagtg | ggtctcatcc | attagtagta | gtagtagtta | catatactac | 180 |
| gcagactcag | tgaagggccg | attcaccatc | tccagagaca | acgccaagaa | ctcactgtat | 240 |
| ctgcaaatga | acagcctgag | agccgaggac | acggcggtgt | actactgcgc | cagatcttac | 300 |
| tacgactacg | atcaaggata | cggaatggac | gtatggggcc | agggaacaac | tgtcaccgtc | 360 |
| tcctcagcta | gcacaaaagg | accaagcgtg | tttccactgg | cacctagcag | caaatccacc | 420 |
| agcggcggaa | cagcagccct | cgggtgcctg | gtgaaggatt | acttccctga | gccagtcaca | 480 |
| gtgtcctgga | actccggagc | cctgacatcc | ggcgtgcaca | ccttccccgc | tgtgctgcaa | 540 |
| tccagcggac | tgtatagcct | cagctccgtc | gtgacagtcc | cttccagcag | cctgggcaca | 600 |
| cagacttaca | tttgcaacgt | gaaccacaaa | ccttccaaca | ctaaggtgga | caaaaaggtg | 660 |
| gaacccaaat | cctgtgataa | gacccataca | tgcccacctt | gtcccgctcc | tgagctgctg | 720 |
| ggggaccctt | ccgtctttct | gtttcctcca | aaaccaaaag | acacactcat | gatcagccgg | 780 |
| acccccgaag | tcacctgtgt | ggtggtggac | gtcagccacg | aagatccaga | ggtcaagttc | 840 |
| aattggtacg | tggatggagt | ggaagtccac | aacgcaaaaa | ccaaacctag | agaagaacag | 900 |
| tacaatagca | catacagggt | ggtgtccgtc | ctgacagtgc | tccaccagga | ctggctcaat | 960 |
| ggcaaagagt | ataagtgcaa | ggtgagcaac | aaggccctgc | ctgcaccaat | tgagaaaaca | 1020 |
| attagcaagg | caaggggca | gccacgggaa | ccccaggtgt | ataccctgcc | cccaagccgg | 1080 |
| gatgaactga | ccaaaaacca | ggtcagcctg | acatgcctgg | tgaaagggtt | ttacccaagc | 1140 |
| gatattgccg | tcgagtggga | gagcaacgga | cagccagaaa | acaattacaa | aaccacccca | 1200 |
| cctgtgctgg | actccgatgg | gagctttttc | ctgtacagca | agctcacagt | ggacaagtcc | 1260 |
| agatggcaac | agggcaacgt | gttttcctgc | tccgtgatgc | acgaggccct | ccacaaccac | 1320 |
| tatacacaaa | agtccctctc | cctcagccca | gga | | | 1353 |

<210> SEQ ID NO 46
<211> LENGTH: 1356
<212> TYPE: DNA
<213> ORGANISM: Artificial Sequence
<220> FEATURE:
<223> OTHER INFORMATION: DNA encoding alpha-FXI-13654p IgG1 HC
      C-terminal K

<400> SEQUENCE: 46

| | | | | | |
|---|---|---|---|---|---|
| gaggtgcagc | tggtggagtc | tgggggaggc | ctggtcaagc | ctgggggtc | cctgagactc | 60 |
| tcctgtgcag | cctctggatt | caccttcagt | agctatagca | tgaactgggt | ccgccaggct | 120 |
| ccagggaagg | ggctggagtg | ggtctcatcc | attagtagta | gtagtagtta | catatactac | 180 |
| gcagactcag | tgaagggccg | attcaccatc | tccagagaca | acgccaagaa | ctcactgtat | 240 |
| ctgcaaatga | acagcctgag | agccgaggac | acggcggtgt | actactgcgc | cagatcttac | 300 |
| tacgactacg | atcaaggata | cggaatggac | gtatggggcc | agggaacaac | tgtcaccgtc | 360 |
| tcctcagcta | gcacaaaagg | accaagcgtg | tttccactgg | cacctagcag | caaatccacc | 420 |
| agcggcggaa | cagcagccct | cgggtgcctg | gtgaaggatt | acttccctga | gccagtcaca | 480 |

```
gtgtcctgga actccggagc cctgacatcc ggcgtgcaca ccttccccgc tgtgctgcaa      540
tccagcggac tgtatagcct cagctccgtc gtgacagtcc cttccagcag cctgggcaca      600
cagacttaca tttgcaacgt gaaccacaaa ccttccaaca ctaaggtgga caaaaaggtg      660
gaacccaaat cctgtgataa gacccataca tgcccacctt gtcccgctcc tgagctgctg      720
gggggacctt ccgtctttct gtttcctcca aaaccaaaag acacactcat gatcagccgg      780
acccccgaag tcacctgtgt ggtggtggac gtcagccacg aagatccaga ggtcaagttc      840
aattggtacg tggatggagt ggaagtccac aacgcaaaaa ccaaacctag agaagaacag      900
tacaatagca catacagggt ggtgtccgtc ctgacagtgc tccaccagga ctggctcaat      960
ggcaaagagt ataagtgcaa ggtgagcaac aaggccctgc ctgcaccaat tgagaaaaca     1020
attagcaagg caaaggggca gccacgggaa ccccaggtgt ataccctgcc cccaagccgg     1080
gatgaactga ccaaaaacca ggtcagcctg acatgcctgg tgaaagggtt ttacccaagc     1140
gatattgccg tcgagtggga gagcaacgga cagccagaaa acaattacaa aaccaccccc     1200
cctgtgctgg actccgatgg gagcttttc ctgtacagca agctcacagt ggacaagtcc     1260
agatggcaac agggcaacgt gttttcctgc tccgtgatgc acgaggccct ccacaaccac     1320
tatacacaaa agtccctctc cctcagccca ggaaag                              1356
```

<210> SEQ ID NO 47
<211> LENGTH: 1350
<212> TYPE: DNA
<213> ORGANISM: Artificial Sequence
<220> FEATURE:
<223> OTHER INFORMATION: DNA encoding alpha-FXI-13716p IgG4 HC
      C-terminal K-less

<400> SEQUENCE: 47

```
caggtccagc tcgtgcagag cggagccgag gtgaagaagc ccggagcctc cgtcaaagtg       60
agctgtaaag ccagcggcta caccttcaca tcctacagca tgcactgggt gaggcaggct      120
cctggccaag gcctggagtg gatgggcatt atcaacccca gcggcggctc cacctcctac      180
gctcagaagt tccagggcag ggtgaccatg accagagaca ccagcaccag caccgtgtat      240
atggagctga gctccctgag gagcgaggac acagccgtgt actactgcgc tagggggcgcc      300 tacctgatgg agctgtacta ctactacgga atggatgtgt ggggccaggg caccaccgtg      360
acagtctcca gcgccagcac caaaggccct tccgtgttc cctggccccc tgcagcagg      420 agcaccagcg aaagcacagc cgccctgggc tgtctggtga aggactactt ccccgaaccc      480
gtgaccgtga gctggaacag cggagctctg acctccggcg tgcacacatt tccgccgtg      540 ctgcagtcca gcggactgta cagcctgtcc agcgtggtga ccgtcccag ctccagcctg      600 ggcaccaaga cctacacctg taacgtggat cataagccca gcaacaccaa ggtggacaag      660
agagtggaga gcaaatacgg ccctccctgt ccccccttgtc ccgctcccga atttctgggc      720
ggcccttccg tgttcctgtt ccccctaag cccaaggaca cctgatgat cagcagaacc      780 cccgaagtca catgcgtggt ggtcgacgtg agccaggagg accccgaggt ccagtttaac      840
tggtacgtgg acggagtgga agtgcacaac gccaagacaa agcccaggga ggagcagttc      900
aacagcacct acagagtggt gtccgtgctc accgtgctgc accaggattg gctgaacgga      960
aaggagtaca agtgtaaggt gagcaacaaa ggcctccca gcagcatcga aaagaccatc     1020
tccaaagcta agggacagcc cagagagccc caggtgtaca cactgccccc cagccaggag     1080
gagatgacca agaatcaggt gtccctgacc tgcctggtga aaggctttta ccctccgac     1140
```

```
attgccgtcg aatgggagtc caacggccag cctgagaaca actataagac aaccccccct   1200
gtgctggaca gcgacggctc cttctttctg tactccaggc tgaccgtcga caaatccagg   1260
tggcaggagg gaaacgtgtt cagctgcagc gtgatgcacg aggccctgca caaccactac   1320
acccagaaga gcctgtccct gagcctcggc                                   1350
```

<210> SEQ ID NO 48
<211> LENGTH: 1353
<212> TYPE: DNA
<213> ORGANISM: Artificial Sequence
<220> FEATURE:
<223> OTHER INFORMATION: DNA encoding alpha-FXI-13716p IgG4 HC
      C-terminal K

<400> SEQUENCE: 48

```
caggtccagc tcgtgcagag cggagccgag gtgaagaagc ccggagcctc cgtcaaagtg     60
agctgtaaag ccagcggcta caccttcaca tcctacagca tgcactgggt gaggcaggct    120
cctggccaag gctggagtg gatgggcatt atcaaccca gcggcggctc cacctcctac     180
gctcagaagt tccagggcag ggtgaccatg accagagaca ccagcaccag caccgtgtat    240
atggagctga gctccctgag gagcgaggac acagccgtgt actactgcgc taggggcgcc    300
tacctgatgg agctgtacta ctactacgga tggatgtgt ggggccaggg caccaccgtg     360
acagtctcca gcgccagcac caaaggccct tccgtgttc cctggcccc ctgcagcagg      420 agcaccagcg aaagcacagc cgccctgggc tgtctggtga aggactactt ccccgaaccc    480
gtgaccgtga gctggaacag cggagctctg acctccggcg tgcacacatt tccgccgtg    540 ctgcagtcca gcggactgta cagcctgtcc agcgtggtga ccgtcccag ctccagcctg    600 ggcaccaaga cctacacctg taacgtggat cataagccca gcaacaccaa ggtggacaag    660
agagtggaga gcaaatacgg ccctcccgt ccccttgtc ccgctcccga atttctgggc      720
ggcccttccg tgttcctgtt ccccctaag cccaaggaca cctgatgat cagcagaacc      780 cccgaagtca catgcgtggt ggtcgacgtg agccaggagg accccgaggt ccagtttaac    840
tggtacgtgg acggagtgga agtgcacaac gccaagacaa agcccaggga ggagcagttc    900
aacagcacct acagagtggt gtccgtgctc accgtgctgc accaggattg gctgaacgga    960
aaggagtaca agtgtaaggt gagcaacaaa ggcctcccca gcagcatcga aaagaccatc   1020
tccaaagcta agggacagcc cagagagccc caggtgtaca cactgccccc cagccaggag   1080
gagatgacca gaatcaggt gtccctgacc tgcctggtga aaggctttta ccctccgac     1140 attgccgtcg aatgggagtc caacggccag cctgagaaca actataagac aaccccccct   1200
gtgctggaca gcgacggctc cttctttctg tactccaggc tgaccgtcga caaatccagg   1260
tggcaggagg gaaacgtgtt cagctgcagc gtgatgcacg aggccctgca caaccactac   1320
acccagaaga gcctgtccct gagcctcggc aag                                1353
```

<210> SEQ ID NO 49
<211> LENGTH: 642
<212> TYPE: DNA
<213> ORGANISM: Artificial Sequence
<220> FEATURE:
<223> OTHER INFORMATION: DNA encoding alpha-FXI-13716p LC

<400> SEQUENCE: 49

```
gagatcgtca tgacccagag ccctgctacc ctgagcgtga gccctggcga aagggccacc     60
ctgtcctgta gggccagcca gagcgtgtcc agcaacctgg cctggtatca gcagaagcct    120
```

```
ggccaggccc ctaggctgct gatctacggc gccagcacca gagctaccgg catccctgct      180
aggttctccg gaagcggctc cggcaccgag ttcaccctga ccattagctc cctgcagagc      240
gaggacttcg ccgtgtacta ctgccagcag ttcaacgact ggcccctgac cttcggcgga      300
ggcaccaagg tggagatcaa gaggaccgtg gccgctcctt ccgtgttcat cttcccccc      360 agcgacgagc agctgaagtc cggcacagcc tccgtggtgt gcctgctgaa caacttctac      420
cccagggagg ccaaggtgca gtggaaggtg gacaacgccc tgcaaagcgg caacagccag      480
gagtccgtga ccgagcagga cagcaaggac tccacctact ccctgagctc caccctgacc      540
ctgagcaagg ccgattacga gaagcacaag gtgtacgcct gcgaggtgac ccaccaggga      600
ctgagcagcc ccgtgaccaa gagcttcaac aggggcgaat gc                        642
```

```
<210> SEQ ID NO 50
<211> LENGTH: 1359
<212> TYPE: DNA
<213> ORGANISM: Artificial Sequence
<220> FEATURE:
<223> OTHER INFORMATION: DNA encoding alpha-FXI-13716p IgG1 HC
      C-terminal K-less

<400> SEQUENCE: 50
```

```
caggtgcagc tggtgcagtc tggggctgag gtgaagaagc ctggggcctc agtgaaggtt      60
tcctgcaagg catctggata caccttcacc agctacagca tgcactgggt gcgacaggcc     120
cctggacaag gcttgagtg gatgggaata atcaaccccta gtggtggtag cacaagctac     180
gcacagaagt tccagggcag agtcaccatg accagggaca cgtccacgag cacagtctac     240
atggagctga gcagcctgag atctgaggac acggcggtgt actactgcgc cagaggtgct     300
tatctaatgg agttatacta ctattacggt atggatgtct ggggccaggg aacaactgtc     360
accgtctcct cagctagcac aaaaggacca agcgtgttc cactggcacc tagcagcaaa     420
tccaccagcg gcgaacagc agccctcggg tgcctggtga aggattactt ccctgagcca      480
gtcacagtgt cctggaactc cggagccctg acatccggcg tgcacacctt ccccgctgtg     540
ctgcaatcca gcggactgta tagcctcagc tccgtcgtga cagtcccttc agcagcctg      600 ggcacacaga cttacatttg caacgtgaac cacaaacctt ccaacactaa ggtggacaaa     660
aaggtggaac ccaaatcctg tgataagacc catacatgcc caccttgtcc cgctcctgag     720 ctgctgggggg gaccttccgt ctttctgtttt cctccaaaac caaaagacac actcatgatc     780
agccggaccc ccgaagtcac ctgtgtggtg gtggacgtca gccacgaaga tccagaggtc     840
aagttcaatt ggtacgtgga tggagtggaa gtccacaacg caaaaaccaa acctagagaa     900
gaacagtaca atagccacata cagggtggtg tccgtcctga cagtgctcca ccaggactgg    960
ctcaatggca agagtataa gtgcaaggtg agcaacaagg ccctgcctgc accaattgag    1020
aaaacaatta gcaaggcaaa ggggcagcca cgggaacccc aggtgtatac cctgccccca    1080
agccgggatg aactgaccaa aaaccaggtc agcctgacat gcctggtgaa agggtttttac    1140 ccaagcgata ttgccgtcga gtgggagagc aacggacagc cagaaaacaa ttacaaaacc    1200
accccacctg tgctggactc cgatgggagc ttttctcctgt acagcaagct cacagtggac    1260
aagtccagat ggcaacaggg caacgtgttt tcctgctccg tgatgcacga ggccctccac    1320
aaccactata cacaaaagtc cctctcccct agcccagga                           1359
```

```
<210> SEQ ID NO 51
<211> LENGTH: 1362
```

<212> TYPE: DNA
<213> ORGANISM: Artificial Sequence
<220> FEATURE:
<223> OTHER INFORMATION: DNA encoding alpha-FXI-13716p IgG1 HC
    C-terminal K

<400> SEQUENCE: 51

```
caggtgcagc tggtgcagtc tggggctgag gtgaagaagc ctggggcctc agtgaaggtt      60
tcctgcaagg catctggata caccttcacc agctacagca tgcactgggt gcgacaggcc     120
cctggacaag gcttgagtg gatgggaata atcaaccta gtggtggtag cacaagctac       180
gcacagaagt tccagggcag agtcaccatg accagggaca cgtccacgag cacagtctac     240
atggagctga gcagcctgag atctgaggac acggcggtgt actactgcgc cagaggtgct     300
tatctaatgg agttatacta ctattacggt atggatgtct ggggccaggg aacaactgtc     360
accgtctcct cagctagcac aaaaggacca agcgtgtttc cactggcacc tagcagcaaa     420
tccaccagcg gcggaacagc agccctcggg tgcctggtga aggattactt ccctgagcca     480
gtcacagtgt cctggaactc cggagccctg acatccggcg tgcacacctt cccgctgtg     540
ctgcaatcca cggactgta tagcctcagc tccgtcgtga cagtcccttc agcagcctg      600
ggcacacaga cttacatttg caacgtgaac cacaaaccctt ccaacactaa ggtggacaaa   660
aaggtggaac ccaaatcctg tgataagacc catacatgcc caccttgtcc cgctcctgag   720
ctgctggggg gaccttccgt cttctgttt cctccaaaac caaaagacac actcatgatc     780
agccggaccc ccgaagtcac ctgtgtggtg gtggacgtca gccacgaaga tccagaggtc   840
aagttcaatt ggtacgtgga tggagtgaa gtccacaacg caaaaaccaa acctagagaa     900
gaacagtaca atagcacata cagggtggtg tccgtcctga cagtgctcca ccaggactgg   960
ctcaatggca agagtataa gtgcaaggtg agcaacaagg ccctgcctgc accaattgag    1020
aaaacaatta gcaaggcaaa ggggcagcca cgggaacccc aggtgtatac cctgcccca   1080
agccgggatg aactgaccaa aaaccaggtc agcctgacat gcctggtgaa agggttttac   1140
ccaagcgata ttgccgtcga gtgggagagc aacggacagc cagaaaacaa ttacaaaacc   1200
accccacctg tgctggactc cgatgggagc ttttttcctgt acagcaagct cacagtggac   1260
aagtccagat ggcaacaggg caacgtgttt tcctgctccg tgatgcacga ggccctccac   1320
aaccactata cacaaaagtc cctctcccctc agcccaggaa ag                      1362
```

<210> SEQ ID NO 52
<211> LENGTH: 1350
<212> TYPE: DNA
<213> ORGANISM: Artificial Sequence
<220> FEATURE:
<223> OTHER INFORMATION: DNA encoding alpha-FXI-13716p IgG4 HC S228P Q1E
    M103L C-terminal K-less

<400> SEQUENCE: 52

```
gaggtgcagc tggtccagag cggagccgag gtgaagaaac ccggagccag cgtcaaggtg      60
agctgcaagg cctccggcta caccttcaca tcctatagca tgcactgggt gaggcaggct    120
cctggccagg gcctggaatg gatgggcatc atcaacccca gcggcggctc cacatcctac    180
gcccagaaat tcaggggaag ggtcaccatg accaggggata catccaccag caccgtgtac    240
atggagctgt ccagcctgag gtccgaggac accgctgtgt actactgcgc cagaggcgcc    300
tatctgctgg agctgtacta ctactacgga atggacgtgt ggggccaggg cacaaccgtg    360
accgtgagca gcgccagcac caagggacct tccgtgttcc cctggccccc ttgtagcaga    420
```

```
tccacctccg aatccaccgc cgctctgggc tgtctcgtca aggattattt ccccgagcct    480
gtgaccgtgt cctggaactc cggagccctc acctccggcg tgcatacctt ccctgccgtg    540
ctccagtcca gcggcctgta ctccctcagc agcgtggtga ccgtgccctc agcagcctg     600 ggcaccaaaa cctatacctg caatgtggac cacaagccca gcataccaa ggtggacaag     660 agggtggagt ccaaatacgg acctccctgt cccccctgcc ccgctcccga atttctggga    720
ggcccctccg tgttcctgtt ccctcccaag cccaaggaca cactgatgat ttccaggacc    780
cctgaggtga cctgcgtggt ggtggacgtc agccaggaag atcctgaggt gcagttcaac    840
tggtacgtgg atggcgtgga agtgcataac gccaagacca gcccaggga ggaacagttc     900 aacagcacct acagagtggt cagcgtgctg acagtcctgc accaggactg gctgaacggc    960
aaggaataca agtgcaaggt gtccaacaag gactcccct cctccatcga gaaaacaatc     1020
agcaaggcca aaggccagcc cagagaacct caagtctata ccctcccccc tagccaggag    1080
gagatgacca gaaccaagt gagcctgacc tgcctggtga agggcttttta ccccagcgac    1140 atcgccgtgg aatgggagtc caacggacag cccgagaaca actataagac aaaccccccc   1200
gtgctcgact ccgatggaag ctttttcctc tacagcaggc tgaccgtgga caagagcaga    1260
tggcaggagg gaaatgtgtt cagctgcagc gtgatgcacg aagccctgca caaccactac    1320
acccaaaaaa gcctgagcct gagcctggga                                     1350
```

<210> SEQ ID NO 53  
<211> LENGTH: 1353  
<212> TYPE: DNA  
<213> ORGANISM: Artificial Sequence  
<220> FEATURE:  
<223> OTHER INFORMATION: DNA encoding alpha-FXI-13716p IgG4 HC S228P Q1E M103L C-terminal K

<400> SEQUENCE: 53

```
gaggtgcagc tggtccagag cggagccgag gtgaagaaac ccggagccag cgtcaaggtg     60
agctgcaagg cctccggcta caccttcaca tcctatagca tgcactgggt gaggcaggct    120
cctggccagg cctggaatg gatgggcatc atcaaccca gcggcggctc cacatcctac     180
gcccagaaat ttcagggaag ggtcaccatg accaggata catccaccag caccgtgtac    240
atggagctgt ccagcctgag gtccgaggac accgctgtgt actactgcgc cagaggcgcc    300
tatctgctgg agctgtacta ctactacgga atggacgtgt ggggccaggg cacaaccgtg    360
accgtgagca gcgccagcac caagggacct tccgtgttcc ccctggcccc ttgtagcaga    420
tccacctccg aatccaccgc cgctctgggc tgtctcgtca aggattattt ccccgagcct    480
gtgaccgtgt cctggaactc cggagccctc acctccggcg tgcataccett ccctgccgtg   540 ctccagtcca gcggcctgta ctccctcagc agcgtggtga ccgtgccctc agcagcctg    600 ggcaccaaaa cctatacctg caatgtggac cacaagccca gcataccaa ggtggacaag    660 agggtggagt ccaaatacgg acctccctgt cccccctgcc ccgctcccga atttctggga    720
ggcccctccg tgttcctgtt ccctcccaag cccaaggaca cactgatgat ttccaggacc    780
cctgaggtga cctgcgtggt ggtggacgtc agccaggaag atcctgaggt gcagttcaac    840
tggtacgtgg atggcgtgga agtgcataac gccaagacca gcccaggga ggaacagttc    900 aacagcacct acagagtggt cagcgtgctg acagtcctgc accaggactg gctgaacggc    960
aaggaataca agtgcaaggt gtccaacaag gactcccct cctccatcga gaaaacaatc     1020
agcaaggcca aaggccagcc cagagaacct caagtctata ccctcccccc tagccaggag    1080
```

| | |
|---|---|
| gagatgacca agaaccaagt gagcctgacc tgcctggtga agggctttta ccccagcgac | 1140 |
| atcgccgtgg aatgggagtc caacggacag cccgagaaca actataagac aacccctccc | 1200 |
| gtgctcgact ccgatggaag cttttttcctc tacagcaggc tgaccgtgga caagagcaga | 1260 |
| tggcaggagg gaaatgtgtt cagctgcagc gtgatgcacg aagccctgca caaccactac | 1320 |
| acccaaaaaa gcctgagcct gagcctggga aag | 1353 |

<210> SEQ ID NO 54
<211> LENGTH: 1362
<212> TYPE: DNA
<213> ORGANISM: Artificial Sequence
<220> FEATURE:
<223> OTHER INFORMATION: DNA encoding alpha-FXI-13716 IgG1 HC Q1E M103L
      C-terminal K-less

<400> SEQUENCE: 54

| | |
|---|---|
| gaggtgcagc tggtccagag cggagccgag gtgaagaaac ccggagccag cgtcaaggtg | 60 |
| agctgcaagg cctccggcta caccttcaca tcctatagca tgcactgggt gaggcaggct | 120 |
| cctggccagg gcctggaatg gatgggcatc atcaaccca gcggcggctc cacatcctac | 180 |
| gcccagaaat ttcagggaag ggtcaccatg accaggata catccaccag caccgtgtac | 240 |
| atggagctgt ccagcctgag gtccgaggac accgctgtgt actactgcgc cagaggcgcc | 300 |
| tatctgctgg agctgtacta ctactacgga atggacgtgt ggggccaggg cacaaccgtg | 360 |
| accgtgagca gcgccgctag cacaaaagga ccaagcgtgt tccactggc acctagcagc | 420 |
| aaatccacca gcggcggaac agcagccctc gggtgcctgg tgaaggatta cttccctgag | 480 |
| ccagtcacag tgtcctggaa ctccggagcc ctgacatccg gcgtgcacac cttccccgct | 540 |
| gtgctgcaat ccagcggact gtatagcctc agctccgtcg tgacagtccc ttccagcagc | 600 |
| ctgggcacac agacttacat ttgcaacgtg aaccacaaac cttccaacac taaggtggac | 660 |
| aaaaaggtgg aacccaaatc ctgtgataag acccatacat gccaccttg tcccgctcct | 720 |
| gagctgctgg ggggaccttc cgtctttctg tttcctccaa aaccaaaga cacactcatg | 780 |
| atcagccgga cccccgaagt cacctgtgtg gtggtggacg tcagccacga agatccagag | 840 |
| gtcaagttca attggtacgt ggatggcgtg gaagtccaca cgcaaaaaac caaacctaga | 900 |
| gaagaacagt acaatagcac atacagggtg gtgtccgtcc tgacagtgct ccaccaggac | 960 |
| tggctcaatg gcaaagagta taagtgcaag gtgagcaaca aggccctgcc tgcaccaatt | 1020 |
| gagaaaacaa ttagcaaggc aaaggggcag ccacgggaac cccaggtgta ccctgccc | 1080 |
| ccaagccggg atgaactgac caaaaaccag gtcagcctga catgcctggt gaagggtttt | 1140 |
| tacccaagcg atattgccgt cgagtgggag agcaacggac agccagaaaa caattacaaa | 1200 |
| accacccccac ctgtgctgga ctccgatggg agcttttttcc tgtacagcaa gctcacagtg | 1260 |
| gacaagtcca gatggcaaca gggcaacgtg ttttcctgct ccgtgatgca cgaggccctc | 1320 |
| cacaaccact atacacaaaa gtccctctcc ctcagcccag ga | 1362 |

<210> SEQ ID NO 55
<211> LENGTH: 1365
<212> TYPE: DNA
<213> ORGANISM: Artificial Sequence
<220> FEATURE:
<223> OTHER INFORMATION: DNA encoding alpha-FXI-13716 IgG1 HC Q1E M103L
      C-terminal K

<400> SEQUENCE: 55

| | |
|---|---|
| gaggtgcagc tggtccagag cggagccgag gtgaagaaac ccggagccag cgtcaaggtg | 60 |

```
agctgcaagg cctccggcta caccttcaca tcctatagca tgcactgggt gaggcaggct    120
cctggccagg gcctggaatg gatgggcatc atcaaccccca gcggcggctc cacatcctac   180
gcccagaaat tcagggaag ggtcaccatg accagggata catccaccag caccgtgtac    240
atggagctgt ccagcctgag gtccgaggac accgctgtgt actactgcgc cagaggcgcc   300
tatctgctgg agctgtacta ctactacgga atggacgtgt ggggccaggg cacaaccgtg    360
accgtgagca gcgccgctag cacaaaagga ccaagcgtgt tccactggca cctagcagc    420 aaatccacca gcggcggaac agcagccctc gggtgcctgg tgaaggatta cttccctgag    480
ccagtcacag tgtcctggaa ctccggagcc ctgacatccg gcgtgcacac cttccccgct    540
gtgctgcaat ccagcggact gtatagcctc agctccgtcg tgacagtccc ttccagcagc    600
ctgggcacac agacttacat ttgcaacgtg aaccacaaac cttccaacac taaggtggac    660
aaaaaggtgg aacccaaatc ctgtgataag acccatacat gcccaccttg tccgctcct     720 gagctgctgg ggggaccttc cgtctttctg tttcctccaa aaccaaagga cacactcatg    780
atcagccgga cccccgaagt cacctgtgtg gtggtggacg tcagccacga agatccagag    840
gtcaagttca attggtacgt ggatggagtg gaagtccaca cgcaaaaac caaacctaga    900 gaagaacagt acaatagcac atacagggtg gtgtccgtcc tgacagtgct ccaccaggac    960
tggctcaatg gcaaagagta taagtgcaag gtgagcaaca aggccctgcc tgcaccaatt    1020
gagaaaacaa ttagcaaggc aaaggggcag ccacgggaac cccaggtgta ccctgccc     1080 ccaagccggg atgaactgac caaaaaccag gtcagcctga catgcctggt gaaagggttt    1140
tacccaagcg atattgccgt cgagtgggag agcaacggac agccagaaaa caattacaaa    1200 accacccccac ctgtgctgga ctccgatggg agctttttcc tgtacagcaa gctcacagtg    1260
gacaagtcca gatggcaaca gggcaacgtg ttttcctgct ccgtgatgca cgaggccctc    1320
cacaaccact atacacaaaa gtccctctcc ctcagcccag gaaag                   1365
```

<210> SEQ ID NO 56
<211> LENGTH: 20
<212> TYPE: PRT
<213> ORGANISM: Artificial Sequence
<220> FEATURE:
<223> OTHER INFORMATION: Leader Sequence A

<400> SEQUENCE: 56

Met Ser Val Pro Thr Gln Val Leu Gly Leu Leu Leu Leu Trp Leu Thr
1               5                   10                  15

Asp Ala Arg Cys
            20

<210> SEQ ID NO 57
<211> LENGTH: 19
<212> TYPE: PRT
<213> ORGANISM: Artificial Sequence
<220> FEATURE:
<223> OTHER INFORMATION: Leader Sequence B

<400> SEQUENCE: 57

Met Glu Trp Ser Trp Val Phe Leu Phe Phe Leu Ser Val Thr Thr Gly
1               5                   10                  15

Val His Ser

<210> SEQ ID NO 58
<211> LENGTH: 19

<212> TYPE: PRT
<213> ORGANISM: Artificial Sequence
<220> FEATURE:
<223> OTHER INFORMATION: Leader Sequence C

<400> SEQUENCE: 58

Met Glu Leu Gly Leu Cys Trp Val Phe Leu Val Ala Ile Leu Glu Gly
1               5                   10                  15

Val Gln Cys

<210> SEQ ID NO 59
<211> LENGTH: 449
<212> TYPE: PRT
<213> ORGANISM: Artificial Sequence
<220> FEATURE:
<223> OTHER INFORMATION: alpha-FXI-13654p-IgG4 HC S228P
<220> FEATURE:
<221> NAME/KEY: MISC_FEATURE
<222> LOCATION: (449)..(449)
<223> OTHER INFORMATION: Xaa is Lys or absent

<400> SEQUENCE: 59

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Tyr Tyr Asp Tyr Asp Gln Gly Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

```
Ala Lys Thr Lys Pro Arg Glu Glu Gln Phe Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Gln Glu Glu Met Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
                420                 425                 430

Ala Leu His Asn His Tyr Thr Gln Lys Ser Leu Ser Leu Ser Leu Gly
                435                 440                 445

Xaa

<210> SEQ ID NO 60
<211> LENGTH: 451
<212> TYPE: PRT
<213> ORGANISM: Artificial Sequence
<220> FEATURE:
<223> OTHER INFORMATION: alpha-FXI-13716p-IgG4 HC S228P
<220> FEATURE:
<221> NAME/KEY: MISC_FEATURE
<222> LOCATION: (451)..(451)
<223> OTHER INFORMATION: Xaa is Lys or absent

<400> SEQUENCE: 60

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ser Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ala Tyr Leu Met Glu Leu Tyr Tyr Tyr Gly Met Asp
                100                 105                 110

Val Trp Gly Gln Gly Thr Thr Val Thr Val Ser Ser Ala Ser Thr Lys
            115                 120                 125

Gly Pro Ser Val Phe Pro Leu Ala Pro Cys Ser Arg Ser Thr Ser Glu
        130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175
```

Phe Pro Ala Val Leu Gln Ser Ser Gly Leu Tyr Ser Leu Ser Ser Val
                180                 185                 190

Val Thr Val Pro Ser Ser Ser Leu Gly Thr Lys Thr Tyr Thr Cys Asn
            195                 200                 205

Val Asp His Lys Pro Ser Asn Thr Lys Val Asp Lys Arg Val Glu Ser
210                 215                 220

Lys Tyr Gly Pro Pro Cys Pro Pro Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly Xaa
    450

<210> SEQ ID NO 61
<211> LENGTH: 451
<212> TYPE: PRT
<213> ORGANISM: Artificial Sequence
<220> FEATURE:
<223> OTHER INFORMATION: alpha-FXI-13716-IgG4 HC  S228P 1Q1E M103L
<220> FEATURE:
<221> NAME/KEY: MISC_FEATURE
<222> LOCATION: (451)..(451)
<223> OTHER INFORMATION: Xaa is Lys or absent

<400> SEQUENCE: 61

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ser Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe

```
            50                  55                  60
Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                     85                  90                  95

Ala Arg Gly Ala Tyr Leu Leu Glu Leu Tyr Tyr Tyr Gly Met Asp
                100                 105                 110

Val Trp Gly Gln Gly Thr Thr Val Thr Val Ser Ser Ala Ser Thr Lys
                115                 120                 125

Gly Pro Ser Val Phe Pro Leu Ala Pro Cys Ser Arg Ser Thr Ser Glu
            130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Lys Thr Tyr Thr Cys Asn
                195                 200                 205

Val Asp His Lys Pro Ser Asn Thr Lys Val Asp Lys Arg Val Glu Ser
210                 215                 220

Lys Tyr Gly Pro Pro Cys Pro Pro Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
                260                 265                 270

Glu Asp Pro Glu Val Gln Phe Asn Trp Tyr Val Asp Gly Val Glu Val
                275                 280                 285

His Asn Ala Lys Thr Lys Pro Arg Glu Glu Gln Phe Asn Ser Thr Tyr
                290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Gln Glu Glu Met Thr Lys Asn Gln Val Ser
                355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
                420                 425                 430

His Glu Ala Leu His Asn His Tyr Thr Gln Lys Ser Leu Ser Leu Ser
                435                 440                 445

Leu Gly Xaa
    450

<210> SEQ ID NO 62
```

```
<211> LENGTH: 452
<212> TYPE: PRT
<213> ORGANISM: Artificial Sequence
<220> FEATURE:
<223> OTHER INFORMATION: alpha-FXI-13654p-IgG1 HC
<220> FEATURE:
<221> NAME/KEY: MISC_FEATURE
<222> LOCATION: (452)..(452)
<223> OTHER INFORMATION: Xaa is Lys or absent

<400> SEQUENCE: 62
```

| Glu | Val | Gln | Leu | Val | Glu | Ser | Gly | Gly | Gly | Leu | Val | Lys | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | Tyr |
|---|---|---|---|---|---|---|---|---|---|---|---|---|---|---|---|
| | | | 20 | | | | | 25 | | | | | 30 | | |

| Ser | Met | Asn | Trp | Val | Arg | Gln | Ala | Pro | Gly | Lys | Gly | Leu | Glu | Trp | Val |
| | | 35 | | | | | 40 | | | | | 45 | | | |

| Ser | Ser | Ile | Ser | Ser | Ser | Ser | Tyr | Ile | Tyr | Tyr | Ala | Asp | Ser | Val |
| 50 | | | | | 55 | | | | | 60 | | | | |

| Lys | Gly | Arg | Phe | Thr | Ile | Ser | Arg | Asp | Asn | Ala | Lys | Asn | Ser | Leu | Tyr |
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |

| Ala | Arg | Ser | Tyr | Tyr | Asp | Tyr | Asp | Gln | Gly | Tyr | Gly | Met | Asp | Val | Trp |
| | | | 100 | | | | | 105 | | | | | 110 | | |

| Gly | Gln | Gly | Thr | Thr | Val | Thr | Val | Ser | Ser | Ala | Ser | Thr | Lys | Gly | Pro |
| | | | 115 | | | | | 120 | | | | | 125 | | |

| Ser | Val | Phe | Pro | Leu | Ala | Pro | Ser | Ser | Lys | Ser | Thr | Ser | Gly | Gly | Thr |
| 130 | | | | | 135 | | | | | 140 | | | | | |

| Ala | Ala | Leu | Gly | Cys | Leu | Val | Lys | Asp | Tyr | Phe | Pro | Glu | Pro | Val | Thr |
| 145 | | | | 150 | | | | | 155 | | | | | 160 | |

| Val | Ser | Trp | Asn | Ser | Gly | Ala | Leu | Thr | Ser | Gly | Val | His | Thr | Phe | Pro |
| | | | | 165 | | | | | 170 | | | | | 175 | |

| Ala | Val | Leu | Gln | Ser | Ser | Gly | Leu | Tyr | Ser | Leu | Ser | Ser | Val | Val | Thr |
| | | | 180 | | | | | 185 | | | | | 190 | | |

| Val | Pro | Ser | Ser | Ser | Leu | Gly | Thr | Gln | Thr | Tyr | Ile | Cys | Asn | Val | Asn |
| | | 195 | | | | | 200 | | | | | 205 | | | |

| His | Lys | Pro | Ser | Asn | Thr | Lys | Val | Asp | Lys | Lys | Val | Glu | Pro | Lys | Ser |
| 210 | | | | | 215 | | | | | 220 | | | | | |

| Cys | Asp | Lys | Thr | His | Thr | Cys | Pro | Pro | Cys | Pro | Ala | Pro | Glu | Leu | Leu |
| 225 | | | | | 230 | | | | | 235 | | | | | 240 |

| Gly | Gly | Pro | Ser | Val | Phe | Leu | Phe | Pro | Pro | Lys | Pro | Lys | Asp | Thr | Leu |
| | | | | 245 | | | | | 250 | | | | | 255 | |

| Met | Ile | Ser | Arg | Thr | Pro | Glu | Val | Thr | Cys | Val | Val | Val | Asp | Val | Ser |
| | | | | 260 | | | | | 265 | | | | | 270 | |

| His | Glu | Asp | Pro | Glu | Val | Lys | Phe | Asn | Trp | Tyr | Val | Asp | Gly | Val | Glu |
| | | | 275 | | | | | 280 | | | | | 285 | | |

| Val | His | Asn | Ala | Lys | Thr | Lys | Pro | Arg | Glu | Glu | Gln | Tyr | Asn | Ser | Thr |
| | | | 290 | | | | | 295 | | | | | 300 | | |

| Tyr | Arg | Val | Val | Ser | Val | Leu | Thr | Val | Leu | His | Gln | Asp | Trp | Leu | Asn |
| 305 | | | | | 310 | | | | | 315 | | | | | 320 |

| Gly | Lys | Glu | Tyr | Lys | Cys | Lys | Val | Ser | Asn | Lys | Ala | Leu | Pro | Ala | Pro |
| | | | | 325 | | | | | 330 | | | | | 335 | |

| Ile | Glu | Lys | Thr | Ile | Ser | Lys | Ala | Lys | Gly | Gln | Pro | Arg | Glu | Pro | Gln |
| | | | 340 | | | | | 345 | | | | | 350 | | |

| Val | Tyr | Thr | Leu | Pro | Pro | Ser | Arg | Asp | Glu | Leu | Thr | Lys | Asn | Gln | Val |

```
                355                 360                 365
Ser Leu Thr Cys Leu Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Xaa
        450

<210> SEQ ID NO 63
<211> LENGTH: 454
<212> TYPE: PRT
<213> ORGANISM: Artificial Sequence
<220> FEATURE:
<223> OTHER INFORMATION: alpha-FXI-13716p-IgG1 HC
<220> FEATURE:
<221> NAME/KEY: MISC_FEATURE
<222> LOCATION: (454)..(454)
<223> OTHER INFORMATION: Xaa is Lys or absent

<400> SEQUENCE: 63

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ser Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ala Tyr Leu Met Glu Leu Tyr Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240
```

-continued

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
        260                 265                 270

Val Ser His Glu Asp Pro Glu Val Lys Phe Asn Trp Tyr Val Asp Gly
    275                 280                 285

Val Glu Val His Asn Ala Lys Thr Lys Pro Arg Glu Glu Gln Tyr Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Xaa
    450

<210> SEQ ID NO 64
<211> LENGTH: 454
<212> TYPE: PRT
<213> ORGANISM: Artificial Sequence
<220> FEATURE:
<223> OTHER INFORMATION: alpha-FXI-13716-IgG1 HC 1Q1E M103L
<220> FEATURE:
<221> NAME/KEY: MISC_FEATURE
<222> LOCATION: (454)..(454)
<223> OTHER INFORMATION: Xaa is 454 or absent

<400> SEQUENCE: 64

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ser Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ala Tyr Leu Leu Glu Leu Tyr Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
            130                 135                 140
Gly Thr Ala Ala Leu Gly Cys Leu Val Lys Asp Tyr Phe Pro Glu Pro
145                 150                 155                 160
Val Thr Val Ser Trp Asn Ser Gly Ala Leu Thr Ser Gly Val His Thr
                165                 170                 175
Phe Pro Ala Val Leu Gln Ser Ser Gly Leu Tyr Ser Leu Ser Ser Val
            180                 185                 190
Val Thr Val Pro Ser Ser Leu Gly Thr Gln Thr Tyr Ile Cys Asn
        195                 200                 205
Val Asn His Lys Pro Ser Asn Thr Lys Val Asp Lys Lys Val Glu Pro
210                 215                 220
Lys Ser Cys Asp Lys Thr His Thr Cys Pro Pro Cys Pro Ala Pro Glu
225                 230                 235                 240
Leu Leu Gly Gly Pro Ser Val Phe Leu Phe Pro Pro Lys Pro Lys Asp
                245                 250                 255
Thr Leu Met Ile Ser Arg Thr Pro Glu Val Thr Cys Val Val Val Asp
            260                 265                 270
Val Ser His Glu Asp Pro Glu Val Lys Phe Asn Trp Tyr Val Asp Gly
        275                 280                 285
Val Glu Val His Asn Ala Lys Thr Lys Pro Arg Glu Glu Gln Tyr Asn
290                 295                 300
Ser Thr Tyr Arg Val Val Ser Val Leu Thr Val Leu His Gln Asp Trp
305                 310                 315                 320
Leu Asn Gly Lys Glu Tyr Lys Cys Lys Val Ser Asn Lys Ala Leu Pro
                325                 330                 335
Ala Pro Ile Glu Lys Thr Ile Ser Lys Ala Lys Gly Gln Pro Arg Glu
            340                 345                 350
Pro Gln Val Tyr Thr Leu Pro Pro Ser Arg Asp Glu Leu Thr Lys Asn
        355                 360                 365
Gln Val Ser Leu Thr Cys Leu Val Lys Gly Phe Tyr Pro Ser Asp Ile
370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
                405                 410                 415
Leu Thr Val Asp Lys Ser Arg Trp Gln Gln Gly Asn Val Phe Ser Cys
            420                 425                 430
Ser Val Met His Glu Ala Leu His Asn His Tyr Thr Gln Lys Ser Leu
        435                 440                 445
Ser Leu Ser Pro Gly Xaa
    450

<210> SEQ ID NO 65
<211> LENGTH: 453
<212> TYPE: PRT
<213> ORGANISM: Artificial Sequence
<220> FEATURE:
<223> OTHER INFORMATION: alpha-FXI-13716 IgG1 HC Q1E C-terminal K-less

<400> SEQUENCE: 65

Glu Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30

-continued

```
Ser Met His Trp Val Arg Gln Ala Pro Gly Gln Gly Leu Glu Trp Met
        35                  40                  45
Gly Ile Ile Asn Pro Ser Gly Gly Ser Thr Ser Tyr Ala Gln Lys Phe
 50                  55                  60
Gln Gly Arg Val Thr Met Thr Arg Asp Thr Ser Thr Ser Thr Val Tyr
 65                  70                  75                  80
Met Glu Leu Ser Ser Leu Arg Ser Glu Asp Thr Ala Val Tyr Tyr Cys
                 85                  90                  95
Ala Arg Gly Ala Tyr Leu Met Glu Leu Tyr Tyr Tyr Gly Met Asp
                100                 105                 110
Val Trp Gly Gln Gly Thr Thr Val Thr Val Ser Ser Ala Ser Thr Lys
            115                 120                 125
Gly Pro Ser Val Phe Pro Leu Ala Pro Ser Ser Lys Ser Thr Ser Gly
        130                 135                 140
Gly Thr Ala Ala Leu Gly Cys Leu Val Lys Asp Tyr Phe Pro Glu Pro
145                 150                 155                 160
Val Thr Val Ser Trp Asn Ser Gly Ala Leu Thr Ser Gly Val His Thr
                165                 170                 175
Phe Pro Ala Val Leu Gln Ser Ser Gly Leu Tyr Ser Leu Ser Ser Val
            180                 185                 190
Val Thr Val Pro Ser Ser Ser Leu Gly Thr Gln Thr Tyr Ile Cys Asn
        195                 200                 205
Val Asn His Lys Pro Ser Asn Thr Lys Val Asp Lys Val Glu Pro
210                 215                 220
Lys Ser Cys Asp Lys Thr His Thr Cys Pro Pro Cys Pro Ala Pro Glu
225                 230                 235                 240
Leu Leu Gly Gly Pro Ser Val Phe Leu Phe Pro Pro Lys Pro Lys Asp
                245                 250                 255
Thr Leu Met Ile Ser Arg Thr Pro Glu Val Thr Cys Val Val Val Asp
            260                 265                 270
Val Ser His Glu Asp Pro Glu Val Lys Phe Asn Trp Tyr Val Asp Gly
        275                 280                 285
Val Glu Val His Asn Ala Lys Thr Lys Pro Arg Glu Glu Gln Tyr Asn
290                 295                 300
Ser Thr Tyr Arg Val Val Ser Val Leu Thr Val Leu His Gln Asp Trp
305                 310                 315                 320
Leu Asn Gly Lys Glu Tyr Lys Cys Lys Val Ser Asn Lys Ala Leu Pro
                325                 330                 335
Ala Pro Ile Glu Lys Thr Ile Ser Lys Ala Lys Gly Gln Pro Arg Glu
            340                 345                 350
Pro Gln Val Tyr Thr Leu Pro Pro Ser Arg Asp Glu Leu Thr Lys Asn
        355                 360                 365
Gln Val Ser Leu Thr Cys Leu Val Lys Gly Phe Tyr Pro Ser Asp Ile
370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
                405                 410                 415
Leu Thr Val Asp Lys Ser Arg Trp Gln Gln Gly Asn Val Phe Ser Cys
            420                 425                 430
Ser Val Met His Glu Ala Leu His Asn His Tyr Thr Gln Lys Ser Leu
        435                 440                 445
```

Ser Leu Ser Pro Gly
    450

<210> SEQ ID NO 66
<211> LENGTH: 454
<212> TYPE: PRT
<213> ORGANISM: Artificial Sequence
<220> FEATURE:
<223> OTHER INFORMATION: alpha-FXI-13716 IgG1 HC Q1E C-terminal K

<400> SEQUENCE: 66

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ser Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ala Tyr Leu Met Glu Leu Tyr Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

```
Pro Gln Val Tyr Thr Leu Pro Pro Ser Arg Asp Glu Leu Thr Lys Asn
                355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 67
<211> LENGTH: 450
<212> TYPE: PRT
<213> ORGANISM: Artificial Sequence
<220> FEATURE:
<223> OTHER INFORMATION: alpha-FXI-13716-IgG4 HC S228P Q1E C-terminal
      K-less

<400> SEQUENCE: 67

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ser Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ala Tyr Leu Met Glu Leu Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Pro Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255
```

```
Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly
    450

<210> SEQ ID NO 68
<211> LENGTH: 451
<212> TYPE: PRT
<213> ORGANISM: Artificial Sequence
<220> FEATURE:
<223> OTHER INFORMATION: alpha-FXI-13716-IgG4 HC S228P Q1E C-terminal K

<400> SEQUENCE: 68

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ser Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ala Tyr Leu Met Glu Leu Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160
```

Val Thr Val Ser Trp Asn Ser Gly Ala Leu Thr Ser Gly Val His Thr
            165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
            195                 200                 205

Val Asp His Lys Pro Ser Asn Thr Lys Val Asp Lys Arg Val Glu Ser
            210                 215                 220

Lys Tyr Gly Pro Pro Cys Pro Pro Cys Pro Ala Pro Glu Phe Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
            275                 280                 285

His Asn Ala Lys Thr Lys Pro Arg Glu Glu Gln Phe Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
            405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
            435                 440                 445

Leu Gly Lys
450

<210> SEQ ID NO 69
<211> LENGTH: 450
<212> TYPE: PRT
<213> ORGANISM: Artificial Sequence
<220> FEATURE:
<223> OTHER INFORMATION: alpha-FXI-13716-IgG4 HC S228P M103L C-terminal
      K-less

<400> SEQUENCE: 69

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ser Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe

```
            50                  55                  60
Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Ala Tyr Leu Leu Glu Leu Tyr Tyr Tyr Gly Met Asp
                100                 105                 110

Val Trp Gly Gln Gly Thr Thr Val Thr Val Ser Ser Ala Ser Thr Lys
                115                 120                 125

Gly Pro Ser Val Phe Pro Leu Ala Pro Cys Ser Arg Ser Thr Ser Glu
            130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Lys Thr Tyr Thr Cys Asn
                195                 200                 205

Val Asp His Lys Pro Ser Asn Thr Lys Val Asp Lys Arg Val Glu Ser
210                 215                 220

Lys Tyr Gly Pro Pro Cys Pro Pro Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
                260                 265                 270

Glu Asp Pro Glu Val Gln Phe Asn Trp Tyr Val Asp Gly Val Glu Val
                275                 280                 285

His Asn Ala Lys Thr Lys Pro Arg Glu Glu Gln Phe Asn Ser Thr Tyr
                290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Gln Glu Glu Met Thr Lys Asn Gln Val Ser
                355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
                420                 425                 430

His Glu Ala Leu His Asn His Tyr Thr Gln Lys Ser Leu Ser Leu Ser
                435                 440                 445

Leu Gly
    450

<210> SEQ ID NO 70
```

<211> LENGTH: 451
<212> TYPE: PRT
<213> ORGANISM: Artificial Sequence
<220> FEATURE:
<223> OTHER INFORMATION: alpha-FXI-13716-IgG4 HC S228P M103L C-terminal K

<400> SEQUENCE: 70

```
Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Ser Tyr
            20                  25                  30

Ser Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ala Tyr Leu Leu Glu Leu Tyr Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Pro Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
```

```
                370                 375                 380
Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
                420                 425                 430

His Glu Ala Leu His Asn His Tyr Thr Gln Lys Ser Leu Ser Leu Ser
                435                 440                 445

Leu Gly Lys
        450

<210> SEQ ID NO 71
<211> LENGTH: 232
<212> TYPE: PRT
<213> ORGANISM: Artificial Sequence
<220> FEATURE:
<223> OTHER INFORMATION: anti-RSV Kappa Light Chain

<400> SEQUENCE: 71

Met Ala Pro Val Gln Leu Leu Gly Leu Leu Val Leu Phe Leu Pro Ala
1               5                   10                  15

Met Arg Cys Asp Ile Gln Met Thr Gln Ser Pro Ser Thr Leu Ser Ala
                20                  25                  30

Ser Val Gly Asp Arg Val Thr Ile Thr Cys Lys Cys Gln Leu Ser Val
            35                  40                  45

Gly Tyr Met His Trp Tyr Gln Gln Lys Pro Gly Lys Ala Pro Lys Leu
        50                  55                  60

Leu Ile Tyr Asp Thr Ser Lys Leu Ala Ser Gly Val Pro Ser Arg Phe
65                  70                  75                  80

Ser Gly Ser Gly Ser Gly Thr Glu Phe Thr Leu Thr Ile Ser Ser Leu
                85                  90                  95

Gln Pro Asp Asp Phe Ala Thr Tyr Tyr Cys Phe Gln Gly Ser Gly Tyr
                100                 105                 110

Pro Phe Thr Phe Gly Gly Gly Thr Lys Leu Glu Ile Lys Arg Thr Val
            115                 120                 125

Ala Ala Pro Ser Val Phe Ile Phe Pro Pro Ser Asp Glu Gln Leu Lys
        130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
                180                 185                 190

Leu Ser Ser Thr Leu Thr Leu Ser Lys Ala Asp Tyr Glu Lys His Lys
            195                 200                 205

Val Tyr Ala Cys Glu Val Thr His Gln Gly Leu Ser Ser Pro Val Thr
        210                 215                 220

Lys Ser Phe Asn Arg Gly Glu Cys
225                 230

<210> SEQ ID NO 72
<211> LENGTH: 466
<212> TYPE: PRT
<213> ORGANISM: Artificial Sequence
<220> FEATURE:
<223> OTHER INFORMATION: anti-RSV IgG4 HC S228P
```

<400> SEQUENCE: 72

```
Met Ala Val Val Gln Leu Leu Gly Leu Leu Val Leu Phe Leu Pro Ala
1               5                   10                  15

Met Arg Cys Gln Val Thr Leu Arg Glu Ser Gly Pro Ala Leu Val Lys
            20                  25                  30

Pro Thr Gln Thr Leu Thr Leu Thr Cys Thr Phe Ser Gly Phe Ser Leu
        35                  40                  45

Ser Thr Ser Gly Met Ser Val Gly Trp Ile Arg Gln Pro Pro Gly Lys
    50                  55                  60

Ala Leu Glu Trp Leu Ala Asp Ile Trp Trp Asp Asp Lys Lys Asp Tyr
65                  70                  75                  80

Asn Pro Ser Leu Lys Ser Arg Leu Thr Ile Ser Lys Asp Thr Ser Lys
                85                  90                  95

Asn Gln Val Val Leu Lys Val Thr Asn Met Asp Pro Ala Asp Thr Ala
            100                 105                 110

Thr Tyr Tyr Cys Ala Arg Ser Met Ile Thr Asn Trp Tyr Phe Asp Val
        115                 120                 125

Trp Gly Ala Gly Thr Thr Val Thr Val Ser Ser Ala Ser Thr Lys Gly
130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Lys Thr Tyr Thr Cys Asn Val
    210                 215                 220

Asp His Lys Pro Ser Asn Thr Lys Val Asp Lys Arg Val Glu Ser Lys
225                 230                 235                 240

Tyr Gly Pro Pro Cys Pro Pro Cys Pro Ala Pro Glu Phe Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser Gln Glu
        275                 280                 285

Asp Pro Glu Val Gln Phe Asn Trp Tyr Val Asp Gly Val Glu Val His
290                 295                 300

Asn Ala Lys Thr Lys Pro Arg Glu Glu Gln Phe Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Gly Leu Pro Ser Ser Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Gln Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
```

-continued

```
                405                 410                 415
Leu Asp Ser Asp Gly Ser Phe Phe Leu Tyr Ser Arg Leu Thr Val Asp
            420                 425                 430

Lys Ser Arg Trp Gln Glu Gly Asn Val Phe Ser Cys Ser Val Met His
            435                 440                 445

Glu Ala Leu His Asn His Tyr Thr Gln Lys Ser Leu Ser Leu Ser Leu
    450                 455                 460

Gly Lys
465
```

ANTI-COAGULATION FACTOR XI ANTIBODIES

CROSS REFERENCE TO RELATED APPLICATIONS

This application claims benefit of U.S. Provisional Patent Application No. 62/281,842 filed Jan. 22, 2016, which is herein incorporated by reference in its entirety.

REFERENCE TO SEQUENCE LISTING SUBMITTED ELECTRONICALLY

The sequence listing of the present application is submitted electronically via EFS-Web as an ASCII formatted sequence listing with a file name "23617WOPCTSEQ", creation date of Dec. 1, 2016, and a size of 160 Kb. This sequence listing submitted via EFS-Web is part of the specification and is herein incorporated by reference in its entirety.

BACKGROUND OF THE INVENTION (1) Field of the Invention

The present invention relates to antibodies that bind the apple 2 domain of human coagulation factor XI (FXI) and inhibit activation of FXI by coagulation factor XIIa.

(2) Description of Related Art

Thromboembolic disorders, including both venous and arterial thrombosis, remain the leading cause of morbidity and mortality in the Western world despite the availability of numerous class of anticoagulants, such as vitamin K antagonists (VKAs), heparins, and direct thrombin inhibitors (Weitz et al., Chest 2008, 133: 234S-256S; Hawkins, Pharmacotherapy 2004, 24:62S-65S). These drugs are effective in reducing risks of thrombosis but they are associated with multiple limitations. For example, the VKAs (e.g. warfarin) have been the mainstay for oral anticoagulation yet the management of VKA therapy is complicated due to its significant bleeding risk, slow onset and offset of action, and multiple dietary and drug interactions (Hawkins, op. cit.; Ansell J et al., Chest 2008, 133:160S-198S). The new oral anticoagulants (NOACs, including rivaroxaban, apixaban, edoxaban, and dabigatran) have demonstrated at least non-inferior efficacy compared to warfarin, with less food and drug interactions and no need for monitoring. However, the NOACs still increase the risk of bleeding as demonstrated by the close to 18% annual incidence of major or nonmajor clinically relevant bleeding in their registration trials for stroke prevention in atrial fibrillation (Connolly et al., N Engl J Med 2009, 361:1139-1151; Patel et al., N Engl J Med 2011, 365:883-891; Granger et al., N Engl J Med 2011, 365:981-992; Giugliano et al., N Engl J Med 2013, 369: 2093-2104). This is largely ascribed to the fact that the NOACs target proteins (coagulation Factor Xa (FXa) and thrombin) that are essential for normal coagulation (hemostasis). Novel therapy with better safety profiles in prevention and treatment of thrombotic diseases or disorders is thus an unmet need.

In the classic waterfall model of the blood clotting cascade (FIG. 1A), coagulation is triggered by either the extrinsic (tissue factor (TF)-activated) pathway or the intrinsic (contact-activated) pathway, both feeding into the common pathway that culminates in thrombin generation and fibrin formation (Furie & Furie, Cell 1988, 53:505-518; Gailani & Renne, J Thromb Haemost 2007, 5:1106-1112). The extrinsic cascade is initiated when TF that is present in the subendothelium and atherosclerotic lesions becomes exposed to flowing blood and forms a complex with coagulation Factor VIIa (FVIIa). The TF-FVIIa complex (extrinsic tenase complex) then triggers the common pathway, i.e. activation of FX to form FXa which in turn converts prothrombin to thrombin. The TF-FVIIa complex can also activate coagulation Factor IX (FIX) to form FIXa. FIXa in complex with coagulation Factor VIII (FVIIIa) (intrinsic tenase complex) can cleave the FX substrate as well. The intrinsic cascade is initiated when FXIIa is formed via contact activation from negatively charged surfaces (e.g. collagen and glycosaminoglycans) and propagates thrombin generation by sequential activation of FXI, FIX, FX, and prothrombin. Thrombin, as the terminal protease in the clotting cascade, may further contribute to FXIa generation by direct activation of FXI in a feedback mechanism. Platelets, another important hemostatic component in whole blood, can be activated by thrombin and may subsequently support FXIa formation as well. FXI-dependent amplification of thrombin generation may indirectly regulate fibrinolysis via activation of the thrombin-activatable fibrinolysis inhibitor (TAFI). FXI thus interacts with several components in the hemostatic system and plays a pivotal role in blood coagulation and thrombosis (Gailani & Renne op. cit.; Emsley et al., Blood 2010, 115:2569-2577).

Coagulation Factor XI (FXI) is a dimer composed of identical 80 KDa subunits, and each subunit starting from the N-terminus consists of four apple domains (A1, A2, A3, and A4) and a catalytic domain (See FIG. 1B). FXI is a zymogen that circulates in complex with High Molecular Weight Kininogen (HK). HK binds to the A2 domain in FXI and is a physiological cofactor for FXIIa activation of FXI to FXIa. The remaining apple domains in FXI also mediate important physiological functions. For example, FIX-binding exosite is localized in A3, whereas FXIIa-binding site is in A4. Residues that are critical for FXI dimerization are also localized in A4 (Emsley et al., op. cit.).

In recent years multiple lines of effort have demonstrated that FXI plays a pivotal role in the pathological process of thrombus formation with relatively small contribution to hemostasis and is thus a promising target for thrombosis. Key data supporting this notion are summarized in the following: (1) in Ionis Pharmaceuticals Inc. FXI antisense oligonucleotide (ASO) Phase II trial (Buller et al., N Engl J Med 2015, 372:232-240), FXI ASO produced significant reduction in venous thromboembolism (VTE), with a trend toward less bleeding, compared to enoxaparin, in patients undergoing total knee arthroplasty; (2) Human genetics and epidemiological studies (Duga et al., Semin Thromb Hemost 2013;

Chen et al., Drug Discov Today 2014; Key, Hematology Am Soc Hematol Educ Program 2014, 2014:66-70) indicated that severe FXI deficiency (hemophilia C) confers reduced risk of ischemic stroke and deep vein thrombosis; conversely, increased levels of FXI are associated with a higher risk for VTE and ischemic stroke; and (3) Numerous lines of preclinical studies demonstrated that FXI(a) inhibition or loss-of-function mediate profound thromboprotection without compromising hemostasis (Chen et al. op. cit.). Of note, monoclonal antibodies 14E11 and 1A6 produced significant thrombus reduction in the baboon AV shunt thrombosis model (U.S. Pat. No. 8,388,959; Tucker et al., Blood 2009, 113:936-944; Cheng et al., Blood 2010, 116: 3981-3989). Moreover, 14E11 (as it cross-reacts with mouse FXI) provided protection in an experimental model of acute ischemic stroke in mice (Leung et al., Transl Stroke Res 2012, 3:381-389). Additional FXI-targeting mAbs have also been reported in preclinical models that validate FXI as an antithrombotic target with minimal bleeding risk (van Montfoort et al., Thromb Haemost 2013, 110; Takahashi et al., Thromb Res 2010, 125:464-470; van Montfoort, Ph.D. Thesis, University of Amsterdam, Amsterdam, Netherlands, 14 Nov. 2014). Inhibition of FXI is thus a promising strategy for novel antithrombotic therapy with an improved benefit-risk profile compared to current standard-of-care anticoagulants.

BRIEF SUMMARY OF THE INVENTION

The present invention provides human antibodies and antigen binding fragments capable of selectively binding to coagulation Factor XI (anti-FXI antibodies) and inhibiting blood coagulation and associated thrombosis without compromising hemostasis, preferably, effecting a reduction in blood clotting and associated thrombosis while inducing little or no detectable bleeding. Compositions include anticoagulation Factor XI antibodies and antigen binding fragments capable of binding to a defined epitope of the apple 2 domain of coagulation Factor XI. These antibodies and antigen binding fragments exhibit neutralizing activity by inhibiting the conversion of the zymogen form of coagulation factor XI to its activated form, coagulation Factor XIa, via the coagulation Factor FXIIa.

The antibodies and antigen binding fragments are useful for the treatment and/or prevention of thrombotic disorders and diseases, including but not limited to, myocardial infarction, ischemic stroke, pulmonary thromboembolism, venous thromboembolism (VTE), atrial fibrillation, disseminated intravascular coagulation, medical device-related thromboembolic disorders, severe systemic inflammatory response syndrome, metastatic cancer, and infectious disease. The antibodies and antigen binding fragments are particularly useful for Stroke Prevention in Atrial Fibrillation (SPAF).

The present invention provides an antibody or antigen binding fragment comprising at least the six complementarity determining regions (CDRs) of antibody αFXI-13654p, αFXI-13716p, or αFXI-13716 or at least the six complementarity determining regions (CDRs) of antibody αFXI-13654p, AD-13716p, or αFXI-13716 wherein one or more of the six CDRs has one, two, or three amino acid substitutions, additions, deletions, or combinations thereof, wherein antibody αFXI-13654p comprises a heavy chain (HC) having the amino acid sequence shown in SEQ ID NO:18, 26, 31, or 32 and a light chain (LC) having the amino acid sequence shown in SEQ ID NO:19; wherein antibody αFXI-13716p comprises an HC having the amino acid sequence shown in SEQ ID NO:22, 27, 33, or 34 and a LC having the amino acid sequence shown in SEQ ID NO:23; wherein antibody αFXI-13716 comprises an HC having the amino acid sequence shown in SEQ ID NO:25, 28, 35, or 36 and a LC having the amino acid sequence shown in SEQ ID NO:23; wherein optionally one or more of the six CDRs has one, two, or three amino acid substitutions, additions, deletions, or combinations thereof; and, wherein the antibody or antigen binding fragment of (i), (ii) or (iii) binds the apple 2 domain of coagulation factor XI (FXI) and inhibits activation of FXI.

The present invention provides an antibody or antigen binding fragment comprising at least the six complementarity determining regions (CDRs) of antibody αFXI-13654p, αFXI-13716p, or αFXI-13716 or at least the six complementarity determining regions (CDRs) of antibody αFXI-13654p, AD-13716p, or αFXI-13716 wherein one or more of the six CDRs has one, two, or three amino acid substitutions, additions, deletions, or combinations thereof relative to the CDRs of αFXI-13654p, αFXI-13716p, or αFXI-13716, wherein antibody αFXI-13654p comprises a heavy chain (HC) having the amino acid sequence shown in SEQ ID NO:18 or 31 and a light chain (LC) having the amino acid sequence shown in SEQ ID NO:19; wherein antibody αFXI-13716p comprises an HC having the amino acid sequence shown in SEQ ID NO:22 or 33 and a LC having the amino acid sequence shown in SEQ ID NO:23; wherein antibody αFXI-13716 comprises an HC having the amino acid sequence shown in SEQ ID NO:25 or 35 and a LC having the amino acid sequence shown in SEQ ID NO:23; wherein optionally one or more of the six CDRs has one, two, or three amino acid substitutions, additions, deletions, or combinations thereof; and, wherein the antibody or antigen binding fragment of (i), (ii) or (iii) binds the apple 2 domain of coagulation factor XI (FXI) and inhibits activation of FXI.

In further aspects or embodiments of the invention, the six CDRs comprise CDR1, CDR2, and CDR3 of the HC of antibody αFXI-13654p, αFXI-13716p, or αFXI-13716 and CDR1, CDR2, and CDR3 of the LC of antibody αFXI-13654p, αFXI-13716p, or αFXI-13716. In further embodiments, the six CDRs comprise CDR1, CDR2, and CDR3 of the HC of antibody αFXI-13654p, αFXI-13716p, or αFXI-13716 wherein one or more of the three CDRs has one, two, or three amino acid substitutions, additions, deletions, or combinations thereof; and CDR1, CDR2, and CDR3 of the LC of antibody αFXI-13654p, αFXI-13716p, or αFXI-13716, wherein one or more of the three CDRs has one, two, or three amino acid substitutions, additions, deletions, or combinations thereof relative to the CDRs of αFXI-13654p, αFXI-13716p, or αFXI-13716.

In further aspects or embodiments of the invention, the antibody or antigen binding fragment comprises (i) the HC CDRs having the amino acid sequences set forth in SEQ ID NO:1, SEQ ID NO:2, and SEQ ID NO:3 for HC CDR1, CDR2 and CDR3 respectively and the LC CDRs having the amino acid sequences set forth in SEQ ID NO:4, SEQ ID NO:5, and SEQ ID NO:6 for LC CDR1, CDR2 and CDR3 respectively, wherein optionally one or more of the six CDRs has one, two, or three amino acid substitutions, additions, deletions, or combinations thereof; (ii) the HC CDRs having the amino acid sequences set forth in SEQ ID NO:7, SEQ ID NO:8, and SEQ ID NO:9 for HC CDR1, CDR2 and CDR3 respectively and the LC CDRs having the amino acid sequences set forth in SEQ ID NO:10, SEQ ID NO:11, and SEQ ID NO:12 for LC CDR1, CDR2 and CDR3 respectively, wherein optionally one or more of the six CDRs has one, two, or three amino acid substitutions, additions, deletions, or combinations thereof; or, (iii) the HC CDRs having the amino acid sequences set forth in SEQ ID NO:7, SEQ ID NO:8, and SEQ ID NO:13 for HC CDR1, CDR2 and CDR3 respectively and the LC CDRs having the amino acid sequences set forth in SEQ ID NO:10, SEQ ID NO:11, and SEQ ID NO:12 for LC CDR1, CDR2 and CDR3 respectively, wherein optionally one or more of the six CDRs has one, two, or three amino acid substitutions, additions, deletions, or combinations thereof.

In further aspects or embodiments of the invention, the antibody or antigen binding fragment comprises (i) the HC CDRs having the amino acid sequences set forth in SEQ ID NO:1, SEQ ID NO:2, and SEQ ID NO:3 for HC CDR1, CDR2 and CDR3 respectively and the LC CDRs having the amino acid sequences set forth in SEQ ID NO:4, SEQ ID NO:5, and SEQ ID NO:6 for HC CDR1, CDR2 and CDR3 respectively, wherein one or more of the six CDRs has one, two, or three amino acid substitutions, additions, deletions, or combinations thereof; (ii) the HC CDRs having the amino acid sequences set forth in SEQ ID NO:7, SEQ ID NO:8, and SEQ ID NO:9 and the LC CDRs having the amino acid sequences set forth in SEQ ID NO:10, SEQ ID NO:11, and SEQ ID NO:12 for HC CDR1, CDR2 and CDR3 respectively, wherein one or more of the six CDRs has one, two, or three amino acid substitutions, additions, deletions, or combinations thereof; or, (iii) the HC CDRs having the amino acid sequences set forth in SEQ ID NO:7, SEQ ID NO:8, and SEQ ID NO:13 and the LC CDRs having the amino acid sequences set forth in SEQ ID NO:10, SEQ ID NO:11, and SEQ ID NO:12 for LC CDR1, CDR2 and CDR3 respectively, wherein one or more of the six CDRs has one, two, or three amino acid substitutions, additions, deletions, or combinations thereof.

In further aspects or embodiments of the invention, the antibody or antigen binding fragment comprises CDR1, CDR2, and CDR3 of the HC of antibody αFXI-13654p, αFXI-13716p, or αFXI-13716 in a HC variable domain having the amino acid sequence shown in SEQ ID NO:16 for antibody αFXI-13654p, SEQ ID NO:20 antibody αFXI-1371p, or SEQ ID NO:24 antibody αFXI-13716 and CDR1, CDR2, and CDR3 of the LC of antibody αFXI-13654p, αFXI-13716p, or αFXI-13716 in a LC variable domain having amino acid sequence shown in SEQ ID NO:17 for antibody αFXI-13654p or SEQ ID NO:21 for antibody αFXI-13716p or antibody αFXI-13716.

In further aspects or embodiments of the invention, the antibody comprises a HC constant domain comprising the amino acid sequence shown in SEQ ID NO:14 or 40 or variant thereof in which the constant domain comprises 1, 2, 3, 4, 5, 6, 7, 8, 9, or 10 amino acid substitutions, additions, deletions, or combinations thereof.

In further aspects or embodiments of the invention, the antibody comprises a LC constant domain comprising the amino acid sequence shown in SEQ ID NO:15 or variant thereof in which the constant domain comprises 1, 2, 3, 4, 5, 6, 7, 8, 9, or 10 amino acid substitutions, additions, deletions, or combinations thereof.

The present invention further provides an antibody or antigen binding fragment comprising at least the six complementarity determining regions (CDRs) of antibody αFXI-13654p, αFXI-13716p, or αFXI-13716; wherein antibody αFXI-13654p comprises a heavy chain (HC) having the amino acid sequence shown in SEQ ID NO:18, 26, 31, or 32 and a light chain (LC) having the amino acid sequence shown in SEQ ID NO:19; wherein antibody αFXI-13716p comprises an HC having the amino acid sequence shown in SEQ ID NO:22, 27, 33, or 34 and a LC having the amino acid sequence shown in SEQ ID NO:23; wherein antibody αFXI-13716 comprises an HC having the amino acid sequence shown in SEQ ID NO:25, 28, 35, or 36 and a LC having the amino acid sequence shown in SEQ ID NO:23; wherein optionally one or more of the six CDRs has one, two, or three amino acid substitutions, additions, deletions, or combinations thereof; and, wherein the antibody or antigen binding fragment binds the apple 2 domain of coagulation factor XI (FXI) and inhibits activation of FXI.

In further aspects or embodiments of the invention, the HC CDRs of antibody αFXI-13654p have the amino acid sequences set forth in SEQ ID NO:1, SEQ ID NO:2, and SEQ ID NO:3 and the LC CDRs of antibody αFXI-13654p have the amino acid sequences set forth in SEQ ID NO:4, SEQ ID NO:5, and SEQ ID NO:6, wherein optionally one or more of the six CDRs has one, two, or three amino acid substitutions, additions, deletions, or combinations thereof, the HC CDRs of antibody αFXI-13716p have the amino acid sequences set forth in SEQ ID NO:7, SEQ ID NO:8, and SEQ ID NO:9 and the LC CDRs of antibody αFXI-13716p have the amino acid sequences set forth in SEQ ID NO:10, SEQ ID NO:11, and SEQ ID NO:12, wherein optionally one or more of the six CDRs has one, two, or three amino acid substitutions, additions, deletions, or combinations thereof, and, the HC CDRs of antibody αFXI-13716 have the amino acid sequences set forth in SEQ ID NO:7, SEQ ID NO:8, and SEQ ID NO:13 and the LC CDRs of antibody αFXI-13716 have the amino acid sequences set forth in SEQ ID NO:10, SEQ ID NO:11, and SEQ ID NO:12, wherein optionally one or more of the six CDRs has one, two, or three amino acid substitutions, additions, deletions, or combinations thereof.

In further aspects or embodiments of the invention, the αFXI-13654p antibody comprises an HC variable domain having the amino acid sequence shown in SEQ ID NO:16 and an LC variable domain having amino acid sequence shown in SEQ ID NO:17 wherein optionally one or both of the variable domains has 1, 2, 3, 4, 5, 6, 7, 8, 9, or 10 amino acid substitutions, additions, deletions, or combinations thereof with the proviso that no CDR in the variable domains has more than three amino acid substitutions, additions, deletions; the αFXI-13716p antibody comprises an HC variable domain having the amino acid sequence shown in SEQ ID NO:20 and an LC variable domain having amino acid sequence shown in SEQ ID NO:21, wherein optionally one or both of the variable domains has 1, 2, 3, 4, 5, 6, 7, 8, 9, or 10 amino acid substitutions, additions, deletions, or combinations thereof with the proviso that no CDR in the variable domains has more than three amino acid substitutions, additions, deletions; and the αFXI-13716 antibody comprises an HC variable domain having the amino acid sequence shown in SEQ ID NO:24 and an LC variable domain having amino acid sequence shown in SEQ ID NO:21, wherein optionally one or both of the variable domains has 1, 2, 3, 4, 5, 6, 7, 8, 9, or 10 amino acid substitutions, additions, deletions, or combinations thereof with the proviso that no CDR in the variable domains has more than three amino acid substitutions, additions, deletions. In a further embodiment, the aforementioned HC or LC variable domains may comprise one, two or three amino acid substitutions, additions, deletions, or combinations thereof in the framework regions of said variable domains.

In further aspects or embodiments of the invention, the αFXI-13654p antibody, αFXI-13716p antibody, and αFXI-13716p antibody each comprises an HC constant domain having the amino acid sequence shown in SEQ ID NO:14 or 40 or variant thereof in which the constant domain comprises 1, 2, 3, 4, 5, 6, 7, 8, 9, or 10 amino acid substitutions, additions, deletions, or combinations thereof.

In further aspects or embodiments of the invention, the αFXI-13654p antibody, αFXI-13716p antibody, and αFXI-13716p antibody each comprises an LC constant domain comprising the amino acid sequence shown in SEQ ID NO:15 or variant thereof in which the constant domain comprises 1, 2, 3, 4, 5, 6, 7, 8, 9, or 10 amino acid substitutions, additions, deletions, or combinations thereof.

The present invention further provides an antibody or antigen binding fragment comprising (a) a heavy chain variable domain having the amino acid sequence shown in SEQ ID NO: 16 and a light chain variable domain having the amino acid sequence shown in SEQ ID NO:17, wherein optionally one or both of the variable domains has 1, 2, 3, 4, 5, 6, 7, 8, 9, or 10 amino acid substitutions, additions, deletions, or combinations thereof with the proviso that no CDR in the variable domains has more than three amino acid substitutions, additions, deletions, or combinations thereof; (b) a heavy chain variable domain having the amino acid sequence shown in SEQ ID NO:20 and a light chain variable domain having the amino acid sequence shown in SEQ ID NO:21, wherein optionally one or both of the variable domains has 1, 2, 3, 4, 5, 6, 7, 8, 9, or 10 amino acid substitutions, additions, deletions, or combinations thereof with the proviso that no CDR in the variable domains has more than three amino acid substitutions, additions, deletions, or combinations thereof; or (c) a heavy chain variable domain having the amino acid sequence shown in SEQ ID NO: 24 and a light chain variable domain having the amino acid sequence shown in SEQ ID NO:21, and wherein optionally one or both of the variable domains has 1, 2, 3, 4, 5, 6, 7, 8, 9, or 10 amino acid substitutions, additions, deletions, or combinations thereof with the proviso that no CDR in the variable domains has more than three amino acid substitutions, additions, deletions, or combinations thereof. In a further embodiment, the aforementioned HC or LC variable domains may comprise one, two or three amino acid substitutions, additions, deletions, or combinations thereof. In the framework regions of said variable domains.

In further aspects or embodiments of the invention, the antibody further comprises a HC constant domain comprising the amino acid sequence shown in SEQ ID NO:14 or 40 and may optionally include 1, 2, 3, 4, 5, 6, 7, 8, 9, or 10 amino acid substitutions, additions, deletions, or combinations thereof.

In further aspects or embodiments of the invention, the antibody further comprises a LC constant domain comprising the amino acid sequence shown in SEQ ID NO:15 and may optionally include 1, 2, 3, 4, 5, 6, 7, 8, 9, or 10 amino acid substitutions, additions, deletions, or combinations thereof.

In particular embodiments, the HC and LC constant domains may comprise 1, 2, 3, 4, 5, 6, 7, 8, 9, or 10 amino acid substitutions, additions, deletions, or combinations thereof. In further aspects, the HC constant domain may comprise a C-terminal lysine or may lack a C-terminal lysine.

The present invention further provides an antibody or antigen binding fragment comprising (a) a heavy chain having a variable domain comprising a heavy chain complementarity determining region (HC-CDR) 1 having the amino acid sequence shown in SEQ ID NO:1, a HC-CDR 2 having the amino acid sequence shown in SEQ ID NO:2, and a HC-CDR 3 having the amino acid sequence shown in SEQ ID NO:3, wherein optionally one or more of the HC-CDRs has one, two, or three amino acid substitutions, additions, deletions, or combinations thereof (b) a heavy chain having a variable domain comprising a heavy chain complementarity determining region (HC-CDR) 1 having the amino acid sequence shown in SEQ ID NO:7, a HC-CDR 2 having the amino acid sequence shown in SEQ ID NO:8, and a HC-CDR 3 having the amino acid sequence shown in SEQ ID NO:9, wherein optionally one or more of the HC-CDRs has one, two, or three amino acid substitutions, additions, deletions, or combinations thereof; or (c) a heavy chain having a variable domain comprising a heavy chain complementarity determining region (HC-CDR) 1 having the amino acid sequence shown in SEQ ID NO:7, a HC-CDR 2 having the amino acid sequence shown in SEQ ID NO:8, and a HC-CDR 3 having the amino acid sequence shown in SEQ ID NO:13, wherein optionally one or more of the HC-CDRs has one, two, or three amino acid substitutions, additions, deletions, or combinations thereof, and wherein optionally one or both of the variable domains has 1, 2, 3, 4, 5, 6, 7, 8, 9, or 10 amino acid substitutions, additions, deletions, or combinations thereof with the proviso that no CDR in the variable domains has more than three amino acid substitutions, additions, deletions, and wherein the antibody or antigen binding fragment binds the apple 2 domain of coagulation factor XI (FXI) and inhibits activation of FXI.

In further aspects or embodiments of the invention, the antibody comprises a heavy chain constant domain of the human IgG1, IgG2, IgG3, or IgG4 isotype. In further aspects, the constant domain may comprise 1, 2, 3, 4, 5, 6, 7, 8, 9, or 10 amino acid substitutions, additions, deletions, or combinations thereof. In particular aspects, the constant domain may comprise a C-terminal lysine or may lack a C-terminal lysine.

In further aspects or embodiments of the invention, the antibody comprises a heavy chain constant domain of the human IgG1 or IgG4 isotype. In a further aspect, the heavy chain constant domain is of the IgG4 isotype and further includes a substitution of the serine residue at position 228 (EU numbering) with proline, which corresponds to position 108 of SEQ ID NO:41 (Serine at position 108) or SEQ ID NO:14 (proline at position 108) and may optionally include 1, 2, 3, 4, 5, 6, 7, 8, 9, or 10 amino acid substitutions, additions, deletions, or combinations thereof.

In further aspects or embodiments of the invention, the antibody comprises a heavy chain constant domain comprising the amino acid sequence shown in SEQ ID NO:14 or 40 and may optionally include 1, 2, 3, 4, 5, 6, 7, 8, 9, or 10 amino acid substitutions, additions, deletions, or combinations thereof.

The present invention further provides an antibody or antigen binding fragment comprising (a) a light chain having a variable domain comprising a light chain complementarity determining region (LC-CDR) 1 having the amino acid sequence shown in SEQ ID NO:4, a LC-CDR 2 having the amino acid sequence shown in SEQ ID NO:5, and a LC-CDR 3 having the amino acid sequence shown in SEQ ID NO:6, wherein optionally one or more of the LC-CDRs has one, two, or three amino acid substitutions, additions, deletions, or combinations thereof or (b) a light chain having a variable domain comprising a light chain complementarity determining region (LC-CDR) 1 having the amino acid sequence shown in SEQ ID NO:10, a LC-CDR 2 having the amino acid sequence shown in SEQ ID NO:11, and a LC-CDR 3 having the amino acid sequence shown in SEQ ID NO:12, wherein optionally one or more of the LC-CDRs has one, two, or three amino acid substitutions, additions, deletions, or combinations thereof, and wherein optionally one or both of the variable domains has 1, 2, 3, 4, 5, 6, 7, 8, 9, or 10 amino acid substitutions, additions, deletions, or combinations thereof with the proviso that no CDR in the variable domains has more than three amino acid substitutions, additions, deletions, wherein the antibody or antigen binding fragment binds the apple 2 domain of coagulation factor XI (FXI) and inhibits activation of FXI. In a further embodiment, the aforementioned HC or LC variable domains may comprise one, two or three amino acid substitutions, additions, deletions, or combinations thereof in the framework regions of said variable domains.

In further aspects or embodiments of the invention, the light chain comprises a human kappa light chain or human lambda light chain. In particular aspects, the light chain constant domain may comprise 1, 2, 3, 4, 5, 6, 7, 8, 9, or 10 amino acid substitutions, additions, deletions, or combinations thereof.

In further aspects or embodiments of the invention, the antibody comprises a light chain constant domain comprising the amino acid sequence shown in SEQ ID NO:15. The present invention further provides an antibody or antigen binding fragment comprising (a) a heavy chain having a variable domain comprising a heavy chain complementarity determining region (HC-CDR) 1 having the amino acid sequence shown in SEQ ID NO:1, a HC-CDR 2 having the amino acid sequence shown in SEQ ID NO:2, and a HC-CDR 3 having the amino acid sequence shown in SEQ ID NO:3, wherein optionally one or more of the HC-CDRs has one, two, or three amino acid substitutions, additions, deletions, or combinations thereof and (b) a light chain having a variable domain comprising a light chain complementarity determining region (LC-CDR) 1 having the amino acid sequence shown in SEQ ID NO:4, a LC-CDR 2 having the amino acid sequence shown in SEQ ID NO:5, and a LC-CDR 3 having the amino acid sequence shown in SEQ ID NO:6, wherein optionally one or more of the LC-CDRs has one, two, or three amino acid substitutions, additions, deletions, or combinations thereof, and wherein optionally one or both of the variable domains has 1, 2, 3, 4, 5, 6, 7, 8, 9, or 10 amino acid substitutions, additions, deletions, or combinations thereof with the proviso that no CDR in the variable domains has more than three amino acid substitutions, additions, deletions, or combinations thereof. In a further embodiment, the aforementioned HC or LC variable domains may comprise one, two or three amino acid substitutions, additions, deletions, or combinations thereof in the framework regions of said variable domains.

In further aspects or embodiments of the invention, the antibody comprises a heavy chain constant domain of the IgG1, IgG2, IgG3, or IgG4 isotype. In particular aspects, the constant domain may comprise 1, 2, 3, 4, 5, 6, 7, 8, 9, or 10 amino acid substitutions, additions, deletions, or combinations thereof. In further aspects, the constant domain may comprise a C-terminal lysine or may lack a C-terminal lysine.

In further aspects or embodiments of the invention, the antibody comprises a heavy chain constant domain of the human IgG1 or IgG4 isotype. In a further aspect, the heavy chain constant domain is of the IgG4 isotype and further includes a substitution of the serine residue at position 228 (EU numbering) with proline, which corresponds to position 108 of SEQ ID NO:41 (Serine at position 108) or SEQ ID NO:14 (proline at position 108) and may optionally include 1, 2, 3, 4, 5, 6, 7, 8, 9, or 10 amino acid substitutions, additions, deletions, or combinations thereof.

In further aspects or embodiments of the invention, the antibody comprises a heavy chain constant domain comprising the amino acid sequence shown in SEQ ID NO:14 or 40, which in particular embodiments may comprise 1, 2, 3, 4, 5, 6, 7, 8, 9, or 10 amino acid substitutions, additions, deletions, or combinations thereof.

In further aspects or embodiments of the invention, the light chain comprises a human kappa light chain constant domain or human lambda light chain constant domain, which in particular embodiments may comprise 1, 2, 3, 4, 5, 6, 7, 8, 9, or 10 amino acid substitutions, additions, deletions, or combinations thereof.

In further aspects or embodiments of the invention, the antibody comprises a light chain constant domain comprising the amino acid sequence shown in SEQ ID NO:15, which in particular embodiments may comprise 1, 2, 3, 4, 5, 6, 7, 8, 9, or 10 amino acid substitutions, additions, deletions, or combinations thereof.

The present invention further provides an antibody or antigen binding fragment comprising (a) a heavy chain having a variable domain comprising a heavy chain complementarity determining region (HC-CDR) 1 having the amino acid sequence shown in SEQ ID NO:7, a HC-CDR 2 having the amino acid sequence shown in SEQ ID NO:8, and a HC-CDR 3 having the amino acid sequence shown in SEQ ID NO:9 or 13, wherein optionally one or more of the HC-CDRs has one, two, or three amino acid substitutions, additions, deletions, or combinations thereof; and (b) a light chain having a variable domain comprising a light chain complementarity determining region (LC-CDR) 1 having the amino acid sequence shown in SEQ ID NO:10, a LC-CDR 2 having the amino acid sequence shown in SEQ ID NO:11, and a LC-CDR 3 having the amino acid sequence shown in SEQ ID NO:12, wherein optionally one or more of the HLC-CDRs has one, two, or three amino acid substitutions, additions, deletions, or combinations thereof, and wherein optionally one or both of the variable domains has 1, 2, 3, 4, 5, 6, 7, 8, 9, or 10 amino acid substitutions, additions, deletions, or combinations thereof with the proviso that no CDR in the variable domains has more than three amino acid substitutions, additions, deletions. In a further embodiment, the aforementioned HC or LC variable domains may comprise one, two or three amino acid substitutions, additions, deletions, or combinations thereof in the framework regions of said variable domains.

In further aspects or embodiments of the invention, the antibody comprises an heavy chain constant domain of the IgG1, IgG2, IgG3, or IgG4 isotype, which in particular embodiments may comprise 1, 2, 3, 4, 5, 6, 7, 8, 9, or 10 amino acid substitutions, additions, deletions, or combinations thereof. In particular aspects, the constant domain may comprise a C-terminal lysine or may lack a C-terminal lysine.

In further aspects or embodiments of the invention, the antibody comprises a heavy chain constant domain of the human IgG1 or IgG4 isotype or variant thereof comprising a constant domain having 1, 2, 3, 4, 5, 6, 7, 8, 9, or 10 amino acid substitutions, additions, deletions, or combinations thereof. In a further aspect, the heavy chain constant domain is of the IgG4 isotype and further includes a substitution of the serine residue at position 228 (EU numbering) with proline, which corresponds to position 108 of SEQ ID NO:41 (Serine at position 108) or SEQ ID NO:14 (proline at position 108) and may optionally include 1, 2, 3, 4, 5, 6, 7, 8, 9, or 10 amino acid substitutions, additions, deletions, or combinations thereof.

In further aspects or embodiments of the invention, the antibody comprises a heavy chain constant domain comprising the amino acid sequence shown in SEQ ID NO:14 or 40 or variant thereof comprising a constant domain having 1, 2, 3, 4, 5, 6, 7, 8, 9, or 10 amino acid substitutions, additions, deletions, or combinations thereof.

In further aspects or embodiments of the invention, the light chain comprises a human kappa light chain constant domain or human lambda light chain constant domain, which in particular aspects may comprise 1, 2, 3, 4, 5, 6, 7, 8, 9, or 10 amino acid substitutions, additions, deletions, or combinations thereof.

In further aspects or embodiments of the invention, the antibody comprises a light chain constant domain comprising the amino acid sequence shown in SEQ ID NO:15 or variant thereof comprising a constant domain having 1, 2, 3, 4, 5, 6, 7, 8, 9, or 10 amino acid substitutions, additions, deletions, or combinations thereof.

The present invention further provides an antibody comprising a heavy chain having the amino acid sequence shown in SEQ ID NO: 18, 26, 31, or 32; and a light chain having the amino acid sequence shown in SEQ ID NO: 19 or variant thereof comprising a constant domain having 1, 2, 3, 4, 5, 6, 7, 8, 9, or 10 amino acid substitutions, additions, deletions, or combinations thereof.

The present invention further provides an antibody comprising a heavy chain having the amino acid sequence shown in SEQ ID NO:22, 25, 27, 28, 33, 34, 35, or 36; and a light chain having the amino acid sequence shown in SEQ ID NO:23 or variant thereof comprising a constant domain having 1, 2, 3, 4, 5, 6, 7, 8, 9, or 10 amino acid substitutions, additions, deletions, or combinations thereof.

The present invention further provides an antibody comprising a heavy chain having the amino acid sequence shown in SEQ ID NO:22; and a light chain having the amino acid sequence shown in SEQ ID NO:23.

The present invention further provides an antibody comprising a heavy chain having the amino acid sequence shown in SEQ ID NO:25; and a light chain having the amino acid sequence shown in SEQ ID NO:23.

The present invention further provides an antibody comprising a heavy chain (HC) having the amino acid sequence shown in SEQ ID NO: 27; and a light chain (LC) having the amino acid sequence shown in SEQ ID NO:23. In a further embodiment, the aforementioned HC and/or LC may comprise 1, 2, 3, 4, 5, 6, 7, 8, 9, or 10 amino acid substitutions, additions, deletions, or combinations thereof with the proviso that the complementarity determining regions (CDRs) of the aforementioned antibody may comprise no more than one, two or three amino acid substitutions, additions, deletions, or combinations thereof.

The present invention further provides an antibody comprising a heavy chain having the amino acid sequence shown in SEQ ID NO:28; and a light chain having the amino acid sequence shown in SEQ ID NO:23. In a further embodiment, the aforementioned HC and/or LC may comprise 1, 2, 3, 4, 5, 6, 7, 8, 9, or 10 amino acid substitutions, additions, deletions, or combinations thereof with the proviso that the complementarity determining regions (CDRs) of the aforementioned antibody may comprise no more than one, two or three amino acid substitutions, additions, deletions, or combinations thereof.

The present invention further provides an antibody comprising a heavy chain having the amino acid sequence shown in SEQ ID NO:33; and a light chain having the amino acid sequence shown in SEQ ID NO:23. In a further embodiment, the aforementioned HC and/or LC may comprise 1, 2, 3, 4, 5, 6, 7, 8, 9, or 10 amino acid substitutions, additions, deletions, or combinations thereof with the proviso that the complementarity determining regions (CDRs) of the aforementioned antibody may comprise no more than one, two or three amino acid substitutions, additions, deletions, or combinations thereof.

The present invention further provides an antibody comprising a heavy chain having the amino acid sequence shown in SEQ ID NO:34; and a light chain having the amino acid sequence shown in SEQ ID NO:23. In a further embodiment, the aforementioned HC and/or LC may comprise 1, 2, 3, 4, 5, 6, 7, 8, 9, or 10 amino acid substitutions, additions, deletions, or combinations thereof with the proviso that the complementarity determining regions (CDRs) of the aforementioned antibody may comprise no more than one, two or three amino acid substitutions, additions, deletions, or combinations thereof.

The present invention further provides an antibody comprising a heavy chain having the amino acid sequence shown in SEQ ID NO:35; and a light chain having the amino acid sequence shown in SEQ ID NO:23. In a further embodiment, the aforementioned HC and/or LC may comprise 1, 2, 3, 4, 5, 6, 7, 8, 9, or 10 amino acid substitutions, additions, deletions, or combinations thereof with the proviso that the complementarity determining regions (CDRs) of the aforementioned antibody may comprise no more than one, two or three amino acid substitutions, additions, deletions, or combinations thereof.

The present invention further provides an antibody comprising a heavy chain having the amino acid sequence shown in SEQ ID NO:36; and a light chain having the amino acid sequence shown in SEQ ID NO:23. In a further embodiment, the aforementioned HC and/or LC may comprise 1, 2, 3, 4, 5, 6, 7, 8, 9, or 10 amino acid substitutions, additions, deletions, or combinations thereof with the proviso that the complementarity determining regions (CDRs) of the aforementioned antibody may comprise no more than one, two or three amino acid substitutions, additions, deletions, or combinations thereof.

The present invention further provides an antibody comprising a heavy chain having the amino acid sequence shown in SEQ ID NO:18, 26, 31, or 32; and a light chain having the amino acid sequence shown in SEQ ID NO:19. In a further embodiment, the aforementioned HC and/or LC may comprise 1, 2, 3, 4, 5, 6, 7, 8, 9, or 10 amino acid substitutions, additions, deletions, or combinations thereof with the proviso that the complementarity determining regions (CDRs) of the aforementioned antibody may comprise no more than one, two or three amino acid substitutions, additions, deletions, or combinations thereof.

The present invention further provides an antibody comprising a heavy chain having the amino acid sequence shown in SEQ ID NO:18; and a light chain having the amino acid sequence shown in SEQ ID NO:19. In a further embodiment, the aforementioned HC and/or LC may comprise 1, 2, 3, 4, 5, 6, 7, 8, 9, or 10 amino acid substitutions, additions, deletions, or combinations thereof with the proviso that the complementarity determining regions (CDRs) of the aforementioned antibody may comprise no more than one, two or three amino acid substitutions, additions, deletions, or combinations thereof.

The present invention further provides an antibody comprising a heavy chain having the amino acid sequence shown in SEQ ID NO:26; and a light chain having the amino acid sequence shown in SEQ ID NO:19. In a further embodiment, the aforementioned HC and/or LC may comprise 1, 2, 3, 4, 5, 6, 7, 8, 9, or 10 amino acid substitutions, additions, deletions, or combinations thereof with the proviso that the complementarity determining regions (CDRs) of the aforementioned antibody may comprise no more than one, two or three amino acid substitutions, additions, deletions, or combinations thereof.

The present invention further provides an antibody comprising a heavy chain having the amino acid sequence shown in SEQ ID NO: 31; and a light chain having the amino acid sequence shown in SEQ ID NO:19. In a further embodiment, the aforementioned HC and/or LC may comprise 1, 2, 3, 4, 5, 6, 7, 8, 9, or 10 amino acid substitutions, additions, deletions, or combinations thereof with the proviso that the complementarity determining regions (CDRs) of the aforementioned antibody may comprise no more than one, two or three amino acid substitutions, additions, deletions, or combinations thereof.

The present invention further provides an antibody comprising a heavy chain having the amino acid sequence shown in SEQ ID NO:32; and a light chain having the amino acid sequence shown in SEQ ID NO:19. In a further embodiment, the aforementioned HC and/or LC may comprise 1, 2, 3, 4, 5, 6, 7, 8, 9, or 10 amino acid substitutions, additions, deletions, or combinations thereof with the proviso that the complementarity determining regions (CDRs) of the aforementioned antibody may comprise no more than one, two or three amino acid substitutions, additions, deletions, or combinations thereof.

The present invention further provides an isolated nucleic acid molecule encoding the light chain variable domain or the heavy chain variable of any one of the aforementioned antibodies or antigen binding fragments.

The present invention further provides an antibody or antigen binding fragment that binds to an epitope on coagulation factor XI (FXI) comprising the amino acid sequence YATRQFPSLEHRNICL (SEQ ID NO:38) and amino acid sequence HTQTGTPTRITKL (SEQ ID NO:39) with the proviso that the antibody or antigen binding fragment does not comprise murine or rat amino acid sequences.

In a further embodiment, the antibody or antigen binding fragment does not comprise non-human amino acid sequences. In a further embodiment, the antibody comprises the human IgG1 constant domain or IgG4 constant domain or modified variant thereof. In a further embodiment, the IgG1 or IgG4 constant domain is a variant that comprises at least 1, 2, 3, 4, 5, 6, 7, 8, 9, or 10 amino acid substitutions, additions, deletions, or combinations thereof. In a further embodiment, the IgG1 or IgG4 constant domain is a variant that comprises at least 1, 2, 3, or 4 amino acid substitutions, additions, deletions, or combinations thereof.

In a further embodiment, the IgG4 constant domain is a variant that comprises at least a substitution of the serine at position 228 (EU numbering) or position 108 as shown in SEQ ID NO:14 with a proline residue.

In a further embodiment, the IgG1 or IgG4 constant domain is a variant that at least lacks a lysine at the C-terminus.

In a further embodiment, the antibody or antigen binding fragment comprises variable domain sequences comprising a framework characteristic of human antibodies.

The present invention further provides an antibody or antigen binding fragment that binds to an epitope on coagulation factor XI (FXI) comprising the amino acid sequence YATRQFPSLEHRNICL (SEQ ID NO:38) and amino acid sequence HTQTGTPTRITKL (SEQ ID NO:39) with the proviso that the antibody comprises the human IgG1 constant domain or IgG4 constant domain or modified derivative thereof.

In a further embodiment, the IgG1 or IgG4 constant domain is a variant that comprises at least 1, 2, 3, 4, 5, 6, 7, 8, 9, or 10 amino acid substitutions, additions, deletions, or combinations thereof.

In a further embodiment, the IgG1 or IgG4 constant domain is a variant that comprises at least 1, 2, 3, or 4 amino acid substitutions, additions, deletions, or combinations thereof. In a further embodiment, the IgG4 constant domain is a variant that comprises at least a substitution of the serine at position 228 (EU numbering) or position 108 as shown in SEQ ID NO:14 with a proline residue.

In a further embodiment, the IgG1 or IgG4 constant domain is a variant that at least lacks a lysine at the C-terminus.

In a further embodiment, the antibody or antigen binding fragment comprises variable domain sequences comprising a framework characteristic of human antibodies.

The present invention further provides an antibody or antigen binding fragment that cross-blocks or competes with the binding of a reference antibody to coagulation Factor XI, wherein the reference antibody comprises (i) a heavy chain having the amino acid sequence shown in SEQ ID NO: 18, 26, 31, or 32 and a light chain having the amino acid sequence shown in SEQ ID NO: 19; or (ii) a heavy chain having the amino acid sequence shown in SEQ ID NO:22, 25, 27, 28, 33, 34, 35, or 36 and a light chain having the amino acid sequence shown in SEQ ID NO:23; with the proviso that the antibody or antigen binding fragment does not comprise murine or rat amino acid sequences.

In a further embodiment, the antibody or antigen binding fragment does not comprise non-human amino acid sequences. In a further embodiment, the antibody comprises the human IgG1 constant domain or IgG4 constant domain or modified variant thereof. In a further embodiment, the IgG1 or IgG4 constant domain is a variant that comprises at least 1, 2, 3, 4, 5, 6, 7, 8, 9, or 10 amino acid substitutions, additions, deletions, or combinations thereof. In a further embodiment, the IgG1 or IgG4 constant domain is a variant that comprises at least 1, 2, 3, or 4 amino acid substitutions, additions, deletions, or combinations thereof.

In a further embodiment, the IgG4 constant domain is a variant that comprises at least a substitution of the serine at position 228 (EU numbering) or position 108 as shown in SEQ ID NO:14 with a proline residue.

In a further embodiment, the IgG1 or IgG4 constant domain is a variant that at least lacks a lysine at the C-terminus. In a further embodiment, the antibody or antigen binding fragment comprises variable domain sequences comprising a framework characteristic of human antibodies.

The present invention further provides an antibody or antigen binding fragment that cross-blocks or competes with the binding of a reference antibody to coagulation Factor XI, wherein the reference antibody comprises (i) a heavy chain having the amino acid sequence shown in SEQ ID NO: 18, 26, 31, or 32 and a light chain having the amino acid sequence shown in SEQ ID NO: 19; or (ii) a heavy chain having the amino acid sequence shown in SEQ ID NO:22, 25, 27, 28, 33, complementarity 34, 35, or 36 and a light chain having the amino acid sequence shown in SEQ ID NO:23; with the proviso that the antibody or antigen binding fragment comprises the human IgG1 constant domain or IgG4 constant domain or modified derivative thereof.

In a further embodiment, the IgG1 or IgG4 constant domain is a variant that comprises at least 1, 2, 3, 4, 5, 6, 7, 8, 9, or 10 amino acid substitutions, additions, deletions, or combinations thereof.

In a further embodiment, the IgG1 or IgG4 constant domain is a variant that comprises at least 1, 2, 3, or amino acid substitutions, additions, deletions, or combinations thereof.

In a further embodiment, the IgG4 constant domain is a variant that comprises at least a substitution of the serine at position 228 (EU numbering) or position 108 as shown in SEQ ID NO:14 with a proline residue.

In a further embodiment, the IgG1 or IgG4 constant domain is a variant that at least lacks a lysine at the C-terminus.

In a further embodiment, the antibody or antigen binding fragment comprises variable domain sequences comprising a framework characteristic of human antibodies.

The present invention further provides a method for producing (a) an antibody or antigen binding fragment comprising (i) a heavy chain having variable domain comprising a heavy chain complementarity determining region (HC-CDR) 1 having the amino acid sequence shown in SEQ ID NO:7, a HC-CDR 2 having the amino acid sequence shown in SEQ ID NO:8, and a HC-CDR 3 having the amino acid sequence shown in SEQ ID NO:9 or 13 wherein optionally one or more of the HC-CDRs has one, two, or three amino acid substitutions, additions, deletions, or combinations thereof; and (ii) a light chain having a variable domain comprising a light chain complementarity determining region (LC-CDR) 1 having the amino acid sequence shown in SEQ ID NO:10, a LC-CDR 2 having the amino acid sequence shown in SEQ ID NO:11, and a LC-CDR 3 having the amino acid sequence shown in SEQ ID NO:12 wherein optionally one or more of the HC-CDRs has one, two, or three amino acid substitutions, additions, deletions, or combinations thereof, or (b) an antibody or antigen binding fragment comprising (i) a heavy chain having a variable domain comprising a heavy chain comprising a heavy chain complementarity determining region (HC-CDR) 1 having the amino acid sequence shown in SEQ ID NO:1, a HC-CDR 2 having the amino acid sequence shown in SEQ ID NO:2, and a HC-CDR 3 having the amino acid sequence shown in SEQ ID NO:3 wherein optionally one or more of the HC-CDRs has one, two, or three amino acid substitutions, additions, deletions, or combinations thereof; and (ii) a light chain having a variable domain comprising a light chain complementarity determining region (LC-CDR) 1 having the amino acid sequence shown in SEQ ID NO:4, a LC-CDR 2 having the amino acid sequence shown in SEQ ID NO:5, and a LC-CDR 3 having the amino acid sequence shown in SEQ ID NO:6 wherein optionally one or more of the HC-CDRs has one, two, or three amino acid substitutions, additions, deletions, or combinations thereof, the method comprising providing a host cell comprising a nucleic acid molecule encoding the heavy chain and a nucleic acid molecule encoding the light chain; and cultivating the host cell under conditions and a time sufficient to produce the antibody or antigen binding fragment.

In further aspects or embodiments of the invention the antibody comprises a heavy chain constant domain of the IgG1, IgG2, IgG3, or IgG4 isotype or variant thereof in which the constant domain comprises at least 1, 2, 3, 4, 5, 6, 7, 8, 9, or 10 amino acid substitutions, additions, deletions, or combinations thereof.

In further aspects or embodiments of the invention the antibody comprises a heavy chain constant domain of the IgG4 isotype or variant thereof in which the constant domain comprises at least 1, 2, 3, 4, 5, 6, 7, 8, 9, or 10 amino acid substitutions, additions, deletions, or combinations thereof.

In further aspects or embodiments of the invention the antibody comprises a heavy chain constant domain comprising the amino acid sequence shown in SEQ ID NO:14 or 40 or variant thereof in which the constant domain comprises at least 1, 2, 3, 4, 5, 6, 7, 8, 9, or 10 amino acid substitutions, additions, deletions, or combinations thereof.

In further aspects or embodiments of the invention, the light chain comprises a human kappa light chain constant domain or human lambda light chain constant domain or variant thereof in which the constant domain comprises at least 1, 2, 3, 4, 5, 6, 7, 8, 9, or 10 amino acid substitutions, additions, deletions, or combinations thereof.

In further aspects or embodiments of the invention, the antibody comprises a light chain constant domain comprising the amino acid sequence shown in SEQ ID NO:15 or variant thereof in which the constant domain comprises at least 1, 2, 3, 4, 5, 6, 7, 8, 9, or 10 amino acid substitutions, additions, deletions, or combinations thereof.

In further aspects or embodiments of the invention, the host cell is a Chinese hamster ovary cell or a human embryo kidney 293 cell.

In further aspects or embodiments of the invention, the host cell is a yeast or filamentous fungus cell.

The present invention further provides a composition comprising (a) an antibody or antigen binding fragment comprising (i) a heavy chain having a variable domain comprising a heavy chain comprising a heavy chain complementarity determining region (HC-CDR) 1 having the amino acid sequence shown in SEQ ID NO:7, a HC-CDR 2 having the amino acid sequence shown in SEQ ID NO:8, and a HC-CDR 3 having the amino acid sequence shown in SEQ ID NO:9 or 13 wherein optionally one or more of the HC-CDRs has one, two, or three amino acid substitutions, additions, deletions, or combinations thereof; and (ii) a light chain having a variable domain comprising a light chain complementarity determining region (LC-CDR) 1 having the amino acid sequence shown in SEQ ID NO:10, a LC-CDR 2 having the amino acid sequence shown in SEQ ID NO:11, and a LC-CDR 3 having the amino acid sequence shown in SEQ ID NO:12 wherein optionally one or more of the HC-CDRs has one, two, or three amino acid substitutions, additions, deletions, or combinations thereof, or (b) an antibody or antigen binding fragment comprising (i) a heavy chain having a variable domain comprising a heavy chain comprising a heavy chain complementarity determining region (HC-CDR) 1 having the amino acid sequence shown in SEQ ID NO:1, a HC-CDR 2 having the amino acid sequence shown in SEQ ID NO:2, and a HC-CDR 3 having the amino acid sequence shown in SEQ ID NO:3 wherein optionally one or more of the HC-CDRs has one, two, or three amino acid substitutions, additions, deletions, or combinations thereof; and (ii) a light chain having a variable domain comprising a light chain complementarity determining region (LC-CDR) 1 having the amino acid sequence shown in SEQ ID NO:4, a LC-CDR 2 having the amino acid sequence shown in SEQ ID NO:5, and a LC-CDR 3 having the amino acid sequence shown in SEQ ID NO:6 wherein optionally one or more of the HC-CDRs has one, two, or three amino acid substitutions, additions, deletions, or combinations thereof, and wherein the antibody or antigen binding fragment is obtained from a host cell comprising a nucleic acid molecule encoding the heavy chain and a nucleic acid molecule encoding the light chain.

In further aspects or embodiments of the invention the antibody comprises a heavy chain constant domain of the IgG1, IgG2, IgG3, or IgG4 isotype or variant thereof in which the constant domain comprises at least 1, 2, 3, 4, 5, 6, 7, 8, 9, or 10 amino acid substitutions, additions, deletions, or combinations thereof.

In further aspects or embodiments of the invention the antibody comprises a heavy chain constant domain of the IgG4 isotype or variant thereof in which the constant domain comprises at least 1, 2, 3, 4, 5, 6, 7, 8, 9, or 10 amino acid substitutions, additions, deletions, or combinations thereof.

In further aspects or embodiments of the invention the antibody comprises a heavy chain constant domain comprising the amino acid sequence shown in SEQ ID NO:14 or 40 or variant thereof in which the constant domain comprises at least 1, 2, 3, 4, 5, 6, 7, 8, 9, or 10 amino acid substitutions, additions, deletions, or combinations thereof.

In further aspects or embodiments of the invention, the light chain comprises a human kappa light chain constant domain r human lambda light chain constant domain or variant thereof in which the constant domain comprises at least 1, 2, 3, 4, 5, 6, 7, 8, 9, or 10 amino acid substitutions, additions, deletions, or combinations thereof.

In further aspects or embodiments of the invention, the antibody comprises a light chain constant domain comprising the amino acid sequence shown in SEQ ID NO:15 or variant thereof in which the constant domain comprises at least 1, 2, 3, 4, 5, 6, 7, 8, 9, or 10 amino acid substitutions, additions, deletions, or combinations thereof.

In further aspects or embodiments of the invention, the host cell is a Chinese hamster ovary cell or a human embryo kidney 293 cell.

In further aspects or embodiments of the invention, the host cell is a yeast or filamentous fungus cell.

The present invention further provides a composition comprising the antibody or antigen binding fragment of any one of the aforementioned antibodies or antigen binding fragments and a pharmaceutically acceptable carrier or diluent.

The present invention further provides a method of treating a thromboembolic disorder or disease in a subject comprising administering to the subject a therapeutically effective amount of the antibody or antigen binding fragment of any one of the aforementioned antibodies or antigen binding fragments or compositions comprising any one of the aforementioned antibodies or antigen binding fragments.

In further embodiments, the subject is suffering from or at risk of suffering from myocardial infarction, ischemic stroke, pulmonary thromboembolism, venous thromboembolism (VTE), atrial fibrillation, disseminated intravascular coagulation, medical device-related thromboembolic disorders, severe systemic inflammatory response syndrome, metastatic cancer, or an infectious disease.

In further embodiments, the subject has a pathological activation of FXI.

In further embodiments, the antibody or antigen binding fragment or composition disclosed herein is administered to the subject by parenteral administration.

In further embodiments, the antibody or antigen binding fragment is administered in a therapeutically effective amount of about 0.3 to about 3.0 mg of the antibody or antigen binding fragment/kg of the subject (mg/kg).

In further embodiments, the antibody or antigen binding fragment is administered in a therapeutically effective amount of about 1.0 to 2.0 mg/kg.

In further embodiments, the antibody or antigen binding fragment is administered in a therapeutically effective amount of about 1.0 mg/kg.

In further embodiments, the antibody or antigen binding fragment is administered in a therapeutically effective amount of about 1.0, 1.1, 1.2, 1.3, 1.4, 1.5, 1.6, 1.7, 1.8, 1.9, or 2.0 mg/kg.

The present invention further provides a method of treating a thromboembolic disorder or disease in a subject comprising administering to a subject in need thereof a therapeutically effective amount of the antibody or antigen binding fragments of any one of the aforementioned antibodies or antigen binding fragments or compositions comprising any one of the aforementioned antibodies or antibody fragments.

In further embodiments, the subject in need of treatment is a subject suffering from or at risk of suffering from myocardial infarction, ischemic stroke, pulmonary thromboembolism, venous thromboembolism (VTE), atrial fibrillation, disseminated intravascular coagulation, medical device-related thromboembolic disorders, severe systemic inflammatory response syndrome, metastatic cancer, or an infectious disease.

In further embodiments, the subject in need of treatment is a subject with pathological activation of FXI.

In further embodiments, the antibody or antigen binding fragment or composition is administered to the subject by parenteral administration.

In further embodiments, the antibody or antigen binding fragment is administered in a therapeutically effective amount of about 0.3 to about 3.0 mg of the antibody or antigen binding fragment/kg of the subject (mg/kg).

In further embodiments, the antibody or antigen binding fragment is administered in a therapeutically effective amount of about 1.0 to 2.0 mg/kg.

In further embodiments, the antibody or antigen binding fragment is administered in a therapeutically effective amount of about 1.0 mg/kg.

In further embodiments, the antibody or antigen binding fragment is administered in a therapeutically effective amount of about 1.0, 1.1, 1.2, 1.3, 1.4, 1.5, 1.6, 1.7, 1.8, 1.9, or 2.0 mg/kg.

The present invention further provides for the use of an antibody of any one of the aforementioned antibodies or antigen binding fragments or composition comprising any one of the aforementioned antibodies or antigen binding fragments for the manufacture of a medicament for treating a thromboembolic disorder or disease.

In particular embodiments, the thromboembolic disorder or disease is myocardial infarction, ischemic stroke, pulmonary thromboembolism, venous thromboembolism (VTE), atrial fibrillation, disseminated intravascular coagulation, medical device-related thromboembolic disorders, severe systemic inflammatory response syndrome, metastatic cancer, or an infectious disease.

The present invention further provides an antibody of any one of the aforementioned antibodies or antigen binding fragments or composition comprising any one of the aforementioned antibodies or antigen binding fragments for the treatment of a thromboembolic disorder or disease.

In particular embodiments, the thromboembolic disorder or disease is myocardial infarction, ischemic stroke, pulmonary thromboembolism, venous thromboembolism (VTE), atrial fibrillation, disseminated intravascular coagulation, medical device-related thromboembolic disorders, severe systemic inflammatory response syndrome, metastatic cancer, or an infectious disease.

The present invention further provides a method of inhibiting activation of FXI by factor XIIa (FXIIa) in a subject, comprising: (a) selecting a subject in need of treatment, wherein the subject in need of treatment has or is at risk of developing thrombosis; and (b) administering to the subject an inhibitory amount of any one of the aforementioned antibodies or antigen binding fragments or composition comprising any one of the aforementioned antibodies or antigen binding fragments, thereby inhibiting activation of FXI by FXIIa.

In further embodiments, the subject in need of treatment is a subject suffering from or at risk of suffering from myocardial infarction, ischemic stroke, pulmonary thromboembolism, venous thromboembolism (VTE), atrial fibrillation, disseminated intravascular coagulation, medical device-related thromboembolic disorders, severe systemic inflammatory response syndrome, metastatic cancer, or an infectious disease.

In further embodiments, the subject in need of treatment is a subject with pathological activation of FXI.

In further embodiments, the inhibitory amount of the antibody or antigen binding fragment or composition is an amount sufficient to inhibit activation of FXI by at least 50%.

In further embodiments, the antibody or antigen binding fragment or composition is administered to the subject by parenteral administration.

In further embodiments, the antibody or antigen binding fragment is administered in an inhibitory amount of about 0.3 to about 3.0 mg of the antibody or antigen binding fragment/kg of the subject (mg/kg).

In further embodiments, the antibody or antigen binding fragment is administered in an inhibitory amount of about 1.0 to 2.0 mg/kg.

In further embodiments, the antibody or antigen binding fragment is administered in an inhibitory amount of about 1.0 mg/kg.

In further embodiments, the antibody or antigen binding fragment is administered in an inhibitory amount of about 1.0, 1.1, 1.2, 1.3, 1.4, 1.5, 1.6, 1.7, 1.8, 1.9, or 2.0 mg/kg.

The present invention further provides a method for inhibiting blood coagulation and associated thrombosis without compromising hemostasis in a subject in need thereof, comprising administering to the subject a therapeutically effective amount of any one of the aforementioned antibodies or antigen binding fragments or composition comprising any one of the aforementioned antibodies or antigen binding fragments, thereby inhibiting blood coagulation and associated thrombosis without compromising hemostasis in the subject.

In further embodiments, the subject is suffering from or at risk of suffering from myocardial infarction, ischemic stroke, pulmonary thromboembolism, venous thromboembolism (VTE), atrial fibrillation, disseminated intravascular coagulation, medical device-related thromboembolic disorders, severe systemic inflammatory response syndrome, metastatic cancer, or an infectious disease.

In further embodiments, the subject has a pathological activation of FXI.

In further embodiments, the antibody or antigen binding fragment or composition is administered in an amount sufficient to inhibit activation of FXI by at least 50%.

In further embodiments, the antibody or antigen binding fragment or the composition is administered to the subject by parenteral administration.

In further embodiments, the antibody or antigen binding fragment is administered in a therapeutically effective amount of about 0.1 to about 10 mg of the antibody or antigen binding fragment/kg of the subject (mg/kg).

In further embodiments, the antibody or antigen binding fragment is administered in a therapeutically effective amount of about 1.0 to 2.0 mg/kg. In further embodiments, the antibody or antigen binding fragment is administered in a therapeutically effective amount of about 1.0 mg/kg. In further embodiments, the antibody or antigen binding fragment is administered in a therapeutically effective amount of about 1.0, 1.1, 1.2, 1.3, 1.4, 1.5, 1.6, 1.7, 1.8, 1.9, or 2.0 mg/kg.

The present invention further provides for the use of any one of the aforementioned antibodies or antigen binding fragments or composition comprising any one of the aforementioned antibodies or antigen binding fragments for the manufacture of a medicament for inhibiting blood coagulation and associated thrombosis without compromising hemostasis.

The present invention further provides any one of the aforementioned antibodies or antigen binding fragments or composition comprising any one of the aforementioned antibodies or antigen binding fragments for the inhibiting blood coagulation and associated thrombosis without compromising hemostasis.

Definitions

As used herein, "antibody" refers both to an entire immunoglobulin, including recombinantly produced forms and includes any form of antibody that exhibits the desired biological activity. Thus, it is used in the broadest sense and specifically covers, but is not limited to, monoclonal antibodies (including full length monoclonal antibodies), polyclonal antibodies, multispecific antibodies (e.g., bispecific antibodies), humanized, fully human antibodies, biparatopic antibodies, and chimeric antibodies. "Parental antibodies" are antibodies obtained by exposure of an immune system to an antigen prior to modification of the antibodies for an intended use, such as humanization of an antibody for use as a human therapeutic antibody.

As used herein, "antigen binding fragment" refers to fragments of antibodies, i.e. antibody fragments that retain the ability to bind specifically to the antigen bound by the full-length antibody, e.g. fragments that retain one or more CDR regions. Examples of antibody binding fragments include, but are not limited to, Fab, Fab', F(ab')$_2$, and Fv fragments; diabodies; single-chain antibody molecules, e.g., sc-Fv; nanobodies and multispecific antibodies formed from antibody fragments.

As used herein, a "Fab fragment" is comprised of one light chain and the $C_H1$ and variable regions of one heavy chain. The heavy chain of a Fab molecule cannot form a disulfide bond with another heavy chain molecule. A "Fab fragment" can be the product of papain cleavage of an antibody.

As used herein, a "Fab' fragment" contains one light chain and a portion or fragment of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a F(ab')$_2$ molecule.

As used herein, a "F(ab')$_2$ fragment" contains two light chains and two heavy chains containing the $V_H$ domain and a portion of the constant region between the $C_H1$ and $C_H2$ domains, such that an interchain disulfide bond is formed between the two heavy chains. An F(ab')$_2$ fragment thus is composed of two Fab' fragments that are held together by a disulfide bond between the two heavy chains. An "F(ab')$_2$ fragment" can be the product of pepsin cleavage of an antibody.

As used herein, an "Fv region" comprises the variable regions from both the heavy and light chains, but lacks the constant regions.

As used herein, an "Fc" region contains two heavy chain fragments comprising the $C_H1$ and $C_H2$ domains of an antibody. The two heavy chain fragments are held together by two or more disulfide bonds and by hydrophobic interactions of the $C_H3$ domains.

As used herein, a "diabody" refers to a small antibody fragment with two antigen-binding sites, which fragments comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementarity domains of another chain and create two antigen-binding sites. Diabodies are described more fully in, e.g., EP 404, 097; WO 93/11161; and Holliger et al. (1993) *Proc. Natl. Acad. Sci. USA* 90: 6444-6448. For a review of engineered antibody variants generally see Holliger and Hudson (2005) *Nat. Biotechnol.* 23:1126-1136.

As used herein, a "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens. In an embodiment of the invention, the domain antibody is a single domain antibody or nanobody. In an embodiment of the invention, a domain antibody is a nanobody comprising at least the heavy chain CDRs of the disclosed antibodies αFXI-13654p, αFXI-13716p, or αFXI-13716, said heavy chain CDRs wherein optionally one or more of the CDRs has one, two, or three amino acid substitutions, additions, deletions, or combinations thereof.

As used herein, a "bivalent antibody" comprises two antigen-binding sites. In some instances, the two binding sites have the same antigen specificities. However, bivalent antibodies may be bispecific (e.g., with affinity for FXI and another antigen).

As used herein, a "bispecific antibody" is an artificial hybrid antibody having two different heavy/light chain pairs and thus two different binding sites. For example, a bispecific antibody may comprise a first heavy/light chain pair comprising one heavy and one light chain of a first antibody comprising at least the six CDRs of antibody αFXI-13654p, αFXI-13716p, or αFXI-13716 or embodiments wherein one or more of the six CDRs has one, two, or three amino acid substitutions, additions, deletions, or combinations thereof along with a second heavy/light chain pair comprising one heavy and one light chain of a second antibody having specificity for an antigen of interest other than FXI. Bispecific antibodies can be produced by a variety of methods including fusion of hybridomas or linking of Fab' fragments. See, e.g., Songsivilai, et al., (1990) Clin. Exp. Immunol. 79: 315-321, Kostelny, et al., (1992) J Immunol. 148:1547-1553. In addition, bispecific antibodies may be formed as "diabodies" (Holliger, et al., (1993) PNAS USA 90:6444-6448) or as "Janusins" (Traunecker, et al., (1991) EMBO J. 10:3655-3659 and Traunecker, et al., (1992) Int. J. Cancer Suppl. 7:51-52).

As used herein, a "biparatopic antibody is an antibody having binding specificity for different epitopes on the same antigen.

As used herein, "isolated" antibodies or antigen-binding fragments thereof are at least partially free of other biological molecules from the cells or cell cultures in which they are produced. Such biological molecules include nucleic acids, proteins, lipids, carbohydrates, or other material such as cellular debris and growth medium. An isolated antibody or antigen-binding fragment may further be at least partially free of expression system components such as biological molecules from a host cell or of the growth medium thereof. Generally, the term "isolated" is not intended to refer to a complete absence of such biological molecules or to an absence of water, buffers, or salts or to components of a pharmaceutical formulation that includes the antibodies or fragments.

As used herein, a "monoclonal antibody" refers to a population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies having different amino acid sequences in their variable domains that are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256: 495, or may be made by recombinant DNA methods (see, e.g., U.S. Pat. No. 4,816,567). The "monoclonal antibodies" may also be isolated from phage antibody libraries using the techniques described in Clackson et al. (1991) *Nature* 352: 624-628 and Marks et al. (1991) *J. Mol. Biol.* 222: 581-597, for example. See also Presta (2005) *J. Allergy Clin. Immunol.* 116:731.

As used herein, a "chimeric antibody" is an antibody having the variable domain from a first antibody and the constant domain from a second antibody wherein (i) the first and second antibodies are from different species (U.S. Pat. No. 4,816,567; and Morrison et al., (1984) *Proc. Natl. Acad. Sci. USA* 81: 6851-6855) or (ii) the first and second antibodies are from different isotypes, e.g., variable domain from an IgG1 antibody and the constant domains from an IgG4 antibody, for example αFXI-13465p-IgG4 (S228P). In one aspect, the variable domains are obtained from a human antibody (the "parental antibody"), and the constant domain sequences are obtained from a non-human antibody (e.g., mouse, rat, dog, monkey, gorilla, horse). In another aspect, the variable domains are obtained from a non-human antibody (the "parental antibody") (e.g., mouse, rat, dog, monkey, gorilla, horse), and the constant domain sequences are obtained from a human antibody. In a further aspect, the variable domains are obtained from a human IgG1 antibody (the "parental antibody"), and the constant domain sequences are obtained from human IgG4 antibody.

As used herein, a "humanized antibody" refers to forms of antibodies that contain sequences from both human and non-human (e.g., murine, rat) antibodies. In general, the humanized antibody will comprise all of at least one, and typically two, variable domains, in which the hypervariable loops correspond to those of a non-human immunoglobulin, and all or substantially all of the framework (FR) regions are those of a human immunoglobulin sequence. The humanized antibody may optionally comprise at least a portion of a human immunoglobulin constant region (Fc).

As used herein, a "fully human antibody" refers to an antibody that comprises human immunoglobulin amino acid sequences or variant sequences thereof comprising mutations introduced recombinantly to provide a fully human antibody with modified function or efficacy compared to the antibody lacking said mutations. A fully human antibody does not comprise non-human immunoglobulin amino acid sequences, e.g., constant domains and variable domains, including CDRs comprise human sequences apart from that generated from the mutations discussed above. A fully human antibody may include amino acid sequences of antibodies or immunoglobulins obtained from a fully human antibody library where diversity in the library is generated in silico (See for example, U.S. Pat. No. 8,877,688 or U.S. Pat. No. 8,691,730). A fully human antibody includes such antibodies produced in a non-human organism, for example, a fully human antibody may contain murine carbohydrate chains if produced in a mouse, in a mouse cell, or in a hybridoma derived from a mouse cell. Similarly, "mouse or murine antibody" refers to an antibody that comprises mouse or murine immunoglobulin sequences only. Alternatively, a fully human antibody may contain rat carbohydrate chains if produced in a rat, in a rat cell, or in a hybridoma derived from a rat cell. Similarly, "rat antibody" refers to an antibody that comprises rat immunoglobulin sequences only.

As used herein, "non-human amino acid sequences" with respect to antibodies or immunoglobulins refers to an amino acid sequence that is characteristic of the amino acid sequence of a non-human mammal. The term does not include amino acid sequences of antibodies or immunoglobulins obtained from a fully human antibody library where diversity in the library is generated in silico (See for example, U.S. Pat. No. 8,877,688 or U.S. Pat. No. 8,691,730).

In general, the basic antibody structural unit comprises a tetramer. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of the heavy chain may define a constant region primarily responsible for effector function. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989).

As used herein, "effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

The variable regions of each light/heavy chain pair form the antibody binding site. Thus, in general, an intact antibody has two binding sites. Except in bifunctional or bispecific antibodies, the two binding sites are, in general, the same.

Typically, the variable domains of both the heavy and light chains comprise three hypervariable regions, also called complementarity determining regions (CDRs), located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of *Sequences of Proteins of Immunological Interest*, Kabat, et al.; National Institutes of Health, Bethesda, Md.; 5th ed.; NIH Publ. No. 91-3242 (1991); Kabat (1978) Adv. Prot. Chem. 32:1-75; Kabat, et al., (1977) J. Biol. Chem. 252: 6609-6616; Chothia, et al., (1987) J Mol. Biol. 196:901-917 or Chothia, et al., (1989) Nature 342:878-883.

As used herein, "hypervariable region" refers to the amino acid residues of an antibody that are responsible for antigen-binding. The hypervariable region comprises amino acid residues from a "complementarity determining region" or "CDR" (i.e. CDRL1, CDRL2 and CDRL3 in the light chain variable domain and CDRH1, CDRH2 and CDRH3 in the heavy chain variable domain). See Kabat et al. (1991) Sequences of Proteins of Immunological Interest, 5th Ed. Public Health Service, National Institutes of Health, Bethesda, Md. (defining the CDR regions of an antibody by sequence); see also Chothia and Lesk (1987) *J. Mol. Biol.* 196: 901-917 (defining the CDR regions of an antibody by structure).

As used herein, "framework" or "FR" residues refers to those variable domain residues other than the hypervariable region residues defined herein as CDR residues.

As used herein, "conservatively modified variants" or "conservative substitution" refers to substitutions of amino acids with other amino acids having similar characteristics (e.g. charge, side-chain size, hydrophobicity/hydrophilicity, backbone conformation and rigidity, etc.), such that the changes can frequently be made without altering the biological activity of the protein. Those of skill in this art recognize that, in general, single amino acid substitutions in non-essential regions of a polypeptide do not substantially alter biological activity (see, e.g., Watson et al. (1987) *Molecular Biology of the Gene*, The Benjamin/Cummings Pub. Co., p. 224 (4th Ed.)). In addition, substitutions of structurally or functionally similar amino acids are less likely to disrupt biological activity. Exemplary conservative substitutions are set forth in the table below.

| Original residue | Conservative substitution |
| --- | --- |
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

As used herein, the term "epitope", as used herein, is defined in the context of a molecular interaction between an "antigen binding molecule", such as an antibody (Ab), and its corresponding "antigen" (Ag). Generally, "epitope" refers to the area or region on an Ag to which an Ab specifically binds, i.e. the area or region in physical contact with the Ab. Physical contact may be defined through distance criteria (e.g. a distance cut-off of 4 Å) for atoms in the Ab and Ag molecules.

The epitope for a given antibody (Ab)/antigen (Ag) pair can be defined and characterized at different levels of detail using a variety of experimental and computational epitope mapping methods. The experimental methods include mutagenesis, X-ray crystallography, Nuclear Magnetic Resonance (NMR) spectroscopy and Hydrogen deuterium exchange Mass Spectrometry (HX-MS), methods that are known in the art. As each method relies on a unique principle, the description of an epitope is intimately linked to the method by which it has been determined. Thus, depending on the epitope mapping method employed, the epitope for a given Ab/Ag pair will be described differently.

The epitope for a given antibody (Ab)/antigen (Ag) pair may be described by routine methods. For example, the overall location of an epitope may be determined by assessing the ability of an antibody to bind to different fragments or variants of the antigen. The specific amino acids within the antigen that make contact with an antibody (epitope) may also be determined using routine methods. For example, the Ab and Ag molecules may be combined and the Ab/Ag complex may be crystallized. The crystal structure of the complex may be determined and used to identify specific sites of interaction between the Ab and Ag.

As used herein, "specifically binds" refers, with respect to an antigen such as FXI, to the preferential association of an antibody or other ligand, in whole or part, with a cell or tissue bearing that antigen and not to cells or tissues lacking that antigen. It is recognized that a certain degree of non-specific interaction may occur between a molecule and a non-target cell or tissue. Nevertheless, specific binding may be distinguished as mediated through specific recognition of the antigen. Although selectively reactive antibodies bind antigen, they may do so with low affinity. On the other hand, specific binding results in a much stronger association between the antibody (or other ligand) and cells bearing the antigen than between the bound antibody (or other ligand) and cells lacking the antigen. Specific binding typically results in greater than 2-fold, such as greater than 5-fold, greater than 10-fold, or greater than 100-fold increase in amount of bound antibody or other ligand (per unit time) to a cell or tissue comprising FXI as compared to a cell or tissue lacking FXI. Specific binding to a protein under such conditions requires an antibody that is selected for its specificity for a particular protein. A variety of immunoassay formats are appropriate for selecting antibodies or other ligands specifically immunoreactive with a particular protein. For example, solid-phase ELISA immunoassays are routinely used to select monoclonal antibodies specifically immunoreactive with a protein. See Harlow & Lane, Antibodies, A Laboratory Manual, Cold Spring Harbor Publications, New York (1988), for a description of immunoassay formats and conditions that can be used to determine specific immunoreactivity.

As used herein, "isolated nucleic acid molecule" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty or more other proteins or portions or fragments thereof, or may include operably linked regulatory sequences that control expression of the coding region of the recited nucleic acid sequences, and/or may include vector sequences.

As used herein, "treat" or "treating" means to administer a therapeutic agent, such as a composition containing any of the antibodies or antigen binding fragments thereof of the present invention, internally or externally to a subject or patient having one or more disease symptoms, or being suspected of having a disease, for which the agent has therapeutic activity or prophylactic activity. Typically, the agent is administered in an amount effective to alleviate one or more disease symptoms in the treated subject or population, whether by inducing the regression of or inhibiting the progression of such symptom(s) by any clinically measurable degree. The amount of a therapeutic agent that is effective to alleviate any particular disease symptom may vary according to factors such as the disease state, age, and weight of the patient, and the ability of the drug to elicit a desired response in the subject. Whether a disease symptom has been alleviated can be assessed by any clinical measurement typically used by physicians or other skilled healthcare providers to assess the severity or progression status of that symptom. The term further includes a postponement of development of the symptoms associated with a disorder and/or a reduction in the severity of the symptoms of such disorder. The terms further include ameliorating existing uncontrolled or unwanted symptoms, preventing additional symptoms, and ameliorating or preventing the underlying causes of such symptoms. Thus, the terms denote that a beneficial result has been conferred on a human or animal subject with a disorder, disease or symptom, or with the potential to develop such a disorder, disease or symptom.

As used herein, "treatment," as it applies to a human or veterinary subject, refers to therapeutic treatment, as well as diagnostic applications. "Treatment" as it applies to a human or veterinary subject, encompasses contact of the antibodies or antigen binding fragments of the present invention to a human or animal subject.

As used herein, "therapeutically effective amount" refers to a quantity of a specific substance sufficient to achieve a desired effect in a subject being treated. For instance, this may be the amount necessary to inhibit activation of FXI or the amount necessary to inhibit coagulation for at least 192 to 288 hours as determined in an aPTT assay. When administered to a subject, a dosage will generally be used that will achieve target tissue concentrations that have been shown to achieve a desired in vitro effect.

As used herein, "thrombosis" refers to the formation or presence of a clot (also called a "thrombus") inside a blood vessel, obstructing the flow of blood through the circulatory system. Thrombosis is usually caused by abnormalities in the composition of the blood, quality of the vessel wall and/or nature of the blood flow. The formation of a clot is often caused by an injury to the vessel wall (such as from trauma or infection) and by the slowing or stagnation of blood flow past the point of injury. In some cases, abnormalities in coagulation cause thrombosis.

As used herein, "without compromising hemostasis" means little or no detectable bleeding is observed in a subject or patient following administration of an antibody or antibody fragment disclosed herein to the subject or patient. In case of targeting Factor XI, inhibiting Factor XI conversion to Factor XIa or activation of Factor IX by Factor XIa inhibits coagulation and associated thrombosis without bleeding. In contrast, inhibiting Factor XI conversion or activity inhibits coagulation but also induces bleeding or increases the risk of bleeding.

BRIEF DESCRIPTION OF THE DRAWINGS

FIG. 1A is a cartoon depicting FXI in the coagulation cascade (that is composed of the intrinsic and extrinsic pathways). An FXI binding antibody such as those disclosed herein may exert functional neutralization via blocking FXI activation by FXIIa and thus reduced subsequent activation of FIX to FIXa. The four NOACs (rivaroxaban, apixaban, edoxaban, dabigatran) targeting either FXa or thrombin are shown. FIG. 1B shows the domain structure of FXI. FXI is a dimer composed of identical 80 kDa subunits, and each subunit starting from the N-terminus consists of the four apple domains (1, 2, 3, and 4) and a catalytic domain (CAT). The antibodies and antigen binding fragments disclosed herein bind the apple 2 domain.

FIG. 7 shows the amino acid sequence for the αFXI-13654p heavy chain (HC) variable domain having the amino acid shown in SEQ ID NO:16 and the light chain (LC) variable domain having the amino acid sequence shown in SEQ ID NO:17. The CDRs for the variable regions and their respective KABAT numbering are shown.

FIG. 8 shows the amino acid sequence of αFXI-13654p-IgG4 (S228P)/kappa comprising a heavy chain having the amino acid sequence show in SEQ ID NO:59 and a light chain having the amino acid sequence shown in SEQ ID NO:19. The variable domains are in italics and the proline residue at S228P in the heavy chain constant domain is shown in bold and underlined.

FIG. 9 shows the amino acid sequence for the αFXI-13716p heavy chain (HC) variable domain having the amino acid shown in SEQ ID NO:20 and the light chain (LC) variable domain having the amino acid sequence shown in SEQ ID NO:21. The CDRs for the variable regions and their respective KABAT numbering are shown.

FIG. 10 shows the amino acid sequence of αFXI-13716p-IgG4 (S228P)/kappa comprising a heavy chain having the amino acid sequence show in SEQ ID NO:60 and a light chain having the amino acid sequence shown in SEQ ID NO:23. The variable domains are in italics and the proline residue at S228P in the heavy chain constant domain is shown in bold and underlined.

FIG. 11 shows the amino acid sequence for the αFXI-13716 heavy chain (HC) variable domain having the amino acid shown in SEQ ID NO:24 and the light chain (LC) variable domain having the amino acid sequence shown in SEQ ID NO:21. The CDRs for the variable regions and their respective KABAT numbering are shown.

FIG. 12 shows the amino acid sequence of αFXI-13716p-IgG4 (S228P) Q1E M103L/kappa comprising a heavy chain having the amino acid sequence show in SEQ ID NO:61 and a light chain having the amino acid sequence shown in SEQ ID NO:23. The variable domains are in italics and the proline residue at S228P in the heavy chain constant domain is shown in bold and underlined.

FIG. 13 shows the amino acid sequence of αFXI-13654p-IgG1/kappa comprising a heavy chain having the amino acid sequence show in SEQ ID NO:62 and a light chain having the amino acid sequence shown in SEQ ID NO:19. The variable domains are in italics.

FIG. 14 shows the amino acid sequence of αFXI-13716p-IgG1/kappa comprising a heavy chain having the amino acid sequence show in SEQ ID NO:63 and a light chain having the amino acid sequence shown in SEQ ID NO:23. The variable domains are in italics.

FIG. 15 shows the amino acid sequence of αFXI-13716-IgG1 Q1E M103L/kappa comprising a heavy chain having the amino acid sequence show in SEQ ID NO:64 and a light chain having the amino acid sequence shown in SEQ ID NO:23. The variable domains are in italics.

FIG. 19A shows the clot weight (mg) measured after 2 consecutive AV shunts in the same animal. The animals were administered vehicle during the first shunt (Shunt #1), followed by the administration of αFXI-13716-IgG4 (S228P) Q1E M103L (K)/kappa (at dosages of 0.01 (–△–), 0.03 (–■–), 0.05 (–▼–), 0.6 (--▲--), 0.8 (–■–), 0.1 (–●–), and 1.0 (--◆--) mg/kg IV) as shown during the second shunt (Shunt #2). FIG. 19B shows the percent inhibition of clot weight. FIG. 19C shows the percent change in aPTT with increasing plasma concentration of αFXI-13716-IgG4 (S228P) Q1E M103L (K–)/kappa. FIG. 19D shows percent change in PT with increasing concentrations of αFXI-13716-IgG4 (S228P) Q1E M103L (K–)/kappa.

DETAILED DESCRIPTION OF THE INVENTION

The present invention provides anti-coagulation Factor XI antibodies and antigen binding fragments that bind the apple 2 domain of coagulation Factor XI (FXI). These anti-FXI antibodies and antigen binding fragments are inhibitors of FXI activation by Factor XIIa and are useful for inhibiting blood coagulation and associated thrombosis without compromising hemostasis (i.e., for anti-thrombotic indications). For example, the anti-FXI antibodies and antigen binding fragments may be used for treatment and/or prevention of thromboembolic disorders or diseases, including but not limited to, myocardial infarction, ischemic stroke, pulmonary thromboembolism, venous thromboembolism (VTE), atrial fibrillation, disseminated intravascular coagulation, medical device-related thromboembolic disorders, severe systemic inflammatory response syndrome, metastatic cancer, and infectious disease. The antibodies and antigen binding fragments are particularly useful for Stroke Prevention in Atrial Fibrillation (SPAF). The antibodies and antigen binding fragments may also be used to treat or prevent thrombosis associated with disease or injury to the veins in the legs; immobility for any reason; fracture; certain medications; obesity; inherited disorders or inherited predisposition; autoimmune disorders that predispose to dotting; medications, such as certain contraceptives, that increase the risk of clotting; and, smoking. Therefore, the anti-FXI antibodies and antigen binding fragments disclosed herein are useful in therapies for treating a thromboembolic disorder or disease in a patient or subject in need of such therapies.

Figure 1A:
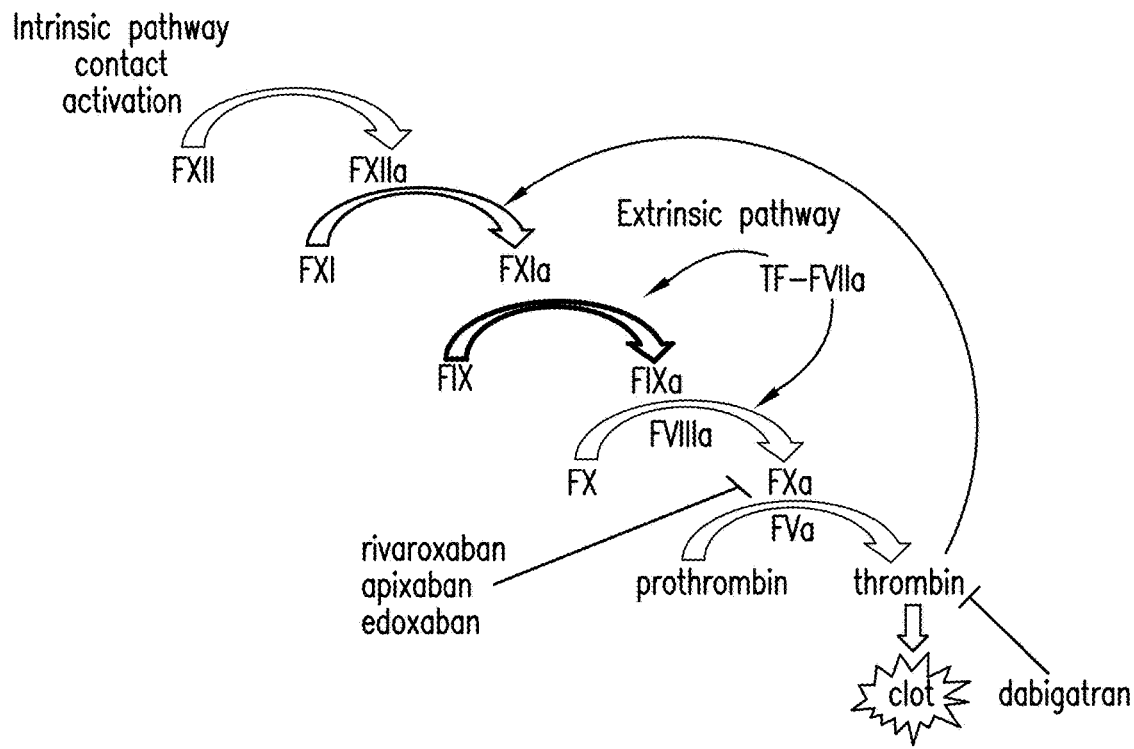
FIG. 1A and FIG. 1B show the coagulation cascade, FXI structure, and the location where four new oral anticoagulants (NOACs) exert their inhibitory effect.
Figure 1B:
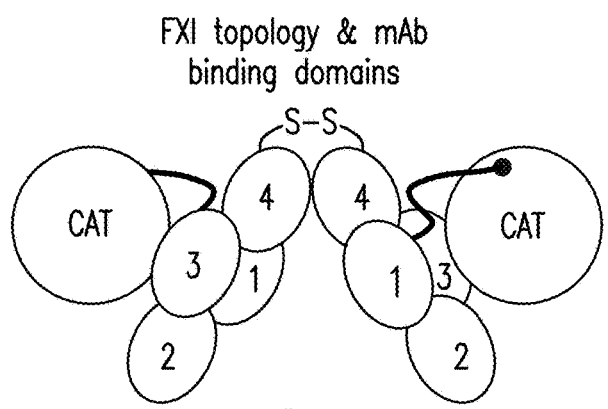

FXI is a homodimeric serine protease having the domain structure shown in FIG. 1B and an integral component of the intrinsic pathway of the coagulation cascade. FXI zymogen can be cleaved by Factor XIIa to its activated form FXIa. FXIa then activates Factor IX and ultimately triggers thrombin generation and clot formation. The anti-FXI antibodies and antigen binding fragments disclosed herein inhibit the conversion of FXI to FXIa (See FIG. 1A).

Anti-FXI antibody molecules were obtained from a fully human synthetic IgG1/kappa library displayed at the surface of engineered yeast strains. The library was screened with FXI or FXIa to identify antibodies capable of binding to human FXI at subnanomolar affinity to human and non-human primate (NHP) FXI and having no binding to human and NHP plasma kallikrein (a protein displaying 56% amino acid identity to FXI), or to other human coagulation cascade proteins (FII//IIa, FVII/VIIa, FIX/IXa, FX/Xa, and FXII/XIIa). Two antibodies were identified that had these properties: αFXI-13654p and αFXI-13716p. These antibodies are fully human antibodies comprising a human kappa (κ) light chain and a human IgG1 (γ1) isotype heavy chain. The antibodies selectively bind to the FXI zymogen an epitope comprising SEQ ID NOs:37 and 38 located in the apple 2 domain of FXI. These antibodies also bind FXIa with comparable affinity to FXI zymogen.

Antibody αFXI-13654p comprises heavy chain (HC) complementarity determining regions (CDRs) 1, 2, and 3 having the amino acid sequences shown in SEQ ID NO:1, SEQ ID NO:2, and SEQ ID NO:3, respectively, and light chain (LC) CDRs 1, 2, and 3 having the amino acid sequences shown in SEQ ID NO:4, SEQ ID NO:5, and SEQ ID NO:6, respectively. αFXI-13654p comprises a heavy chain (HC) variable domain comprising the amino acid sequence shown in SEQ ID NO:16 and a light chain (LC) variable domain comprising the amino acid sequence in SEQ ID NO:17. αFXI-13654p comprises a LC comprising the amino acid sequence shown in SEQ ID NO:19 and a HC comprising the amino acid sequence shown in SEQ ID NO:31.

Antibody αFXI-13716p comprises HC CDRs 1, 2, and 3 having the amino acid sequences shown in SEQ ID NO:7, SEQ ID NO:8, and SEQ ID NO:9, respectively, and LC CDRs 1, 2, and 3 having the amino acid sequences shown in SEQ ID NO:10, SEQ ID NO:11, and SEQ ID NO:12, respectively. αFXI-13716p comprises a heavy chain (HC) variable domain comprising the amino acid sequence shown in SEQ ID NO:20 and a light chain (LC) variable domain comprising the amino acid sequence in SEQ ID NO:21. αFXI-13716p comprises a LC comprising the amino acid sequence shown in SEQ ID NO:23 and a HC comprising the amino acid sequence shown in SEQ ID NO:33.

In particular embodiments, the HC CDR 3 (SEQ ID NO:9) of αFXI-13716p was modified to replace the first methionine (Met) residue within CDR3 with a leucine residue to provide antibody αFXI-13716 (Met at position 103 of SEQ ID NO:20 or position 5 of SEQ ID NO:13). Antibody αFXI-13716 comprises HC CDRs 1, 2, and 3 having the amino acid sequences shown in SEQ ID NO:7, SEQ ID NO:8, and SEQ ID NO:13, respectively, and LC CDRs 1, 2, and 3 having the amino acid sequences shown in SEQ ID NO:10, SEQ ID NO:11, and SEQ ID NO:12, respectively. αFXI-13716 comprises a heavy chain (HC) variable domain comprising the amino acid sequence shown in SEQ ID NO:24 and a light chain (LC) variable domain comprising the amino acid sequence in SEQ ID NO:21. αFXI-13716 comprises a LC comprising the amino acid sequence shown in SEQ ID NO:23 and a HC comprising the amino acid sequence shown in SEQ ID NO:35. Substitution of the Met at position 5 of SEQ ID NO:9 with Val, Ile, Asn, Asp, or Glu reduced efficacy of the antibody in an aPTT assay.

The present invention provides anti-FXI antibodies and antigen binding fragments having a variable region comprising at least the six CDRs of anti-FXI antibody αFXI-13654p, αFXI-13716p, or αFXI-13716 or embodiments wherein one or more of the six CDRs has one, two, or three amino acid substitutions, additions, deletions, or combinations thereof wherein the antibody or antigen binding fragment binds the apple 2 domain of coagulation factor XI (FXI) and methods of using the antibody for treating anti-thrombotic indications, e.g., thromboembolic disorders or diseases such as myocardial infarction, ischemic stroke, pulmonary thromboembolism, venous thromboembolism (VTE), atrial fibrillation, disseminated intravascular coagulation, medical device-related thromboembolic disorders, severe systemic inflammatory response syndrome, metastatic cancer, or an infectious disease, or for example Stroke Prevention in Atrial Fibrillation (SPAF).

The present invention provides anti-FXI antibodies and antigen binding fragments having a variable region comprising at least the three HC-CDRs of anti-FXI antibody αFXI-13654p, αFXI-13716p, or αFXI-13716 or embodiments wherein one or more of the three HC-CDRs has one, two, or three amino acid substitutions, additions, deletions, or combinations thereof wherein the antibody or antigen binding fragment binds the apple 2 domain of coagulation factor XI (FXI) and methods of using the antibody for treating anti-thrombotic indications, e.g., thromboembolic disorders or diseases such as myocardial infarction, ischemic stroke, pulmonary thromboembolism, venous thromboembolism (VTE), atrial fibrillation, disseminated intravascular coagulation, medical device-related thromboembolic disorders, severe systemic inflammatory response syndrome, metastatic cancer, or an infectious disease, or for example Stroke Prevention in Atrial Fibrillation (SPAF).

In particular aspects, the anti-FXI antibodies or antigen binding fragment comprise at least the HC variable domain of anti-FXI antibody αFXI-13654p, αFXI-13716p, or αFXI-13716 or a variant of the HC variable domain comprising 1, 2, 3, 4, 5, 6, 7, 8, 9, or 10 amino acid substitutions, additions, deletions, or combinations thereof relative to the amino acid sequence of the HC of αFXI-13716p, or αFXI-13716.

In particular aspects, the anti-FXI antibodies or antigen binding fragment comprise comprise at least the LC variable domain of anti-FXI antibody αFXI-13654p, αFXI-13716p, or αFXI-13716 or a variant of the LC variable domain comprising 1, 2, 3, 4, 5, 6, 7, 8, 9, or 10 amino acid substitutions, additions, deletions, or combinations thereof relative to the amino acid sequence of the LC of αFXI-13654p, αFXI-13716p, or αFXI-13716.

In particular aspects, the anti-FXI antibodies or antigen binding fragment comprise comprise at least the HC variable domain of anti-FXI antibody αFXI-13654p, αFXI-13716p, or αFXI-13716 or a variant of the HC variable domain comprising 1, 2, 3, 4, 5, 6, 7, 8, 9, or 10 amino acid substitutions, additions, deletions, or combinations thereof relative to the amino acid sequence of the HC of αFXI-13654p, αFXI-13716p, or αFXI-13716 and the LC variable domain of anti-FXI antibody αFXI-13654p, αFXI-13716p, or αFXI-13716 or a variant of the LC variable domain comprising 1, 2, 3, 4, 5, 6, 7, 8, 9, or 10 amino acid substitutions, additions, deletions, or combinations thereof relative to the amino acid sequence of the LC of αFXI-13654p, αFXI-13716p, or αFXI-13716.

In particular embodiments, the antibodies or antigen binding fragment comprise herein comprise at least the six CDRs of antibody αFXI-13654p, αFXI-13716p, or αFXI-13716 or ealternatively the six CDRs wherein one or more of the six CDRs has one, two, or three amino acid substitutions, additions, deletions, or combinations thereof and further comprise a heavy chain (HC) that is of the human IgG1, IgG2, IgG3, or IgG4 isotype and the light chain (LC) may be of the kappa type or lambda type. In other embodiments, the antibodies comprise at least the six CDRs of antibody αFXI-13654p, αFXI-13716p, or αFXI-13716 or alternatively the six CDRs wherein one or more of the six CDRs has one, two, or three amino acid substitutions, additions, deletions, or combinations thereof and further may be of the IgM, IgD, IgA, or IgE class. In particular embodiments, the human IgG1, IgG2, IgG3, or IgG4 isotype may include 1 2, 3, 4, 5, 6, 7, 8, 9, or 10 amino acid substitutions, additions, deletions, or combinations thereof.

In particular embodiments, the antibodies or antigen binding fragment comprise may comprise at least the six CDRs of antibody αFXI-13654p, αFXI-13716p, or αFXI-13716 or alternatively the six CDRs wherein one or more of the six CDRs has one, two, or three amino acid substitutions, additions, deletions, or combinations thereof and further comprise an HC constant domain that is of the IgG4 isotype. An IgG4 framework provides an antibody with little or no effector function. In a further aspect of the invention, the antibodies may comprise at least the six CDRs of antibody αFXI-13654p, αFXI-13716p, or αFXI-13716 or alternatively the six CDRs wherein one or more of the six CDRs has one, two, or three amino acid substitutions, additions, deletions, or combinations thereof and further comprise HC constant domain that is of the IgG4 isotype fused to an HC variable domain that is of the IgG1 isotype. In a further aspect of the invention, the antibodies may comprise at least the HC variable domain and LC variable domain of antibody αFXI-13654p, αFXI-13716p, or αFXI-13716 or variants thereof in which the HC and/or LC variable domains independently comprise 1, 2, 3, 4, 5, 6, 7, 8, 9, or 10 amino acid substitutions, additions, deletions, or combinations thereof and further comprise an HC constant domain that is of the IgG4 isotype. In a further aspect of the invention, the antibodies may comprise at least the HC variable domain and LC of antibody αFXI-13654p, αFXI-13716p, or αFXI-13716 or variants thereof in which the HC and/or LC independently comprise 1, 2, 3, 4, 5, 6, 7, 8, 9, or 10 amino acid substitutions, additions, deletions, or combinations thereof and further comprise an HC constant domain that is of the IgG4 isotype.

The antibodies of the present invention further includes, but are not limited to, monoclonal antibodies (including full length monoclonal antibodies), polyclonal antibodies, multispecific antibodies (e.g., bispecific antibodies), biparatopic antibodies, fully human antibodies, and chimeric antibodies.

In general, the amino acid sequence of the heavy chain of an antibody such as IgG1 or IgG4 has a lysine at the C-terminus of the heavy chain constant domain. In some instances, to improve the homogeneity of an antibody product, the antibody may be produced lacking a C-terminal lysine. The anti-FXI antibodies of the present invention include embodiments in which the C-terminal lysine is present and embodiments in which the C-terminal lysine is absent. For example, an IgG1 HC constant domain may have amino acid sequence shown in SEQ ID NO:40 and an IgG4 HC constant domain may have the amino acid sequence shown in SEQ ID NO:14, wherein in each case wherein X is lysine or absent.

In particular embodiments, the N-terminal amino acid of the HC may be a glutamine residue. In particular embodiments, the N-terminal amino acid of the HC may be a glutamic acid residue. In particular aspects, the N-terminal amino acid is modified to be a glutamic acid residue.

The present invention further provides anti-FXI antigen-binding fragments that comprise at least the six CDRs of anti-FXI antibody αFXI-13654p, αFXI-13716p, or αFXI-13716 or alternatively the six CDRs wherein one or more of the six CDRs has one, two, or three amino acid substitutions, additions, deletions, or combinations thereof.

The present invention further provides anti-FXI Fab fragments that comprise at least the six CDRs of anti-FXI antibody αFXI-13654p, αFXI-13716p, or αFXI-13716 or alternatively the six CDRs wherein one or more of the six CDRs has one, two, or three amino acid substitutions, additions, deletions, or combinations thereof.

The present invention further provides anti-FXI antibodies that comprise at least the six CDRs of antibody αFXI-13654p, αFXI-13716p, or αFXI-13716 or alternatively the six CDRs wherein one or more of the six CDRs has one, two, or three amino acid substitutions, additions, deletions, or combinations thereof and antigen-binding fragments thereof which comprise an Fc region and methods of use thereof.

The present invention further provides anti-FXI Fab' fragments that comprise at least the six CDRs of anti-FXI antibody αFXI-13654p, αFXI-13716p, or αFXI-13716 or alternatively the six CDRs wherein one or more of the six CDRs has one, two, or three amino acid substitutions, additions, deletions, or combinations thereof.

The present invention further provides anti-FXI F(ab')$_2$ that comprise at least the six CDRs of anti-FXI antibody αFXI-13654p, αFXI-13716p, or αFXI-13716 or alternatively the six CDRs wherein one or more of the six CDRs has one, two, or three amino acid substitutions, additions, deletions, or combinations thereof.

The present invention further provides anti-FXI FV fragments that comprise at least the six CDRs of anti-FXI antibody αFXI-13654p, αFXI-13716p, or αFXI-13716 or alternatively the six CDRs wherein one or more of the six CDRs has one, two, or three amino acid substitutions, additions, deletions, or combinations thereof.

The present invention further provides anti-FXI scFv fragments that comprise at least the six CDRs of anti-FXI antibody αFXI-13654p, αFXI-13716p, or αFXI-13716 or alternatively the six CDRs wherein one or more of the six CDRs has one, two, or three amino acid substitutions, additions, deletions, or combinations thereof.

The present invention further provides anti-FXI domain antibodies that comprise at least the three HC CDRs or three LC CDRs of antibody αFXI-13654p, αFXI-13716p, or αFXI-13716 or alternatively the six CDRs wherein one or more of the HC or LC CDRs has one, two, or three amino acid substitutions, additions, deletions, or combinations thereof.

The present invention further provides anti-FXI bivalent antibodies that comprise at least the six CDRs of antibody αFXI-13654p, αFXI-13716p, or αFXI-13716 or alternatively the six CDRs wherein one or more of the six CDRs has one, two, or three amino acid substitutions, additions, deletions, or combinations thereof.

The present invention further provides bispecific antibodies and antigen-binding fragments having a binding specificity for FXI and another antigen of interest and methods of use thereof.

The present invention further provides biparatopic antibodies having first heavy/light chain pair of a first antibody that comprises at least the six CDRs of antibody αFXI-13654p, αFXI-13716p, or αFXI-13716 or alternatively the six CDRs wherein one or more of the CDRs has one, two, or three amino acid substitutions, additions, deletions, or combinations thereof and a second heavy/light chain pair of a second antibody having specificity for an FXI epitope which is different from the epitope recognized by the first heavy/light chain pair.

The present invention further provides anti-FXI antibodies and antigen-binding fragments thereof comprising a first heavy/light chain pair of an antibody that comprises at least the six CDRs of antibody αFXI-13654p or alternatively the six CDRs wherein one or more of the CDRs has one, two, or three amino acid substitutions, additions, deletions, or combinations thereof and a second heavy/light chain pair of an antibody that comprises at least the six CDRs of antibody αFXI-13716p or αFXI-13716 or alternatively the six CDRs wherein one or more of the CDRs has one, two, or three amino acid substitutions, additions, deletions, or combinations thereof.

The present invention further provides anti-FXI diabodies that comprise at least the six CDRs of antibody αFXI-13654p, αFXI-13716p, or αFXI-13716 or alternatively the six CDRs wherein one or more of the six CDRs has one, two, or three amino acid substitutions, additions, deletions, or combinations thereof.

An antibody that comprises at least the six CDRs of antibody αFXI-13654p, αFXI-13716p, or αFXI-13716 or alternatively the six CDRs wherein one or more of the CDRs has one, two, or three amino acid substitutions, additions, deletions, or combinations thereof may be modified in some way such that it retains at least 10% of its FXI binding activity (when compared to the parental antibody) when that activity is expressed on a molar basis. Preferably, an antibody or antigen-binding fragment of the invention retains at least 20%, 50%, 70%, 80%, 90%, 95%, or 100% or more of the FXI binding affinity as the parental antibody. It is also intended that an antibody or antigen-binding fragment of the invention can include conservative or non-conservative amino acid substitutions (referred to as "conservative variants" or "function conserved variants" of the antibody) that do not substantially alter its biologic activity.

The present invention further provides isolated anti-FXI antibodies that comprise at least the six CDRs of antibody αFXI-13654p, αFXI-13716p, or αFXI-13716 or alternatively the six CDRs wherein one or more of the six CDRs has one, two, or three amino acid substitutions, additions, deletions, or combinations thereof and antigen-binding fragments thereof and methods of use thereof as well as isolated polypeptide immunoglobulin chains thereof and isolated polynucleotides encoding such antibodies, antigen binding fragments and isolated polypeptide immunoglobulin chains and isolated vectors including such polynucleotides.

The present invention further provides monoclonal anti-FXI antibodies that comprise at least the six CDRs of antibody αFXI-13654p, αFXI-13716p, or αFXI-13716 or alternatively the six CDRs wherein one or more of the six CDRs has one, two, or three amino acid substitutions, additions, deletions, or combinations thereof and antigen-binding fragments thereof as well as monoclonal compositions comprising a plurality of isolated monoclonal antibodies.

The present invention further provides anti-FXI chimeric antibodies that comprise at least the six CDRs of antibody αFXI-13654p, αFXI-13716p, or αFXI-13716 or alternatively the six CDRs wherein one or more of the six CDRs has one, two, or three amino acid substitutions, additions, deletions, or combinations thereof and methods of use thereof.

The present invention includes anti-FXI fully human antibodies that comprise at least the six CDRs of antibody αFXI-13654p, αFXI-13716p, or αFXI-13716 or alternatively the six CDRs wherein one or more of the six CDRs has one, two, or three amino acid substitutions, additions, deletions, or combinations thereof and antigen-binding fragments thereof and methods of use thereof.

In an embodiment of the invention, a fully human anti-FXI antibody or antigen-binding fragment thereof is the product of isolation from a transgenic animal, e.g., a mouse (e.g., a HUMAB mouse, see e.g., U.S. Pat. Nos. 5,545,806; 5,569,825; 5,625,126; 5,633,425; 5,661,016; 5,770,429; 5,789,650; 5,814,318; 5,874,299 and 5,877,397; and Harding, et al., (1995) Ann. NY Acad. Sci. 764:536 546; or a XENOMOUSE, see e.g., Green et al., 1999, J. Immunol. Methods 231:11-23), which has been genetically modified to have fully human immunoglobulin genes; or the product of isolation from a phage or virus which expresses the immunoglobulin chains of the anti-FXI fully human antibody or antigen-binding fragment thereof.

In some embodiments, different constant domains may be appended to $V_L$ and $V_H$ regions derived from the CDRs provided herein. For example, if a particular intended use of an antibody (or fragment) of the present invention were to call for altered effector functions, a heavy chain constant domain other than human IgG1 may be used, or a hybrid IgG1/IgG4 that has altered effector function may be utilized.

Although human IgG1 antibodies provide for long half-life and for effector functions, such as complement activation and antibody-dependent cellular cytotoxicity, such activities may not be desirable for all uses of the antibody. In such instances a human IgG4 constant domain, for example, may be used. The present invention includes anti-FXI antibodies which comprise an IgG4 constant domain and variants thereof wherein the constant domain comprises 1, 2, 3, 4, 5, 6, 7, 8, 9, or 10 amino acid substitutions, additions, deletions, insertions, and combinations thereof.

In one embodiment, the IgG4 constant domain can differ from the native human IgG4 constant domain (Swiss-Prot Accession No. P01861.1) at a position corresponding to position 228 in the EU system and position 241 in the KABAT system, wherein the native serine at position 108 (Ser108) of the HC constant domain as shown in SEQ ID NO:14, for example, is replaced with proline (Pro), in order to prevent a potential inter-chain disulfide bond between the cysteine at position 106 (Cys106) and the cysteine at position 109 (Cys109), which correspond to positions Cys226 and Cys229 in the EU system and positions Cys239 and Cys242 in the KABAT system) that could interfere with proper intra-chain disulfide bond formation. See Angal et al. Mol. Imunol. 30:105 (1993); see also (Schuurman et. al., Mol. Immunol. 38: 1-8, (2001); SEQ ID NOs:14 and 41).

In other instances, a modified IgG1 constant domain which has been modified to reduce effector function may be used, for example, the IgG1 isotype may include substitutions of IgG2 residues at positions 233-236 and IgG4 residues at positions 327, 330 and 331 to greatly reduce ADCC and CDC (as disclosed in Armour et al., Eur J Immunol. 29(8):2613-24 (1999); Shields et al., J Biol Chem. 276(9):6591-604 (2001)). In particular embodiments, the constant domain comprises 1, 2, 3, 4, 5, 6, 7, 8, 9, or 10 amino acid substitutions, additions, deletions, insertions, and combinations thereof.

In another embodiment, the IgG HC is modified genetically to lack N-glycosylation of the asparagine (Asn) residue at around position 297. The consensus sequence for N-glycosylation is Asn-Xaa-Ser/Thr (wherein Xaa is any amino acid except Pro); in IgG1 the N-glycosylation consensus sequence is Asn-Ser-Thr. The modification may be achieved by replacing the codon for the Asn at position 297 in the nucleic acid molecule encoding the HC with a codon for another amino acid, for example Gln. Alternatively, the codon for Ser may be replaced with the codon for Pro or the codon for Thr may be replaced with any codon except the codon for Ser. Such modified IgG1 molecules have little or no detectable effector function. Alternatively, all three codons are modified.

In an embodiment of the invention, the anti-FXI antibodies comprising at least the six CDRs of antibody αFXI-13654p, αFXI-13716p, or αFXI-13716 or alternatively the six CDRs wherein one or more of the six CDRs has one, two, or three amino acid substitutions, additions, deletions, or combinations thereof comprise a full tetrameric structure having two light chains and two heavy chains, including constant regions. The variable regions of each light/heavy chain pair form the antibody binding site. Thus, in general, an intact antibody has two binding sites. Except in bispecific antibodies, the two binding sites are, in general, the same.

In specific embodiments, the present invention provides the following anti-FXI antibodies:

αFXI-13654p (K−)/kappa comprising the IgG1 HC lacking a C-terminal K (K− less) and having the amino acid sequence shown in SEQ ID NO:31 and a kappa LC having amino acid sequence shown in SEQ ID NO:19.

αFXI-13654p(K+)/kappa comprising the IgG1 HC having a C-terminal K and having the amino acid sequence shown in SEQ ID NO:32 and a kappa LC having amino acid sequence shown in SEQ ID NO:19.

αFXI-13654p-IgG4 (S228P) (K−)/kappa comprising the IgG4 HC having mutation S228P and lacking a C-terminal K (K−less) and having the amino acid sequence shown in SEQ ID NO:18 and a kappa LC having the amino acid sequence shown in SEQ ID NO:19.

αFXI-13654p-IgG4 (S228P) (K−+)/kappa comprising the IgG4 HC having mutation S228P and lacking a C-terminal K (C-terminal K) and having the amino acid sequence shown in SEQ ID NO:26 and a kappa LC having the amino acid sequence shown in SEQ ID NO:19.

αFXI-13716p(K−)/kappa comprising the IgG1 HC lacking a C-terminal K (K−less) and having the amino acid sequence shown in SEQ ID NO:33 and a kappa LC having amino acid sequence shown in SEQ ID NO:23.

αFXI-13716p(K+)/kappa comprising the IgG1 HC having a C-terminal K and having the amino acid sequence shown in SEQ ID NO:34 and a kappa LC having amino acid sequence shown in SEQ ID NO:23.

αFXI-13716p-IgG4 (S228P) (K−)/kappa comprising the IgG4 HC having mutation S228P and lacking a C-terminal K (K−less) and having the amino acid sequence shown in SEQ ID NO:22 and a kappa LC having the amino acid sequence shown in SEQ ID NO:23.

αFXI-13716p-IgG4 (S228P) (K+)/kappa comprising the IgG4 HC having mutation S228P and having a C-terminal K and having the amino acid sequence shown in SEQ ID NO:27 and a kappa LC having the amino acid sequence shown in SEQ ID NO:23.

αFXI-13716 M103L(K−)/kappa comprising the IgG1 HC having mutation M103L and lacking a C-terminal K (K−less) and having the amino acid sequence shown in SEQ ID NO:35 and a kappa LC having amino acid sequence shown in SEQ ID NO:23.

αFXI-13716 M103L(K+)/kappa comprising the IgG1 HC having mutation M103L and C-terminal K and having the amino acid sequence shown in SEQ ID NO:36 and a kappa LC having amino acid sequence shown in SEQ ID NO:23.

αFXI-13716 Q1E M103L(K−)/kappa comprising the IgG1 HC having mutation M103L and lacking a C-terminal K (K−less) and having the amino acid sequence shown in SEQ ID NO:54 and a kappa LC having amino acid sequence shown in SEQ ID NO:23.

αFXI-13716 Q1E M103L(K+)/kappa comprising the IgG1 HC having mutation M103L and having a C-terminal K and having the amino acid sequence shown in SEQ ID NO:55 and a kappa LC having amino acid sequence shown in SEQ ID NO:23.

αFXI-13716 Q1E(K−)/kappa comprising the IgG1 HC having mutation Q1E and lacking a C-terminal K (K−less) and having the amino acid sequence shown in SEQ ID NO:65 and a kappa LC having amino acid sequence shown in SEQ ID NO:23.

αFXI-13716 Q1E(K+)/kappa comprising the IgG1 HC having mutation Q1E and a C-terminal K (and having the amino acid sequence shown in SEQ ID NO:66 and a kappa LC having the amino acid sequence shown in SEQ ID NO:23.

αFXI-13716-IgG4 (S228P) Q1E M103L(K−)/kappa comprising the IgG4 HC having mutation S228P Q1E M103L and lacking a C-terminal K (K−less) and having the amino acid sequence shown in SEQ ID NO:25 and a kappa LC having the amino acid sequence shown in SEQ ID NO:23.

αFXI-13716-IgG4 (S228P) Q1E M103L(K+)/kappa comprising the IgG4 HC having mutation S228P Q1E M103L and a C-terminal K and having the amino acid sequence shown in SEQ ID NO:28 and a kappa LC having the amino acid sequence shown in SEQ ID NO:23.

αFXI-13716-IgG4 (S228P) Q1E(K−)/kappa comprising the IgG4 HC having mutation S228P Q1E M103L and lacking a C-terminal K (K−less) and having the amino acid sequence shown in SEQ ID NO:67 and a kappa LC having the amino acid sequence shown in SEQ ID NO:23.

αFXI-13716-IgG4 (S228P) Q1E (K+)/kappa comprising the IgG4 HC having mutation S228P Q1E M103L and C-terminal K and having the amino acid sequence shown in SEQ ID NO:68 and a kappa LC having the amino acid sequence shown in SEQ ID NO:23.

αFXI-13716-IgG4 (S228P) M103L(K−)/kappa comprising the IgG4 HC having mutation S228P Q1E M103L and lacking a C-terminal K (K−less) and having the amino acid sequence shown in SEQ ID NO:69 and a kappa LC having the amino acid sequence shown in SEQ ID NO:23.

αFXI-13716-IgG4 (S228P) M103L(K+)/kappa comprising the IgG4 HC having mutation S228P Q1E M103L and a C-terminal K and having the amino acid sequence shown in SEQ ID NO:70 and a kappa LC having the amino acid sequence shown in SEQ ID NO:23.

FIX is the endogenous protein substrate of FXIa, the active protease of FXI zymogen. FXIa activates FIX to FIXa thereby perpetuating the coagulation cascade. Assays conducted similar to the protocol described in Example 5 showed the αFXI-13716p-IgG4 (S228P) (K−)/kappa, αFXI-13716-IgG4 (S228P) Q1E M103L(K−)/kappa, and αFXI-13654p-IgG4 (S228P) (K−)/kappa antibodies bind to FXI and inhibited FXIIa-mediated activation of FXI in the presence of HMW Kininogen while in the absence of HMW Kininogen, the anti-FXI antibodies did not inhibit FXIIa-mediated activation of FXI to FXIa. FXIa enzymatic assays using FIX full-length or FIX-sequence specific peptide substrates performed in assays similar to those described in Example 6 showed that the αFXI-13716p-IgG4 (S228P) (K−)/kappa, αFXI-13716-IgG4 (S228P) Q1E M103L(K−)/kappa, and αFXI-13654p-IgG4 (S228P) (K−)/kappa antibodies had no detectable inhibitory effect on FIX activation by FXIa. The results suggest that the anti-FXI antibodies functionally neutralize the downstream effects of FXI by preventing FXI activation by FXIIa and have no impact on FXIa catalytic activity.

Epitope mapping by hydrogen-deuterium exchange mass spectrometry (HDX-MS) as described in Example 4 using αFXI-13716-IgG4 (S228P) Q1E M103L(K−)/kappa antibody showed that the anti-FXI antibodies comprising the aforementioned HC and LC CDRs bind to a particular epitope on the apple 2 domain comprising SEQ ID NO:38 and SEQ ID NO:39.

Thus, the antibodies and antigen binding fragments disclosed herein bind to the apple 2 domain of FXI and inhibit FXI activation by FXIIa but not FXIa catalytic activity; these antibodies may leave the hemostatic activation of FXI by thrombin intact, thus conferring minimal bleeding risk. These antibodies are also distinguishable from FXIa activity blockers for which target protein (FXIa) does not exist unless the coagulation cascade is turned on.

Pharmaceutical Compositions and Administration

To prepare pharmaceutical or sterile compositions of the anti-FXI antibodies or antigen binding fragment thereof, the antibody or antigen binding fragments thereof is admixed with a pharmaceutically acceptable carrier or excipient. See, e.g., *Remington's Pharmaceutical Sciences* and *U.S. Pharmacopeia: National Formulary*, Mack Publishing Company, Easton, Pa. (1984).

Formulations of therapeutic and diagnostic agents may be prepared by mixing with acceptable carriers, excipients, or stabilizers in the form of, e.g., lyophilized powders, slurries, aqueous solutions or suspensions (see, e.g., Hardman, et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY;

Weiner and Kotkoskie (2000) *Excipient Toxicity and Safety*, Marcel Dekker, Inc., New York, N.Y.). In one embodiment, anti-FXI antibodies or antigen binding fragments thereof of the present invention are diluted to an appropriate concentration in a sodium acetate solution pH 5-6, and NaCl or sucrose is added for tonicity. Additional agents, such as polysorbate 20 or polysorbate 80, may be added to enhance stability.

Toxicity and therapeutic efficacy of the antibody or antigen binding fragments compositions, administered alone or in combination with another agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index ($LD_{50}/ED_{50}$). In particular aspects, antibodies exhibiting high therapeutic indices are desirable. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration.

In a further embodiment, a composition comprising an antibody or antigen binding fragments disclosed herein is administered to a subject in accordance with the Physicians' Desk Reference 2003 (Thomson Healthcare; 57th edition (Nov. 1, 2002)).

The mode of administration can vary. Suitable routes of administration is preferably parenteral or subcutaneous, Other routes of administration may include oral, transmucosal, intradermal, direct intraventricular, intravenous, intranasal, inhalation, insufflation, or intra-arterial.

In particular embodiments, the anti-FXI antibody or antigen binding fragment thereof can be administered by an invasive route such as by injection (see above). In further embodiments of the invention, an anti-FXI antibody or antigen binding fragment thereof, or pharmaceutical composition thereof, may be administered intravenously, subcutaneously, intraarterially, or by inhalation, aerosol delivery. Administration by non-invasive routes (e.g., orally; for example, in a pill, capsule or tablet) is also within the scope of the present invention.

Compositions can be administered with medical devices known in the art. For example, a pharmaceutical composition of the invention can be administered by injection with a hypodermic needle, including, e.g., a prefilled syringe or autoinjector.

The pharmaceutical compositions disclosed herein may also be administered with a needleless hypodermic injection device; such as the devices disclosed in U.S. Pat. Nos. 6,620,135; 6,096,002; 5,399,163; 5,383,851; 5,312,335; 5,064,413; 4,941,880; 4,790,824 or 4,596,556.

The pharmaceutical compositions disclosed herein may also be administered by infusion. Examples of well-known implants and modules form administering pharmaceutical compositions include: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art.

The administration regimen depends on several factors, including the serum or tissue turnover rate of the therapeutic antibody, the level of symptoms, the immunogenicity of the therapeutic antibody, and the accessibility of the target cells in the biological matrix. Preferably, the administration regimen delivers sufficient therapeutic antibody to effect improvement in the target disease state, while simultaneously minimizing undesired side effects. Accordingly, the amount of biologic delivered depends in part on the particular therapeutic antibody and the severity of the condition being treated. Guidance in selecting appropriate doses of therapeutic antibodies is available (see, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert, et al. (2003) *New Engl. J. Med.* 348:601-608; Milgrom et al. (1999) *New Engl. J. Med.* 341:1966-1973; Slamon et al. (2001) *New Engl. J. Med* 344:783-792; Beniaminovitz et al. (2000) *New Engl. J. Med.* 342:613-619; Ghosh et al. (2003) *New Engl. J. Med.* 348:24-32; Lipsky et al. (2000) *New Engl. J. Med.* 343:1594-1602).

Determination of the appropriate dose is made by the clinician, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. In general, it is desirable that antibody or antigen binding fragment that will be used is derived from the same species as the animal targeted for treatment, thereby minimizing any immune response to the reagent. In the case of human subjects, for example, chimeric, humanized, and fully human antibodies may be desirable.

Anti-FXI antibodies or antigen binding fragments thereof disclosed herein may be provided by doses administered weekly. Doses may be provided subcutaneously. A total weekly dose is generally about 0.3 mg antibody or antigen binding fragment/kg of the subject to 3.0 mg/kg, more preferably about 1.0 to 2.0 mg/kg or between 1.0 mg/kg and 3.0 mg/kg (see, e.g., Yang, et al. (2003) *New Engl. J. Med.* 349:427-434; Herold, et al. (2002) *New Engl. J. Med.* 346:1692-1698; Liu, et al. (1999) *J. Neurol. Neurosurg. Psych.* 67:451-456; Portielji, et al. (20003) *Cancer Immunol. Immunother.* 52:133-144).

Kits

Further provided are kits comprising one or more components that include, but are not limited to, an anti-FXI antibody or antigen binding fragment, as discussed herein in association with one or more additional components including, but not limited to, a further therapeutic agent, as discussed herein. The antibody or fragment and/or the therapeutic agent can be formulated as a pure composition or in combination with a pharmaceutically acceptable carrier, in a pharmaceutical composition.

In one embodiment, the kit includes an anti-FXI antibody or antigen binding fragment thereof or a pharmaceutical composition thereof in one container (e.g., in a sterile glass or plastic vial) and a further therapeutic agent in another container (e.g., in a sterile glass or plastic vial).

In another embodiment, the kit comprises a combination of the invention, including an anti-FXI antibody or antigen binding fragment thereof or pharmaceutical composition thereof in combination with one or more therapeutic agents formulated together, optionally, in a pharmaceutical composition, in a single, common container.

If the kit includes a pharmaceutical composition for parenteral administration to a subject, the kit can include a device for performing such administration. For example, the kit can include one or more hypodermic needles or other injection devices as discussed above. Thus, the present invention includes a kit comprising an injection device and the anti-FXI antibody or antigen-binding fragment thereof, e.g., wherein the injection device includes the antibody or fragment or wherein the antibody or fragment is in a separate vessel.

The kit can include a package insert including information concerning the pharmaceutical compositions and dosage forms in the kit. Generally, such information aids patients and physicians in using the enclosed pharmaceutical compositions and dosage forms effectively and safely. For example, the following information regarding a combination of the invention may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references, manufacturer/distributor information and patent information.

Methods of Making Antibodies and Antigen Binding Fragments Thereof

The anti-FXI antibodies and antigen binding fragments thereof disclosed herein may also be produced recombinantly. In this embodiment, nucleic acids encoding the antibody and antigen binding fragments molecules may be inserted into a vector and expressed in a recombinant host cell. There are several methods by which to produce recombinant antibodies and antigen binding fragments which are known in the art.

Mammalian cell lines available as hosts for expression of the antibodies or antigen binding fragments disclosed herein are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, human embryo kidney 293 (HEK-293) cells and a number of other cell lines. Cell lines of particular preference are selected through determining which cell lines have high expression levels. Other cell lines that may be used are insect cell lines, such as Sf9 cells, amphibian cells, bacterial cells, plant cells, filamentous fungus cells (e.g. *Trichoderma reesei*), and yeast cells (e.g., *Saccharomyces cerevisiae* or *Pichia pastoris*).

When recombinant expression vectors comprising a nucleic acid molecule encoding the heavy chain or antigen binding portion or fragment thereof, the light chain and/or antigen binding fragment thereof are introduced into host cells, the antibodies are produced by culturing the host cells under conditions and for a period of time sufficient to allow for expression of the antibody or antigen binding fragments in the host cells or, more preferably, secretion of the antibody into the culture medium in which the host cells are grown. The antibodies or antigen binding fragments may be recovered from the culture medium and further purified or processed to produce the antibodies of the invention.

In particular aspects the host cells are transfected with an expression vector comprising a nucleic acid molecule in which the HC and LCs are expressed as a fusion protein in which the N-terminus of the HC and the LC are fused to a leader sequence to facilitate the transport of the antibody through the secretory pathway. Examples of leader sequences that may be used include MSVPTQVLGLLLLWLTDARC (SEQ ID NO:56), MEWSWVFLFFLSVTTGVHS (SEQ ID NO:57), or MELGLCWVFLVAILEGVQC (SEQ ID NO:58).

The HC of exemplary antibodies αFXI-13654p-IgG4 (S228P) (K−)/kappa, 13716p-IgG4 (S228P)/kappa, αFXI-13716-IgG4 (S228P) Q1E M103L(K−)/kappa may be encoded by nucleic acid molecules having the nucleotide sequence shown in SEQ ID NOs:42, 47, or 52, respectively.

The LC of exemplary antibodies αFXI-13654p-IgG4 (S228P) (K−)/kappa, 13716p-IgG4 (S228P) (K−)/kappa, αFXI-13716-IgG4 (S228P) Q1E M103L(K−)/kappa may be encoded by nucleic acid molecules having the nucleotide sequence shown in SEQ ID NO:44 or 49, respectively.

The present invention further provides a plasmid or viral vector comprising a nucleic acid molecule having the nucleotide sequence of SEQ ID NOs:42, 47, or 52. In a further embodiment, the present invention provides a plasmid or viral vector comprising a first nucleic acid molecule having the nucleotide sequence of SEQ ID NOs:42 and a second nucleic acid molecule having the nucleotide sequence of SEQ ID NO:44. In a further embodiment, the present invention provides a plasmid or viral vector comprising a first nucleic acid molecule having the nucleotide sequence of SEQ ID NOs:47 or 52 and a second nucleic acid molecule having the nucleotide sequence of SEQ ID NO:49.

The present invention further provides a plasmid or viral vector comprising a nucleic acid molecule encoding the HC of αFXI-13654p-IgG4 (S228P) (K−)/kappa, 13716p-IgG4 (S228P) (K−)/kappa, αFXI-13716-IgG4 (S228P) Q1E M103L(K−)/kappa and a nucleic acid molecule encoding the LC of αFXI-13654p-IgG4 (S228P) (K−)/kappa, 13716p-IgG4 (S228P)v/kappa, αFXI-13716-IgG4 (S228P) Q1E M103L (K−)/kappa.

The present invention further provides a plasmid or viral vector comprising a nucleic acid molecule encoding the HC of αFXI-13654p-IgG4 (S228P) (K−)/kappa, 13716p-IgG4 (S228P) (K−)/kappa, αFXI-13716-IgG4 (S228P) Q1E M103L(K−)/kappa and a plasmid or viral vector comprising a nucleic acid molecule encoding the LC of αFXI-13654p-IgG4 (S228P) (K−)/kappa, 13716p-IgG4 (S228P) (K−)/kappa, αFXI-13716-IgG4 (S228P) Q1E M103L(K−)/kappa.

The present invention further provides a host cell comprising one or more plasmids or viral vectors comprising a nucleic acid molecule encoding the HC of αFXI-13654p-IgG4 (S228P) (K−)/kappa, 13716p-IgG4 (S228P) (K−)/kappa, αFXI-13716-IgG4 (S228P) Q1E M103L(K−)/kappa and a nucleic acid molecule encoding the LC of αFXI-13654p-IgG4 (S228P) (K−)/kappa, 13716p-IgG4 (S228P) (K−)/kappa, αFXI-13716-IgG4 (S228P) Q1E M103L(K−)/kappa. In particular embodiments, the host cell is a CHO or HEK-293 host cell.

The HC of exemplary antibodies αFXI-13654p-IgG4 (S228P) (K+)/kappa, 13716p-IgG4 (S228P)/kappa, αFXI-13716-IgG4 (S228P) Q1E M103L(K+)/kappa may be encoded by nucleic acid molecules having the nucleotide sequence shown in SEQ ID NOs:43, 48, or 53, respectively.

The LC of exemplary antibodies αFXI-13654p-IgG4 (S228P) (K+)/kappa, 13716p-IgG4 (S228P) (K+)/kappa, αFXI-13716-IgG4 (S228P) Q1E M103L(K+)/kappa may be encoded by nucleic acid molecules having the nucleotide sequence shown in SEQ ID NO:44 or 49, respectively.

The present invention further provides a plasmid or viral vector comprising a nucleic acid molecule having the nucleotide sequence of SEQ ID NOs:43, 48, or 53. In a further embodiment, the present invention provides a plasmid or viral vector comprising a first nucleic acid molecule having the nucleotide sequence of SEQ ID NOs:43 and a second nucleic acid molecule having the nucleotide sequence of SEQ ID NO:44. In a further embodiment, the present invention provides a plasmid or viral vector comprising a first nucleic acid molecule having the nucleotide sequence of SEQ ID NOs:48 or 53 and a second nucleic acid molecule having the nucleotide sequence of SEQ ID NO:49.

The present invention further provides a plasmid or viral vector comprising a nucleic acid molecule encoding the HC of αFXI-13654p-IgG4 (S228P) (K+)/kappa, 13716p-IgG4 (S228P) (K+)/kappa, αFXI-13716-IgG4 (S228P) Q1E M103L(K+)/kappa and a nucleic acid molecule encoding the LC of αFXI-13654p-IgG4 (S228P) (K+)/kappa, 13716p-IgG4 (S228P)v/kappa, αFXI-13716-IgG4 (S228P) Q1E M103L (K+)/kappa.

The present invention further provides a plasmid or viral vector comprising a nucleic acid molecule encoding the HC of αFXI-13654p-IgG4 (S228P) (K+)/kappa, 13716p-IgG4 (S228P) (K+)/kappa, αFXI-13716-IgG4 (S228P) Q1E M103L(K+)/kappa and a plasmid or viral vector comprising a nucleic acid molecule encoding the LC of αFXI-13654p-IgG4 (S228P) (K+)/kappa, 13716p-IgG4 (S228P) (K+)/kappa, αFXI-13716-IgG4 (S228P) Q1E M103L(K+)/kappa.

The present invention further provides a host cell comprising one or more plasmids or viral vectors comprising a nucleic acid molecule encoding the HC of αFXI-13654p-IgG4 (S228P) (K+)/kappa, 13716p-IgG4 (S228P) (K+)/kappa, αFXI-13716-IgG4 (S228P) Q1E M103L(K+)/kappa and a nucleic acid molecule encoding the LC of αFXI-13654p-IgG4 (S228P) (K+)/kappa, 13716p-IgG4 (S228P) (K+)/kappa, αFXI-13716-IgG4 (S228P) Q1E M103L(K+)/kappa. In particular embodiments, the host cell is a CHO or HEK+293 host cell.

In particular embodiments, the antibodies may comprise a heavy chain encoded by a nucleotide sequence set forth in SEQ ID NO: 45, 46, 50, 51, 54, or 55. In particular embodiments, a plasmid or viral vector is provided comprising a nucleic acid molecule comprising a nucleotide sequence set forth in SEQ ID NO: 45, 46, 50, 51, 54, or 55. In a further embodiment, a plasmid or viral vector is provided comprising a first nucleic acid molecule comprising a nucleotide sequence set forth in SEQ ID NO: 45 or 46 and a second nucleic acid molecule comprising a nucleotide sequence set forth in SEQ ID NO: 44. In a further embodiment, a plasmid or viral vector is provided comprising a first nucleic acid molecule comprising a nucleotide sequence set forth in SEQ ID NO: 50, 51, 54, or 55 and a second nucleic acid molecule comprising a nucleotide sequence set forth in SEQ ID NO: 49.

Antibodies or antigen binding fragments can be recovered from the culture medium using standard protein purification methods. Further, expression of antibodies of the invention (or other moieties therefrom) from production cell lines can be enhanced using a number of known techniques. For example, the glutamine synthetase gene expression system (the GS system) is a common approach for enhancing expression under certain conditions.

In general, glycoproteins produced in a particular cell line or transgenic animal will have a glycosylation pattern that is characteristic for glycoproteins produced in the cell line or transgenic animal (See for example, Croset et al., J. Biotechnol. 161: 336-348 (2012)). Therefore, the particular glycosylation pattern of an antibody or antigen binding fragments will depend on the particular cell line or transgenic animal used to produce the antibody or antigen binding fragments. However, all antibodies and antigen binding fragments encoded by the nucleic acid molecules provided herein, or comprising the amino acid sequences provided herein, comprise the instant invention, independent of the glycosylation pattern the antibodies or antigen binding fragments may have.

The following examples are intended to promote a further understanding of the present invention.

General Methods

Standard methods in molecular biology are described Sambrook, Fritsch and Maniatis (1982 & 1989 2nd Edition, 2001 3rd Edition) Molecular Cloning, A Laboratory Manual, Cold Spring Harbor Laboratory Press, Cold Spring Harbor, N.Y.; Sambrook and Russell (2001) Molecular Cloning, 3rd ed., Cold Spring Harbor Laboratory Press, Cold Spring Harbor, N.Y.; Wu (1993) Recombinant DNA, Vol. 217, Academic Press, San Diego, Calif.). Standard methods also appear in Ausbel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) Current Protocols in Protein Science, Vol. 1, John Wiley and Sons, Inc., New York). Chemical analysis, chemical modification, post-translational modification, production of fusion proteins, glycosylation of proteins are described (see, e.g., Coligan, et al. (2000) Current Protocols in Protein Science, Vol. 2, John Wiley and Sons, Inc., New York; Ausubel, et al. (2001) Current Protocols in Molecular Biology, Vol. 3, John Wiley and Sons, Inc., NY, N.Y., pp. 16.0.5-16.22.17; Sigma-Aldrich, Co. (2001) Products for Life Science Research, St. Louis, Mo.; pp. 45-89; Amersham Pharmacia Biotech (2001) BioDirectory, Piscataway, N.J., pp. 384-391). Production, purification, and fragmentation of polyclonal and monoclonal antibodies are described (Coligan, et al. (2001) Current Protocols in Immunology, Vol. 1, John Wiley and Sons, Inc., New York; Harlow and Lane (1999) Using Antibodies, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) Current Protocols in Immunology, Vol. 4, John Wiley, Inc., New York).

Monoclonal, polyclonal, and humanized antibodies can be prepared (see, e.g., Sheperd and Dean (eds.) (2000) Monoclonal Antibodies, Oxford Univ. Press, New York, N.Y.; Kontermann and Dubel (eds.) (2001) Antibody Engineering, Springer-Verlag, New York; Harlow and Lane (1988) Antibodies A Laboratory Manual, Cold Spring Harbor Laboratory Press, Cold Spring Harbor, N.Y., pp. 139-243; Carpenter, et al. (2000) J. Immunol. 165:6205; He, et al. (1998) J. Immunol. 160:1029; Tang et al. (1999) J. Biol. Chem. 274:27371-27378; Baca et al. (1997) J. Biol. Chem. 272:10678-10684; Chothia et al. (1989) Nature 342:877-883; Foote and Winter (1992) J. Mol. Biol. 224:487-499; U.S. Pat. No. 6,329,511).

An alternative to humanization is to use human antibody libraries displayed on phage or human antibody libraries in transgenic mice (Vaughan et al. (1996) Nature Biotechnol. 14:309-314; Barbas (1995) Nature Medicine 1:837-839; Mendez et al. (1997) Nature Genetics 15:146-156; Hoogenboom and Chames (2000) Immunol. Today 21:371-377; Barbas et al. (2001) Phage Display: A Laboratory Manual, Cold Spring Harbor Laboratory Press, Cold Spring Harbor, N.Y.; Kay et al. (1996) Phage Display of Peptides and Proteins: A Laboratory Manual, Academic Press, San Diego, Calif.; de Bruin et al. (1999) Nature Biotechnol. 17:397-399).

Antibodies can be conjugated, e.g., to small drug molecules, enzymes, liposomes, polyethylene glycol (PEG). Antibodies are useful for therapeutic, diagnostic, kit or other purposes, and include antibodies coupled, e.g., to dyes, radioisotopes, enzymes, or metals, e.g., colloidal gold (see, e.g., Le Doussal et al. (1991) J. Immunol. 146:169-175; Gibellini et al. (1998) J. Immunol. 160:3891-3898; Hsing and Bishop (1999) J. Immunol. 162:2804-2811; Everts et al. (2002) J. Immunol. 168:883-889).

Methods for flow cytometry, including fluorescence activated cell sorting (FACS), are available (see, e.g., Owens, et al. (1994) Flow Cytometry Principles for Clinical Laboratory Practice, John Wiley and Sons, Hoboken, N.J.; Givan (2001) Flow Cytometry, 2nd ed.; Wiley-Liss, Hoboken, N.J.; Shapiro (2003) Practical Flow Cytometry, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (Molecular Probes (2003) Catalogue, Molecular Probes, Inc., Eugene, Oreg.; Sigma-Aldrich (2003) Catalogue, St. Louis, Mo.).

Standard methods of histology of the immune system are described (see, e.g., Muller-Harmelink (ed.) (1986) Human Thymus: Histopathology and Pathology, Springer Verlag, New York, N.Y.; Hiatt, et al. (2000) Color Atlas of Histology, Lippincott, Williams, and Wilkins, Phila, Pa.; Louis, et al. (2002) Basic Histology: Text and Atlas, McGraw-Hill, New York, N.Y.).

Software packages and databases for determining, e.g., antigenic fragments, leader sequences, protein folding, functional domains, glycosylation sites, and sequence alignments, are available (see, e.g., GenBank, Vector NTI® Suite (Informax, Inc, Bethesda, Md.); GCG Wisconsin Package (Accelrys, Inc., San Diego, Calif.); DeCypher® (TimeLogic Corp., Crystal Bay, Nev.); Menne, et al. (2000) Bioinformatics 16: 741-742; Menne, et al. (2000) Bioinformatics Applications Note 16:741-742; Wren, et al. (2002) Comput. Methods Programs Biomed. 68:177-181; von Heijne (1983) Eur. J. Biochem. 133:17-21; von Heijne (1986) Nucleic Acids Res. 14:4683-4690).

Example 1

Binding Kinetics, Bioactivity and Mode of Blockade of the Anti-FXI Antibodies to Human and Bon-Human Primate (NHP) FXI and FXIa.

Binding kinetics and affinity of the protein-protein interaction between αFXI-13716p-IgG4 (S228P)(K−)/kappa, αFXI-13716-IgG4 (S228P) Q1E M103L(K−)/kappa, and αFXI-13654p-IgG4 (S228P)(K−)/kappa and human FXI zymogen were determined using the ProteOn XPR36 (Bio-Rad), an SPR-based (surface plasmon resonance) optical biosensor.

Briefly, a GLC low-density sensor chip is washed across all vertical and horizontal flow channels with 0.5% sodium dodecyl-sulfate, 50 mM sodium hydroxide, and 100 mM hydrochloric acid for 60 seconds at 30 μL/sec flow rate. The alginate chip surface for all six vertical flow channels (L1-L6) is subsequently activated with 1×EDC/sNHS at 30 μL/sec flow rate for 150 seconds. A murine Fc-directed anti-human IgG polyclonal antibody (capture antibody), diluted to 1.25 μg/mL in 10 mM sodium acetate, pH 5.0, is then injected across all six vertical flow channels for 300 seconds at a flow rate of 25 μL/second to bind approximately 300 response units (RU) of capture antibody to the activated chip surface per flow channel by amine-coupling to endogenous lysine. 1 M ethanolamine HCl is then injected across all six vertical flow channels to neutralize remaining reactive surface amines. The anti-FXI antibodies are then injected at 25 μL/minutes for 60 seconds, each into a distinct vertical flow channel coated with capture antibody (L2, L3, L4, L5, or L6), at a concentration of 5 μg/mL in 10 mM sodium acetate, pH 5.0, to achieve saturating capture levels of approximately 80 RU; vertical flow channel L1 is injected with 10 mM sodium acetate, pH 5.0 (buffer alone), as a reference control. After capture of anti-FXI antibodies, running buffer (1×HBS-N, 5 mM $CaCl_2$, 0.005% P20, pH 7.4) is injected across all horizontal flow channels (A1-A6) for 5 minutes and allowed to dissociate for 20 minutes at 25 μL/minutes to remove any non-specifically bound anti-FXI antibodies from the chip surface. To measure on-rate ($k_a$) of human FXI to captured anti-FXI antibodies, a 6-point titration of human FXI zymogen (0, 0.25, 0.5, 1.0, 2.0, 4.0 nM diluted in running buffer) is subsequently injected horizontally across all six vertical flow channels for 8 minutes; the bound zymogen is then allowed to dissociate for 60 minutes in running buffer at 25 μL/min to measure off-rate ($k_d$). Binding kinetics and affinity ($K_D$) may be determined using instrument-specific software (Bio-Rad).

Binding kinetics and affinity of the protein-protein interaction between anti-FXI human αFXI-13716p-IgG4 (S228P) (K−)/kappa, αFXI-13716-IgG4 (S228P) Q1E M103L (K−)/kappa, and αFXI-13654p-IgG4 (S228P) (K−)/kappa antibodies and non-human primate (NHP) FXI zymogen (cynomolgus and rhesus) may be determined using the ProteOn XPR36 (Bio-Rad), an SPR-based (surface plasmon resonance) optical biosensor. A GLC low-density sensor chip is washed across all vertical and horizontal flow channels with 0.5% sodium dodecyl-sulfate, 50 mM sodium hydroxide, and 100 mM hydrochloric acid for 60 seconds at 30 μL/second flow rate. The alginate chip surface for all six vertical flow channels (L1-L6) is subsequently activated with 1×EDC/sNHS at 30 μL/second flow rate for 150 seconds. A murine Fc-directed anti-human IgG polyclonal antibody (capture antibody), diluted to 30 μg/mL in 10 mM sodium acetate, pH 5.0, is then injected across all six vertical flow channels for 150 seconds at a flow rate of 25 μL/second to achieve saturation-binding of approximately 4500 response units (RU) of capture antibody to the activated chip surface per flow channel by amine-coupling to endogenous lysine. 1 M ethanolamine HCl is then injected across all six vertical flow channels to neutralize any remaining reactive surface amines. Anti-FXI antibodies are then injected at 25 μL/minutes for 60 seconds, each into a distinct vertical flow channel coated with capture antibody (L2, L3, L4, L5, or L6), at a concentration of 0.415 μg/mL in running buffer (1×HBS-N, 5 mM $CaCl_2$, 0.005% P20, pH 7.4), to achieve capture levels of approximately 40 RU; vertical flow channel L1 is injected with running buffer alone as a reference control. After capture of anti-FXI antibodies, running buffer is injected across all horizontal flow channels (A1-A6) for 5 minutes and allowed to dissociate for 20 minutes at 25

μL/minute to remove non-specifically bound anti-FXI antibodies from the chip surface. To measure on-rate ($k_a$) of NHP FXI to captured anti-FXI antibodies, a 6-point titration of NHP FXI zymogen (0, 0.25, 0.5, 1.0, 2.0, 4.0 nM diluted in running buffer) is subsequently injected horizontally across all six vertical flow channels for 8 minutes; the bound zymogen is then allowed to dissociate for 60 minutes in running buffer at 25 μL/minutes to measure off-rate ($k_d$). Binding kinetics and affinity ($K_D$) were determined using instrument-specific software (Bio-Rad).

The kinetics of binding of αFXI-13716p-IgG4 (S228P) (K-)/kappa, αFXI-13716-IgG4 (S228P) Q1E M103L(K-)/kappa, and αFXI-13654p-IgG4 (S228P)(K-)/kappa to human, cynomolgus monkey, and rhesus monkey FXI and FXIa measured essentially as described above are shown in (Table 1). The data were fit using Langmuir 1-site model (for $k_{on}$ and $k_{off}$ and equilibrium binding for dissociation constant (KD) determination). Both antibodies bound human FXI/XIa with single digit pM KD. The binding dissociation constants for both antibodies were within 2-fold across FXI/FXIa proteins from NHP species.

TABLE 1

Binding of the Anti-FXI Antibodies to FXI and FXIa

| | | FXI Affinity Mean $K_D \pm$ SD pM | | | FXIa Affinity Mean $K_D \pm$ SD pM | | |
|---|---|---|---|---|---|---|---|
| Target | N | αFXI-13716* | αFXI-13654p‡ | αFXI-13716** | αFXI-13716* | αFXI-13654p‡ | αFXI-13716** |
| Human | 3 | 2.5 ± 0.7 | 26.5 ± 8.6 | 3.5 ± 1.1 | 1.1 ± 0.5 | 9.0 ± 8.2 | 1.3 ± 0.5 |
| Cynomolgus monkey | 3 | 6.9 ± 2.8 | 12.9 ± 14.7 | 7.5 ± 1.4 | 3.3 ± 1.8 | 2.0 ± 1.2 | 3.7 ± 1.8 |
| Rhesus monkey | 3 | 2.0 ± 1.9 | 26.6 ± 19.6 | 3.1 ± 0.9 | ND# | ND# | ND# |

*αFXI-13716-IgG4 (S228P) Q1E M103L (K-)/kappa
‡αFXI-13654p-IgG4 (S228P) (K-)/kappa
**αFXI-13716p-IgG4 (S228P) (K-)/kappa
Not done Example 2

Effect of the Anti-FXI Antibodies on Autoactivation of FXI to FXIa on Dextran Sulfate.

Autoactivation of FXI to FXIa on Dextran Sulfate may be measured as follows. 10-point dose titrations of the αFXI-13716p-IgG4 (S228P) (K-)/kappa, αFXI-13716-IgG4 (S228P) Q1E M103L(K-)/kappa, and αFXI-13654p-IgG4 (S228P) (K-)/kappa antibodies, starting at 1 μM concentration with a 3-fold dilution series, are pre-incubated with human FXI (Haematologic Technologies, Inc., Cat # HCXI-0150, final concentration 30 nM) in 50 mM HEPES, 150 mM NaCl, 5 mM $CaCl_2$, 0.1% PEG-8000, pH 7.4 for 2 hours at 25° C. in Corning 3575 non-binding surface microplate. The auto-activation reaction is then initiated by addition of dextran sulfate (ACROS, Cat #433240250, approximate MW 800 kDa, final concentration 1 nM). The reaction is allow to proceed at 25° C. for 1 hour when newly activated FXIa enzymatic activity may be detected by the rate of cleavage of Z-GPR-AFC substrate (Sigma, Cat # C0980-10MG, final concentration 150 μM) by continuously monitoring the fluorescence at 400/505 nm for 10 min using a Tecan Infinite M200 plate reader. The % Inhibition for each data point may be recalculated from the RFU/minute data and analyzed using the log(inhibitor) vs. response four parameters equation with the GraphPad Prism software. The reported $EC_{50}$ values may be given as mean±SD, n=2. The results are shown in Table 2.

TABLE 2

Effect of the anti-FXI Antibodies on Autoactivation of FXI to FXIa

| Antibody | N | FXIa Activation Inhibition ($EC_{50}$, nM) |
|---|---|---|
| αFXI-13716* | 2 | 11 ± 1 |
| αFXI-13654p‡ | 2 | 10 ± 8 |
| αFXI-13716p** | 2 | 4 ± 2 |

*αFXI-13716-IgG4 (S228P) Q1E M103L(K-)/kappa
‡αFXI-13654p-IgG4 (S228P) (K-)/kappa
**αFXI-13716p-IgG4 (S228) (K-)/kappa Example 3

Activated Partial Thromboplastin Time (aPTT) Assay of the Anti-FXI Antibodies.

The ability of αFXI-13654p-IgG4 (S228P) (K-)/kappa, αFXI-13716p-IgG4 (S228P) (K-)/kappa, and αFXI-13716-IgG4 (S228P) Q1E M103L (K-)/kappa antibodies to block in vitro coagulation was assessed using the activated Partial Thromboplastin Time (aPTT) assay. The aPTT assay measures the activity of the intrinsic and common pathways of coagulation.

The test is performed in sodium citrated plasmas. Briefly, human and NHP (cynomolgus or rhesus monkey) plasma is made by collecting blood from healthy donors of both genders into Na citrate tubes (Sarstedt coagulation 9NC/10 mL). Blood is centrifuged at 1500×g and the plasma is collected. aPTT is checked on each individual donor and those within the normal range (28-40 seconds) are pooled, portions aliquoted and stored at −80 C. Plasma from other species is obtained commercially (Innovative Research). Test samples are prepared by spiking inhibitors or vehicle into plasma. These spiked samples are incubated (60 minutes, room temperature (RT)) then run on a coagulation analyzer (STA-R Evolution, Stago Diagnostica). In general, the analyzer performs the following steps: Factor XII is activated by addition of ellagic acid (Pacific Hemostasis), and then time to clot is measured after re-calcification of the sample. Inhibition of FXI will cause aPTT clot time to be prolonged. The data is expressed as percent increase over vehicle control clot time and the concentration that causes 50% (1.5×) percent increase of clot time are reported.

Figure 3A:
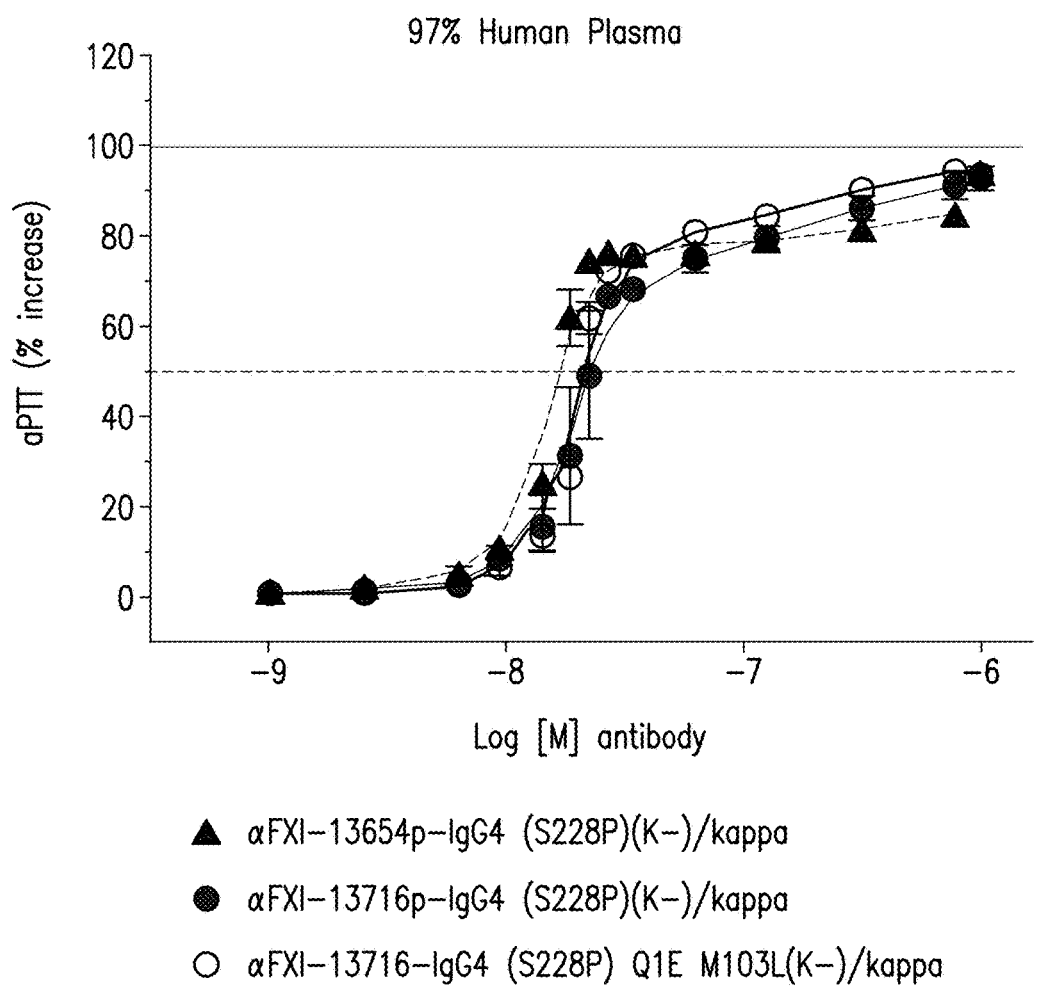
FIG. 3A shows activated Partial Thromboplastin Time (aPTT) assays of αFXI-13654p-IgG4 (S228P) (K−)/kappa (▲), α13716p-IgG4 (S228P) (K−)/kappa (●), αFXI-13716-IgG4 (S228P) Q1E M103L (K−)/kappa (○) in human plasma, expressed as % increase over baseline. (y-axis is aPTT (% increase) and x-axis is Log [M] antibody)
Figure 3B:
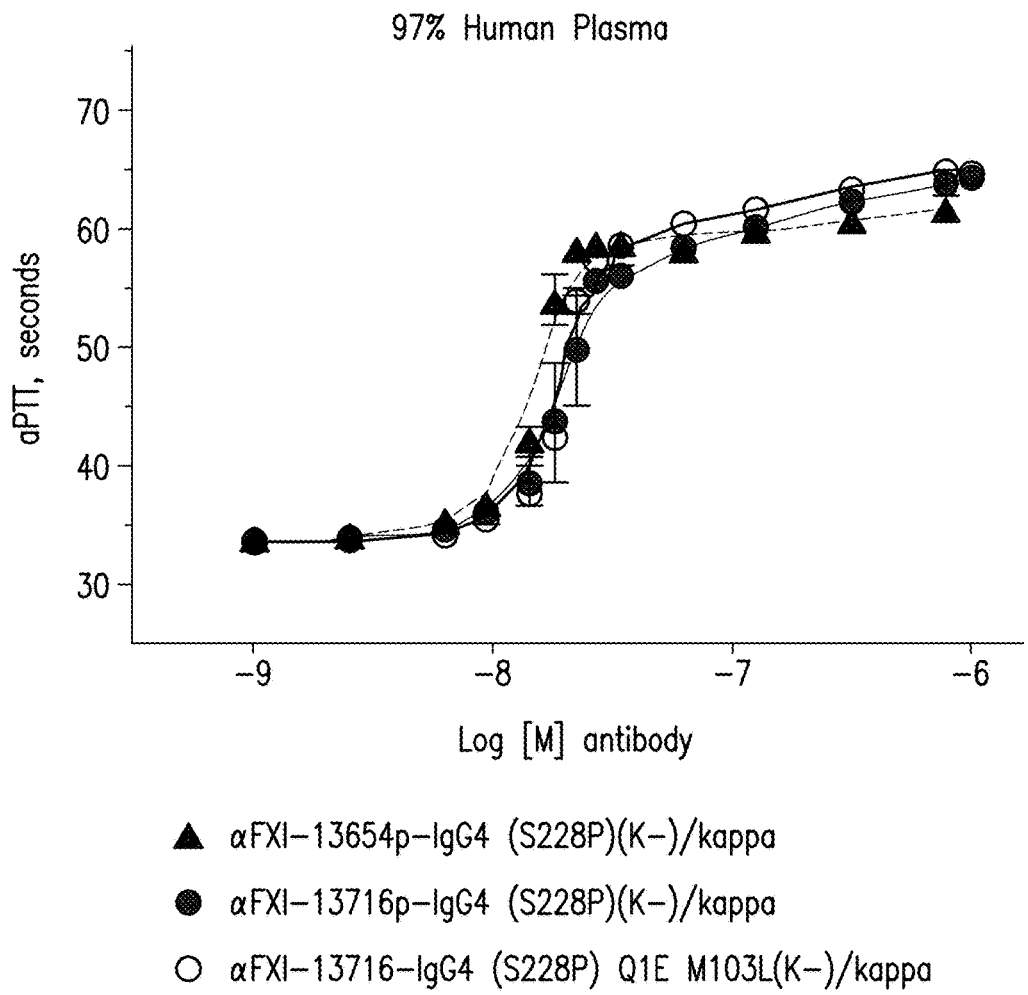
FIG. 3B shows the clotting time of αFXI-13654p-IgG4 (S228P) (K−)/kappa (▲), α13716p-IgG4 (S228P) (K−)/kappa (●), αFXI-13716-IgG4 (S228P) Q1E M103L(K−)/kappa (○) in human plasma as determined from the aPTT assay. (y-axis is aPTT (seconds) and x-axis is Log [M] antibody; aPTT (seconds) may also be expressed as Clot Time (seconds))
Figure 4A:
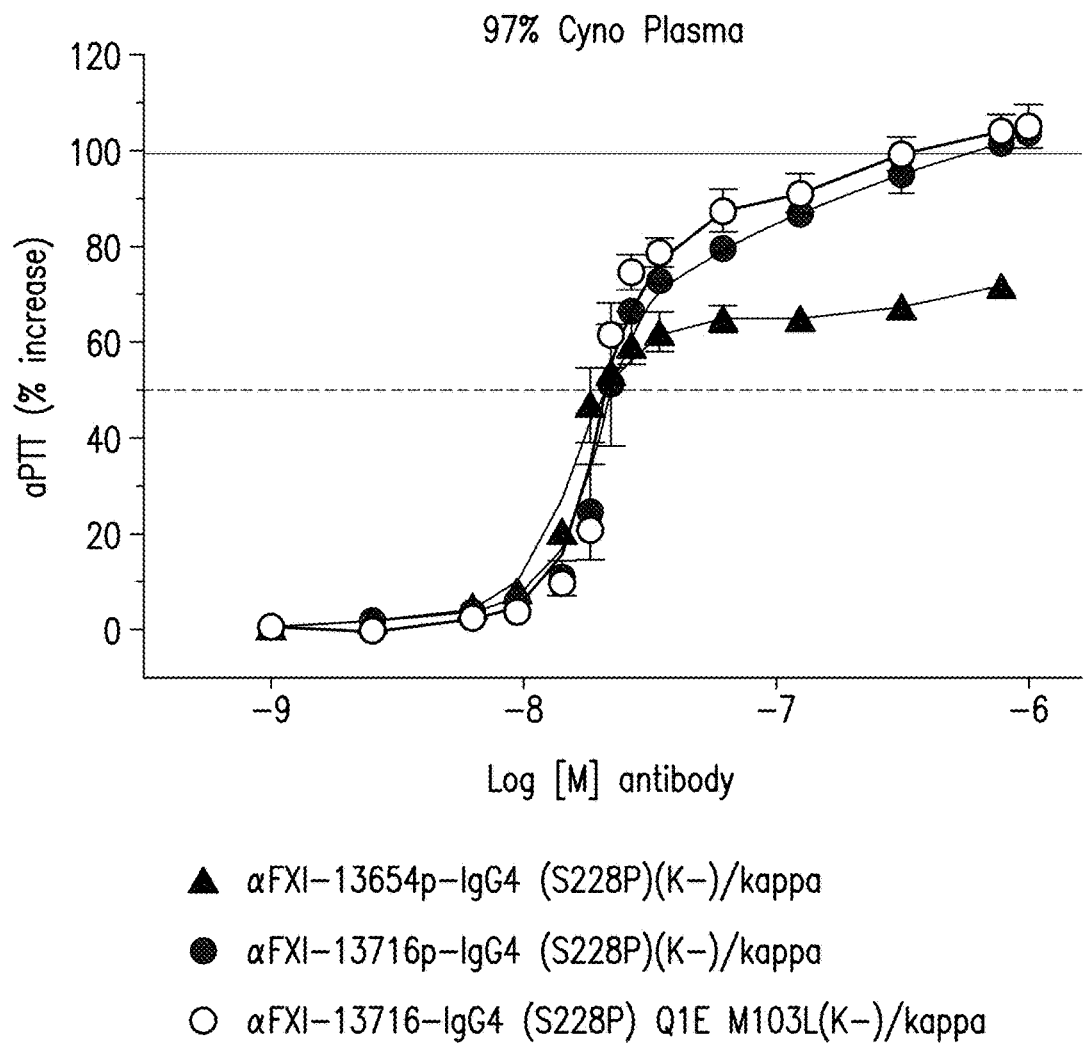
FIG. 4A shows aPTT assays of αFXI-13654p-IgG4 (S228P) (K−)/kappa (▲), α13716p-IgG4 (S228P) (K−)/kappa (●), αFXI-13716-IgG4 (S228P) Q1E M103L (K−)/kappa (0) in cynomolgus monkey plasma, expressed as % increase over baseline. (y-axis is aPTT (% increase) and x-axis is Log [M] antibody)
Figure 4B:
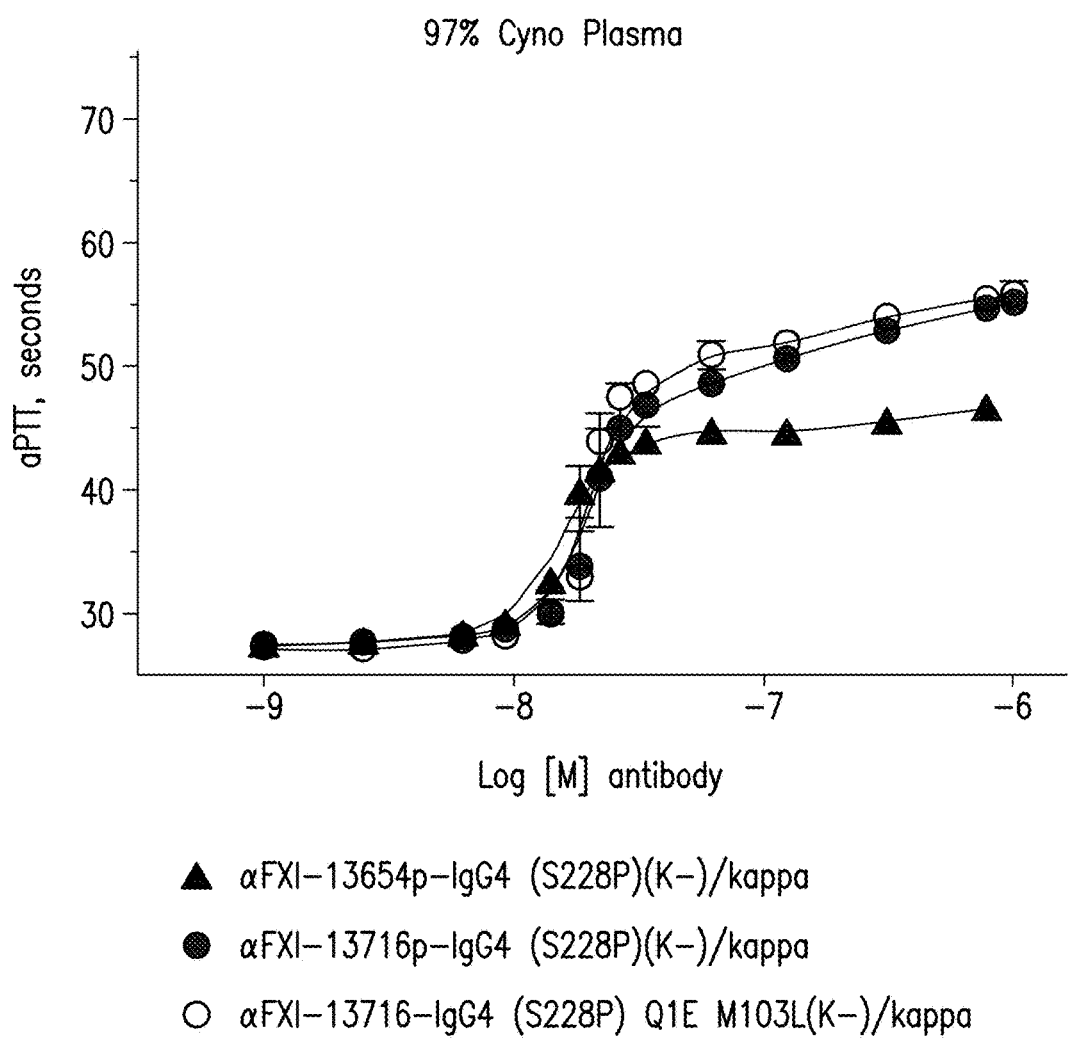
FIG. 4B shows the clotting time of αFXI-13654p-IgG4 (S228P) (K−)/kappa (▲), α13716p-IgG4 (S228P) (K−)/kappa (●), αFXI-13716-IgG4 (S228P) Q1E M103L (K−)/kappa (○) in cynomolgus monkey plasma as determined from the aPTT assay. (y-axis is aPTT (seconds) and x-axis is Log [M] antibody; aPTT (seconds) may also be expressed as Clot Time (seconds))
Figure 5A:
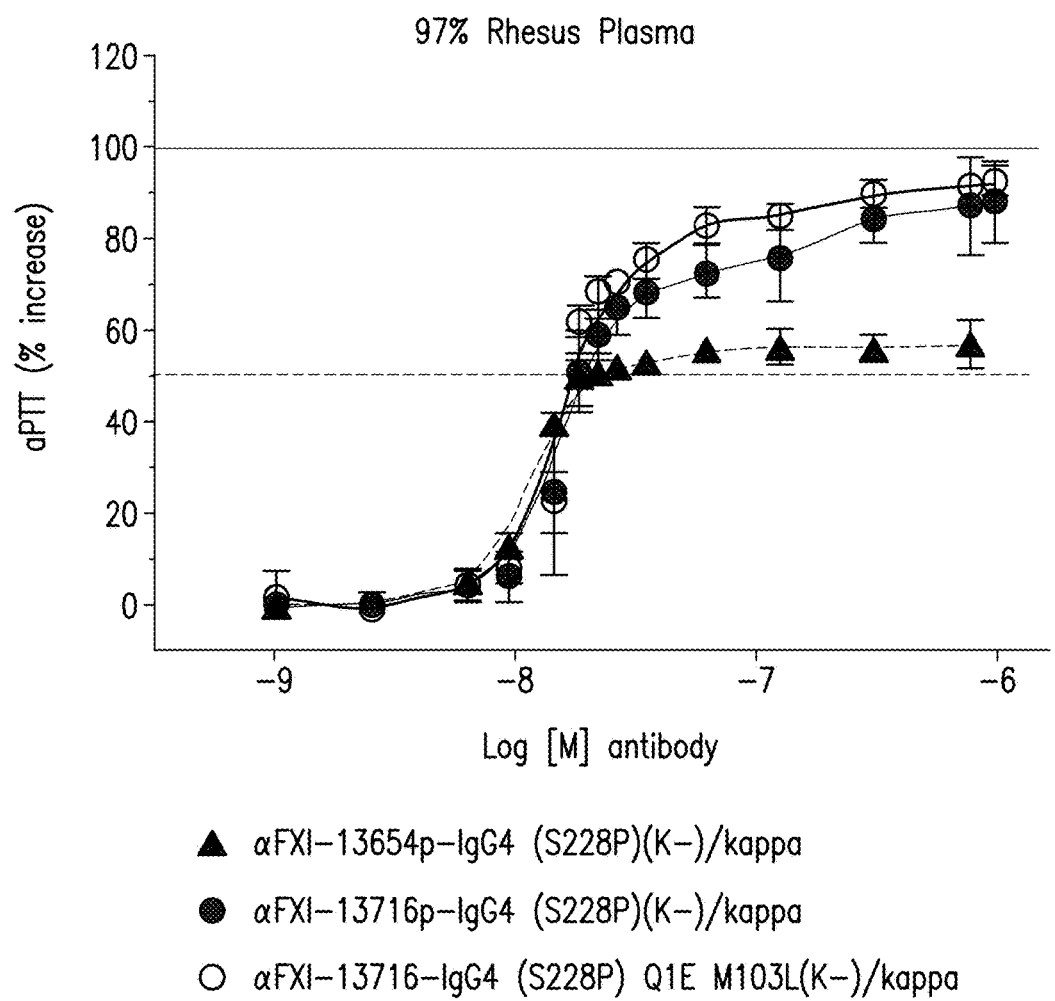
FIG. 5A shows activated aPTT assays of αFXI-13654p-IgG4 (S228P) (K−)/kappa (▲), α13716p-IgG4 (S228P) (K−)/kappa (●), αFXI-13716-IgG4 (S228P) Q1E M103L (K−)/kappa (○) in rhesus monkey plasma, expressed as % increase over baseline.
Figure 5B:
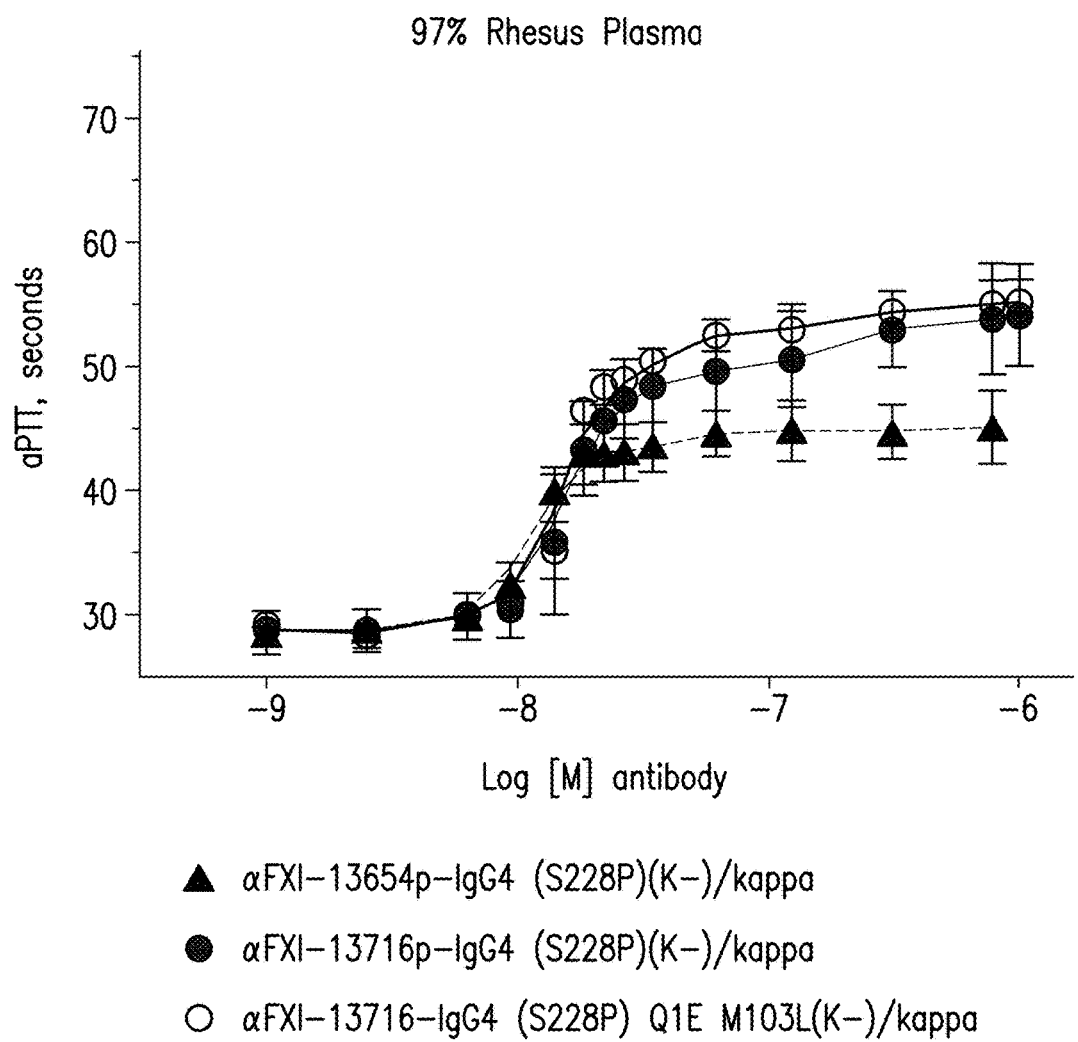
FIG. 5B shows the clotting time of αFXI-13654p-IgG4 (S228P) (K−)/kappa (▲), α13716p-IgG4 (S228P) (K−)/kappa (●), αFXI-13716-IgG4 (S228P) Q1E M103L (K−)/kappa (○) in rhesus monkey plasma as determined from the aPTT assay. (y-axis is aPTT (seconds) and x-axis is Log [M] antibody; aPTT (seconds) may also be expressed as Clot Time (seconds))

Following the above protocol, the concentration of the antibodies required to prolong clotting time by 50% (1.5× concentration) was comparable in 97% human, cynomolgus, and rhesus plasma (FIGS. 3A-3B, FIGS. 4A-4B, and FIGS. 5A-5B). FIGS. 3A, 4A, and 5A express the data as % increase over baseline whereas FIGS. 3B, 4B, and 5B show the raw data (clotting time in seconds). The 1.5× concentrations of the antibodies were comparable (16.8-25 nM) across all human and NHP plasmas, and likely represented the antibody concentration required to titrate one half of the FXI zymogen present in plasma (30-40 nM zymogen). The maximal prolongation in clotting time for the antibodies was comparable between cynomolgus and rhesus plasma. The results are further tabulated in Table 3.

TABLE 3

Concentration Anti-FXI Antibody That Prolongs Clotting Time by 50%

| Antibody | Human 1.5x (nM) | Cynomolgus monkey 1.5x (nM) | Rhesus monkey 1.5x (nM) |
|---|---|---|---|
| αFXI-13654p‡ | 16.8 | 21.6 | 25 |
| αFXI-13716ⁱ | 21.6 | 22.5 | 19.4 |
| αFXI-13716* | 20.9 | 21.1 | 17.4 |

*αFXI-13716-IgG4 (S228P) Q1E M103L(K−)/kappa

‡αFXI-13654p-IgG4 (S228P)(K−)/kappa

ⁱ αFXI-13716p-IgG4 (S228P)(K−)/kappa

Example 4

Epitope Mapping of Anti-FXI Antibodies by Hydrogen Deuterium Exchange Mass Spectrometry.

Contact areas of αFXI-13716p-IgG4 (S228P) (K−)/kappa and αFXI-13654p-IgG4 (S228P) (K−)/kappa antibodies to human FXI were determined by use of hydrogen deuterium exchange mass spectrometry (HDX-MS) analysis. HDX-MS measures the incorporation of deuterium into the amide backbone of the protein and changes in this incorporation are influenced by the hydrogen's solvent exposure. A comparison of the deuterium exchange levels in antigen-alone samples and antibody-bound samples were done to identify antigen regions that may be in contact with the antibody. Human Factor XI has the amino acid sequence shown in SEQ ID NO:37.

Figure 2:
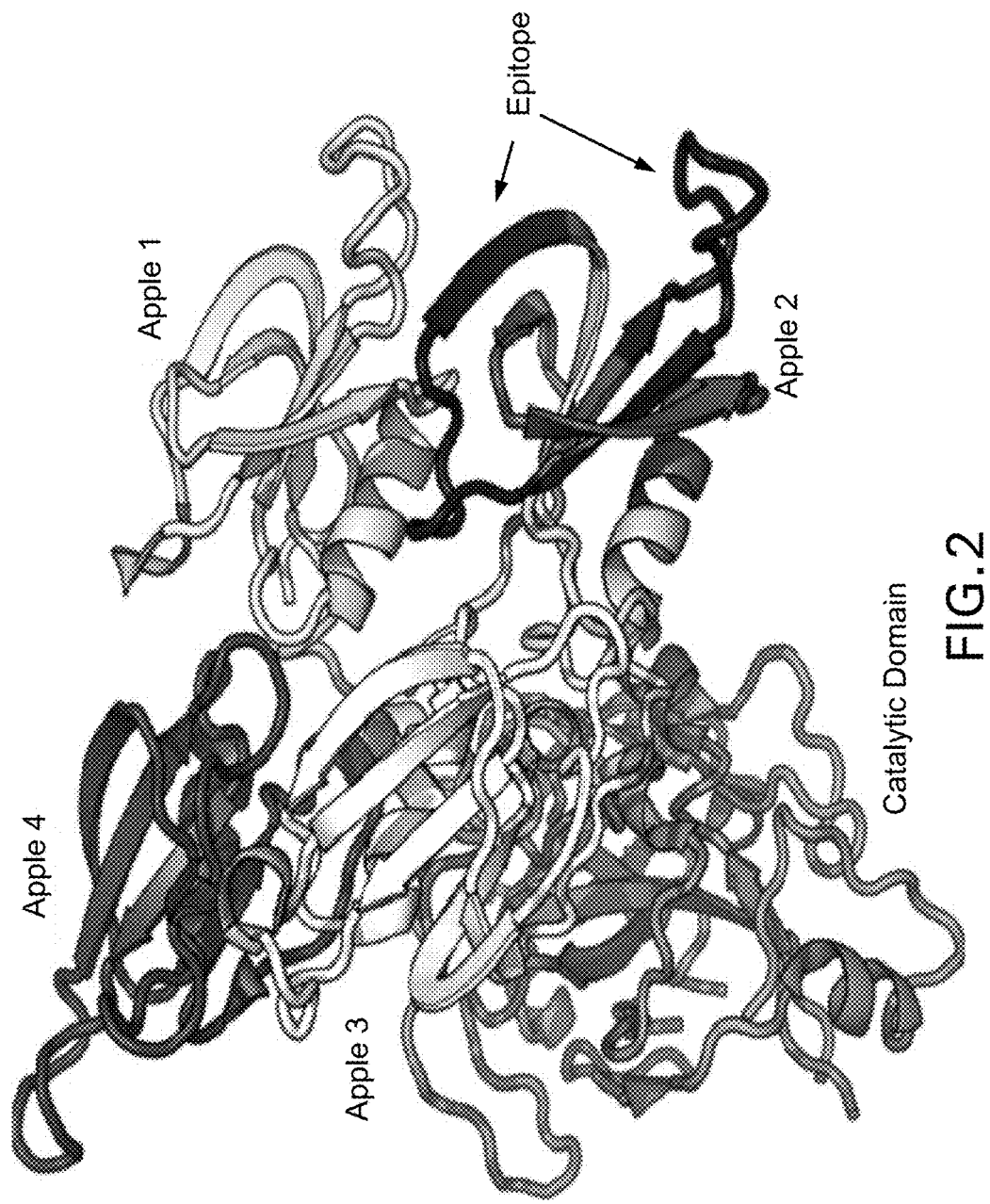
FIG. 2 shows the structure of FXI with the portions of the domain protected from deuteration by αFXI-13716p-IgG4 (S228P) (K−)/kappa or 13654p-IgG4 (S228P) (K−)/kappa colored in black. Peptides in the Apple 2 domain with no deuteration differences are light grey. Peptides where no data was available are colored dark grey.
Figure 6:
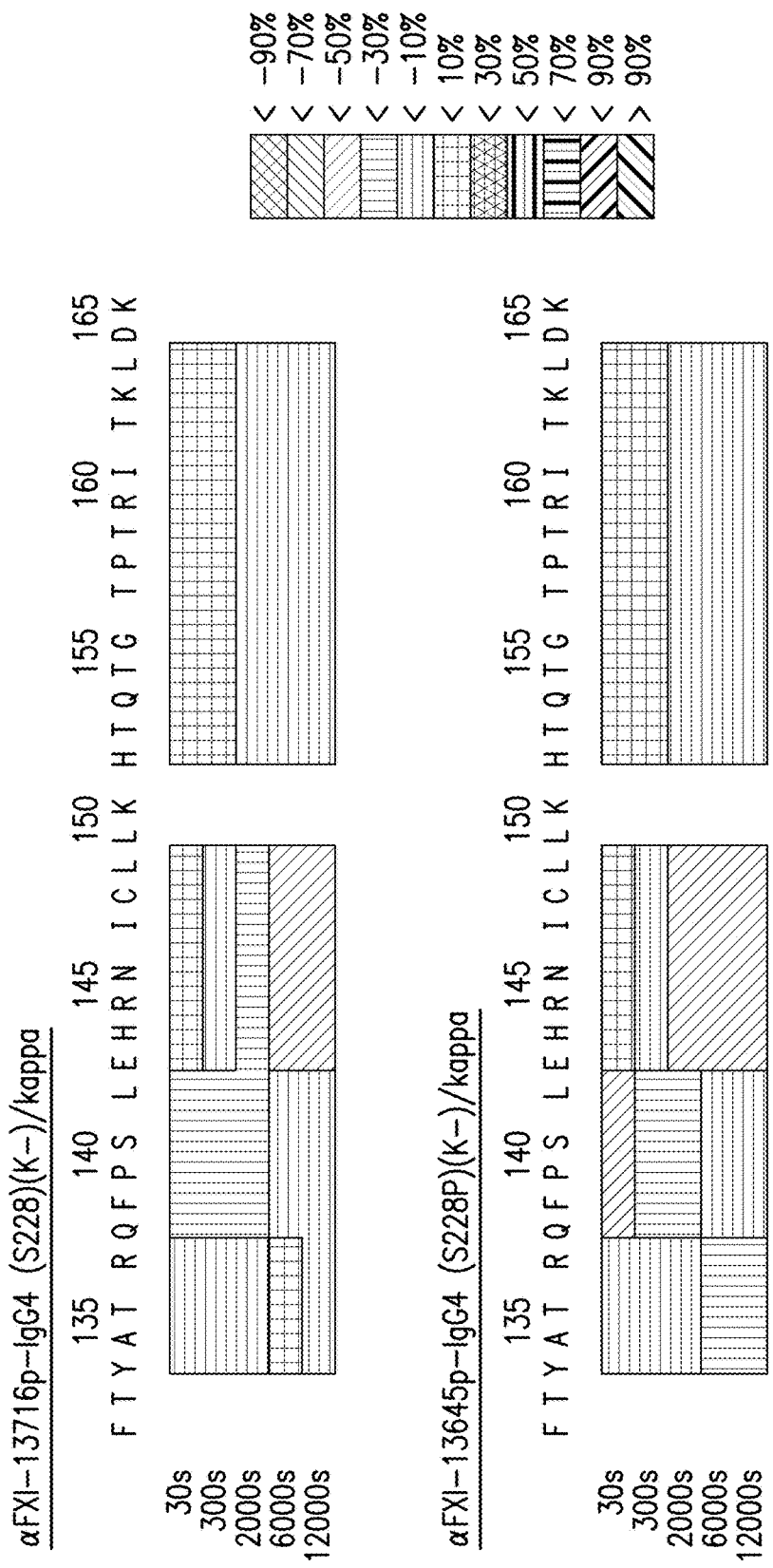
FIG. 6 shows a deuterium labeling difference heatmap of FXI residues 131 to 165 bound by αFXI-13716p-IgG4 (S228P) (K−)/kappa or αFXI-13654p-IgG4 (S228P) (K−)/kappa.

The human Factor XI regions protected from deuteration by the antibodies are Epitope-A YATRQFPSLEHRNICL (Residues 133-148 of Factor XI; SEQ ID NO:38) and Epitope-B HTQTGTPTRITKL (Residues 151-163 of Factor XI; SEQ ID NO:39). These peptides are located on the Apple 2 domain of Factor XI (FIG. 2). No significant deuteration changes were observed in the Apple 1, 3, 4 or catalytic domains, indicating they are not involved in αFXI-13716 binding. FIG. 6 shows a deuterium labeling difference heatmap of Factor XI residues 131 to 165 bound by the antibodies. αFXI-13716p-IgG4 (S228P) (K−)/kappa and αFXI-13654p-IgG4 (S228P) (K−)/kappa antibodies both protected the same regions.

Example 5

Effect of the Anti-FXI Antibodies on Activation of FXI to FXIa by FXIIa in the Presence of HMW Kininogen and Ellagic Acid.

To measure the effects of anti-FXI antibodies on FXI zymogen activation, coupled enzymatic assays that measure FXIa-mediated proteolysis of a tri-peptide fluorophore (GPR-AFC) may be used to determine if the antibodies inhibit FXI activation per se. For these experiments, anti-FXI antibodies are pre-incubated with FXI zymogen for 1 hour. FXI activation to FXIa is induced by the addition of FXIIa in the presence of HMW Kininogen and ellagic acid. FXIa catalytic activity on the tripeptide fluorophore substrate is subsequently measured as a read for zymogen activation. The coupled assay is also run in the absence of HMW Kininogen as a control.

The assay may be performed as follows. 10-point dose titrations of anti-FXI antibodies, starting at 1 µM concentration with a 3-fold dilution series, are pre-incubated with human FXI (Haematologic Technologies, Inc., Cat # HCXI-0150, final concentration 30 nM) and HMW kininogen (Enzyme Research Laboratories, Cat # HK, final concentration 280 nM) in 50 mM HEPES, 150 mM NaCl, 5 mM $CaCl_2$, 0.1% PEG-8000, pH 7.4 for 2 hours at 25° C. in Corning 3575 non-binding surface microplate.

The activation reaction is then initiated by addition of ellagic-acid-containing Pacific Hemostasis APTT-XL reagent (Thermo Scientific, Cat #100403, 100 µM stock concentration, final concentration 2 µM) and freshly diluted coagulation factor XIIa (Enzyme Research Laboratories, Cat # HFXIIa, final concentration 50 pM).

The reaction is allowed to proceed at 25° C. for 1 hour when it may then be quenched by addition of an inhibitor of FXIIa. Inhibitors of FXIIa include, for example, Corn Trypsin Inhibitor (Santa Cruz Biotechnology, Cat# sc-204358), which may be used at a concentration of about 200 nM to inhibit FXIIa and inhibitors disclosed in Published application WO2013113774, for example, H-D-Pro-Phe-Arg-chloromethylketone (PCK), which irreversibly inhibits the amidolytic activity of activated FXII (FXIIa).

The newly activated FXIa enzymatic activity is then detected by measuring the rate of cleavage of Z-GPR-AFC substrate (Sigma, Cat # C0980-10MG, final concentration 150 µM) by continuously monitoring the fluorescence at 400/505 nm for 15 minutes using a Tecan Infinite M200 plate reader. The % Inhibition for each data point may be recalculated from the RFU/min data and analyzed using the log(inhibitor) vs. response four parameters equation with the GraphPad Prism software.

The αFXI-13716p-IgG4 (S228P) (K−)/kappa, αFXI-13716-IgG4 (S228P) Q1E M103L(K−)/kappa, and αFXI-13654p-IgG4 (S228P) (K−)/kappa antibodies were evaluated in assays performed as described above. The results of these assays showed that the anti-FXI antibodies inhibited activation of FXI to FXIa by FXIIa in the presence of HMW kininogen but had no detectable inhibitory effect on FXIIa activation of FXI in the absence of HMW kininogen. These results suggest that the anti-FXI antibodies inhibit FXIIa activation of FXI to FXIa in the presence of HMW kininogen.

Example 6

Effect of the Anti-FXI Antibodies on FXIa Catalytic Activity.

An assay for determining whether an anti-FXI antibody inhibits activity of FXIa may be performed as follows. 10-point dose titrations of anti-FXI antibodies, starting at 1 µM concentration with a 3-fold dilution series, are pre-incubated with human FXI (Haematologic Technologies, Inc., Cat # HCXI-0150, final concentration 30 nM) in 50 mM HEPES, 150 mM NaCl, 5 mM $CaCl_2$, 0.1% PEG-8000, pH 7.4 for 2 hours at 25° C. in Corning 3575 non-binding surface microplate.

The activation reaction is then initiated by addition of freshly diluted coagulation factor XIIa (Enzyme Research Laboratories, Cat # HFXIIa, final concentration 15 nM). The reaction is allowed to proceed at 25° C. for 1 hour when it is then quenched by addition of an inhibitor of FXIIa, for example, Corn Trypsin Inhibitor (Santa Cruz Biotechnology, Cat# sc-204358), which may be used at a concentration of about 200 nM to inhibit FXIIa, or an FXIIa inhibitor such as H-D-Pro-Phe-Arg-chloromethylketone (PCK) disclosed in WO2013113774.

The newly activated FXIa enzymatic activity may then be detected by measuring the rate of cleavage of Z-GPR-AFC substrate (Sigma, Cat # C0980-10MG, final concentration 150 μM) by continuously monitoring the fluorescence at 400/505 nm for 15 minutes using a Tecan Infinite M200 plate reader or the rate of cleavage of or native, intact FIX. The % Inhibition for each data point may be recalculated from the RFU/minute data and analyzed using the log (inhibitor) vs. response four parameters equation with the GraphPad Prism software.

The αFXI-13716-IgG4 (S228P) (K−)/kappa, αFXI-13716-IgG4 (S228P) Q1E M103L(K−)/kappa, and αFXI-13654p-IgG4 (S228P) (K−)/kappa antibodies were evaluated in assays performed as described above. The results revealed that the anti-FXI antibodies did not inhibit the catalytic activity of FXIa.

The results in this example when viewed with the results obtained in Example 5 suggest that the mechanism of action for the anti-FXI antibodies is the inhibition of FXIIa conversion of FXI to FXIa in the presence of HMW kininogen and not the inhibition of FXIa activation of FIX to FIXa.

Example 7

Surface Plasmon Resonance Assay for Assessment of Off-Target Binding of Anti FXI Monoclonal Antibodies to Human and NHP Coagulation Cascade Proteins.

A surface plasmon resonance (SPR)-based assay (Biacore T200) was used to determine the potential non-specific interaction of the anti-Factor FXI mAbs, αFXI-13654p-IgG4 (S228P) (K−)/kappa and αFXI-13716-IgG4 (S228P) Q1E M103L(K−)/kappa to other human and NHP coagulation cascade proteins (Table 4). Anti-FXI mAbs were captured on a CM5 sensor chip immobilized with anti-human IgG (Fc) capture kit (GE Healthcare) at approximately 500 RU to minimize potential background from co-purifying Igs in plasma derived proteins. Negative control antibody, anti-respiratory syncytial virus (RSV) monoclonal antibody (mAb) (lot 23AFE), was used as a reference and to help reduce background binding of plasma-derived proteins. Binding kinetics was measured using an analyte concentration of FXI at 5 nM; all other coagulation cascade proteins were used at an analyte concentration of 500 nM. Single concentration injections (n=2) were run at 30 μL/min, 25° C., HBS-EP+, pH 7.4.

TABLE 4

Recombinant and Plasma Derived Human and NHP Coagulation Cascade Proteins

| Lot No./Catalogue No. | Vendor | Common Name | Description |
| --- | --- | --- | --- |
| 00AJF | Merck | Rhesus monkey Kallikrein | Recombinant protein C- terminal His tagged. NCBI Reference Sequence: EHH26351 |
| 65AJE | Merck | Cynomolgus monkey Kallikrein | Recombinant protein C- terminal His tagged NCBI Reference Sequence: XP_005556538.1 |
| 97AJY/HPK1302 | Enzyme Research Laboratories | Human Prekallikrein | Isolated from human plasma |
| 98AJY/HPKa 1303 | Enzyme Research Laboratories | Human Kallikrein | Isolated from human plasma |
| 41AHG HCP-0010 | Haematologic Technologies Inc. | Human Factor II (Prothrombin) | Isolated from human plasma |
| 00AJZ/HT1002a | Enzyme Research Laboratories | Human Factor II (α-thrombin) | Isolated from human plasma |
| 01AJZ/HFVII 1007 | Enzyme Research Laboratories | Human Factor VII | Isolated from human plasma |
| 03AJZ HFVIIa 4422 | Enzyme Research Laboratories | Human Factor VIIa Protease | Isolated from human plasma |
| 13AJZ/HFIX1009 | Enzyme Research Laboratories | Human Factor IX | Isolated from human plasma |
| 14AJZ/HFIXa 1080 | Enzyme Research Laboratories | Human Factor IXa Protease | Isolated from human plasma |
| 15AJZ/HFX1010 | Enzyme Research Laboratories | Human Factor X | Isolated from human plasma |
| 18AJZ/HFXa 1011 | Enzyme Research Laboratories | Human Factor Xa Protease | Isolated from human plasma |
| 19AJZ/HFXII 1212 | Enzyme Research Laboratories | Human Factor XII | Isolated from human plasma |
| 20AJZ/HFXII 1212a | Enzyme Research Laboratories | Human Factor XIIa Protease | Isolated from human plasma |
| 23AIR/HCXI-0150-C | Haematologic Technologies Inc. | Human FXI | Isolated from human plasma |
| 82AJK/2460-SE | R&D | Human FXI-His tagged | Recombinant protein C- terminal His tagged. Mouse myeloma cell line, NS0 derived. NCBI Reference PO3951. |
| 62AJE | Merck | Rhesus FXI-His (CP, Recomb) | Recombinant protein C- terminal His tagged. NCBI Reference Sequence: EHH26352 |

TABLE 4-continued

Recombinant and Plasma Derived Human and NHP Coagulation Cascade Proteins

| Lot No./ Catalogue No. | Vendor | Common Name | Description |
|---|---|---|---|
| 73AIH | Merck | Cyno FXI-His (CP, Recomb) | Recombinant protein C-terminal His tagged NCBI Reference Sequence: XP_005556540 |
| 23AFE | Merck | Anti-RSV mAb IgG4 | SEQ ID NO: 71 (LC) and SEQ ID NO: 72 (HC) |

Figure 16:
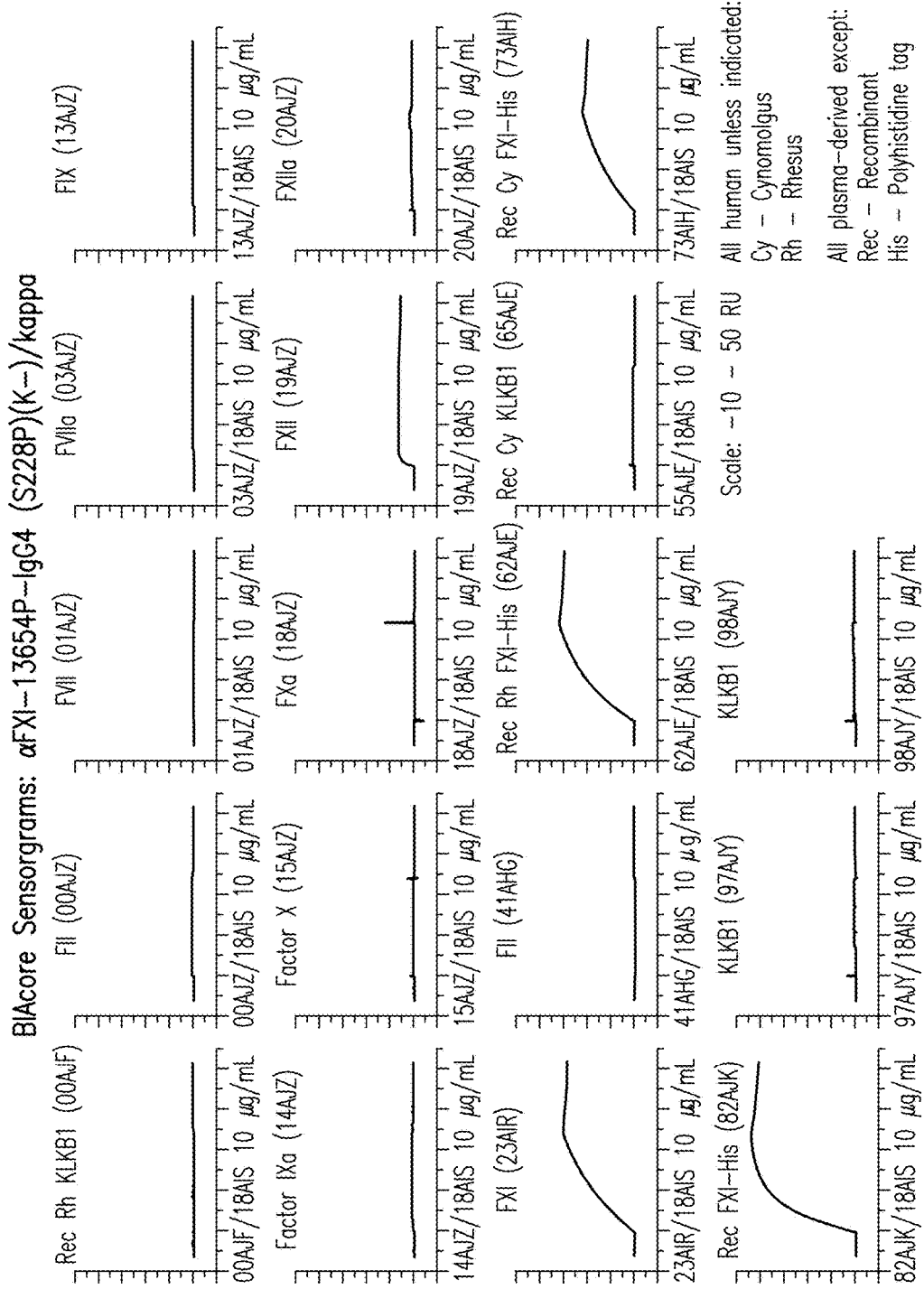
FIG. 16 shows BIAcore Sensorgrams that show the kinetics of binding of αFXI-13654p-IgG4 (S228P) (K−)/kappa to human, cynomolgus and rhesus monkey FXI and other human and NHP coagulation cascade proteins.
Figure 17:
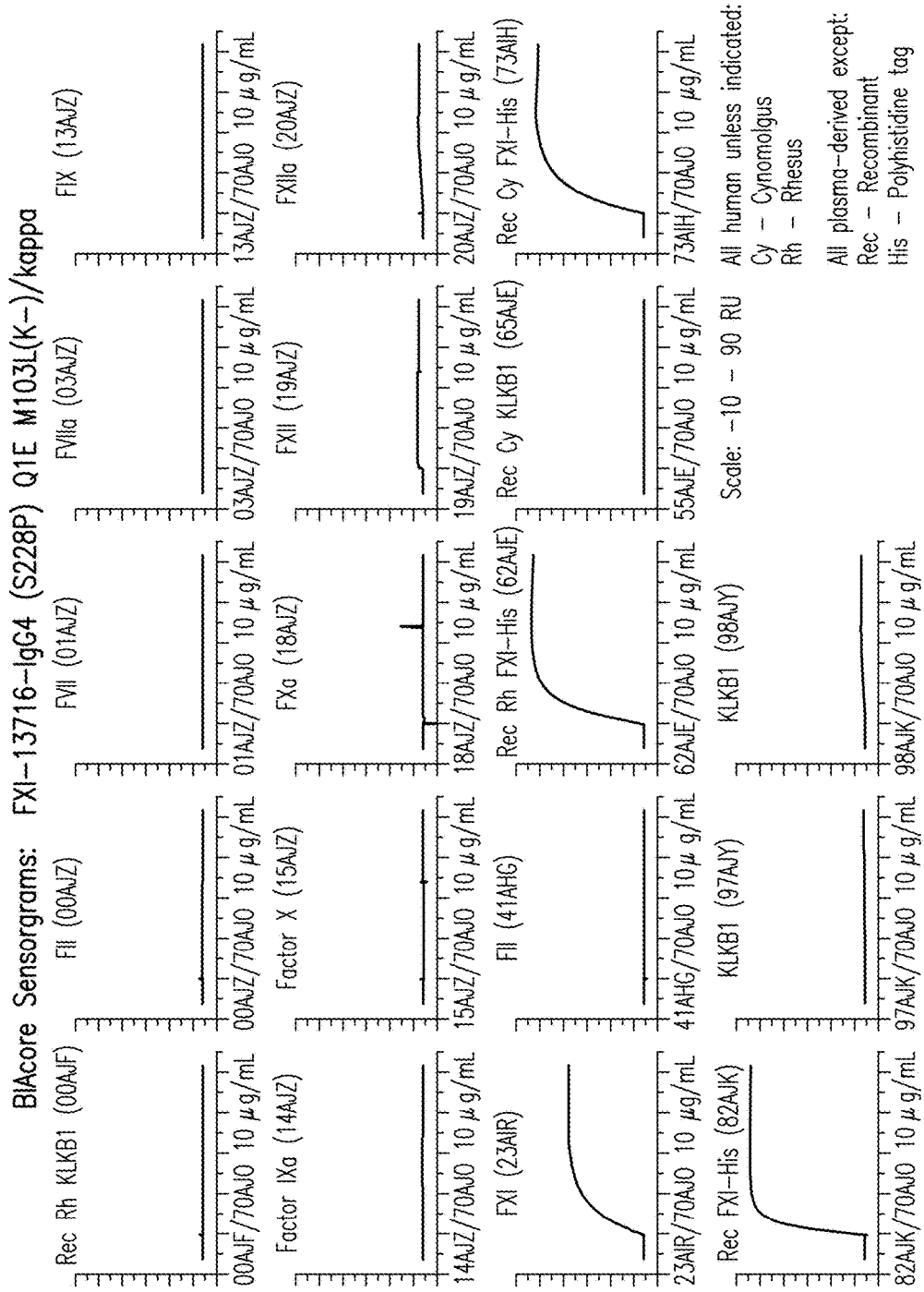
FIG. 17 shows BIAcore Sensorgrams that show the kinetics of binding of αFXI-13716-IgG4 (S228P) Q1E M103L (K−)/kappa to human, cynomolgus and rhesus monkey FXI and other human and NHP coagulation cascade proteins.

The kinetics of binding of the anti-Factor FXI mAbs, αFXI-13654p-IgG4 (S228P) (K−)/kappa and αFXI-13716-IgG4 (S228P) Q1E M103L(K−)/kappa to human, cynomolgus, and rhesus monkey FXI, and other human and NHP coagulation cascade proteins was measured as described above and are shown in FIG. 16 and FIG. 17. Biacore T200 evaluation software was used to fit data to a 1:1 binding model to determine the association rate constant, ka ($M^{-1}$ $s^{-1}$, where "M" equals molar and "s" equals seconds) and the dissociation rate constant, $k_d$ ($s^{-1}$). These rate constants were used to calculate the equilibrium dissociation constant, KD (M).

αFXI-13654p-IgG4 (S228P) (K−)/kappa and αFXI-13716-IgG4 (S228P) Q1E M103L(K−)/kappa captured on chip showed no cross-reactivity against non-FXI coagulation cascade proteins (FIG. 16 and FIG. 17). These monoclonal antibodies showed expected levels of strong binding to human and cynomolgus (and Rhesus) FXI proteins.

Example 8

Cynomolgus Monkey Femoral Arteriovenous (AV) Shunt Thrombosis Model.

The antithrombotic efficacy of αFXI-13716-IgG4 (S228P) Q1E M103L(K−)/kappa was characterized in vivo in a cynomolgus monkey femoral arteriovenous (AV) shunt model developed at the Merck Research Laboratories.

Figure 18:
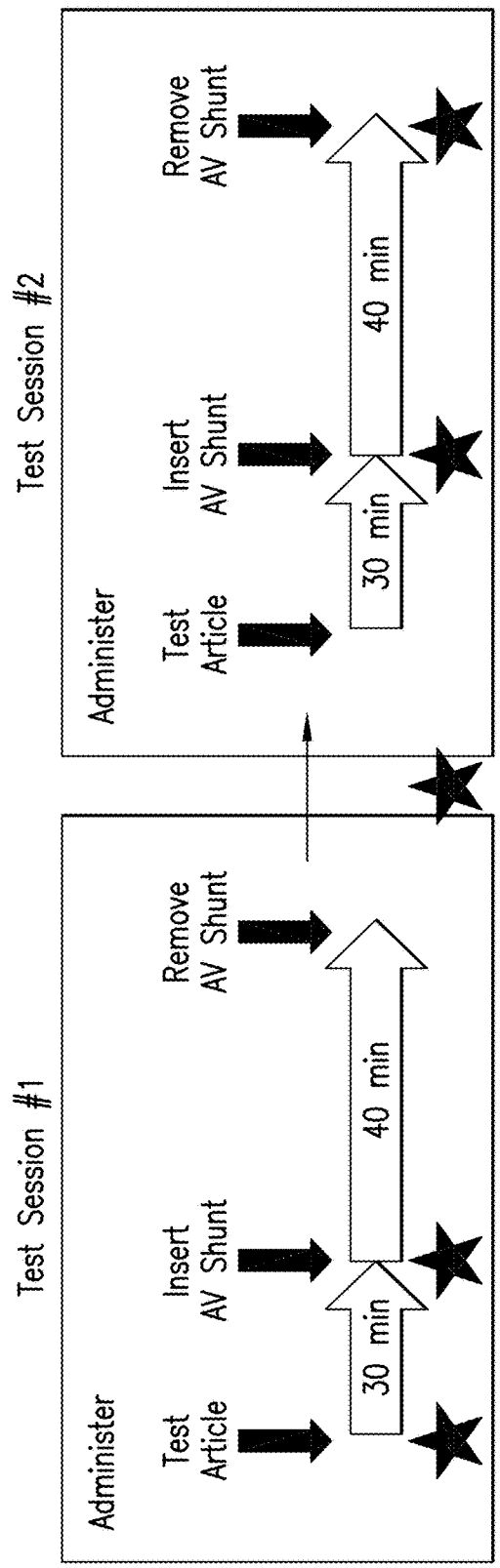
FIG. 18 shows a schematic of the cynomolgus monkey AV shunt test paradigm. Anesthetized monkeys previously instrumented with femoral arterial and venous catheters were administered vehicle or αFXI-13716-IgG4 (S228P) Q1E M103L (K−)/kappa (0.01-1.0 mg/kg) by intravenous bolus (Test Article Administration). An AV shunt was inserted as described in the text (Insert AV shunt). Blood flowed through the AV shunt for 40 minutes. Contact between blood and the silk thread suspended inside of the tubing caused a clot to form. The clots were weighed as described in the text. Blood samples were obtained to measure circulating levels of αFXI-13716-IgG4 (S228P) Q1E M103L (K−)/kappa, aPTT and PT (stars).
Figure 19A:
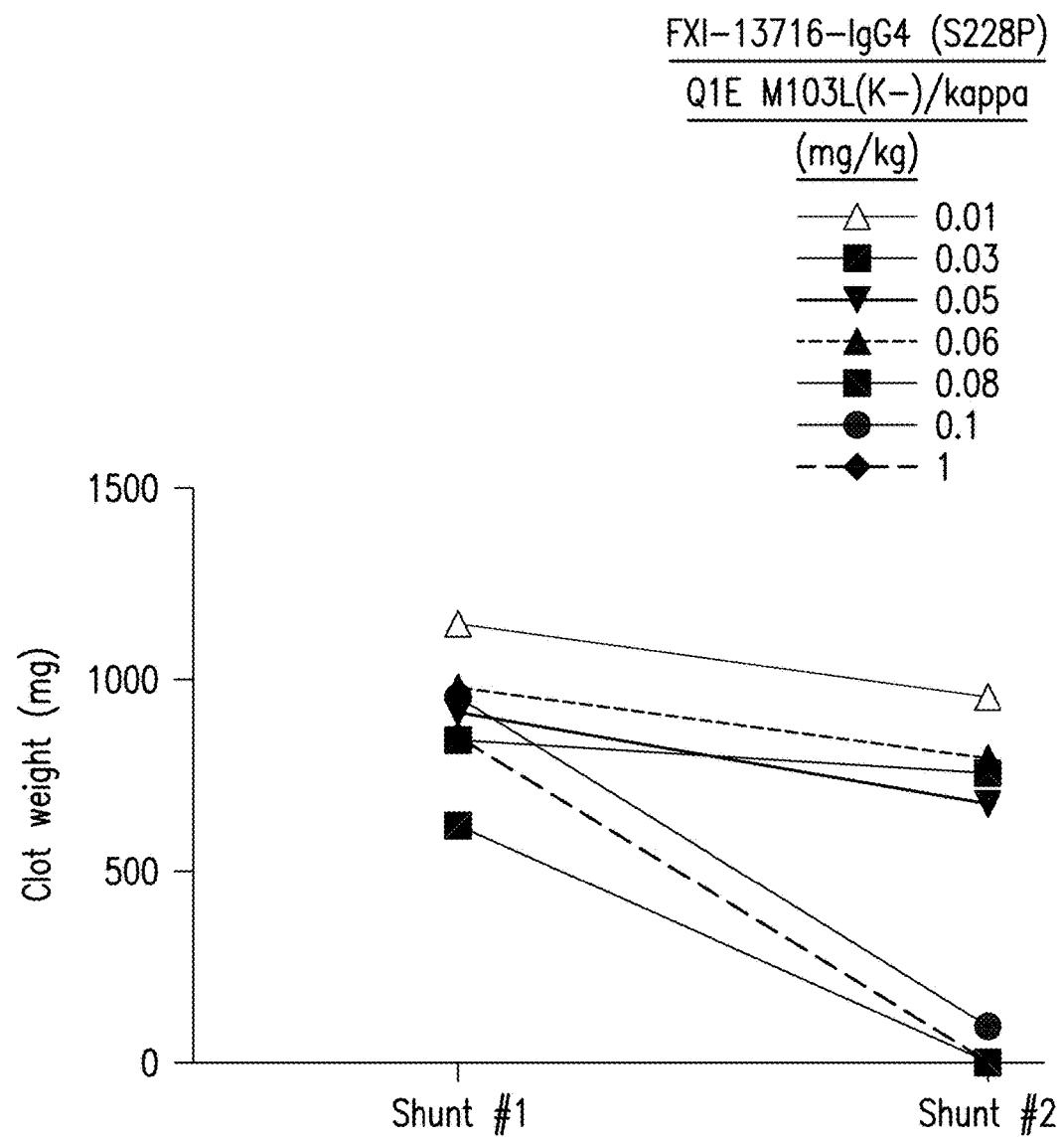
FIG. 19A-D show the effects of αFXI-13716-IgG4 (S228P) Q1E M103L (K−)/kappa on AV shunt clot formation, aPTT and prothrombin time (PT) in the cynomolgus monkey AV shunt model.
Figure 19B:
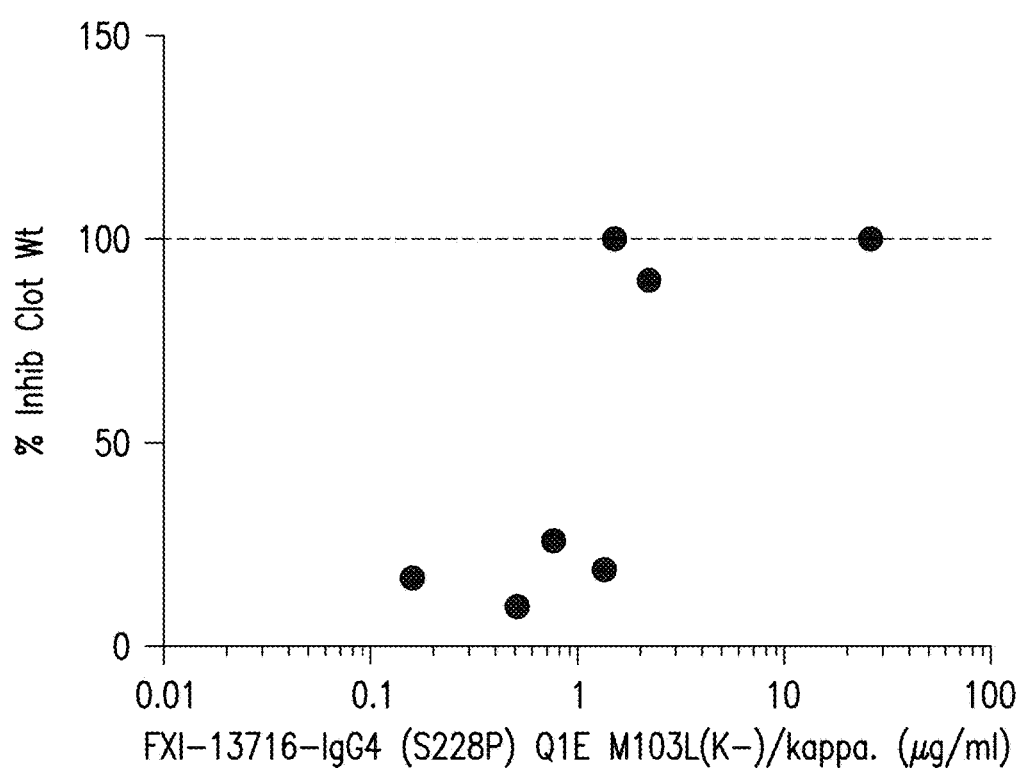
Figure 19C:
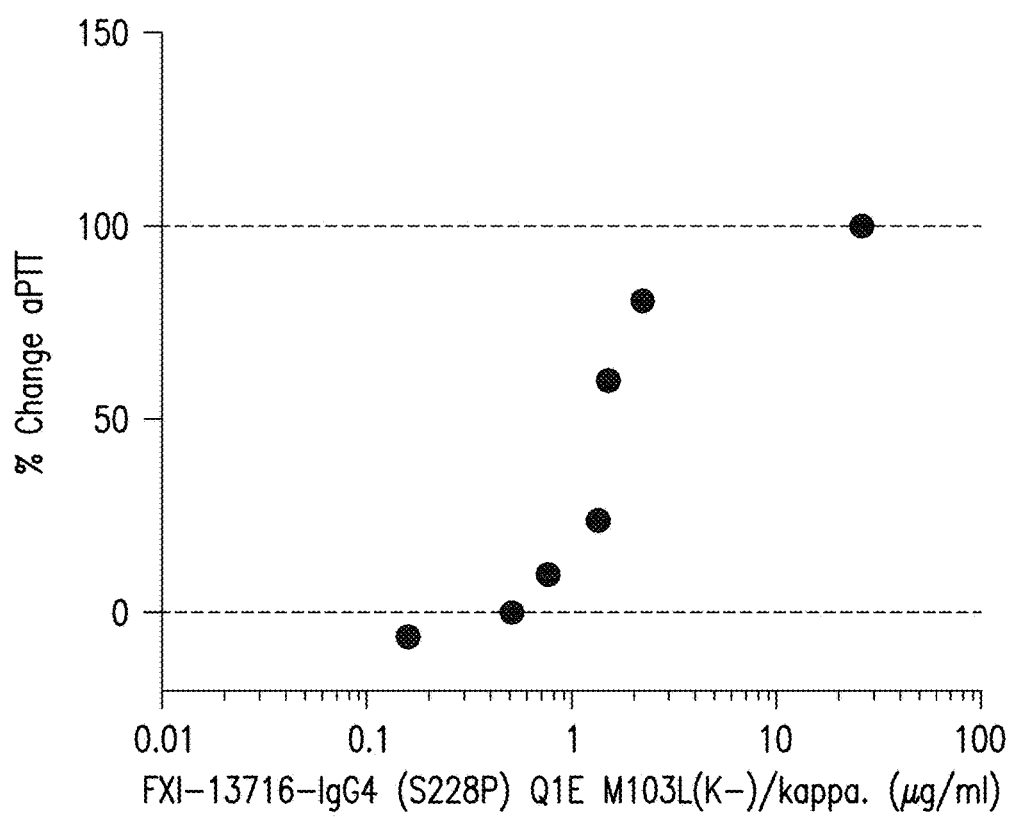
Figure 19D:
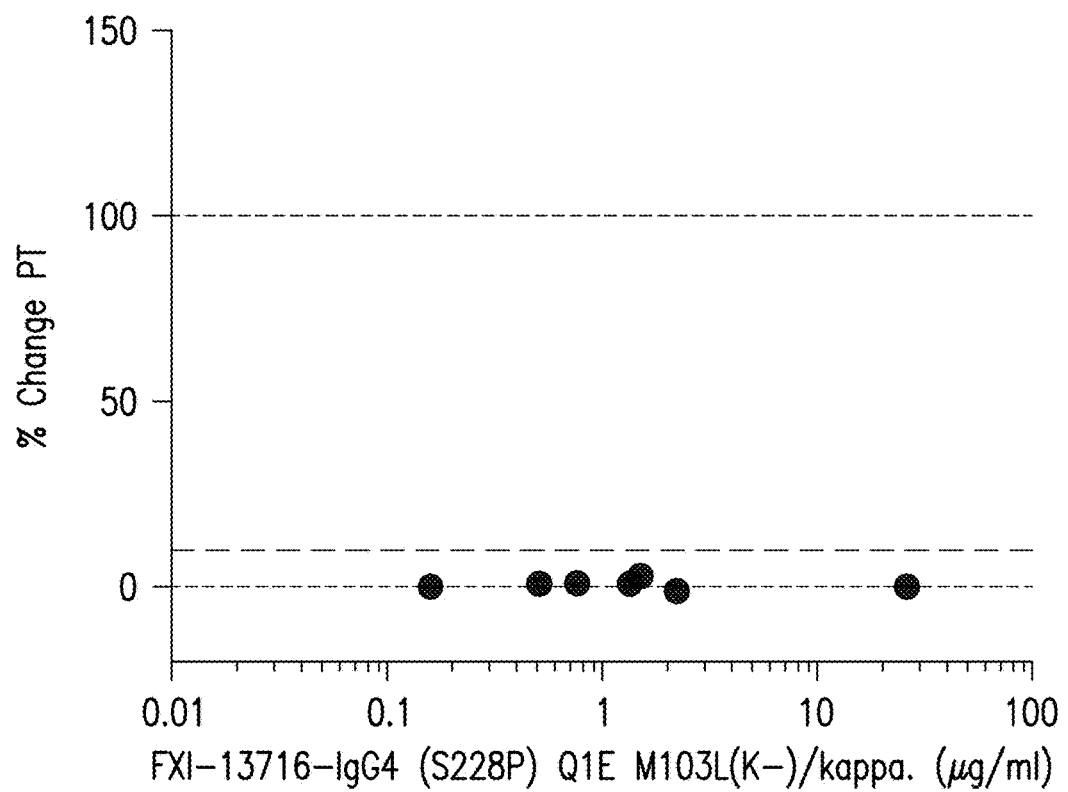

Study Design:

These studies used a repeated design where each animal received 2 shunts over 2 consecutive test periods (See FIG. 18). The monkeys were administered non-compound containing vehicle (20 mM sodium acetate, 9% sucrose, pH 5.5) or αFXI-13716-IgG4 (S228P) Q1E M103L(K−)/kappa (dose range 0.01 to 1.0 mg/kg), during the first and second test periods, respectively. The difference between the clot weight measured during the first (vehicle) and second (αFXI-13716-IgG4 (S228P) Q1E M103L(K−)/kappa) test sessions determined the antithrombotic efficacy. That is, a greater decrease in clot weight during αFXI-13716-IgG4 (S228P) Q1E M103L(K−)/kappa versus vehicle exposure would indicate greater antithrombotic effect. The use of the repeated paired design described above allows for a within animal pre-treatment vs. post-treatment assessment of antithrombotic efficacy.

AV Shunt Placement Procedure Details:

To execute this model, anesthetized cynomolgus monkeys were instrumented with femoral arterial and venous catheters. These catheters enabled the insertion and removal of an AV shunt. The AV shunts were composed of tygon tubing with a piece of silk suture threaded through and suspended across the opening in the tube. To place the AV shunt, both arterial and venous catheters were closed to stop the blood flow. An AV shunt was then placed between the two catheters. The timing of catheter placement and removal is indicated in FIG. 18. Once the shunt was in place, the catheters were opened and blood flowed through the shunt circuit contacting the silk suture. The action of blood contacting the suture promoted clot formation. The AV shunt remained in place for 40 minutes. To remove the AV shunt, both arterial and venous catheters were closed to stop the blood flow through the AV shunt. Then, the shunt was removed and cut open to access the silk suture and blood clot. The blood clot was weighed. The data is reported as the net clot weight which is defined as the total clot weight minus silk suture weight.

The coagulation biomarkers activated partial thromboplastin time (aPTT) and prothrombin time (PT) as well as circulating plasma levels of αFXI-13716-IgG4 (S228P) Q1E M103Lv/kappa were measured from blood samples collected throughout the experiment as depicted in FIG. 18. aPTT and PT were measured from thawed frozen (−80° C.) citrated plasma collected from cynomolgus monkeys using the Sta Compact Max coagulation analyzer (Stago Diagnostic, Inc). The Stago analyzer measures the time of clot formation using an electro-magnetic mechanical clot detection system. For the aPTT assay fifty microliters of plasma was mixed with 50 μL of ellagic acid mixture (APTT-XL, Pacific Hemostasis; Fisher Diagnostics cat #10-0402) at 37° C. for 3 minutes. Fifty microliters of 0.025 M Calcium Chloride (Sta—CaCl2 0.025 M, Stago Diagnostic, Inc., cat#00367) was added to the mixture, and the time to clot formation was measured. For the PT assay fifty microliters of plasma was incubated at 37° C. for 4 minutes. The timing for clot formation was initiated by adding 100 μL of thromboplastin reagent (Neoplastine C1 Plus 10, Stago Diagnostic, Inc., cat#00667). Plasma [αFXI-13716-IgG4 (S228P) Q1E M103L/kappa] was measured as follows. An electrochemiluminescence-based generic hIgG4 immunoassay was used to quantify αFXI-13716-IgG4 (S228P) Q1E M103L (K−)/kappa in cynomolgus monkey plasma. The assay was established with biotinylated goat anti-human IgG(H+L) from Bethyl (cat# A80-319B) as capture reagent, and sulfoTAG labeled mouse anti-human IgG (Fc specific) from Southern Biotech (cat#9190-01) for detection reagent. This assay was qualified and the lower limit of quantification of the assay was determined to be 40 ng/mL with minimum required dilution of 100.

Results:

FIGS. 19A-D summarize the effects of αFXI-13716-IgG4 (S228P) Q1E M103L(K−)/kappa administration on thrombus formation (FIG. 19A, FIG. 19B), aPTT (FIG. 19C) and PT (FIG. 19D). αFXI-13716-IgG4 (S228P) Q1E M103L (K−)/kappa displayed a dose- and plasma concentration-dependent decrease in clot weight with complete efficacy (90-100% clot reduction) observed at plasma [αFXI-13716-IgG4 (S228P) Q1E M103L(K−)/kappa] of >1.5 μg/mL (about 10 nM). αFXI-13716-IgG4 (S228P) Q1E M103L (K−)/kappa displayed a dose- and plasma concentration-dependent increase in aPTT. Plasma concentrations of 26 µg/mL (~180 nM) αFXI-13716-IgG4 (S228P) Q1E M103L (K−)/kappa yielded an approximate 100% increase in aPTT, while 1.5 µg/mL (~10 nM) αFXI-13716-IgG4 (S228P) Q1E M103L(K−)/kappa resulted in an approximate 60% increase in aPTT. Unlike aPTT, PT changed <10% across the concentrations of αFXI-13716-IgG4 (S228P) Q1E M103L (K−)/kappa evaluated, consistent with a selective effect of FXI inhibition on the intrinsic coagulation pathway.

Example 9

Cynomolgus Monkey Template Bleeding Time Model.

The bleeding propensity of the anti-FXI mAb αFXI-13716-IgG4 (S228P) Q1E M103L(K−)/kappa was characterized in vivo in a cynomolgus monkey template bleeding time model developed at the Merck Research Laboratories. This model has been used previously to demonstrate significant increases in template bleeding times at multiple anatomic sites with triple antiplatelet therapy (Cai et al., Eur J Pharmacol 758: 107-114 (2015)).

To execute this model, template bleeding times were determined using spring-loaded lancets on the buccal mucosa (inner lip), finger pad and distal tail at varying time points to induce bleeding.

Bleeding Time Test:

The bleeding time test was performed in anesthetized cynomolgus monkeys as follows. Each test region (buccal mucosa, finger pad or distal tail) was carefully examined to identify a suitable incision site for bleeding inducement. To induce bleeding, a spring-loaded lancet was placed firmly against the selected test site and activated to cause a uniform linear incision. The lancet specifications determined the incision dimensions. Blood from the incision site was allowed to flow freely and was monitored until the bleeding stopped for 30 continuous seconds. This defined the bleeding time (BT). The BT was recorded for each BT site. During the BT determinations, the distal tail incision site was superfused with warm sterile lactated Ringers solution, and the finger pad site was immersed in warm sterile lactated Ringers. Applying lactated ringers improved the ability to see blood flow for these sites.

Figure 20:
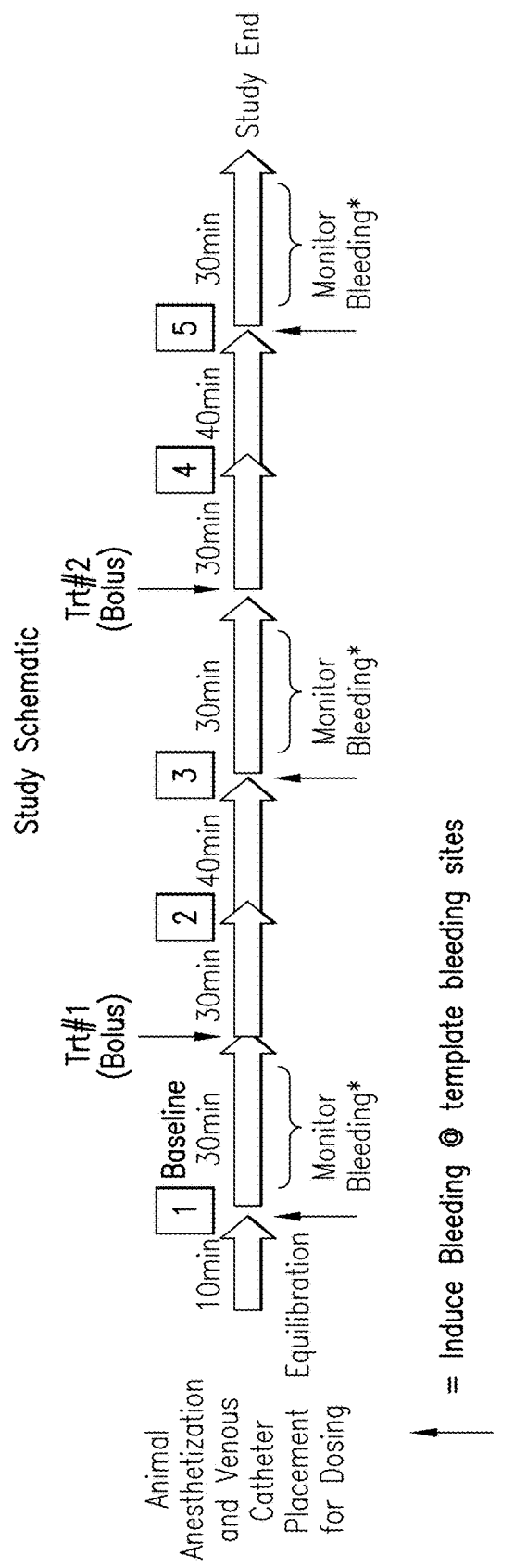
FIG. 20 shows a schematic of the cynomolgus monkey template bleeding time paradigm.
Figure 21A:
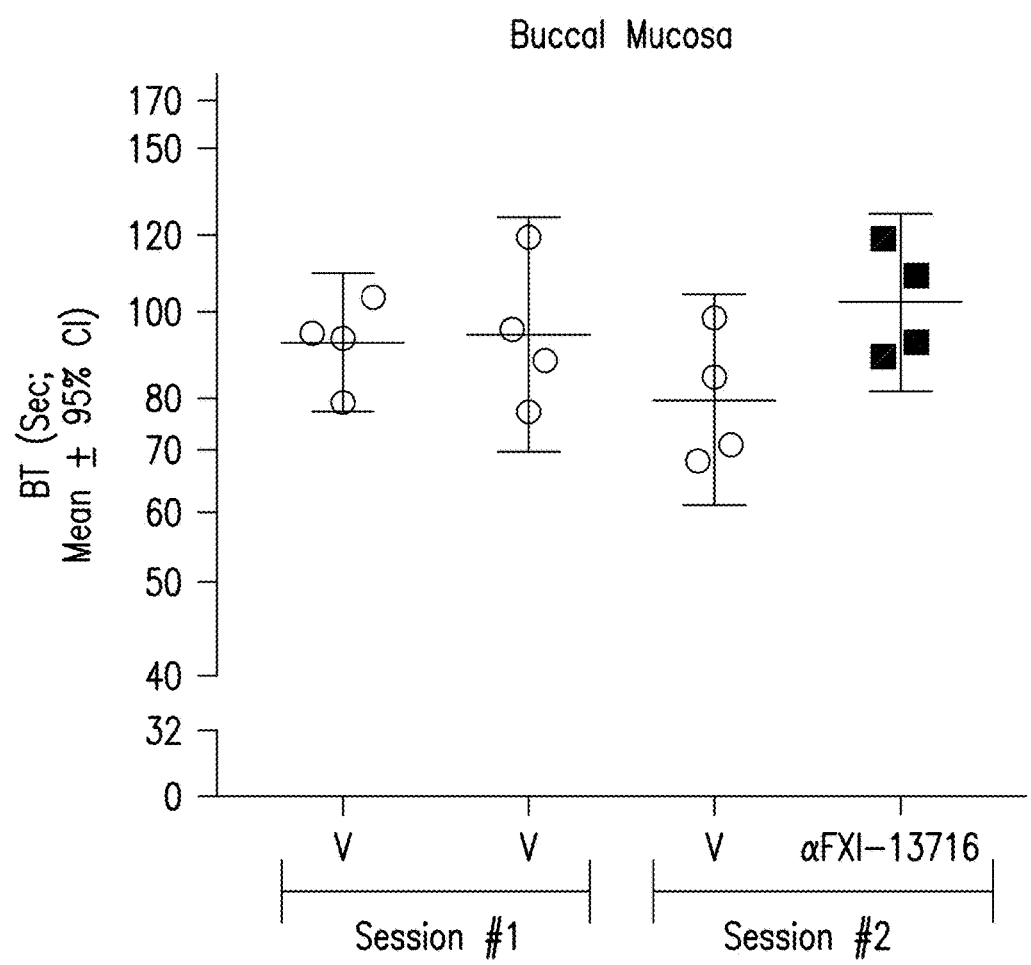
FIG. 21A-F show the effects of αFXI-13716-IgG4 (S228P) Q1E M103L (K–)/kappa on template bleeding time (BT) in seconds measured in cynomolgus monkeys. Template bleeding times were measured in the buccal mucosal (FIG. 21A, FIG. 21D), finger pad (FIG. 21B, FIG. 21E) and distal tail (FIG. 21C, FIG. 21F). Treatment effects (αFXI-13716-IgG4 (S228P) Q1E M103L(K–)/kappa vs. vehicle) on bleeding times were assessed by comparing absolute bleeding times (FIGS. 21A-C) and percentage changes in bleeding times (FIGS. 21D-F), with vehicle-vehicle as Treatments #1 and 2 in study session #1, and vehicle-αFXI-13716-IgG4 (S228P) Q1E M103L(K–)/kappa as Treatments #1 and #2 in study session #2, using a one-tailed paired Students t-test. In the Figs., αFXI-13716-IgG4 (S228P) Q1E M103L (K–)/kappa is indicated by αFXI-13716.
Figure 21B:
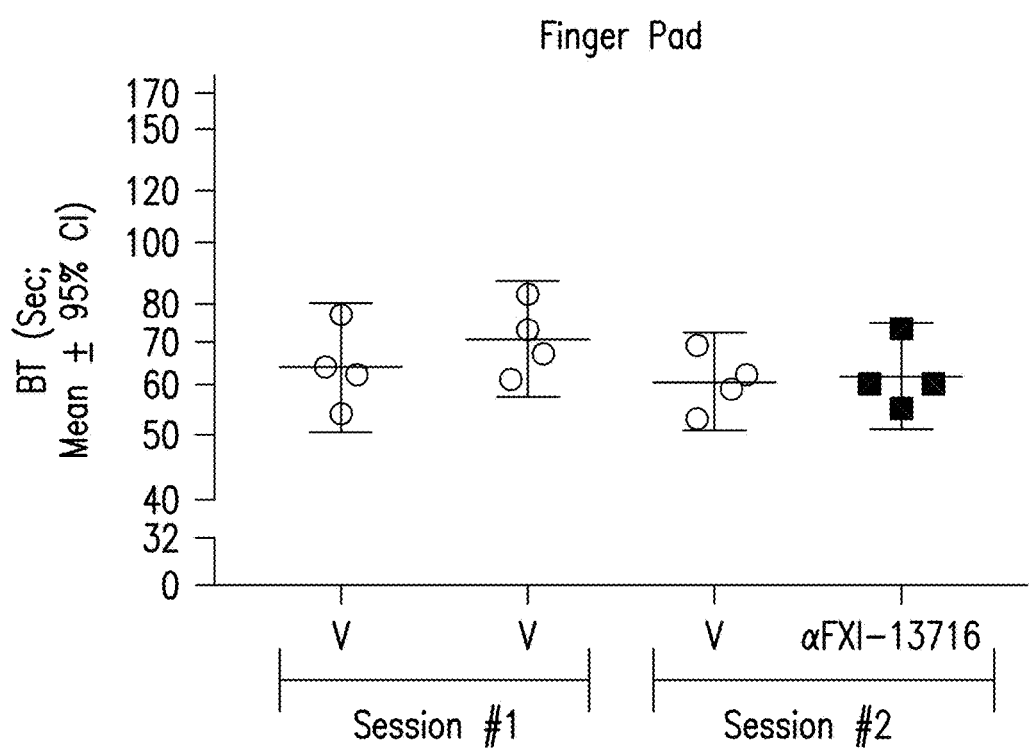
Figure 21C:
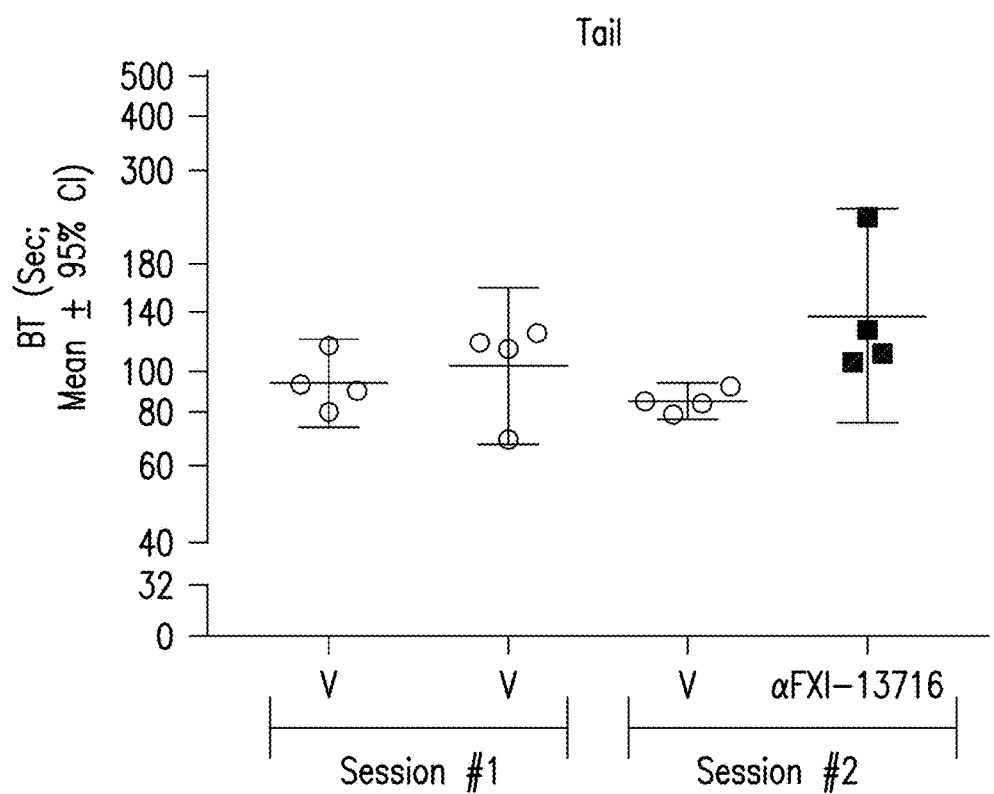
Figure 21D:
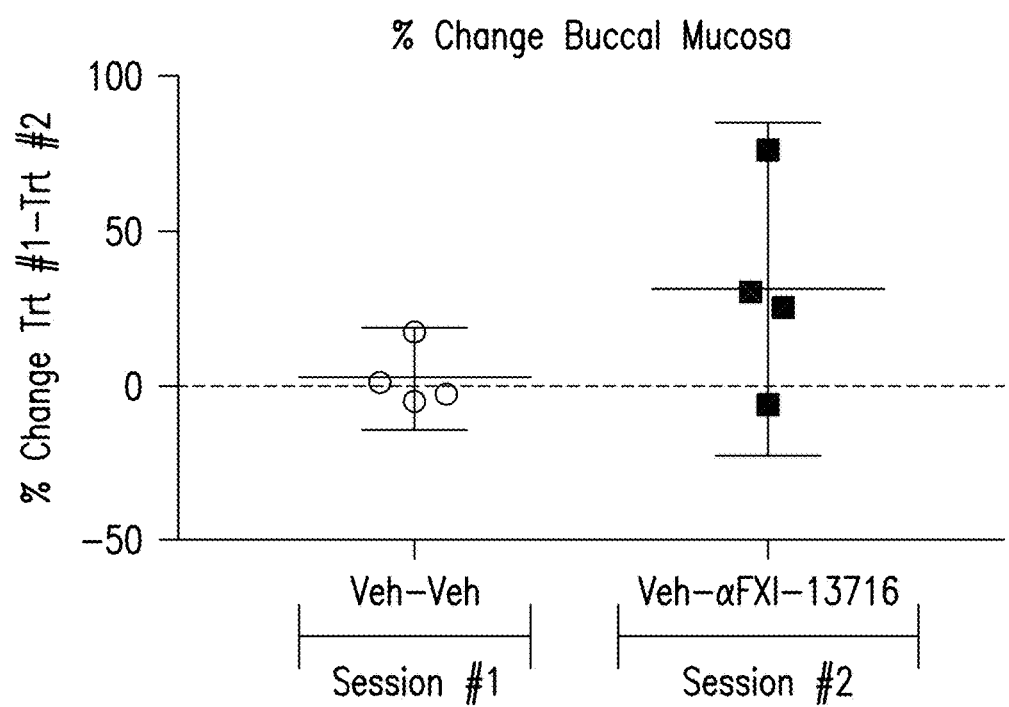
Figure 21E:
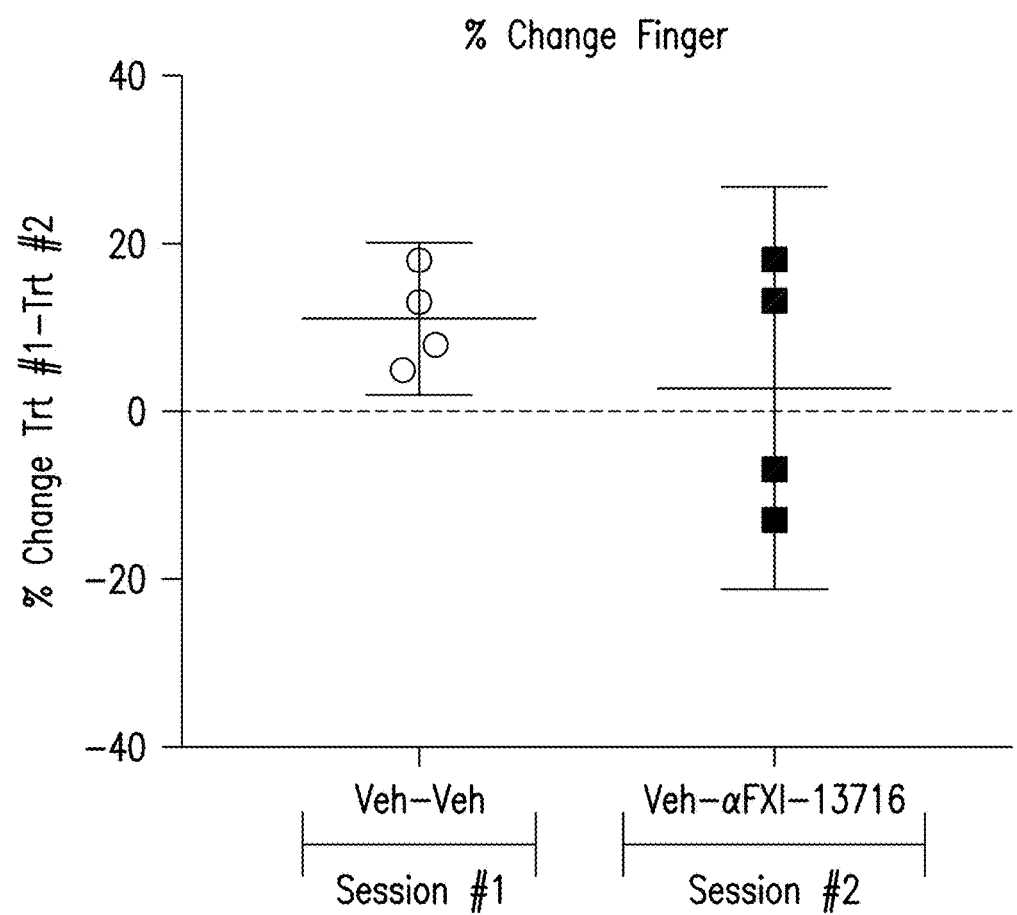
Figure 21F:
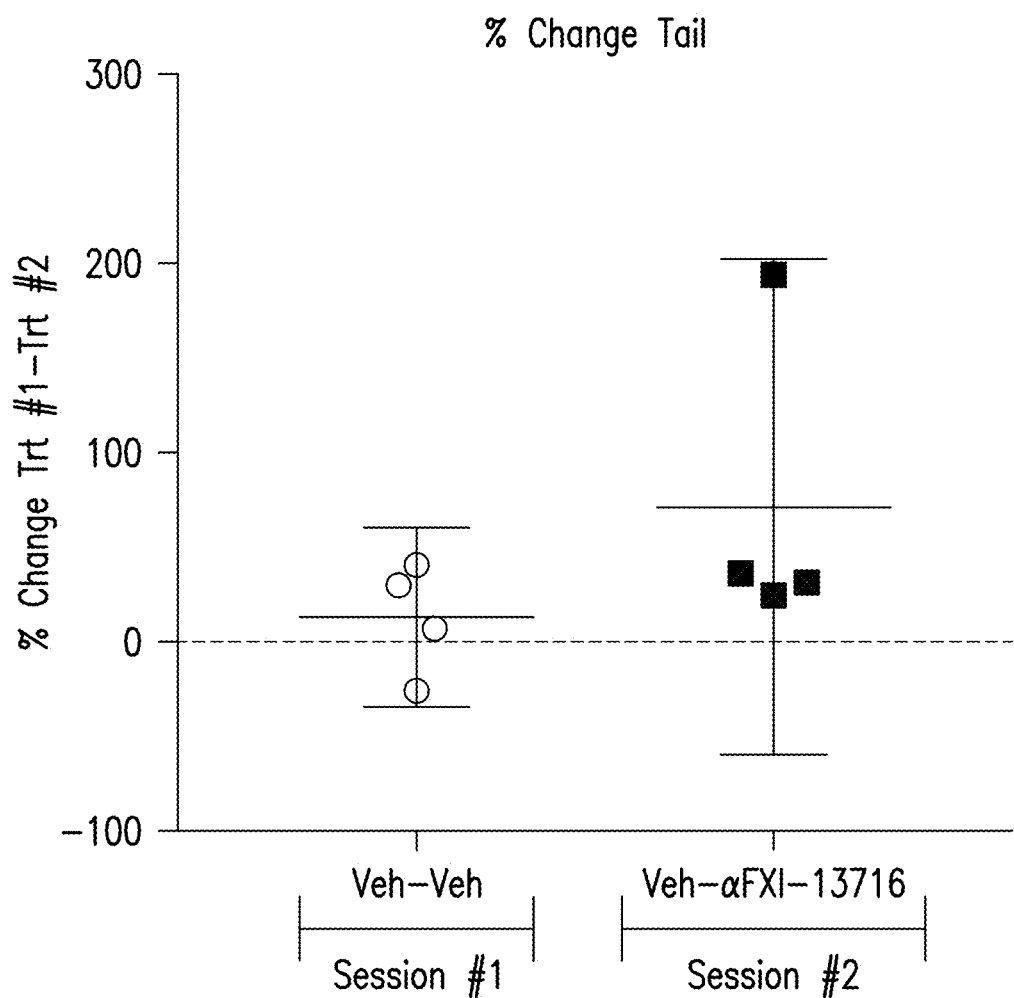

Study Design:

Each study was comprised of three 30 minute template bleeding time tests (BT) at the three test regions (See FIG. 20). The first BT determined Baseline bleeding. The second BT occurred 70 minutes after a 3 minute IV infusion (2.83 mL/kg) of non-compound containing vehicle (20 mM sodium acetate, 9% sucrose, pH 5.5) (Treatment #1). The third BT occurred 70 minutes after a 3 minute IV infusion (2.83 mL/kg) of non-compound containing vehicle or αFXI-13716-IgG4 (S228P) Q1E M103L(K−)/kappa (17 mg/kg) (Treatment #2). Bleeding was monitored and bleeding time recorded as described above. The time when bleeding stopped was recorded for each site. Periodic blood samples were collected to determine circulating plasma levels of αFXI-13716-IgG4 (S228P) Q1E M103L(K−)/kappa, aPTT and PT.

Each test animal had two study sessions. In study session #1, vehicle followed by vehicle constituted Treatment #1 and Treatment #2, respectively. In study session #2, vehicle followed by 17 mg/kg IV αFXI-13716-IgG4 (S228P) Q1E M103L(K−)/kappa constituted Treatment #1 and Treatment #2, respectively.

The 70 minute time period between the end of the test article infusion and initiation of bleeding time assessments mirrored the timing in the AV shunt model for thrombus mass determination (shunt placement 30 min post treatment+40 min blood flow through the shunt). The 17 mg/kg IV test dose of αFXI-13716-IgG4 (S228P) Q1E M103L (K−)/kappa was estimated to achieve 10× the projected human $C_{max}$ αFXI-13716-IgG4 (S228P) Q1E M103L(K−)/kappa based on the PK/PD primate modeling studies described previously.

The coagulation biomarkers activated partial thromboplastin time (aPTT) and prothrombin time (PT) as well as circulating plasma levels of αFXI-13716-IgG4 (S228P) Q1E M103L(K−)/kappa were measured from blood samples collected throughout the experiment as depicted in FIG. 20. aPTT and PT were measured from thawed frozen (−80° C.) citrated plasma collected from the animals using the Sta-R Evolution coagulation analyzer (Stago Diagnostic, Inc). The coagulation analyzer measures the time to clot formation using an electro-magnetic mechanical clot detection system. For the aPTT assay, the analyzer mixes 50 µL of plasma with 50 µL of ellagic acid (APTT-XL, Pacific Hemostasis; Fisher Diagnostics cat #10-0402) in a cuvette which is then incubated at 37° C. for 3 minutes. 50 µL of 0.025M Calcium Chloride (Sta—$CaCl_2$ 0.025 M, Stago Diagnostic, Inc., cat#00367) is then added to the mixture to initiate clotting, and the time to clot formation measured. For the PT assay, 50 µL of plasma was incubated in a cuvette at 37° C. for 4 minutes; clotting was initiated by adding 100 µL of solubilized thromboplastin reagent (Triniclot PT Excel, TCoag, Inc., cat# T1106). Plasma [αFXI-13716-IgG4 (S228P) Q1E M103L(K−)/kappa] was measured as follows. An electrochemiluminescence-based generic hIgG4 immunoassay was used to quantify αFXI-13716-IgG4 (S228P) Q1E M103L (K−)/kappa in cynomolgus monkey plasma. The assay was established with biotinylated goat anti-human IgG(H+L) from Bethyl (cat# A80-319B) as capture reagent, and sulfoTAG labeled mouse anti-human IgG (Fc specific) from Southern Biotech (cat#9190-01) for detection reagent. This assay was qualified and the lower limit of quantification of the assay was determined to be 40 ng/mL with minimum required dilution of 100.

Results:

FIG. 21 summarizes the effects of vehicle and 17 mg/kg IV αFXI-13716-IgG4 (S228P) Q1E M103L(K−)/kappa administration in four cynomolgus monkeys on buccal mucosa (FIG. 21A, FIG. 21 D), finger pad (FIG. 21B, FIG. 21E) and distal tail (FIG. 21C, FIG. 21F) template bleeding times. Effects on bleeding times were assessed by comparing absolute bleeding times (FIGS. 21A-C) and percentage changes in bleeding times (FIGS. 21D-F) with vehicle-vehicle as Treatments #1 and 2 in study session #1, and vehicle-αFXI-13716-IgG4 (S228P) Q1E M103L(K−)/kappa as Treatments #1 and #2 in study session #2. Comparisons of both vehicle vs. αFXI-13716-IgG4 (S228P) Q1E M103L (K−)/kappa absolute bleeding times as well as vehicle-vehicle vs. vehicle-αFXI-13716-IgG4 (S228P) Q1E M103L (K−)/kappa percentage changes in bleeding times detected no statistically significant changes in bleeding times at any of the test sites with αFXI-13716-IgG4 (S228P) Q1E M103L(K−)/kappa administration at this test dose, albeit with non-significant trends in buccal mucosa and distal tail bleeding driven by one animal each at each test site.

The plasma concentration of αFXI-13716-IgG4 (S228P) Q1E M103L(K−)/kappa achieved with the 17 mg/kg IV test dose in the cynomolgus bleeding time study 419±42.4 (mean±SEM) µg/mL (~2807 nM). Plasma aPTT values were 32.7±1.1 sec at baseline vs. 68.6±3.2 sec following 17 mg/kg IV αFXI-13716-IgG4 (S228P) Q1E M103L(K−)/ kappa (2.1-fold increase). Plasma PT values were 12.4±0.22 sec at baseline vs. 12.8±0.24 sec following 17 mg/kg IV αFXI-13716-IgG4 (S228P) Q1E M103L(K−)/kappa (no appreciable increase was observed).

Example 10

Pharmacokinetic (PK) and Pharmacodynamic (PD) Evaluation of αFXI-13716-IgG4 (S228P) Q1E M103L/Kappa Following Multiple Intravenous Administrations in Rhesus Monkeys.

The PKPD properties of αFXI-13716-IgG4 (S228P) Q1E M103L(K-)/kappa were characterized in vivo in rhesus monkey. The objective was to evaluate the PK properties and to establish a PK/PD relationship after a total of two weekly doses.

Study Design:

Rhesus monkeys (four animals per dose group) were administered (IV) non-compound vehicle (10 mM Sodium Acetate, 9% Sucrose, pH 5.5) or αFXI-13716-IgG4 (S228P) Q1E M103L(K-)/kappa at two dose levels of 3 and 6 mg/kg. The duration of the study was 22 days and 1.5 mL of blood was collected for determination of drug levels and activated partial thromboplastin time (aPTT). The coagulation biomarker (aPTT) and circulating plasma levels of αFXI-13716-IgG4 (S228P) Q1E M103L(K+)/kappa were measured from blood samples collected throughout the experiment as depicted in Table 5.

TABLE 5

Sample Collection Schedule

| Collection Type | Time |
| --- | --- |
| PK | Day -3; Day 0: predose (-1 h) and 30 min, 3 h, 6 h, 24 (Day 1), 48 (Day 2), 96 (Day 4) Day 7: predose and 1 h, 6 h, 24 h (Day 8), 48 h (Day 9), 96 h (Day 11), 168 h (Day 14), 264 h (Day 18) and 528 h(Day 22) post second dose |
| PD (evaluation of aPTT) | Day -3; Day 0: predose (-1 h) and 30 min, 3 h, 6 h, 24 (Day 1), 48 (Day 2), 96 (Day 4) Day 7: predose and 1 h, 6 h, 24 h (Day 8), 48 h (Day 9), 96 h (Day 11), 168 h (Day 14), 264 h (Day 18) and 528 h (Day 22) post second dose | aPTT was measured from thawed frozen (-80° C.) citrated plasma collected from the animals using the Sta-R Evolution coagulation analyzer (Stago Diagnostic, Inc). The coagulation analyzer measures the time to clot-formation using an electro-magnetic mechanical clot detection system. For the aPTT assay, the analyzer mixes 50 μL of plasma with 50 μL of ellagic acid (APTT-XL, Pacific Hemostasis; Fisher Diagnostics cat #10-0402) in a cuvette which is then incubated at 37° C. for 3 minutes. 50 μL of 0.025M Calcium Chloride (Sta—CaCl2 0.025M, Stago Diagnostic, Inc., cat#00367) is then added to the mixture to initiate clotting, and the time to clot-formation measured.

An electrochemiluminescence-based generic human IgG4 (huIgG4) immunoassay was used to quantify αFXI-13716-IgG4 (S228P) Q1E M103L(K-)/kappa in cynomolgus monkey plasma. The assay was established with biotinylated goat anti-human IgG(H+L) from Bethyl (cat# A80-319B) as capture reagent, and sulfoTAG labeled mouse anti-human IgG (Fc specific) from Southern Biotech (cat#9190-01) for detection reagent. This assay was qualified and the lower limit of quantification of the assay was determined to be 40 ng/mL with minimum required dilution of 100.

Individual animal plasma concentration-time data for αFXI-13716-IgG4 (S228P) Q1E M103L (K-)/kappa were analyzed using non-compartmental (NCA) methods (Gabrielsson and Weiner, 2000). All PK parameters were estimated or calculated using Phoenix 32 WinNonlin 6.3 (version 6.3.0.395, Certara L. P. St. Louis, Mo., 2012). Noncompartmental analyses utilized Model 201 (IV). All concentration data and PK parameters were rounded to 3 significant figures. Samples with concentration values below the lower limit of quantitation (<LLOQ) were excluded from PK analysis and mean data calculations. For graphical purposes, values <LLOQ were set to be ½ of the minimal reportable concentration for individual animal concentration-time plots.

A sigmoidal $E_{max}$ response (PK/PD) model was used to characterize the relationship between exposure and aPTT using GraphPad Prism version 7.00 (GraphPad Software Inc). In the model, the $E_{max}$ value corresponds to the maximum increase in aPTT achieved from baseline and the $EC_{50}$ value corresponds to the half-maximal effective concentration. Variability was reported as 95% confidence interval (CI) for the $EC_{50}$ value provided by the software.

Figure 22:
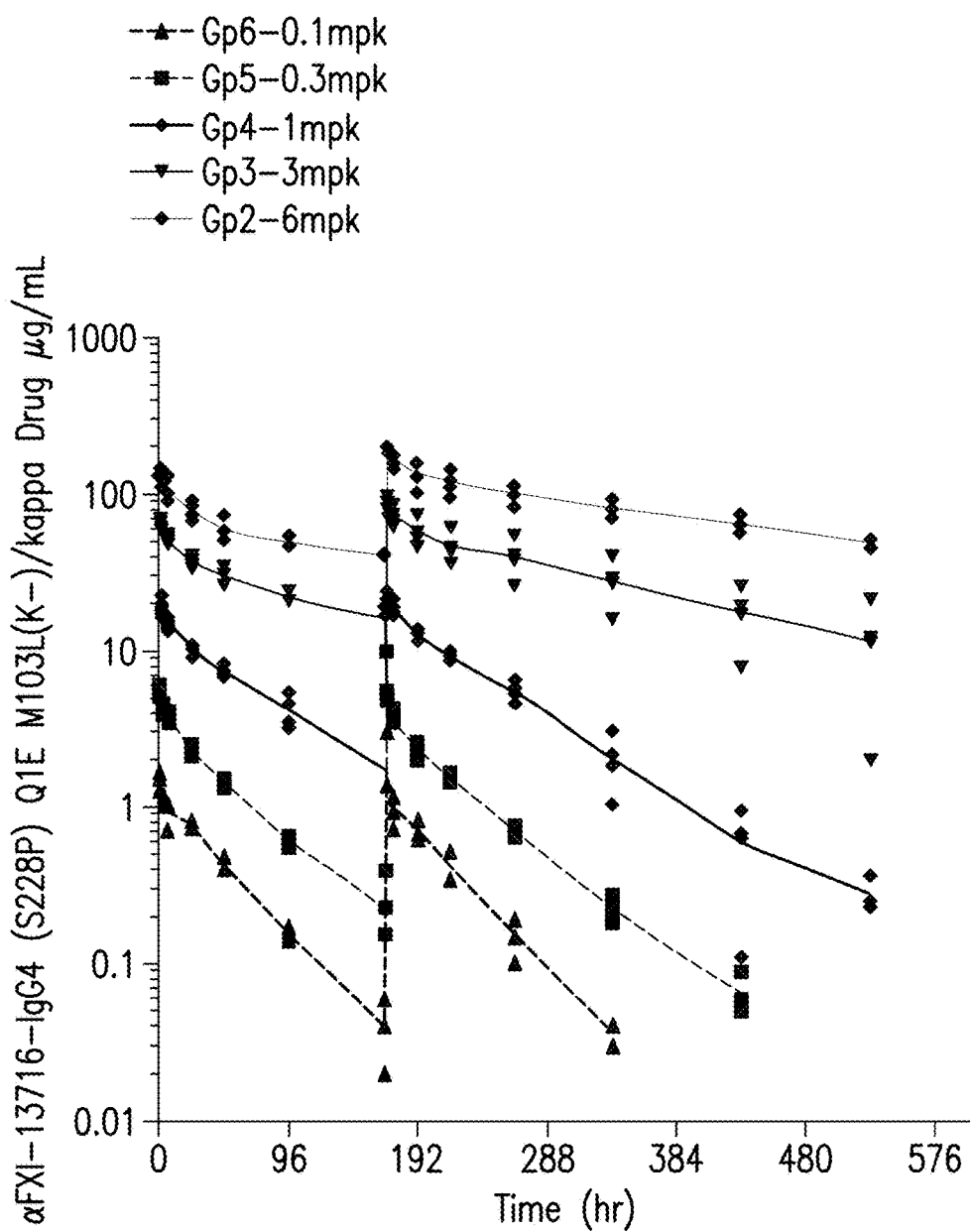
FIG. 22 shows the Concentration-time Profiles following αFXI-13716-IgG4 (S228P) Q1E M103L (K–)/kappa IV administration in Rhesus Monkeys. Plasma concentration-time profiles for αFXI-13716-IgG4 (S228P) Q1E M103L (K–)/kappa in Rhesus monkeys are presented. The data points from individual animals for each dosage are shown: Gp6-0.1 mpk (▲); Gp5-0.3 mpk (■); Gp4-1.0 mpk (◆); Gp3-3.0 mpk (▼); Gp2-6.0 mpk (◆); the lines ━ ━ ━, – – – –, ━━━, ━━━, and ━━━ reflect the group mean for each dosage, respectively. There were 4 animals in each dose groups. hr=hour; y-axis αFXI-13716-IgG4 (S228P) Q1E M103L(K–)/kappa Drug μg/mL.
Figure 23:
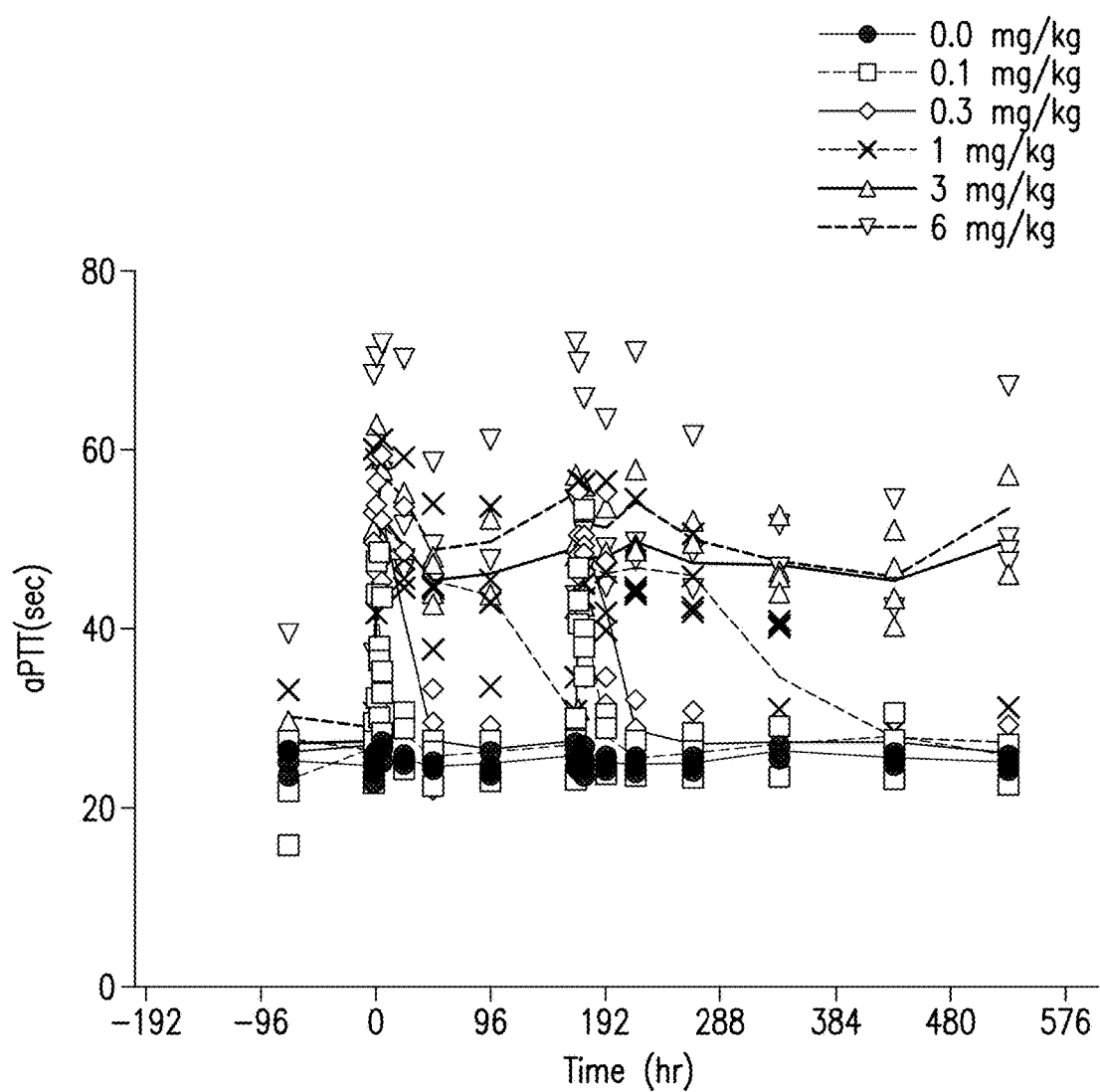
FIG. 23 shows the aPTT-time Profiles in Rhesus Monkey. The aPTT-time profiles for αFXI-13716-IgG4 (S228P) Q1E M103L (K–)/kappa are presented separately for each dose group. There were four animals in each dose group. (y-axis is aPTT (seconds) and X-axis is Time (hours). The lines represent the group mean: (━ ━ ━) 6 mg/kg; (━━━) 3 mg/kg; (– – – –) 1 mg/kg; (━━━) 0.3 mg/kg; (-------) 0.1 kg/mg; and (━━━) 0.0 mg/kg. The individual animal aPTT time profiles for each time point are shown as ∇ (6 mg/kg); Δ (3 mg/kg); X (1 mg/kg); ◇ (0.3 mg/kg); □ (0.1 mg/kg); and ● (0.0 mg/kg).

Results:

The individual concentration-time profiles for αFXI-13716-IgG4 (S228P) Q1E M103L(K-)/kappa are depicted in FIG. 22. Non-linearity was observed for all PK parameters. The mean clearance values decreased from about 40 mL/kg·day for the lowest dose tested (0.1 mg/kg) to about 3 mL/kg·day for the highest dose tested (6 mg/kg). The aPTT concentration-time profiles are depicted in FIG. 23. A dose dependent increase in aPTT was observed. The relationship between plasma concentrations of αFXI-13716-IgG4 (S228P) Q1E M103L(K-)/kappa and aPTT best described by the sigmoidal $E_{max}$ model adequately described this relationship. The estimated $EC_{50}$ value for αFXI-13716-IgG4 (S228P) Q1E M103L(K-)/kappa was about 1.7 ng/mL. Based on the results a therapeutically effective amount may be about 1.0 to 2.0 mg/kg.

TABLE OF SEQUENCES

| SEQ ID NO: | Description | Sequence |
| --- | --- | --- |
| 1 | αFXI-13654p HC-CDR1 | FTFSSYSMN |
| 2 | αFXI-13654p HC-CDR2 | SISSSSSYIYYADSVKG |
| 3 | αFXI-13654p HC-CDR3 | SYYDYDQGYGMDV |

TABLE OF SEQUENCES

| SEQ ID NO: | Description | Sequence |
|---|---|---|
| 4 | αFXI-13654p LC-CDR1 | RASQGISSWLA |
| 5 | αFXI-13654p LC-CDR2 | AASSLQS |
| 6 | αFXI-13654p LC-CDR3 | QQVNSYPIT |
| 7 | αFXI-13716p and αFXI-13716 HC-CDR1 | YTFTSYSMH |
| 8 | αFXI-13716p and αFXI-13716 HC-CDR2 | IINPSGGSTSYAQKFQG |
| 9 | αFXI-13716p HC-CDR3 | GAYLMELYYYYGMDV |
| 10 | αFXI-13716p and αFXI-13716 LC-CDR1 | RASQSVSSNLA |
| 11 | αFXI-136716p and αFXI-13716 LC-CDR2 | GASTRAT |
| 12 | αFXI-13716p and αFXI-13716 LC-CDR3 | QQFNDWPLT |
| 13 | αFXI-13716 HC-CDR3 | GAYLLELYYYYGMDV |
| 14 | Human IgG4 HC constant domain: (S228P) X = K or absent S at position 108 replaced with P | ASTKGPSVFPLAPCSRSTSESTAALGCLVKDYFPEPVTVSWNSGALTSGVHT FPAVLQSSGLYSLSSVVTVPSSSLGTKTYTCNVDHKPSNTKVDKRVESKYGP PCPPCPAPEFLGGPSVFLFPPKPKDTLMISRTPEVTCVVVDVSQEDPEVQFN WYVDGVEVHNAKTKPREEQFNSTYRVVSVLTVLHQDWLNGKEYKCKVSN KGLPSSIEKTISKAKGQPREPQVYTLPPSQEEMTKNQVSLTCLVKGFYPSDIA VEWESNGQPENNYKTTPPVLDSDGSFFLYSRLTVDKSRWQEGNVFSCSVM HEALHNHYTQKSLSLSLGX |
| 15 | Human kappa LC constant domain | RTVAAPSVFIFPPSDEQLKSGTASVVCLLNNFYPREAKVQWKVDNALQSGN SQESVTEQDSKDSTYSLSSTLTLSKADYEKHKVYACEVTHQGLSSPVTKSFN RGEC |

TABLE OF SEQUENCES

| SEQ ID NO: | Description | Sequence |
|---|---|---|
| 16 | αFXI-13654p HC variable region | EVQLVESGGGLVKPGGSLRLSCAASGFTFSSYSMNWVRQAPGKGLEWVSS ISSSSSYIYYADSVKGRFTISRDNAKNSLYLQMNSLRAEDTAVYYCARSYY DYDQGYGMDVWGQGTTVTVSS |
| 17 | αFXI-13654p kappa LC variable region | DIQMTQSPSSVSASVGDRVTITCRASQGISSWLAWYQQKPGKAPKLLIYAA SSLQSGVPSRFSGSGSGTDFTLTISSLQPEDFATYYCQQVNSYPITFGGGTKV EIK |
| 18 | αFXI-13654p-IgG4 HC S228P C-terminal K-less | EVQLVESGGGLVKPGGSLRLSCAASGFTFSSYSMNWVRQAPGKGLEWVSS ISSSSSYIYYADSVKGRFTISRDNAKNSLYLQMNSLRAEDTAVYYCARSYY DYDQGYGMDVWGQGTTVTVSS*ASTKGPSVFPLAPCSRSTSESTAALGCLVKD YFPEPVTVSWNSGALTSGVHTFPAVLQSSGLYSLSSVVTVPSSSLGTKTYTCNVDH KPSNTKVDKRVESKYGPPCPPCPAPEFLGGPSVFLFPPKPKDTLMISRTPEVTCV VVDVSQEDPEVQFNWYVDGVEVHNAKTKPREEQFNSTYRVVSVLTVLHQDWLN GKEYKCKVSNKGLPSSIEKTISKAKGQPREPQVYTLPPSQEEMTKNQVSLTCLVK GFYPSDIAVEWESNGQPENNYKTTPPVLDSDGSFFLYSRLTVDKSRWQEGNVFS CSVMHEALHNHYTQKSLSLSLG* |
| 19 | αFXI-13654p kappa LC | DIQMTQSPSSVSASVGDRVTITCRASQGISSWLAWYQQKPGKAPKLLIYAA SSLQSGVPSRFSGSGSGTDFTLTISSLQPEDFATYYCQQVNSYPITFGGGTKV EIK*RTVAAPSVFIFPPSDEQLKSGTASVVCLLNNEYPREAKVQWKVDNALQSGNS QESVTEQDSKDSTYSLSSTLTLSKADYEKHKVYACEVTHQGLSSPVTKSFNRGEC* |
| 20 | αFXI-13716p HC variable region | QVQLVQSGAEVKKPGASVKVSCKASGYTFTSYSMHWVRQAPGQGLEWM GIINPSGGSTSYAQKFQGRVTMTRDTSTSTVYMELSSLRSEDTAVYYCAR GAYLMELYYYYGMDVWGQGTTVTVSS |
| 21 | αXI-13716p and αFXI-13716 Kappa LC variable region | EIVMTQSPATLSVSPGERATLSCRASQSVSSNLAWYQQKPGQAPRLLIYGA STRATGIPARFSGSGSGTEFTLTISSLQSEDFAVYYCQQFNDWPLTFGGGTK VEIK |
| 22 | αFXI-13716p-IgG4 HC S228P C-terminal K-less | QVQLVQSGAEVKKPGASVKVSCKASGYTFTSYSMHWVRQAPGQGLEWM GIINPSGGSTSYAQKFQGRVTMTRDTSTSTVYMELSSLRSEDTAVYYCAR GAYLMELYYYYGMDVWGQGTTVTVSS*ASTKGPSVFPLAPCSRSTSESTAAL GCLVKDYFPEPVTVSWNSGALTSGVHTFPAVLQSSGLYSLSSVVTVPSSSLGTKTY TCNVDHKPSNTKVDKRVESKYGPPCPPCPAPEFLGGPSVFLFPPKPKDTLA4ISR TPEVTCVVVDVSQEDPEVQFNWYVDGVEVHNAKTKPREEQFNSTYRVVSVLTVL HQDWLNGKEYKCKVSNKGLPSSIEKTISKAKGQPREQVYTLPPSQEEMTKNQV SLTCLVKGFYPSDIAVEWESNGQPENNYKTTPPVLDSDGSFFLYSRLTVDKSRWQ EGNVFSCSVMHEALHNHYTQKSLSLSLG* |
| 23 | αFXI-13716p and αFXI-13716 Kappa LC | EIVMTQSPATLSVSPGERATLSCRASQSVSSNLAWYQQKPGQAPRLLIYGA STRATGIPARFSGSGSGTEFTLTISSLQSEDFAVYYCQQFNDWPLTFGGGTK VEIK*RTVAAPSVHFPPSDEQLKSGTASVVCLLNNFTPREAKVQWKVDNALQSGN SQESVTEQDSKDSTYSLSSTLTLSKADYEKHKVYACEVTHQGLSSPVTKSFNRGEC* |
| 24 | αFXI-13716 HC variable region (Q1E M103L) | EVQLVQSGAEVKKPGASVKVSCKASGYTFTSYSMHWVRQAPGQGLEWM GIINPSGGSTSYAQKFQGRVTMTRDTSTSTVYMELSSLRSEDTAVYYCAR GAYLLELYYYYGMDVWGQGTTVTVSS |
| 25 | αFXI-13716 IgG4 HC Q1E M103L S228P | EVQLVQSGAEVKKPGASVKVSCKASGYTFTSYSMHWVRQAPGQGLEWM GIINPSGGSTSYAQKFQGRVTMTRDTSTSTVYMELSSLRSEDTAVYYCAR GAYLLELYYYYGMDVWGQGTTVTVSS*ASTKGPSVFPLAPCSRSTSESTAALG CLVKDYFPEPVTVSWNSGALTSGVHTFPAVLQSSGLYSLSSVVTVPSSSLGTKTYT CNVDHKPSNTKVDKRVESKYGPPCPPCPAPEFLGGPSVFLFPPKPKDTLA4ISRT PEVTCVVVDVSQEDPEVQFNWYVDGVEVHNAKTKPREEQFNSTYRVVSVLTVLH* |

TABLE OF SEQUENCES

| SEQ ID NO: | Description | Sequence |
|---|---|---|
|  | C-terminal K-less | *QDWLNGKEYKCKVSNKGLPSSIEKTISKAKGQPREPQVYTLPPSQEEMTKNQVS LTCLVKGFYPSDIAVEWESNGQPENNYKTTPPVLDSDGSFFLYSRLTVDKSRWQE GNVFSCSVMHEALHNHYTQKSLSLSLG* |
| 26 | αFXI-13654p-IgG4 HC S228P C-terminal K | EVQLVESGGGLVKPGGSLRLSCAASGFTFSSYSMNWVRQAPGKGLEWVSS ISSSSSYIYYADSVKGRFTISRDNAKNSLYLQMNSLRAEDTAVYYCARSYY DYDQGYGMDVWGQGTTVTVSS*ASTKGPSVFPLAPCSRSTSESTAALGCLVKD YFPEPVTVSWNSGALTSGVHTFPAVLQSSGLYSLSSVVTVPSSSLGTKTYTCNVDH KPSNTKVDKRVESKYGPPCPPCP*APEFLGGPSVFLFPPKPKDTLMISRTPEVTCV VVDVSQEDPEVQFNWYVDGVEVHNAKTKPREEQFNSTYRVVSVLTVLHQDWLN GKEYKCKVSNKGLPSSIEKTISKAKGQPREPQVYTLPPSQEEA4TKNQVSLTCLVK GFYPSDIAVEWESNGQPENNYKTTPPVLDSDGSFFLYSRLTVDKSRWQEGNVFS CSVMHEALHNHYTQKSLSLSLGK* |
| 27 | αFXI-13716p-IgG4 HC S228P C-terminal | QVQLVQSGAEVKKPGASVKVSCKASGYTFTSYSMHWVRQAPGQGLEWM GIINPSGGSTSYAQKFQGRVTMTRDTSTSTVYMELSSLRSEDTAVYYCAR GAYLMELYYYYGMDVWGQGTTVTVSS*ASTKGPSVFPLAPCSRSTSESTAAL GCLVKDYFPEPVTVSWNSGALTSGVHTFPAVLQSSGLYSLSSVVTVPSSSLGTKTY TCNVDHKPSNTKVDKRVESKYGPPCPPPCPAPEFLGGPSVFLEPPKPKDTLMISR TPEVTCVVVDVSQEDPEVQFNWYVDGVEVHNAKTKPREEQFNSTYRVVSVLTVL HQDWLNGKEYKCKVSNKGLPSSIEKTISKAKGQPREPQVYTLPPSQEEMTKNQV SLTCLVKGFYPSDIAVEWESNGQPENNYKTTPPVLDSDGSFFLYSRLTVDKSRWQ EGNVESCSVMHEALHNHYTQKSLSLSLGK* |
| 28 | αFXI-13716 IgG4 HC Q1E M103L S228P C-terminal K | EVQLVQSGAEVKKPGASVKVSCKASGYTFTSYSMHWVRQAPGQGLEWM GIINPSGGSTSYAQKFQGRVTMTRDTSTSTVYMELSSLRSEDTAVYYCAR GAYLLELYYYYGMDVWGQGTTVTVSS*ASTKGPSVFPLAPCSRSTSESTAALG CLVKDYFPEPVTVSWNSGALTSGVHTFPAVLQSSGLYSLSSVVTVPSSSLGTKTYT CNVDHKPSNTKVDKRVESKYGPPCPPCPAPEFLGGPSVFLFPPKPKDTLMISRT PEVTCVVVDVSQEDPEVQFNWYVDGVEVHNAKTKPREEQFNSTYRVVSVLTVLH QDWLNGKEYKCKVSNKGLPSSIEKTISKAKGQPREPQVYTLPPSQEEMTKNQVS LTCLVKGFYPSDIAVEWESNGQPENNYKTTPPVLDSDGSFFLYSRLTVDKSRWQE GNVFSCSVMHEALHNHYTQKSLSLSLGK* |
| 29 | IgG1 HC constant domain C-terminal K-less | ASTKGPSVFPLAPSSKSTSGGTAALGCLVKDYFPEPVTVSWNSGALTSGVHT FPAVLQSSGLYSLSSVVTVPSSSLGTQTYICNVNHKPSNTKVDKKVEPKSCD KTHTCPPCPAPELLGGPSVFLFPPKPKDTLMISRTPEVTCVVVDVSHEDPEV KFNWYVDGVEVHNAKTKPREEQYNSTYRVVSVLTVLHQDWLNGKEYKC KVSNKALPAPIEKTISKAKGQPREPQVYTLPPSRDELTKNQVSLTCLVKGFY PSDIAVEWESNGQPENNYKTTPPVLDSDGSFFLYSKLTVDKSRWQQGNVFS CSVMHEALHNHYTQKSLSLSPG |
| 30 | IgG1 HC constant domain C-terminal K | ASTKGPSVFPLAPSSKSTSGGTAALGCLVKDYFPEPVTVSWNSGALTSGVHT FPAVLQSSGLYSLSSVVTVPSSSLGTQTYICNVNHKPSNTKVDKKVEPKSCD KTHTCPPCPAPELLGGPSVFLFPPKPKDTLMISRTPEVTCVVVDVSHEDPEV KFNWYVDGVEVHNAKTKPREEQYNSTYRVVSVLTVLHQDWLNGKEYKC KVSNKALPAPIEKTISKAKGQPREPQVYTLPPSRDELTKNQVSLTCLVKGFY PSDIAVEWESNGQPENNYKTTPPVLDSDGSFFLYSKLTVDKSRWQQGNVFS CSVMHEALHNHYTQKSLSLSPGK |
| 31 | αFXI-13654p IgG1 HC C-terminal K-less | EVQLVESGGGLVKPGGSLRLSCAASGFTFSSYSMNWVRQAPGKGLEWVSS ISSSSSYIYYADSVKGRFTISRDNAKNSLYLQMNSLRAEDTAVYYCARSYY DYDQGYGMDVWGQGTTVTVSS*ASTKGPSVFPLAPCSRSTSESTAALGCLVKD YFPEPVTVSWNSGALTSGVHTFPAVLQSSGLYSLSSVVTVPSSSLGTKTYTCNVDH KPSNTKVDKRVESKYGPPCPPCPAPEFLGGPSVFLEPPKPKDTLMISRTPEVTCV VVDVSQEDPEVQFNWYVDGVEVHNAKTKPREEQFNSTYRVVSVLTVLHQDWLN GKEYKCKVSNKGLPSSIEKTISKAKGQPREPQVYTLPPSQEEA4TKNQVSLTCLVK GFYPSDIAVEWESNGQPENNYKTTPPVLDSDGSFFLYSRLTVDKSRWQEGNVFS CSVMHEALHNHYTQKSLSLSLG* |
| 32 | αFXI-13654p IgG1 HC C-terminal K | EVQLVESGGGLVKPGGSLRLSCAASGFTFSSYSMNWVRQAPGKGLEWVSS ISSSSSYIYYADSVKGRFTISRDNAKNSLYLQMNSLRAEDTAVYYCARSYY DYDQGYGMDVWGQGTTVTVSS*ASTKGPSVFPLAPCSRSTSESTAALGCLVKD YFPEPVTVSWNSGALTSGVHTFPAVLQSSGLYSLSSVVTVPSSSLGTKTYTCNVDH KPSNTKVDKRVESKYGPPCPPCPAPEFLGGPSVFLEPPKPKDTLAMISRTPEVTCV VVDVSQEDPEVQFNWYVDGVEVHNAKTKPREEQFNSTYRVVSVLTVLHQDWLN GKEYKCKVSNKGLPSSIEKTISKAKGQPREPQVYTLPPSQEEMTKNQVSLTCLVK GFYPSDIAVEWESNGQPENNYKTTPPVLDSDGSFELYSRLTVDKSRWQEGNVES CSVMHEALHNHYTQKSLSLSLGK* |
| 33 | αFXI-13716p IgG1 HC | QVQLVQSGAEVKKPGASVKVSCKASGYTFTSYSMHWVRQAPGQGLEWM GIINPSGGSTSYAQKFQGRVTMTRDTSTSTVYMELSSLRSEDTAVYYCAR GAYLMELYYYYGMDVWGQGTTVTVSS*ASTKGPSVFPLAPSSKSTSGGTAAL* |

| SEQ ID NO: | Description | Sequence |
|---|---|---|
|  | C-terminal K-less | *GCLVKDYFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLEPPKPKDTLAI ISRTPEVTCVVVDVSHEDPEVKFNWYVDGVEVHNAKTKPREEQYNSTYRVVSVLT VLHQDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTVDKSR WQQGNVFSCSVMHEALHNHYTQKSLSLSPG* |
| 34 | αFXI-13716p IgG1 HC C-terminal K | QVQLVQSGAEVKKPGASVKVSCKASGYTFTSYSMHWVRQAPGQGLEWM GIINPSGGSTSYAQKFQGRVTMTRDTSTSTVYMELSSLRSEDTAVYYCAR GAYLMELYYYYGMDVWGQGTTVTVSS*ASTKGPSVFPLAPSSKSTSGGTAAL GCLVKDYFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPKDTLMI ISRTPEVTCVVVDVSHEDPEVKFNWYVDGVEVHNAKTKPREEQYNSTYRVVSVLT VLHQDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTVDKSR WQQGNVFSCSVMHEALHNHYTQKSLSLSPGK* |
| 35 | αFXI-13716 IgG1 HC M103 L C-terminal K-less | QVQLVQSGAEVKKPGASVKVSCKASGYTFTSYSMHWVRQAPGQGLEWM GIINPSGGSTSYAQKFQGRVTMTRDTSTSTVYMELSSLRSEDTAVYYCAR GAYLLELYYYYGMDVWGQGTTVTVSS*ASTKGPSVFPLAPSSKSTSGGTAAL GCLVKDYFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPKDTLIVI ISRTPEVTCVVVDVSHEDPEVKFNWYVDGVEVHNAKTKPREEQYNSTYRVVSVLT VLHQDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTVDKSR WQQGNVESCSVMHEALHNHYTQKSLSLSPG* |
| 36 | αFXI-13716 IgG1 HC M103 L C-terminal K | QVQLVQSGAEVKKPGASVKVSCKASGYTFTSYSMHWVRQAPGQGLEWM GIINPSGGSTSYAQKFQGRVTMTRDTSTSTVYMELSSLRSEDTAVYYCAR GAYLLELYYYYGMDVWGQGTTVTVSS*ASTKGPSVFPLAPSSKSTSGGTAAL GCLVKDYFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPKDTLIVI ISRTPEVTCVVVDVSHEDPEVKFNWYVDGVEVHNAKTKPREEQYNSTYRVVSVLT VLHQDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTVDKSR WQQGNVFSCSVMHEALHNHYTQKSLSLSPGK* |
| 37 | Human FXI | ECVTQLLKDTCFEGGDITTVFTPSAKYCQVVCTYHPRCLLFTFTAESPSEDPT RWFTCVLKDSVTETLPRVNRTAAISGYSFKQCSHQISACNKDIYVDLDMKGI NYNSSVAKSAQECQERCTDDVHCHFFTYATRQFPSLEHRNICLLKHTQTGT PTRITKLDKVVSGFSLKSCALSNLACIRDIFPNTVFADSNIDSVMAPDAFVCG RICTHHPGCLFFTFFSQEWPKESQRNLCLLKTSESGLPSTRIKKSKALSGFSL QSCRHSIPVFCHSSFYHDTDFLGEELDIVAAKSHEACQKLCTNAVRCQFFTY TPAQASCNEGKGKCYLKLSSNGSPTKILHGRGGISGYTLRLCKMDNECTTKI KPRIVGGTASVRGEWPWQVTLHTTSPTQRHLCGGSIIGNQWILTAAHCFYG VESPKILRVYSGILNQSEIKEDTSFFGVQEIIIHDQYKMAESGYDIALLKLETT VNYTDSQRPICLPSKGDRNVIYTDCWVTGWGYRKLRDKIQNTLQKAKIPLV TNEECQKRYRGHKITHKMICAGYREGGKDACKGDSGGPLSCKHNEVWHL VGITSWGEGCAQRERPGVYTNVVEYVDWILEKTQAV |
| 38 | Epitope-A | YATRQFPSLEHRNICL |
| 39 | Epitope-B | HTQTGTPTRITKL |
| 40 | IgG1 HC constant domain X = K or absent | ASTKGPSVFPLAPSSKSTSGGTAALGCLVKDYFPEPVTVSWNSGALTSGVHT FPAVLQSSGLYSLSSVVTVPSSSLGTQTYICNVNHKPSNTKVDKKVEPKSCD KTHTCPPCPAPELLGGPSVFLFPPKPKDTLMISRTPEVTCVVVDVSHEDPEV KFNWYVDGVEVHNAKTKPREEQYNSTYRVVSVLTVLHQDWLNGKEYKC KVSNKALPAPIEKTISKAKGQPREPQVYTLPPSRDELTKNQVSLTCLVKGFY PSDIAVEWESNGQPENNYKTTPPVLDSDGSFFLYSKLTVDKSRWQQGNVFS CSVMHEALHNHYTQKSLSLSPGX |
| 41 | Human IgG4 HC constant domain: S228P X = K or absent | ASTKGPSVFPLAPCSRSTSESTAALGCLVKDYFPEPVTVSWNSGALTSGVHT FPAVLQSSGLYSLSSVVTVPSSSLGTKTYTCNVDHKPSNTKVDKRVESKYGP PCPSCPAPEFLGGPSVFLFPPKPKDTLMISRTPEVTCVVVDVSQEDPEVQFN WYVDGVEVHNAKTKPREEQFNSTYRVVSVLTVLHQDWLNGKEYKCKVSN KGLPSSIEKTISKAKGQPREPQVYTLPPSQEEMTKNQVSLTCLVKGFYPSDIA VEWESNGQPENNYKTTPPVLDSDGSFFLYSRLTVDKSRWQEGNVFSCSVM HEALHNHYTQKSLSLSLGX |
| 42 | DNA encoding αFXI- | GAAGTGCAGCTGGTCGAAAGCGGCGGCGGACTGGTGAAACCCGGAGGA AGCCTGAGGCTGAGCTGTGCCGCCAGCGGCTTTACCTTCAGCTCCTACTC CATGAACTGGGTGAGGCAGGCTCCTGGAAAAGGCCTGGAGTGGGTGAG |

| SEQ ID NO: | Description | Sequence |
|---|---|---|
|  | 13654p IgG4 HC C-terminal K-less | CTCCATCTCCAGCAGCTCCTCCTATATCTACTACGCCGACTCCGTGAAAG GCAGGTTCACCATCAGCAGGGATAATGCCAAGAACAGCCTGTACCTGCA GATGAACTCCCTCAGGGCCGAAGACACAGCCGTGTACTACTGCGCCAGG AGCTATTACGACTACGACCAGGGCTATGGCATGGACGTGTGGGGCCAGG GCACCACAGTCACCGTGAGCTCCGCCTCCACCAAAGGACCCTCCGTGTT TCCCCTGGCCCCCTGTAGCAGATCCACCAGCGAGAGCACCGCCGCTCTG GGCTGTCTCGTGAAGGATTACTTCCCCGAGCCCGTGACCGTGAGCTGGA ACTCTGGCGCCCTGACATCCGGCGTGCACACATTCCCCGCCGTCCTGCA AAGCAGCGGCCTCTATAGCCTGAGCTCCGTGGTGACCGTGCCCTCCAGC AGCCTGGGAACAAAGACCTACACCTGCAACGTGGACCACAAACCCTCCA ACACCAAGGTCGACAAGAGAGTGGAAAGCAAGTACGGCCCTCCTTGTCC CCCTTGCCCTGCTCCTGAGTTCCTGGGCGGACCCAGCGTGTTCCTGTTTC CCCCCAAACCCAAGGACACCCTGATGATCAGCAGAACCCCCGAGGTCAC CTGCGTCGTGGTGGACGTGAGCCAGGAGGACCCCGAAGTGCAGTTCAAC TGGTACGTGGACGGCGTGGAGGTGCACAACGCCAAGACCAAGCCCAGG GAAGAGCAATTCAACTCCACCTACAGGGTGGTGTCCGTCCTGACAGTCC TCCACCAGGACTGGCTGAACGGAAAGGAGTACAAATGTAAGGTGTCCA ACAAGGGCCTGCCCAGCTCCATCGAGAAGACAATCTCCAAGGCTAAGG GCCAGCCCAGAGAGCCCCAGGTGTATACCCTCCCTCCCTCCCAGGAGGA AATGACCAAGAACCAGGTCTCCCTGACCTGCCTGGTGAAGGGCTTCTAT CCCAGCGACATCGCCGTGGAATGGGAATCCAACGGCCAGCCCGAGAAC AACTACAAGACAACACCCCCCGTGCTCGATTCCGACGGTTCTTTCTTCCT GTACTCCAGGCTGACAGTGGACAAAAGCAGGTGGCAGGAGGGCAATGT CTTCAGCTGCAGCGTGATGCATGAGGCCCTGCACAACCACTATACCCAG AAGAGCCTGTCCCTGAGCCTGGGC |
| 43 | DNA encoding αFXI-13654p IgG4 HC C-terminal K | GAAGTGCAGCTGGTCGAAAGCGGCGGCGGACTGGTGAAACCCGGAGGA AGCCTGAGGCTGAGCTGTGCCGCCAGCGGCTTTACCTTCAGCTCCTACTC CATGAACTGGGTGAGGCAGGCTCCTGGAAAAGGCCTGGAGTGGGTGAG CTCCATCTCCAGCAGCTCCTCCTATATCTACTACGCCGACTCCGTGAAAG GCAGGTTCACCATCAGCAGGGATAATGCCAAGAACAGCCTGTACCTGCA GATGAACTCCCTCAGGGCCGAAGACACAGCCGTGTACTACTGCGCCAGG AGCTATTACGACTACGACCAGGGCTATGGCATGGACGTGTGGGGCCAGG GCACCACAGTCACCGTGAGCTCCGCCTCCACCAAAGGACCCTCCGTGTT TCCCCTGGCCCCCTGTAGCAGATCCACCAGCGAGAGCACCGCCGCTCTG GGCTGTCTCGTGAAGGATTACTTCCCCGAGCCCGTGACCGTGAGCTGGA ACTCTGGCGCCCTGACATCCGGCGTGCACACATTCCCCGCCGTCCTGCA AAGCAGCGGCCTCTATAGCCTGAGCTCCGTGGTGACCGTGCCCTCCAGC AGCCTGGGAACAAAGACCTACACCTGCAACGTGGACCACAAACCCTCCA ACACCAAGGTCGACAAGAGAGTGGAAAGCAAGTACGGCCCTCCTTGTCC CCCTTGCCCTGCTCCTGAGTTCCTGGGCGGACCCAGCGTGTTCCTGTTTC CCCCCAAACCCAAGGACACCCTGATGATCAGCAGAACCCCCGAGGTCAC CTGCGTCGTGGTGGACGTGAGCCAGGAGGACCCCGAAGTGCAGTTCAAC TGGTACGTGGACGGCGTGGAGGTGCACAACGCCAAGACCAAGCCCAGG GAAGAGCAATTCAACTCCACCTACAGGGTGGTGTCCGTCCTGACAGTCC TCCACCAGGACTGGCTGAACGGAAAGGAGTACAAATGTAAGGTGTCCA ACAAGGGCCTGCCCAGCTCCATCGAGAAGACAATCTCCAAGGCTAAGG GCCAGCCCAGAGAGCCCCAGGTGTATACCCTCCCTCCCTCCCAGGAGGA AATGACCAAGAACCAGGTCTCCCTGACCTGCCTGGTGAAGGGCTTCTAT CCCAGCGACATCGCCGTGGAATGGGAATCCAACGGCCAGCCCGAGAAC AACTACAAGACAACACCCCCCGTGCTCGATTCCGACGGTTCTTTCTTCCT GTACTCCAGGCTGACAGTGGACAAAAGCAGGTGGCAGGAGGGCAATGT CTTCAGCTGCAGCGTGATGCATGAGGCCCTGCACAACCACTATACCCAG AAGAGCCTGTCCCTGAGCCTGGGCAAG |
| 44 | DNA encoding αFXI-13654p LC | GACATCCAGATGACCCAGAGCCCTTCCTCCGTGAGCGCCAGCGTCGGCG ACAGAGTGACCATCACCTGCAGAGCCAGCCAGGGCATCAGCAGCTGGCT GGCTTGGTACCAGCAGAAGCCCGGCAAGGCCCCCAAGCTGCTGATCTAC GCCGCCAGCAGCCTGCAGAGCGGCGTGCCCTCCAGATTTAGCGGCAGCG GCAGCGGCACCGACTTTACCCTCACAATCAGCAGCCTGCAGCCCGAGGA CTTCGCTACCTACTACTGCCAGCAGGTGAACAGCTACCCTATCACATTCG GCGGCGGCACCAAGGTGGAGATCAAGAGAACCGTGGCCGCCCCCAGCG TGTTCATCTTCCCCCCCTCCGATGAGCAGCTGAAAAGCGGCACCGCCAG CGTCGTGTGCCTGCTGAACAACTTCTACCCCAGGGAGGCCAAAGTGCAG TGGAAGGTCGACAACGCCCTGCAGTCCGGCAACAGCCAAGAAAGCGTC ACCGAGCAGGACAGCAAGGACTCCACCTACAGCCTGTCCAGCACCCTGA CCCTGAGCAAGGCCGACTACGAGAAGCACAAGGTGTACGCCTGCGAGG TGACACACCAGGGCCTGAGCTCCCCCGTGACCAAGAGCTTCAATAGGGG CGAGTGC |
| 45 | DNA encoding αFXI- | GAGGTGCAGCTGGTGGAGTCTGGGGGAGGCCTGGTCAAGCCTGGGGGG TCCCTGAGACTCTCCTGTGCAGCCTCTGGATTCACCTTCAGTAGCTATAG CATGAACTGGGTCCGCCAGGCTCCAGGGAAGGGGCTGGAGTGGGTCTCA |

| SEQ ID NO: | Description | Sequence |
|---|---|---|
|  | 13654p IgG1 HC C-terminal K-less | TCCATTAGTAGTAGTAGTAGTTACATATACTACGCAGACTCAGTGAAGG<br>GCCGATTCACCATCTCCAGAGACAACGCCAAGAACTCACTGTATCTGCA<br>AATGAACAGCCTGAGAGCCGAGGACACGGCGGTGTACTACTGCGCCAG<br>ATCTTACTACGACTACGATCAAGGATACGGAATGGACGTATGGGGCCAG<br>GGAACAACTGTCACCGTCTCCTCAgctagcacaaaaggaccaagcgtgtttccactggcaccta<br>gcagcaaatccaccagcggcggaacagcagccctcgggtgcctggtgaaggattacttccctgagccagtcacagtgt<br>cctggaactccggagccctgacatccggcgtgcacaccttccccgctgtgctgcaatccagcggactgtatagcctcag<br>ctccgtcgtgacagtcccttccagcagcctgggcacacagactttacatttgcaacgtgaaccacaaaaccttccaacacta<br>aggtggacaaaaaggtggaacccaaatcctgtgataagacccatacatgcccaccttgtcccgctcctgagctgctggg<br>gggaccttccgtctttctgtttcctccaaaaccaaaagacacactcatgatcagccggaccccgaagtcacctgtgtggt<br>ggtggacgtcagccacgaagatccagaggtcaagttcaattggtacgtggatggagtggaagtccacaacgcaaaaac<br>caaacctagagaagaacagtacaatagcacatacagggtggtgtccgtcctgacagtgctccaccaggactggctcaat<br>ggcaaagagtataagtgcaaggtgagcaacaaggccctgcctgcaccaattgagaaaacaattagcaaggcaaaggg<br>gcagccacgggaaccccaggtgtataccctgccccaagccgggatgaactgaccaaaaaccaggtcagcctgacat<br>gcctggtgaaagggttttacccaagcgatattgccgtcgagtgggagagcaacggacagccagaaaacaattacaaaa<br>ccaccccacctgtgctggactccgatgggagctattcctgtacagcaagctcacgtggacaagtccagatggcaaca<br>gggcaacgtgttttcctgctccgtgatgcacgaggccctccacaaccactatacacaaaagtccctctccctcagcccag<br>ga |
| 46 | DNA encoding αFXI-13654p IgG1 HC C-terminal K | GAGGTGCAGCTGGTGGAGTCTGGGGGAGGCCTGGTCAAGCCTGGGGGG<br>TCCCTGAGACTCTCCTGTGCAGCCTCTGGATTCACCTTCAGTAGCTATAG<br>CATGAACTGGGTCCGCCAGGCTCCAGGGAAGGGGCTGGAGTGGGTCTCA<br>TCCATTAGTAGTAGTAGTAGTTACATATACTACGCAGACTCAGTGAAGG<br>GCCGATTCACCATCTCCAGAGACAACGCCAAGAACTCACTGTATCTGCA<br>AATGAACAGCCTGAGAGCCGAGGACACGGCGGTGTACTACTGCGCCAG<br>ATCTTACTACGACTACGATCAAGGATACGGAATGGACGTATGGGGCCAG<br>GGAACAACTGTCACCGTCTCCTCAgctagcacaaaaggaccaagcgtgtttccactggcaccta<br>gcagcaaatccaccagcggcggaacagcagccctcgggtgcctggtgaaggattacttccctgagccagtcacagtgt<br>cctggaactccggagccctgacatccggcgtgcacaccttccccgctgtgctgcaatccagcggactgtatagcctcag<br>ctccgtcgtgacagtcccttccagcagcctgggcacacagactttacatttgcaacgtgaaccacaaaaccttccaacacta<br>aggtggacaaaaaggtggaacccaaatcctgtgataagacccatacatgcccaccttgtcccgctcctgagctgctggg<br>gggaccttccgtctttctgtttcctccaaaaccaaaagacacactcatgatcagccggaccccgaagtcacctgtgtggt<br>ggtggacgtcagccacgaagatccagaggtcaagttcaattggtacgtggatggagtggaagtccacaacgcaaaaac<br>caaacctagagaagaacagtacaatagcacatacagggtggtgtccgtcctgacagtgctccaccaggactggctcaat<br>ggcaaagagtataagtgcaaggtgagcaacaaggccctgcctgcaccaattgagaaaacaattagcaaggcaaaggg<br>gcagccacgggaaccccaggtgtataccctgccccaagccgggatgaactgaccaaaaaccaggtcagcctgacat<br>gcctggtgaaagggttttacccaagcgatattgccgtcgagtgggagagcaacggacagccagaaaacaattacaaaa<br>ccaccccacctgtgctggactccgatgggagctattcctgtacagcaagctcacgtggacaagtccagatggcaaca<br>gggcaacgtgttacctgctccgtgatgcacgaggccctccacaaccactatacacaaaagtccctctccctcagcccag<br>gaaag |
| 47 | DNA encoding αFXI-13716p IgG4 HC C-terminal K-less | CAGGTCCAGCTCGTGCAGAGCGGAGCCGAGGTGAAGAAGCCCGGAGCC<br>TCCGTCAAAGTGAGCTGTAAAGCCAGCGGCTACACCTTCACATCCTACA<br>GCATGCACTGGGTGAGGCAGGCTCCTGGCCAAGGCCTGGAGTGGATGG<br>GCATTATCAACCCCAGCGGCGGCTCCACCTCCTACGCTCAGAAGTTCCA<br>GGGCAGGGTGACCATGACCAGAGACACCAGCACCAGCACCGTGTATAT<br>GGAGCTGAGCTCCCTGAGGAGCGAGGACACAGCCGTGTACTACTGCGCT<br>AGGGGGCGCCTACCTGATGGAGCTGTACTACTACTACGGAATGGATGTGT<br>GGGGCCAGGGCACCACCGTGACAGTCTCCAGCGCCAGCACCAAAGGCC<br>CTTCCGTGTTTCCCCTGGCCCCCTGCAGCAGGAGCACCAGCGAAAGCAC<br>AGCCGCCCTGGGCTGTCTGGTGAAGGACTACTTCCCCGAACCCGTGACC<br>GTGAGCTGGAACAGCGGAGCTCTGACCTCCGGCGTGCACACATTTCCCG<br>CCGTGCTGCAGTCCAGCGGACTGTACAGCCTGTCCAGCGTGGTGACCGT<br>CCCCAGCTCCAGCCTGGGCACCAAGACCTACACCTGTAACGTGGATCAT<br>AAGCCCAGCAACACCAAGGTGGACAAGAGAGTGGAGAGCAAATACGGC<br>CCTCCCTGTCCCCCTTGTCCCGCTCCCGAATTTCTGGGCGGCCCTTCCGT<br>GTTCCTGTTCCCCCCTAAGCCCAAGGACACCCTGATGATCAGCAGAACC<br>CCCGAAGTCACATGCGTGGTGGTCGACGTGAGCCAGGAGGACCCCGAG<br>GTCCAGTTTAACTGGTACGTGGACGGAGTGGAAGTGCACAACGCCAAGA<br>CAAAGCCCAGGGAGGAGCAGTTCAACAGCACCTACAGAGTGGTGTCCG<br>TGCTCACCGTGCTGCACCAGGATTGGCTGAACGGAAAGGAGTACAAGTG<br>TAAGGTGAGCAACAAAGGCCTCCCAGCAGCATCGAAAAGACCATCTCC<br>AAAGCTAAGGGACAGCCCAGAGAGCCCCAGGTGTACACACTGCCCCCC<br>AGCCAGGAGGAGATGACCAAGAATCAGGTGTCCCTGACCTGCCTGGTGA<br>AAGGCTTTTACCCCTCCGACATTGCCGTCGAATGGGAGTCCAACGGCCA<br>GCCTGAGAACAACTATAAGACAACCCCCCCTGTGCTGGACAGCGACGGC<br>TCCTTCTTTCTGTACTCCAGGCTGACCGTCGACAAATCCAGGTGGCAGGA<br>GGGAAACGTGTTCAGCTGCAGCGTGATGCACGAGGCCCTGCACAACCAC<br>TACACCCAGAAGAGCCTGTCCCTGAGCCTCGGC |
| 48 | DNA encoding aFXI- | CAGGTCCAGCTCGTGCAGAGCGGAGCCGAGGTGAAGAAGCCCGGAGCC<br>TCCGTCAAAGTGAGCTGTAAAGCCAGCGGCTACACCTTCACATCCTACA<br>GCATGCACTGGGTGAGGCAGGCTCCTGGCCAAGGCCTGGAGTGGATGG |

| SEQ ID NO: | Description | Sequence |
|---|---|---|
|  | 13716p IgG4 HC C-terminal K | GCATTATCAACCCCAGCGGCGGCTCCACCTCCTACGCTCAGAAGTTCCA GGGCAGGGTGACCATGACCAGAGACACCAGCACCAGCACCGTGTATAT GGAGCTGAGCTCCCTGAGGAGCGAGGACACAGCCGTGTACTACTGCGCT AGGGGCGCCTACCTGATGGAGCTGTACTACTACTACGGAATGGATGTGT GGGGCCAGGGCACCACCGTGACAGTCTCCAGCGCCAGCACCAAAGGCC CTTCCGTGTTTCCCCTGGCCCCCTGCAGCAGGAGCACCAGCGAAAGCAC AGCCGCCCTGGGCTGTCTGGTGAAGGACTACTTCCCCGAACCCGTGACC GTGAGCTGGAACAGCGGAGCTCTGACCTCCGGCGTGCACACATTTCCCG CCGTGCTGCAGTCCAGCGGACTGTACAGCCTGTCCAGCGTGGTGACCGT CCCCAGCTCCAGCCTGGGCACCAAGACCTACACCTGTAACGTGGATCAT AAGCCCAGCAACACCAAGGTGGACAAGAGAGTGGAGAGCAAATACGGC CCTCCCTGTCCCCCTTGTCCCGCTCCCGAATTTCTGGGCGGCCCTTCCGT GTTCCTGTTCCCCCCTAAGCCCAAGGACACCCTGATGATCAGCAGAACC CCCGAAGTCACATGCGTGGTGGTCGACGTGAGCCAGGAGGACCCCGAG GTCCAGTTTAACTGGTACGTGGACGGAGTGGAAGTGCACAACGCCAAGA CAAAGCCCAGGGAGGAGCAGTTCAACAGCACCTACAGAGTGGTGTCCG TGCTCACCGTGCTGCACCAGGATTGGCTGAACGGAAAGGAGTACAAGTG TAAGGTGAGCAACAAAGGCCTCCCCAGCAGCATCGAAAAGACCATCTCC AAAGCTAAGGGACAGCCCAGAGAGCCCCAGGTGTACACACTGCCCCCC AGCCAGGAGGAGATGACCAAGAATCAGGTGTCCCTGACCTGCCTGGTGA AAGGCTTTTACCCCTCCGACATTGCCGTCGAATGGGAGTCCAACGGCCA GCCTGAGAACAACTATAAGACAACCCCCCCTGTGCTGGACAGCGACGGC TCCTTCTTTCTGTACTCCAGGCTGACCGTCGACAAATCCAGGTGGCAGGA GGGAAACGTGTTCAGCTGCAGCGTGATGCACGAGGCCCTGCACAACCAC TACACCCAGAAGAGCCTGTCCCTGAGCCTCGGCAAG |
| 49 | DNA encoding αFXI-13716p LC | GAGATCGTCATGACCCAGAGCCCTGCTACCCTGAGCGTGAGCCCTGGCG AAAGGGCCACCCTGTCCTGTAGGGCCAGCCAGAGCGTGTCCAGCAACCT GGCCTGGTATCAGCAGAAGCCTGGCCAGGCCCCTAGGCTGCTGATCTAC GGCGCCAGCACCAGAGCTACCGGCATCCCTGCTAGGTTCTCCGGAAGCG GCTCCGGCACCGAGTTCACCCTGACCATTAGCTCCCTGCAGAGCGAGGA CTTCGCCGTGTACTACTGCCAGCAGTTCAACGACTGGCCCCTGACCTTCG GCGGAGGCACCAAGGTGGAGATCAAGAGGACCGTGGCCGCTCCTTCCGT GTTCATCTTCCCCCCCAGCGACGAGCAGCTGAAGTCCGGCACAGCCTCC GTGGTGTGCCTGCTGAACAACTTCTACCCCAGGGAGGCCAAGGTGCAGT GGAAGGTGGACAACGCCCTGCAAAGCGGCAACAGCCAGGAGTCCGTGA CCGAGCAGGACAGCAAGGACTCCACCTACTCCCTGAGCTCCACCCTGAC CCTGAGCAAGGCCGATTACGAGAAGCACAAGGTGTACGCCTGCGAGGT GACCCACCAGGGACTGAGCAGCCCCGTGACCAAGAGCTTCAACAGGGG CGAATGC |
| 50 | DNA encoding αFXI-13716p IgG1 HC C-terminal K-less | CAGGTGCAGCTGGTGCAGTCTGGGGCTGAGGTGAAGAAGCCTGGGGCCT CAGTGAAGGTTTCCTGCAAGGCATCTGGATACACCTTCACCAGCTACAG CATGCACTGGGTGCGACAGGCCCCTGGACAAGGGCTTGAGTGGATGGG AATAATCAACCCTAGTGGTGGTAGCACAAGCTACGCACAGAAGTTCCAG GGCAGAGTCACCATGACCAGGGACACGTCCACGAGCACAGTCTACATG GAGCTGAGCAGCCTGAGATCTGAGGACACGGCGGTGTACTACTGCGCCA GAGGTGCTTATCTAATGGAGTTATACTACTATTACGGTATGGATGTCTGG GGCCAGGGAACAACTGTCACCGTCTCCTCAgctagcacaaaaggaccaagcgtgtttccac tggcacctagcagcaaatccaccagcggcggaacagcagccctcgggtgcctggtgaaggattacttccctgagcca gtcacagtgtcctggaactccggagcccgacatcggcgtgcacaccttccccgctgtgctgcaatccagcggactgt atagcctcagctccgtcgtgacagtcccttccagcagcctgggcacacagacttacatttgcaacgtgaaccacaaacct tccaacactaaggtggacaaaaaggtggaacccaaatcctgtgataagacccatacatgccacctgtcccgctcctga gctgctggggggaccttccgtctttctgttctctccaaaaccaaaagacacactcatgatcagccggaccccccgaagtca cctgtgtggtggtggacgtcagccacgaagatccagaggtcaagttcaattggtacgtggatggagtggaagtccacaa cgcaaaaaaccaaacctagagaagaacagtacaatagcacatacagggtggtgtccgtcctgacagtgctccaccagga ctggctcaatggcaaagagtataagtgcaaggtgagcaacaaggccctgcctgcaccaattgagaaaacaattagcaa ggcaaagggccagccacgggaacccaggtgtatacctgccccccaagccgggatgaactgaccaaaaaccaggtc agcctgacatgcctggtgaaagggttttacccaagcgatattgccgtcgagtgggagagcaacggacagccagaaaac aattacaaaaccacccccacctgtgctggactccgatgggagctattcctgtacagcaagctcacagtggacaagtccag atggcaacagggcaacgtgttttcctgctccgtgatgcacgaggcccttccacaaccactatacacaaaagtccctctccc tcagcccagga |
| 51 | DNA encoding αFXI-13716p IgG1 HC C-terminal K | CAGGTGCAGCTGGTGCAGTCTGGGGCTGAGGTGAAGAAGCCTGGGGCCT CAGTGAAGGTTTCCTGCAAGGCATCTGGATACACCTTCACCAGCTACAG CATGCACTGGGTGCGACAGGCCCCTGGACAAGGGCTTGAGTGGATGGG AATAATCAACCCTAGTGGTGGTAGCACAAGCTACGCACAGAAGTTCCAG GGCAGAGTCACCATGACCAGGGACACGTCCACGAGCACAGTCTACATG GAGCTGAGCAGCCTGAGATCTGAGGACACGGCGGTGTACTACTGCGCCA GAGGTGCTTATCTAATGGAGTTATACTACTATTACGGTATGGATGTCTGG GGCCAGGGAACAACTGTCACCGTCTCCTCAgctagcacaaaaggaccaagcgtgtttccac tggcacctagcagcaaatccaccagcggcggaacagcagccctcgggtgcctggtgaaggattacttccctgagcca gtcacagtgtcctggaactccggagcccgacatcggcgtgcacaccttccccgctgtgctgcaatccagcggactgt |

TABLE OF SEQUENCES

| SEQ ID NO: | Description | Sequence |
|---|---|---|
| | | atagcctcagctccgtcgtgacagtcccttccagcagcctgggcacacagacttacatttgcaacgtgaaccacaaacct<br>tccaacactaaggtggacaaaaaggtggaacccaaatcctgtgataagacccatacatgcccaccttgtcccgctcctga<br>gctgctggggggaccttccgtctcttctgtttcctccaaaaccaaaagacacactcatgatcagccggaccccgaagtca<br>cctgtgtggtggtggacgtcagccacgaagatccagaggtcaagttcaattggtacgtggatggagtggagtccacaa<br>cgcaaaaaccaaacctagagaagaacagtacaatagcacatacagggtggtgtccgtcctgacagtgctccaccagga<br>ctggctcaatggcaaagagtataagtgcaaggtgagcaacaaggccctgcctgcaccaattgagaaaacaattagcaa<br>ggcaaaggggcagccacgggaacccaggtgtataccctgcccccaagccgggatgaactgaccaaaaaccaggtc<br>agcctgacatgcctggtgaaagggttttacccaagcgatattgccgtcgagtgggagagcaacggacagccagaaac<br>aattacaaaaccacccacctgtgctggactccgatgggagctattcctgtacagcaagctcacgtggacaagtccag<br>atggcaacagggcaacgtgttttcctgctccgtgatgcacgaggccctccacaaccactatacacaaaagtccctctccc<br>tcagcccaggaaag |
| 52 | DNA encoding αFXI-13716 IgG4 HC S228P Q1E M103L C-terminal K-less | GAGGTGCAGCTGGTCCAGAGCGGAGCCGAGGTGAAGAAACCCGGAGCC<br>AGCGTCAAGGTGAGCTGCAAGGCCTCCGGCTACACCTTCACATCCTATA<br>GCATGCACTGGGTGAGGCAGGCTCCTGGCCAGGGCCTGGAATGGATGG<br>GCATCATCAACCCCAGCGGCGGCTCCACATCCTACGCCCAGAAATTTCA<br>GGGAAGGGTCACCATGACCAGGGATACATCCACCAGCACCGTGTACATG<br>GAGCTGTCCAGCCTGAGGTCCGAGGACACCGCTGTGTACTACTGCGCCA<br>GAGGCGCCTATCTGCTGGAGCTGTACTACTACTACGGAATGGACGTGTG<br>GGGCCAGGGCACAACCGTGACCGTGAGCAGCGCCAGCACCAAGGGACC<br>TTCCGTGTTCCCCCTGGCCCCTTGTAGCAGATCCACCTCCGAATCCACCG<br>CCGCTCTGGGCTGTCTCGTCAAGGATTATTTCCCCGAGCCTGTGACCGTG<br>TCCTGGAACTCCGGAGCCCTCACCTCCGGCGTGCATACCTTCCCTGCCGT<br>GCTCCAGTCCAGCGGCCTGTACTCCCTCAGCAGCGTGGTGACCGTGCCC<br>TCCAGCAGCCTGGGCACCAAAACCTATACCTGCAATGTGGACCACAAGC<br>CCAGCAATACCAAGGTGGACAAGAGGGTGGAGTCCAAATACGGACCTC<br>CCTGTCCCCCTGCCCCGCTCCCGAATTTCTGGGAGGCCCCTCCGTGTTC<br>CTGTTCCCTCCCAAGCCCAAGGACACACTGATGATTTCCAGGACCCCTG<br>AGGTGACCTGCGTGGTGGTGGACGTCAGCCAGGAAGATCCTGAGGTGCA<br>GTTCAACTGGTACGTGGATGGCGTGGAAGTGCATAACGCCAAGACCAAG<br>CCCAGGGAGGAACAGTTCAACAGCACCTACAGAGTGGTCAGCGTGCTG<br>ACAGTCCTGCACCAGGACTGGCTGAACGGCAAGGAATACAAGTGCAAG<br>GTGTCCAACAAGGGACTCCCCTCCTCCATCGAGAAAACAATCAGCAAGG<br>CCAAAGGCCAGCCCAGAGAACCTCAAGTCTATACCCTCCCCCCTAGCCA<br>GGAGGAGATGACCAAGAACCAAGTGAGCCTGACCTGCCTGGTGAAGGG<br>CTTTTACCCCAGCGACATCGCCGTGGAATGGGAGTCCAACGGACAGCCC<br>GAGAACAACTATAAGACAACCCCTCCCGTGCTCGACTCCGATGGAAGCT<br>TTTTTCCTCTACAGCAGGCTGACCGTGGACAAGAGCAGATGGCAGGAGGG<br>AAATGTGTTCAGCTGCAGCGTGATGCACGAAGCCCTGCACAACCACTAC<br>ACCCAAAAAAGCCTGAGCCTGAGCCTGGGA |
| 53 | DNA encoding αFXI-13716 IgG4 HC S228P Q1E M103L C-terminal K | GAGGTGCAGCTGGTCCAGAGCGGAGCCGAGGTGAAGAAACCCGGAGCC<br>AGCGTCAAGGTGAGCTGCAAGGCCTCCGGCTACACCTTCACATCCTATA<br>GCATGCACTGGGTGAGGCAGGCTCCTGGCCAGGGCCTGGAATGGATGG<br>GCATCATCAACCCCAGCGGCGGCTCCACATCCTACGCCCAGAAATTTCA<br>GGGAAGGGTCACCATGACCAGGGATACATCCACCAGCACCGTGTACATG<br>GAGCTGTCCAGCCTGAGGTCCGAGGACACCGCTGTGTACTACTGCGCCA<br>GAGGCGCCTATCTGCTGGAGCTGTACTACTACTACGGAATGGACGTGTG<br>GGGCCAGGGCACAACCGTGACCGTGAGCAGCGCCAGCACCAAGGGACC<br>TTCCGTGTTCCCCCTGGCCCCTTGTAGCAGATCCACCTCCGAATCCACCG<br>CCGCTCTGGGCTGTCTCGTCAAGGATTATTTCCCCGAGCCTGTGACCGTG<br>TCCTGGAACTCCGGAGCCCTCACCTCCGGCGTGCATACCTTCCCTGCCGT<br>GCTCCAGTCCAGCGGCCTGTACTCCCTCAGCAGCGTGGTGACCGTGCCC<br>TCCAGCAGCCTGGGCACCAAAACCTATACCTGCAATGTGGACCACAAGC<br>CCAGCAATACCAAGGTGGACAAGAGGGTGGAGTCCAAATACGGACCTC<br>CCTGTCCCCCTGCCCCGCTCCCGAATTTCTGGGAGGCCCCTCCGTGTTC<br>CTGTTCCCTCCCAAGCCCAAGGACACACTGATGATTTCCAGGACCCCTG<br>AGGTGACCTGCGTGGTGGTGGACGTCAGCCAGGAAGATCCTGAGGTGCA<br>GTTCAACTGGTACGTGGATGGCGTGGAAGTGCATAACGCCAAGACCAAG<br>CCCAGGGAGGAACAGTTCAACAGCACCTACAGAGTGGTCAGCGTGCTG<br>ACAGTCCTGCACCAGGACTGGCTGAACGGCAAGGAATACAAGTGCAAG<br>GTGTCCAACAAGGGACTCCCCTCCTCCATCGAGAAAACAATCAGCAAGG<br>CCAAAGGCCAGCCCAGAGAACCTCAAGTCTATACCCTCCCCCCTAGCCA<br>GGAGGAGATGACCAAGAACCAAGTGAGCCTGACCTGCCTGGTGAAGGG<br>CTTTTACCCCAGCGACATCGCCGTGGAATGGGAGTCCAACGGACAGCCC<br>GAGAACAACTATAAGACAACCCCTCCCGTGCTCGACTCCGATGGAAGCT<br>TTTTTCCTCTACAGCAGGCTGACCGTGGACAAGAGCAGATGGCAGGAGGG<br>AAATGTGTTCAGCTGCAGCGTGATGCACGAAGCCCTGCACAACCACTAC<br>ACCCAAAAAAGCCTGAGCCTGAGCCTGGGAAAG |
| 54 | DNA encoding aFXI- | GAGGTGCAGCTGGTCCAGAGCGGAGCCGAGGTGAAGAAACCCGGAGCC<br>AGCGTCAAGGTGAGCTGCAAGGCCTCCGGCTACACCTTCACATCCTATA<br>GCATGCACTGGGTGAGGCAGGCTCCTGGCCAGGGCCTGGAATGGATGG |

| TABLE OF SEQUENCES | | |
|---|---|---|
| SEQ ID NO: | Description | Sequence |
| | 13716 IgG1 HC Q1E M103L C-terminal K-less | GCATCATCAACCCCAGCGGCGGCTCCACATCCTACGCCCAGAAATTTCA<br>GGGAAGGGTCACCATGACCAGGGATACATCCACCAGCACCGTGTACATG<br>GAGCTGTCCAGCCTGAGGTCCGAGGACACCGCTGTGTACTACTGCGCCA<br>GAGGCGCCTATCTGCTGGAGCTGTACTACTACTACGGAATGGACGTGTG<br>GGGCCAGGGCACAACCGTGACCGTGAGCAGCGCCgctagcacaaaaggaccaagcg<br>tgtttccactggcacctagcagcaaatccaccagcggcggaacagcagccctcgggtgcctggtgaaggattactccc<br>tgagccagtcacagtgtcctggaactccggagccctgacatccggcgtgcacaccttccccgctgtgctgcaatccagc<br>ggactgtatagcctcagctccgtcgtgacagtcccttccagcagcctgggcacacagacttacatttgcaacgtgaacca<br>caaaccttccaacactaaggtggacaaaaaggtggaacccaaatcctgtgataagacccatacatgcccaccttgtccc<br>gctcctgagctgctggggggaccttccgtcttctgtttcctccaaaaccaaaagacacactcatgatcagccggacccc<br>cgaagtcacctgtgtggtggtggacgtcagccacgaagatccagaggtcaagttcaattggtacgtggatggagtggaa<br>gtccacaacgcaaaaaccaaacctagagaagaacagtacaatagcacatacagggtggtgtccgtcctgacagtgctc<br>caccaggactggctcaatggcaaagagtataagtgcaaggtgagcaacaaggcccgcctgcaccaattgagaaaac<br>aattagcaaggcaaaggggcagccacgggaaccccaggtgtataccctgccccaagccgggatgaactgaccaaa<br>aaccaggtcagcctgacatgcctggtgaaagggttttacccaagcgatattgccgtcgagtgggagagcaacggacag<br>ccagaaaacaattacaaaaaccacccccacctgtgctggactccgatgggagctattcctgtacagcaagctcacagtgga<br>caagtccagatggcaacagggcaacgtgttttcctgctccgtgatgcacgaggccctccacaaccactatacacaaaag<br>tccctctccctcagcccagga |
| 55 | DNA encoding αFXI- 13716 IgG1 HC Q1E M103L C-terminal K | GAGGTGCAGCTGGTCCAGAGCGGAGCCGAGGTGAAGAAACCCGGAGCC<br>AGCGTCAAGGTGAGCTGCAAGGCCTCCGGCTACACCTTCACATCCTATA<br>GCATGCACTGGGTGAGGCAGGCTCCTGGCCAGGGCCTGGAATGGATGG<br>GCATCATCAACCCCAGCGGCGGCTCCACATCCTACGCCCAGAAATTTCA<br>GGGAAGGGTCACCATGACCAGGGATACATCCACCAGCACCGTGTACATG<br>GAGCTGTCCAGCCTGAGGTCCGAGGACACCGCTGTGTACTACTGCGCCA<br>GAGGCGCCTATCTGCTGGAGCTGTACTACTACTACGGAATGGACGTGTG<br>GGGCCAGGGCACAACCGTGACCGTGAGCAGCGCCgctagcacaaaaggaccaagcg<br>tgtttccactggcacctagcagcaaatccaccagcggcggaacagcagccctcgggtgcctggtgaaggattactccc<br>tgagccagtcacagtgtcctggaactccggagccctgacatccggcgtgcacaccttccccgctgtgctgcaatccagc<br>ggactgtatagcctcagctccgtcgtgacagtcccttccagcagcctgggcacacagacttacatttgcaacgtgaacca<br>caaaccttccaacactaaggtggacaaaaaggtggaacccaaatcctgtgataagacccatacatgcccaccttgtccc<br>gctcctgagctgctggggggaccttccgtcttctgtttcctccaaaaccaaaagacacactcatgatcagccggacccc<br>cgaagtcacctgtgtggtggtggacgtcagccacgaagatccagaggtcaagttcaattggtacgtggatggagtggaa<br>gtccacaacgcaaaaaccaaacctagagaagaacagtacaatagcacatacagggtggtgtccgtcctgacagtgctc<br>caccaggactggctcaatggcaaagagtataagtgcaaggtgagcaacaaggcccgcctgcaccaattgagaaaac<br>aattagcaaggcaaaggggcagccacgggaaccccaggtgtataccctgccccaagccgggatgaactgaccaaa<br>aaccaggtcagcctgacatgcctggtgaaagggttttacccaagcgatattgccgtcgagtgggagagcaacggacag<br>ccagaaaacaattacaaaaaccacccccacctgtgctggactccgatgggagctattcctgtacagcaagctcacagtgga<br>caagtccagatggcaacagggcaacgtgttttcctgctccgtgatgcacgaggccctccacaaccactatacacaaaag<br>tccctctccctcagcccaggaaag |
| 56 | Leader Sequence A | MSVPTQVLGLLLLWLTDARC |
| 57 | Leader Sequence B | MEWSWVFLFFLSVTTGVHS |
| 58 | Leader Sequence C | MELGLCWVFLVAILEGVQC |
| 59 | αFXI- 13654p- IgG4 HC S228P X = K or absent | EVQLVESGGGLVKPGGSLRLSCAASGFTFSSYSMNWVRQAPGKGLEWVSSI<br>SSSSSYIYYADSVKGRFTISRDNAKNSLYLQMNSLRAEDTAVYYCARSYYD<br>YDQGYGMDVWGQGTTVTVSSASTKGPSVFPLAPCSRSTSESTAALGCLVK<br>DYFPEPVTVSWNSGALTSGVHTFPAVLQSSGLYSLSSVVTVPSSSLGTKTYT<br>CNVDHKPSNTKVDKRVESKYGPPCPPCPAPEFLGGPSVFLFPPKPKDTLMIS<br>RTPEVTCVVVDVSQEDPEVQFNWYVDGVEVHNAKTKPREEQFNSTYRVVS<br>VLTVLHQDWLNGKEYKCKVSNKGLPSSIEKTISKAKGQPREPQVYTLPPSQ<br>EEMTKNQVSLTCLVKGFYPSDIAVEWESNGQPENNYKTTPPVLDSDGSFFL<br>YSRLTVDKSRWQEGNVFSCSVMHEALHNHYTQKSLSLSLGX |
| 60 | αFXI- 13716p- IgG4 HC S228P X = K or absent | QVQLVQSGAEVKKPGASVKVSCKASGYTFTSYSMHWVRQAPGQGLEWM<br>GIIINPSGGSTSYAQKFQGRVTMTRDTSTSTVYMELSSLRSEDTAVYYCARG<br>AYLMELYYYYGMDVWGQGTTVTVSSASTKGPSVFPLAPCSRSTSESTAAL<br>GCLVKDYFPEPVTVSWNSGALTSGVHTFPAVLQSSGLYSLSSVVTVPSSSLG<br>TKTYTCNVDHKPSNTKVDKRVESKYGPPCPPCPAPEFLGGPSVFLFPPKPKD<br>TLMISRTPEVTCVVVDVSQEDPEVQFNWYVDGVEVHNAKTKPREEQFNST<br>YRVVSVLTVLHQDWLNGKEYKCKVSNKGLPSSIEKTISKAKGQPREPQVYT<br>LPPSQEEMTKNQVSLTCLVKGFYPSDIAVEWESNGQPENNYKTTPPVLDSD<br>GSFFLYSRLTVDKSRWQEGNVFSCSVMHEALHNHYTQKSLSLSLGX |

TABLE OF SEQUENCES

| SEQ ID NO: | Description | Sequence |
|---|---|---|
| 61 | αFXI-13716-IgG4 HC S228P 1Q1E M103L X = K or absent | EVQLVQSGAEVKKPGASVKVSCKASGYTFTSYSMHWVRQAPGQGLEWMG IINPSGGSTSYAQKFQGRVTMTRDTSTSTVYMELSSLRSEDTAVYYCARGA YLLELYYYYGMDVWGQGTTVTVSSASTKGPSVFPLAPCSRSTSESTAALGC LVKDYFPEPVTVSWNSGALTSGVHTFPAVLQSSGLYSLSSVVTVPSSSLGTK TYTCNVDHKPSNTKVDKRVESKYGPPCPPCPAPEFLGGPSVFLFPPKPKDTL MISRTPEVTCVVVDVSQEDPEVQFNWYVDGVEVHNAKTKPREEQFNSTYR VVSVLTVLHQDWLNGKEYKCKVSNKGLPSSIEKTISKAKGQPREPQVYTLP PSQEEMTKNQVSLTCLVKGFYPSDIAVEWESNGQPENNYKTTPPVLDSDGS FFLYSRLTVDKSRWQEGNVFSCSVMHEALHNHYTQKSLSLSLGX |
| 62 | αFXI-13654p-IgG1 HC X = K or absent | EVQLVESGGGLVKPGGSLRLSCAASGFTFSSYSMNWVRQAPGKGLEWVSSI SSSSSYIYYADSVKGRFTISRDNAKNSLYLQMNSLRAEDTAVYYCARSYYD YDQGYGMDVWGQGTTVTVSSASTKGPSVFPLAPSSKSTSGGTAALGCLVK DYFPEPVTVSWNSGALTSGVHTFPAVLQSSGLYSLSSVVTVPSSSLGTQTYI CNVNHKPSNTKVDKKVEPKSCDKTHTCPPCPAPELLGGPSVFLFPPKPKDTL MISRTPEVTCVVVDVSHEDPEVKFNWYVDGVEVHNAKTKPREEQYNSTYR VVSVLTVLHQDWLNGKEYKCKVSNKALPAPIEKTISKAKGQPREPQVYTLP PSRDELTKNQVSLTCLVKGFYPSDIAVEWESNGQPENNYKTTPPVLDSDGSF FLYSKLTVDKSRWQQGNVFSCSVMHEALHNHYTQKSLSLSPGX |
| 63 | αFXI-13716p-IgG1 HC X = K or absent | QVQLVQSGAEVKKPGASVKVSCKASGYTFTSYSMHWVRQAPGQGLEWM GIINPSGGSTSYAQKFQGRVTMTRDTSTSTVYMELSSLRSEDTAVYYCARG AYLMELYYYYGMDVWGQGTTVTVSSASTKGPSVFPLAPSSKSTSGGTAAL GCLVKDYFPEPVTVSWNSGALTSGVHTFPAVLQSSGLYSLSSVVTVPSSSLG TQTYICNVNHKPSNTKVDKKVEPKSCDKTHTCPPCPAPELLGGPSVFLFPPK PKDTLMISRTPEVTCVVVDVSHEDPEVKFNWYVDGVEVHNAKTKPREEQY NSTYRVVSVLTVLHQDWLNGKEYKCKVSNKALPAPIEKTISKAKGQPREPQ VYTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPGX |
| 64 | αFXI-13716-gG1 HC 1Q 1E M103L X = K or absent | EVQLVQSGAEVKKPGASVKVSCKASGYTFTSYSMHWVRQAPGQGLEWMG IINPSGGSTSYAQKFQGRVTMTRDTSTSTVYMELSSLRSEDTAVYYCARGA YLLELYYYYGMDVWGQGTTVTVSSASTKGPSVFPLAPSSKSTSGGTAALGC LVKDYFPEPVTVSWNSGALTSGVHTFPAVLQSSGLYSLSSVVTVPSSSLGTQ TYICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYNS TYRVVSVLTVLHQDWLNGKEYKCKVSNKALPAPIEKTISKAKGQPREPQVY TLPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGX |
| 65 | αFXI-13716 IgG1 HC Q1E C-terminal K-less | EVQLVQSGAEVKKPGASVKVSCKASGYTFTSYSMHWVRQAPGQGLEWM GIINPSGGSTSYAQKFQGRVTMTRDTSTSTVYMELSSLRSEDTAVYYCAR GAYLMELYYYYGMDVWGQGTTVTVSS*ASTKGPSVFPLAPSSKSTSGGTAAL GCLVKDYFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPKDTLM ISRTPEVTCVVVDVSHEDPEVKFNWYVDGVEVHNAKTKPREEQYNSTYRVVSVLT VLHQDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTVDKSR WQQGNVFSCSVMHEALHNHYTQKSLSLSPG* |
| 66 | αFXI-13716 IgG1 HC Q1E C-terminal K | EVQLVQSGAEVKKPGASVKVSCKASGYTFTSYSMHWVRQAPGQGLEWM GHNPSGGSTSYAQKFQGRVTMTRDTSTSTVYMELSSLRSEDTAVYYCAR GAYLMELYYYYGMDVWGQGTTVTVSS*ASTKGPSVFPLAPSSKSTSGGTAAL GCLVKDYFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPKDTLM ISRTPEVTCVVVDVSHEDPEVKFNWYVDGVEVHNAKTKPREEQYNSTYRVVSVLT VLHQDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTVDKSR WQQGNVFSCSVMHEALHNHYTQKSLSLSPGK* |
| 67 | αFXI-13716-IgG4 HC S228P Q1E C-terminal K-less | EVQLVQSGAEVKKPGASVKVSCKASGYTFTSYSMHWVRQAPGQGLEWM GIINPSGGSTSYAQKFQGRVTMTRDTSTSTVYMELSSLRSEDTAVYYCAR GAYLMELYYYYGMDVWGQGTTVTVSS*ASTKGPSVFPLAPCSRSTSESTAAL GCLVKDYFPEPVTVSWNSGALTSGVHTFPAVLQSSGLYSLSSVVTVPSSSLGTKTY TCNVDHKPSNTKVDKRVESKYGPPCPPCPAPEFLGGPSVFLFPPKPKDTLMISR TPEVTCVVVDVSQEDPEVQFNWYVDGVEVHNAKTKPREEQFNSTYRVVSVLTVL HQDWLNGKEYKCKVSNKGLPSSIEKTISKAKGQPREPQVYTLPPSQEEMTKNQV SLTCLVKGFYPSDIAVEWESNGQPENNYKTTPPVLDSDGSFFLYSRLTVDKSRWQ EGNVFSCSVMHEALHNHYTQKSLSLSLG* |
| 68 | αFXI-13716-IgG4 HC | EVQLVQSGAEVKKPGASVKVSCKASGYTFTSYSMHWVRQAPGQGLEWM GIINPSGGSTSYAQKFQGRVTMTRDTSTSTVYMELSSLRSEDTAVYYCAR GAYLMELYYYYGMDVWGQGTTVTVSS*ASTKGPSVFPLAPCSRSTSESTAAL* |

TABLE OF SEQUENCES

| SEQ ID NO: | Description | Sequence |
|---|---|---|
| | S228P Q1E C-terminal K | GCLVKDYFPEPVTVSWNSGALTSGVHTFPAVLQSSGLYSLSSVVTVPSSSLGTKTY TCNVDHKPSNTKVDKRVESKYGPPCPPCPAPEFLGGPSVFLFPPKPKDTLMISR TPEVTCVVVDVSQEDPEVQFNWYVDGVEVHNAKTKPREEQFNSTYRVVSVLTVL HQDWLNGKEYKCKVSNKGLPSSIEKTISKAKGQPREPQVYTLPPSQEEMTKNQV SLTCLVKGFYPSDIAVEWESNGQPENNYKITTPPVLDSDGSFFLYSRLTVDKSRWQ EGNVFSCSVMHEALHNHYTQKSLSLSLGK |
| 69 | αFXI-13716-IgG4 HC S228P M103L C-terminal K-less | QVQLVQSGAEVKKPGASVKVSCKASGYTFTSYSMHWVRQAPGQGLEWM GIINPSGGSTSYAQKFQGRVTMTRDTSTSTVYMELSSLRSEDTAVYYCAR GAYLLELYYYYGMDVWGQGTTVTVSS*ASTKGPSVFPLAPCSRSTSESTAALG CLVKDYFPEPVTVSWNSGALTSGVHTFPAVLQSSGLYSLSSVVTVPSSSLGTKTYT CNVDHKPSNTKVDKRVESKYGPPCPPCPAPEFLGGPSVFLEPPKPKDTLMISRT PEVTCVVVDVSQEDPEVQFNWYVDGVEVHNAKTKPREEQFNSTYRVVSVLTVLH QDWLNGKEYKCKVSNKGLPSSIEKTISKAKGQPREPQVYTLPPSQEEMTKNQVS LTCLVKGFYPSDIAVEWESNGQPENNYKTTPPVLDSDGSFFLYSRLTVDKSRWQE GNVFSCSVMHEALHNHYTQKSLSLSLG* |
| 70 | αFXI-13716-IgG4 HC S228P M103 L C-terminal K | QVQLVQSGAEVKKPGASVKVSCKASGYTFTSYSMHWVRQAPGQGLEWM GIINPSGGSTSYAQKFQGRVTMTRDTSTSTVYMELSSLRSEDTAVYYCAR GAYLLELYYYYGMDVWGQGTTVTVSS*ASTKGPSVFPLAPCSRSTSESTAALG CLVKDYFPEPVTVSWNSGALTSGVHTFPAVLQSSGLYSLSSVVTVPSSSLGTKTYT CNVDHKPSNTKVDKRVESKYGPPCPPCPAPEFLGGPSVFLEPPKPKDTLMISRT PEVTCVVVDVSQEDPEVQFNWYVDGVEVHNAKTKPREEQFNSTYRVVSVLTVLH QDWLNGKEYKCKVSNKGLPSSIEKTISKAKGQPREPQVYTLPPSQEEMTKNQVS LTCLVKGFYPSDIAVEWESNGQPENNYKTTPPVLDSDGSFFLYSRLTVDKSRWQE GNVFSCSVMHEALHNHYTQKSLSLSLGK* |
| 71 | anti-RSV Kappa Light Chain | MAPVQLLGLLVLFLPAMRCDIQMTQSPSTLSASVGDRVTITCKCQLSVGYM HWYQQKPGKAPKLLIYDTSKLASGVPSRFSGSGSGTEFTLTISSLQPDDFAT YYCFQGSGYPFTFGGGTKLEIK*RTVAAPSVHFPPSDEQLKSGTASVVCLLNNFY PREAKVQWKVDNALQSGNSQESVTEQDSKDSTYSLSSTLTLSKADYEKHKVYACE VTHQGLSSPVTKSFNRGEC* |
| 72 | anti-RSV IgG4 HC S228P | MAVVQLLGLLVLFLPAMRCQVTLRESGPALVKPTQTLTLTCTFSGFSLSTSG MSVGWIRQPPGKALEWLADIWWDDKKDYNPSLKSRLTISKDTSKNQVVLK VTNMDPADTATYYCARSMITNWYFDVWGAGTTVTVSS*ASTKGPSVFPLAPC SRSTSESTAALGCLVKDYFPEPVTVSWNSGALTSGVHTFPAVLQSSGLYSLSSVVT VPSSSLGTKTYTCNVDHKPSNTKVDKRVESKYGPPCPPCPAPEFLGGPSVFLFPP KPKDTLMISRTPEVTCVVVDVSQEDPEVQFNWYVDGVEVHNAKTKPREEQENS TYRVVSVLTVLHQDWLNGKEYKCKVSNKGLPSSIEKTISKAKGQPREPQVYTLPP SQEEMTKNQVSLTCLVKGFYPSDIAVEWESNGQPENNYKTTPPVLDSDGSFFLYS RLTVDKSRWQEGNVESCSVMHEALHNHYTQKSLSLSLGK* |

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed:

1. An antibody or antigen binding fragment comprising:
a heavy chain (HC) variable domain comprising
an HC complementarity determining region (HC CDR) 1 having the amino acid sequence set forth in SEQ ID NO:7, an HC CDR 2 having the amino acid sequence set forth in SEQ ID NO:8, and an HC CDR 3 having the amino acid sequence set forth in SEQ ID NO:9 or 13 and
a light chain (LC) variable domain comprising an LC CDR 1 having the amino acid sequence set forth in SEQ ID NO:10, an LC CDR 2 having the amino acid sequence set forth in SEQ ID NO:11, and an LC CDR 3 having the amino acid sequence set forth in SEQ ID NO:12; and,
wherein the antibody or antigen binding fragment binds the apple 2 domain of coagulation factor XI (FXI) and inhibits activation of FXI.

2. The antibody or antigen binding fragment of claim 1, wherein the antibody or antigen binding fragment comprises:
an HC variable domain having the amino acid sequence shown in SEQ ID NO:24 or 20 and an LC variable domain having amino acid sequence shown in SEQ ID NO:21.

3. The antibody or antigen binding fragment of claim 1, which is an antibody, wherein the antibody comprises an HC constant domain having the amino acid sequence shown in SEQ ID NO:14 or 40 or variant thereof in which the constant domain comprises 1, 2, 3, 4, 5, 6, 7, 8, 9, or 10 amino acid substitutions, additions, deletions, or combinations thereof.

4. The antibody or antigen binding fragment of claim 1, which is an antibody, wherein the antibody comprises an LC constant domain comprising the amino acid sequence shown in SEQ ID NO:15 or variant thereof in which the constant domain comprises 1, 2, 3, 4, 5, 6, 7, 8, 9, or 10 amino acid substitutions, additions, deletions, or combinations thereof.

5. The antibody or antigen binding fragment of claim 1, which is an antibody wherein the antibody comprises a heavy chain constant domain of the human IgG1, IgG2, IgG3, or IgG4 isotype or variant thereof in which the constant domain comprises 1, 2, 3, 4, 5, 6, 7, 8, 9, or 10 amino acid substitutions, additions, deletions, or combinations thereof.

6. The antibody or antigen binding fragment of claim 1, which is an antibody wherein the antibody comprises a heavy chain constant domain of the human IgG4 isotype or variant thereof in which the constant domain comprises 1, 2, 3, 4, 5, 6, 7, 8, 9, or 10 amino acid substitutions, additions, deletions, or combinations thereof.

7. The antibody or antigen binding fragment of claim 1, which is an antibody wherein the antibody comprises a heavy chain having the amino acid sequence shown in SEQ ID NO:22, 25, 27, 28, 33, 34, 35, or 36; and a light chain having the amino acid sequence shown in SEQ ID NO:23.

8. A composition comprising an antibody or antigen binding fragment of claim 1 and a pharmaceutically acceptable carrier or diluent.

9. A method of treating a thromboembolic disorder or disease in a subject comprising:
administering to a subject in need thereof a therapeutically effective amount of the antibody or antigen binding fragment of any one of claims 1-7.

10. The method of claim 9, wherein the subject in need of treatment is a subject suffering from or at risk of suffering from myocardial infarction, ischemic stroke, pulmonary thromboembolism, venous thromboembolism (VTE), atrial fibrillation, disseminated intravascular coagulation, medical device-related thromboembolic disorders, severe systemic inflammatory response syndrome, metastatic cancer, or an infectious disease.

11. The method of claim 9, wherein the subject in need of treatment is a subject with pathological activation of FXI.

12. The method of claim 9 wherein the therapeutically effective amount of the antibody or antigen binding fragment comprises about 0.3 to about 3.0 mg of the antibody or antigen binding fragment/kg of the subject.

13. The method of claim 12, wherein the therapeutically effective amount of the antibody or antigen binding fragment comprises about 1.0 to 2.0 mg of the antibody or antigen binding fragment/kg of the subject.

14. An antibody comprising a heavy chain consisting of the amino acid sequence set forth in SEQ ID NO:25 or 28 and a light chain consisting of the amino acid sequence set forth in SEQ ID NO:23.

15. The antibody of claim 14, wherein the heavy chain consists of the amino acid sequence set forth in SEQ ID NO:25.

16. A composition comprising the antibody of claim 14 and a pharmaceutically acceptable carrier.

17. A method of treating a thromboembolic disorder or disease in a subject comprising:
administering to a subject in need thereof a therapeutically effective amount of the antibody or antigen binding fragment of claim 14.

18. The method of claim 17, wherein the subject in need of treatment is a subject suffering from or at risk of suffering from myocardial infarction, ischemic stroke, pulmonary thromboembolism, venous thromboembolism (VTE), atrial fibrillation, disseminated intravascular coagulation, medical device-related thromboembolic disorders, severe systemic inflammatory response syndrome, metastatic cancer, or an infectious disease.

* * * * *